US012649729B2

(12) United States Patent
Shen et al.

(10) Patent No.: US 12,649,729 B2

(45) Date of Patent: Jun. 9, 2026

(54) PYRAZOLE DERIVATIVES USEFUL AS NAMPT MODULATORS

(71) Applicant: Cytokinetics, Inc., South San Francisco, CA (US)

(72) Inventors: Minxing Shen, San Bruno, CA (US); Antonio Romero, San Mateo, CA (US); Pu-Ping Lu, Foster City, CA (US)

(73) Assignee: CYTOKINETICS, INC., South San Francisco, CA (US)

( * ) Notice: Subject to any disclaimer, the term of this patent is extended or adjusted under 35 U.S.C. 154(b) by 320 days.

(21) Appl. No.: 18/268,569

(22) PCT Filed: Dec. 20, 2021

(86) PCT No.: PCT/US2021/064422

§ 371 (c)(1),
(2) Date: Jun. 20, 2023

(87) PCT Pub. No.: WO2022/140290

PCT Pub. Date: Jun. 30, 2022

(65) Prior Publication Data

US 2024/0067631 A1 Feb. 29, 2024

Related U.S. Application Data

(60) Provisional application No. 63/128,756, filed on Dec. 21, 2020.

(51) Int. Cl.

| | |
|---|---|
| ***C07D 401/14*** | (2006.01) |
| ***C07D 403/12*** | (2006.01) |
| ***C07D 403/14*** | (2006.01) |
| ***C07D 405/14*** | (2006.01) |
| ***C07D 409/14*** | (2006.01) |
| ***C07D 413/14*** | (2006.01) |
| ***C07D 417/14*** | (2006.01) |

(52) U.S. Cl.

CPC ......... *C07D 401/14* (2013.01); *C07D 403/12* (2013.01); *C07D 403/14* (2013.01); *C07D 405/14* (2013.01); *C07D 409/14* (2013.01); *C07D 413/14* (2013.01); *C07D 417/14* (2013.01)

(58) Field of Classification Search

CPC .................................................... C07D 401/14

See application file for complete search history.

(56) References Cited

U.S. PATENT DOCUMENTS

| | | | |
|---|---|---|---|
| 5,391,806 | A | 2/1995 | Otsuji et al. |
| 5,846,514 | A | 12/1998 | Foster |
| 6,334,997 | B1 | 1/2002 | Foster |
| 6,531,506 | B1 | 3/2003 | Kroetz et al. |
| 7,074,785 | B2 | 7/2006 | Seitz et al. |
| 9,132,136 | B2 | 9/2015 | Hoener |
| 10,329,275 | B2 | 6/2019 | Bair et al. |
| 11,007,178 | B2 | 5/2021 | Tipparaju et al. |
| 11,452,717 | B2 | 9/2022 | Gardell et al. |
| 11,485,745 | B2 | 11/2022 | Bair et al. |

(Continued)

FOREIGN PATENT DOCUMENTS

| | | | |
|---|---|---|---|
| CA | 2477005 | A1 | 9/2003 |
| CL | 2014003560 | A1 | 11/2015 |

(Continued)

OTHER PUBLICATIONS

Akiu, M. et al. (2021). "Discovery of DS68702229 as a Potent, Orally Available NAMPT (Nicotinamide Phosphoribosyltransferase) Activator," Chem. Pharm. Bull. (Tokyo) 69(11):1110-1122.

Akiu, M. et al. (2022). "Optimization NAMPT (Nicotinamide Phosphoribosyltransferase) Activators: Discover of N,N-Diethyl-1,2-Benzoxazole-3-Carboxamide Derivatives As Potent NAMPT Activators With Mitigated Mutagenic Risks," Heterocycles 104(1):94-122, 29 pages.

Akiu, M. et al. (Jul. 1, 2021, e-pub. Apr. 19, 2021). "Discovery of 1-[2-(1-methyl-1H-pyrazol-5-yl)-[1,2,4]triazolo[1,5-a]pyridin-6-yl]-3-(pyridin-4-ylmethyl)Urea as a Potent NAMPT (Nicotinamide Phosphoribosyltransferase) Activator With Attenuated CYP Inhibition," Bioorganic and Medicinal Chemistry Letters 43:128048, 7 pages.

(Continued)

*Primary Examiner* — John S Kenyon

*Assistant Examiner* — Rehana Ismail

(74) *Attorney, Agent, or Firm* — MORRISON & FOERSTER LLP

(57) ABSTRACT

Provided herein are compounds of formula (A): or a pharmaceutically acceptable salt thereof, wherein X, $R^1$, $R^2$, $R^3$, $R^4$, $R^y$, and $R^z$ are as defined herein. Also provided herein is a pharmaceutically acceptable composition comprising a compound of formula (A), or a pharmaceutically acceptable salt thereof, as well as methods of using a compound of formula (A), or a pharmaceutically acceptable salt thereof, to treat various diseases and conditions mediated by nicotinamide phosphoribosyltransferase (NAMPT).

(A)

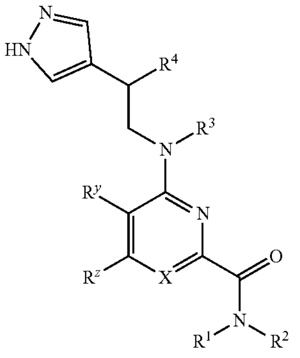

33 Claims, No Drawings

(56) References Cited

U.S. PATENT DOCUMENTS

| | | | |
|---|---|---|---|
| 2006/0205772 | A1 | 9/2006 | Coppola et al. |
| 2007/0287708 | A1 | 12/2007 | Cole et al. |
| 2008/0188561 | A1 | 8/2008 | Vernier et al. |
| 2011/0112080 | A1 | 5/2011 | Galley et al. |
| 2011/0152245 | A1 | 6/2011 | Groebke et al. |
| 2012/0028964 | A1 | 2/2012 | Hoener et al. |
| 2013/0109668 | A1 | 5/2013 | Ceccarelli et al. |
| 2013/0137720 | A1 | 5/2013 | Wang et al. |
| 2013/0317027 | A1 | 11/2013 | Willardsen et al. |
| 2021/0161873 | A1 | 6/2021 | Gardell et al. |
| 2022/0370636 | A1 | 11/2022 | Tipparaju et al. |
| 2023/0116972 | A1 | 4/2023 | Ashcraft et al. |
| 2023/0133132 | A1 | 5/2023 | Romero et al. |
| 2023/0348369 | A1 | 11/2023 | Romero et al. |
| 2024/0279215 | A1 | 8/2024 | Lu et al. |

FOREIGN PATENT DOCUMENTS

| | | | | |
|---|---|---|---|---|
| CN | 1741986 | A | 3/2006 | |
| CN | 103709096 | A | 4/2014 | |
| CN | 104098556 | A | 10/2014 | |
| CN | 106916101 | A | 7/2017 | |
| CN | 111848506 | A | 10/2020 | |
| CN | 113121518 | A | 7/2021 | |
| CN | 115417870 | A | 12/2022 | |
| CN | 115521305 | A | 12/2022 | |
| CN | 111848506 | B | 1/2023 | |
| CN | 116589402 | A | 8/2023 | |
| CN | 118108664 | A | 5/2024 | |
| EP | 2611777 | B1 | 5/2016 | |
| EP | 3568390 | A1 | 11/2019 | |
| GB | 760051 | A | 10/1956 | |
| JP | 2001-525400 | A | 12/2001 | |
| JP | 2005-519079 | A | 6/2005 | |
| JP | 2006-517199 | A | 7/2006 | |
| JP | 2009-506979 | A | 2/2009 | |
| JP | 2009-523812 | A | 6/2009 | |
| JP | 2013-522171 | A | 6/2013 | |
| JP | 2013-536181 | A | 9/2013 | |
| JP | 2013-536868 | A | 9/2013 | |
| JP | 2014-534224 | A | 12/2014 | |
| JP | 2015-508786 | A | 3/2015 | |
| JP | 2015-529224 | A | 10/2015 | |
| WO | 1999029674 | A1 | 12/1997 | |
| WO | 0063157 | A1 | 10/2000 | |
| WO | 0125190 | A1 | 4/2001 | |
| WO | 03024220 | A1 | 3/2003 | |
| WO | 03072098 | A1 | 9/2003 | |
| WO | 2004065351 | A1 | 8/2004 | |
| WO | 2004082677 | A1 | 9/2004 | |
| WO | 2005/058311 | A1 | 6/2005 | |
| WO | 2005073183 | A1 | 8/2005 | |
| WO | 2005087754 | A1 | 9/2005 | |
| WO | 2007026920 | A2 | 3/2007 | |
| WO | 2007084667 | A2 | 7/2007 | |
| WO | WO-2008082487 | A2 * | 7/2008 | .............. A61P 37/06 |
| WO | 2008/103351 | A2 | 8/2008 | |
| WO | 2009015667 | A1 | 2/2009 | |
| WO | 2010036316 | A1 | 4/2010 | |
| WO | 2011/057973 | A1 | 5/2011 | |
| WO | 2011109441 | A1 | 9/2011 | |
| WO | 2012/016879 | A1 | 2/2012 | |
| WO | 2012/031197 | A1 | 3/2012 | |
| WO | 2012031196 | A1 | 3/2012 | |
| WO | 2012/067965 | A1 | 5/2012 | |
| WO | 2012092873 | A1 | 7/2012 | |
| WO | 2013/170112 | A1 | 11/2013 | |
| WO | 2014/004884 | A1 | 1/2014 | |
| WO | 2014039714 | A2 | 3/2014 | |
| WO | 2015105749 | A1 | 7/2015 | |
| WO | 2016087975 | A1 | 6/2016 | |
| WO | 2018132372 | A1 | 7/2018 | |
| WO | 2019101641 | A1 | 5/2019 | |
| WO | 2020010252 | A1 | 1/2020 | |
| WO | 2020/073031 | A1 | 4/2020 | |
| WO | 2021159015 | A1 | 8/2021 | |
| WO | 2021207186 | A1 | 10/2021 | |
| WO | 2021226276 | A2 | 11/2021 | |
| WO | 2022135617 | A1 | 6/2022 | |
| WO | 2022140290 | A1 | 6/2022 | |
| WO | 2022165114 | A1 | 8/2022 | |
| WO | 2023011416 | A1 | 2/2023 | |
| WO | 2023229346 | A1 | 11/2023 | |
| WO | 2024/137981 | A1 | 6/2024 | |
| WO | 2024/166024 | A1 | 8/2024 | |
| WO | 2025/231630 | A1 | 11/2025 | |

OTHER PUBLICATIONS

Artursson, P. et al. (Mar. 29, 1991). "Correlation Between Oral Drug Absorption in Humans and Apparent Drug Permeability Coefficients in Human Intestinal Epithelial (CACO-2) Cells," Biochemical and Biophysical Research Communications 175(3): 880-885.

Berge, S.M. et al. (Jan. 1977). "Pharmaceuticals Salts," J. Pharmaceutical Sciences 66(1):1-19.

Blacher, E. et al. (Aug. 2019). "Potential Roles of Gut Microbiome and Metabolites in Modulating ALS in Mice," Nature 570:474-480, 42 pages.

Braidy, N. et al. (Apr. 2011). "Age Related Changes in NAD+ Metabolism Oxidative Stress and Sirt1 Activity in Wistar Rats," PLoS One 6(4):e19194, 18 pages.

Bu, X-B. et al. (2017). "Rhodium-Catalyzed Oxidative Coupling Reaction of Isocyanides with Alcohols or Amines and Molecular Oxygen as Oxygen Source: Synthesis of Carbamates and Ureas," European Journal of Organic Chemistry 7:1132-1138.

Cerutti, R. et al. (Jun. 3, 2014). "NAD+-Dependent Activation of Sirt1 Corrects the Phenotype in a Mouse Model of Mitochondrial Disease," Cell Metab. 19(6):1042-1049.

Dean, D.C. (Jul. 2000). "Recent Advances in the Synthesis and Applications of Radiolabeled Compounds for Drug Discovery and Development," Current Pharm. Des. 6(10):113, TOC Only, 2 pages.

Diguet, N. et al. (May 22, 2018, e-pub. Dec. 7, 2017). "Nicotinamide Riboside Preserves Cardiac Function in a Mouse Model of Dilated Cardiomyopathy," Circulation 137(21):2256-2273, 31 pages.

European Examination Report mailed on Nov. 21, 2023, for EP Patent Application No. 21710105.4, 13 pages.

Evans, A.E. (Mar. 1981, e-pub. Jan. 9, 2007). "Synthesis of Radiolabelled Compounds," J Radio Anal. Chem. 64(1-2):9-32.

Fang, E. F. et al. (May 8, 2014). "Defective Mitophagy in XPA via PARP-1 Hyperactivation and NAD(+)/SIRT1 Reduction," Cell 157(4):882-896, 29 pages.

Fang, E.F. et al. (Oct. 2017). "NAD+ In Aging: Molecular Mechanisms and Translational Implications," Trends Mol. Med. 23(10):899-916, 33 pages.

Fulco, M. et al. (May 2008). "Glucose Restriction Inhibits Skeletal Myoblast Differentiation by Activating SIRT1 Through AMPK-Mediated Regulation of Nampt," Dev. Cell. 14(5):661-673.

Galli, U. et al. (May 12, 2020). "Recent Advances in NAMPT Inhibitors: A Novel Immunotherapic Strategy," Frontiers In Pharmacology 11:656, 20 pages.

Gardell, S.J. et al. (2019). "Boosting NAD+ With A Small Molecule That Activated NAMPT," Nature Communications 10:3241, 12 pages.

Ghosh, D. et al. (Apr. 25, 2012). "A Reversible Early Oxidized Redox State That Precedes Macromolecular ROS Damage in Aging Nontransgenic and 3xTg-AD Mouse Neurons," J. Neurosci. 32(17):5821-5832.

Gillig, A. et al. (2012). "Synthesis of a C-Iminoribofuranoside Analog of the Nicotinamide Phosphoribosyltransferase (NAMPT) Inhibitor FK866," HCA 95:34-42.

Goring, S. et al. (Mar. 2014, e-pub. Feb. 10, 2015). "Computer-Guided Design, Synthesis, and Biological Evaluation of Quinoxalinebisarylureas as FLT3 Inhibitors," Chem Med Chem 10(3): 511-522.

Greene, T.W. et al. (1999). Protective Groups in Organic Synthesis, 3. Ed., John Wiley & Sons, Cover & Contents pages, 20 pages.

(56) References Cited

OTHER PUBLICATIONS

Guarino, M. et al. (Sep. 10, 2019). "Nicotinamide and NAFLD: Is There Nothing New Under the Sun?," Metabolites 9(9):180, 17 pages.
Harlan, B.A. et al. (May 13, 2016). "Enhancing NAD+ Salvage Pathway Reverts the Toxicity of Primary Astrocytes Expressing Amyotrophic Lateral Sclerosis-linked Mutant Superoxide Dismutase 1 (SOD1)," J. Biol. Chem. 291 (20):10836-10846.
Harlan, B.A. et al. (May 2020). "Evaluation and the NAD+ Biosynthetic Pathway in ALS Patents and Effect of Modulating NAD+ Levels in hSOD1-Linked ALS Mouse Models," Exp Neurol. 327:113219, 25 pages.
Imai, S-I. (2009). "Nicotinamide Phosphoribosyltransferase (Nampt): A Link Between NAD Biology, Metabolism, and Disease," Curr. Pharm. Des. 15(1):20-28, 16 pages.
International Preliminary Report on Patentability issue date of Jul. 28, 2022 for Patent Application No. PCT/US2021/016948, filed Feb. 5, 2021, 12 pages.
International Preliminary Report on Patentability issue date of Nov. 8, 2022 for Patent Application No. PCT/US2021/030950, filed May 5, 2021, 11 pages.
International Preliminary Report on Patentability issued on Jun. 13, 2023, for PCT Application No. PCT/US2021/064422, filed on Dec. 20, 2021, 6 pages.
International Search Report and Written Opinion mailed on Mar. 14, 2022, for PCT Application No. PCT/US2021/064422, filed on Dec. 20, 2021, 13 pages.
International Search Report and Written Opinion mailed on Sep. 27, 2021, for PCT Application No. PCT/US2021/030950, filed on May 5, 2021, 15 pages.
International Search Report and Written Opinion of the International Searching Authority mailed Jul. 12, 2021, for International Application No. PCT/US2021/016948, filed Feb. 5, 2021, 18 pages.
Invitation to Pay, ISA form 206 mailed Aug. 2, 2021 for International Patent Application No. PCT/US2021/030950, filed May 5, 2021, 13 pages.
Johnson, S. et al. (2018, e-pub. Nov. 8, 2018). "CA1 Nampt Knockdown Recapitulates Hippocampal Cognitive Phenotypes in Old Mice Which Nicotinamide Mononucleotide Improves," NPJ Aging Mech. Dis. 4:10, 12 pages.
Kabalka, G.W. et al. (1989). "The Synthesis of Radiolabeled Compounds via Organometallic Intermediates," Tetrahedron 45(21):6601-6621.
Khan, N. A. et al. (Jun. 2014). "Effective Treatment Of Mitochondrial Myopathy By Nicotinamide Riboside, A Vitamin B3," Embo Mol Med. 6(6):721-731.
Massudi, H. et al. (Jul. 2012)." Age-Associated Changes In Oxidative Stress and NAD+ Metabolism In Human Tissue," PLoS One 7(7):e42357, 9 pages.
Mavrodin, A. et al. (1965). "N-Phenylsulfonylphenyl-O-Alkslarylated Urethans. Synthesis Of Some New Anticancer Compounds," Revue Roumaine de Chimie 10(10):1025-1033, with English Abstract.
Mehr, A. P. et al. (Sep. 2018, e-pub. Aug. 20, 2018). "De Novo NAD+ Biosynthetic Impairment In Acute Kidney Injury In Humans," Nat Med. 24(9):1351-1359, 27 pages.
Mennie, K. M. et al. (Jan. 17, 2020, e-pub. Jan. 7, 2020). "Reductive sp3-sp2 Coupling Reactions Enable Late-Stage Modification of Pharmaceuticals," Organic Letters 22(2):556-559.
Mohamed, J.S. et al. (Oct. 2014). "Dysregulation of SIRT-1 in Aging Mice Increases Skeletal Muscle Fatigue by a PARP-1-Dependent Mechanism," Aging 6(10):820-834.
Papageorgiou, E. A. et al. (Apr. 20, 2000, e-pub. Mar. 18, 2000). "Selective Hydrogenolysis of Novel Benzyl Carbamate Protecting Groups," Org Lett. 2(8):1049-1051.
Peek, C.B. et al. (Nov. 1, 2013). "Circadian Clock NAD+ Cycle Drives Mitochondrial Oxidative Metabolism in Mice," Science 342(6158):1243417, 17 pages.
Pi, C. et al. (Jun. 7, 2019). "Nicotinamide Phosphoribosyltransferase Postpones Rat Bone Marrow Mesenchymal Stem Cell Senescence By Mediating NAD+-Sirt1 Signaling," Aging 11(11):3505-3522.
Pinkerton, A. B. et al. (2021). "Optimization of a Urea-Containing Series of Nicotinamide Phosphoribosyltransferase (NAMPT) Activators," Bioorganic and Medicinal Chemistry Letters 41:128007, 23 pages.
Pinkerton, A. B. et al. (Jun. 1, 2021, e-pub. Mar. 31, 2021). "Optimization of a Urea-Containing Series of Nicotinamide Phosphoribosyltransferase (NAMPT) Activators," Bioorganic and Medicinal Chemistry Letters 41:128007, 5 pages.
Pubchem (Jul. 12, 2014). CID: 75363707 "N-[4-(2-methylbutan-2-yl)cyclohexyl]-2-(1,2,4-triazol-1-yl)pyridine-4-carboxamide," 9 pages.
Pubchem (Jun. 21, 2010). CID: 45834917 "N-(4-methylcyclohexyl)-2-(1,2,4-triazol-1-yl)pyridine-4-carboxamide," 9 pages.
Ralto, K.M. et al. (Feb. 2020, e-pub. Oct. 31, 2019). "NAD+ Homeostasis in Renal Health and Disease." Nat. Rev. Nephrol. 16(2):99-111.
Revollo, J.R. et al. (Dec. 3, 2004). "The NAD Biosynthesis Pathway Mediated by Nicotinamide Phosphoribosyltransferase Regulates Sir2 Activity in Mammalian Cells," J. Biol. Chem. 279(49):50754-50763.
Revollo, J.R. et al. (Nov. 2007). "Nampt/PBEF/visfatin Regulates Insulin Secretion in β Cells as a Systemic NAD Biosynthetic Enzyme," Cell Matab. 6(5);363-375, 24 pages.
Ryu, D. et al. (Oct. 19, 2016). "NAD+ Repletion Improves Muscle Function In Muscular Dystrophy And Counters Global PARylation," Sci. Transl. Med. 8(361):361ra139, 29 pages.
Smyrnias, I. et al. (Apr. 16, 2019). "Cardioprotective Effect of the Mitochondrial Unfolded Protein Response During Chronic Pressure Overload," J Am Coll Cardiol. 73(14):1795-1806.
Stromland, O. et al. (Feb. 2019). "Keeping the Balance in NAD Metabolism," Biochem. Soc. Trans. 47(1):119-130, 22 pages.
Takei, H. et al. (Nov. 1965). "The Preparation Of Iminosulfonic Acid Derivatives By Means Of Sulfinamides and N-Bromosuccinimide," Bulletin of the Chemical Society of Japan 38(11):1989-1993.
U.S. Appl. No. 18/393,327, filed Dec. 21, 2023, for Pu-Ping Lu et al. U.S. Patent Application is not submitted herewith pursuant to the waiver of 37 C.F.R. § 1.98(a)(2)(iii) issued by the Office on Sep. 21, 2004.
Van Der Veer, E. et al. (Apr. 13, 2007). "Extension of Human Cell Lifespan by Nicotinamide Phosphoribosyltransferase," J. Biol. Chem. 282(15):10841-10845.
Verdin, E. (Dec. 4, 2015). "NAD+ in Aging, Metabolism, and Neurodegeneration," Science 350 (6265):1208-1213.
Williams, P.A. et al. (Apr. 25, 2017). "Nicotinamide and WLDS Act Together to Prevent Neurodegeneration in Glaucoma," Front. Neurosci. 11:232, 10 pages.
Xu, T-Y. et al. (Jun. 4, 2015). "Discovery And Characterization Of Novel Small-Molecule Inhibitors Targeting Nicotinamide Phosphoribosyltransferase," Sci Rep. 5:10043, 14 pages.
Yang, H. et al. (Sep. 21, 2007). "Nutrient-Sensitive Mitochondrial NAD+ Levels Dictate Cell Survival," Cell 130(6):1095-1107.
Yang, Y. et al. (Dec. 2016). "NAD+ Metabolism: Bioenergetics, Signaling and Manipulation for Therapy," Biophys. Acta. 1864(12):1787-1800, 31 pages.
Yin, Y. et al. (Jul. 8, 2010. e-pub Apr. 5, 2010). "Discovery of Potent and Selective Urea-Based ROCK Inhibitors and Their Effects on Intraocular Pressure in Rats," ACS Med Chem Lett. 1(4): 175-179.
Yoshino, J. et al. (Oct. 5, 2011). "Nicotinamide Mononucleotide, a Key NAD+ Intermediate, Treats the Pathophysiology of Diet- and Age-Induced Diabetes in Mice," Cell Metab. 74(4):528-536.
Zak, M. et al. (Sep. 22, 2016). "Minimizing CYP2C9 Inhibition of Exposed-Pyridine NAMPT (Nicotinamide Phosphoribosyltransferase) Inhibitors," Journal of Medical Chemistry 59(18):8345-8368.
Zhao, Y. et al. (Jul. 2015). "Regenerative Neurogenesis After Ischemic Stroke Promoted by Nicotinamide Phosphoribosyltransferase-Nicotinamide Adenine Dinucleotide Cascade," Stroke 46(7):1966-1974.
Zheng, D. et al. (Jul. 15, 2019). "Nicotinamide Riboside Promotes Auolysosome Clearance in Preventing Doxorubicin-Indued Cardiotoxicity," Clin. Sci. (Lond). 133(13):1505-1521, 27 pages.

(56) References Cited

OTHER PUBLICATIONS

Zheng, X. et al. (Apr. 25, 2013. e-pub. Jun. 13, 2013). "Structure-Based Identification Of Ureas As Novel Nicotinamide Phosphoribosyltransferase (Nampt) Inhibitors," J Med Chem. 56(12):4921-4937.
CAS Registry No. 1071363-30-8 (Nov. 7, 2008). "Urea, N-cyclohexyl-N'-[[4-(1-methylethoxy)phenyl]methyl]-," 2 pages.
CAS Registry No. 1111205-27-6 (Feb. 24, 2009). "Urea, N-[(4-methoxyphenyl)methyl]-N'-[4-(5-methyl-1,2,4-oxadiazol-3-yl)phenyl]-," 1 page.
CAS Registry No. 1111205-36-7 (Feb. 24, 2009). "Urea, N-[(4-chlorophenyl)methyl]-N'-[4-(5-cyclobutyl-1,2,4-oxadiazol-3-yl)phenyl]-," 1 page.
CAS Registry No. 1119367-55-3 (Mar. 12, 2009). "2-methyl-N-[4-[[[[(4-methylcyclohexyl)amino]carbonyl]amino]methyl]phenyl]-," 1 page.
CAS Registry No. 1147664-42-3 (May 20, 2009). "Urea, N-[4-(1,1-dioxido-2-isothiazolidinyl)phenyl]-N'-[(4-methoxyphenyl)methyl]-," 1 page.
CAS Registry No. 1170809-16-1 (Jul. 31, 2009). "Urea, N-[(4-methoxyphenyl)methyl]-N'-[4-[4-(2-pyridinyl)-1-piperazinyl]methyl]phenyl]-," 1 page.
CAS Registry No. 1170972-21-0 (Jul. 31, 2009). "Urea, N-[(4-chlorophenyl)methyl]-N'-[4-[[4-(2-furanylmethyl)-1-piperazinyl]methyl]phenyl]-," 1 page.
CAS Registry No. 1171471-94-5 (Aug. 2, 2009). "Urea, N-[4-[[4-(2-furanylmethyl)-1-piperazinyl]methyl]phenyl]-N'-[(4-methoxyphenyl)methyl]-," 2 pages.
CAS Registry No. 1172336-21-8 (Aug. 4, 2009). "Urea, N-[(4-methoxyphenyl)methyl]-N'-[4-{(4-methyl-1-piperazinyl)methyl]phenyl]-," 1 page.
CAS Registry No. 1172544-60-3 (Aug. 4, 2009). "Urea, N-[(4-flurophenyl)methyl]-N'-[(4- (4-methyl-1-piperazinyl) methyl]phenyl]-," 1 page.
CAS Registry No. 1183542-51-9 (Sep. 13, 2009). "Urea, N-cyclohexyl-N'-(IH-pyrazol-4-ylmethyl)-," 2 pages.
CAS Registry No. 1203067-82-6 (Jan. 24, 2010). "Urea, N-[(4-Chlorophenyl)methyl]-N'-[4-(1, 1-dioxido-2-isothiazolidinyl)phenyl]-," 1 page.
CAS Registry No. 1280964-65-9 (Apr. 17, 2011). "Benzamide, 4-[[[(cyclohexylamino)carbonyl]amino]methyl]-N-ethyl-," 1 page.
CAS Registry No. 1303650-36-3 (Jun. 1, 2011). "Urea, N- [(4-bromophenyl) methyl] -N' -cyclohexyl-," 2 pages.
CAS Registry No. 1371486-55-3 (Apr. 30, 2012). "Urea, N-[(4-fluorophenyl)methyl]-N'-[4-(1-piperidinyl)phenyl]-," 1 page.
CAS Registry No. 1385988-48-6 (Aug. 3, 2012). "Urea, N-[3-chloro-4-(1-pyrrolidinyl)phenyl]-N'-[(4-fluorophenyl)methyl]-," 1 page.
CAS Registry No. 1387015-63-5 (Aug. 6, 2012). "Urea, N-[(4-fluorophenyl)methyl]-N'-[4-(4-methyl-2-pyrimidinyl)phenyl]," 1 page.
CAS Registry No. 1387054-86-5 (Aug. 6, 2012). "Urea, N-[(4-chlorophenyl)methyl]-N'-[4-(3,5-dimethyl-1H-pyrazol-1-yl)-3-flurophenyl]-," 2 pages.
CAS Registry No. 1387106-46-8 (Aug. 7, 2012). "Urea, N-cyclohexyl-N'-[6-(I-methylethoxy)-3-pyridinyl]methyl]-, " 1 page.
CAS Registry No. 1387176-98-8 (Aug. 7, 2012). "Urea, N-cyclohexyl-N'-[4-(2-methylpropoxy)phenyl]methyl]-," 1 page.
CAS Registry No. 1389145-02-1 (Aug. 12, 2012). "Urea, N-[4-(3,5-dimethyl-1H-pyrazol-1-yl)-3-fluorophenyl]-N'-[(4-fluoropheny)methyl]-," 1 page.
CAS registry No. 1389213-95-9 (Aug. 10, 2012). "Urea, N-[(4-chlorophenyl)methyl]-N'-[4-(2-oxo-3-oxazolidinyl)phenyl]-," 2 pages.
CAS Registry No. 1646963-03-2 (Feb. 13, 2015). "Urea, N-[(6-chloro-3-pyridinyl)methyl]-N'-(3-cyclohexylpropyl)-," 1 page.
CAS Registry No. 1713221-96-5 (May 26, 2015). "Urea, N-cyclohexyl-N'-[(6-methoxy-3-pyridinyl)methyl]-," 1 page.
CAS Registry No. 1898739-21-3 (Apr. 27, 2016). "Urea, N-[(4-fluorophenyl)methyl]-N'-[4-(4-methyl-1-piperazinyl)phenyl]-," 1 page.
CAS Registry No. 1899425-35-4 (Apr. 28, 2016). "Urea, N-(cyclohexylmethyl)-N'-[(4-methoxyphenyl)methyl]-, " 2 pages.
CAS registry No. 1902512-90-6 (May 3, 2016). "Urea, N-[(4-methoxyphenyl)methyl]-N'-[4-(4-methyl-1-piperazinyl)phenyl]-," 2 pages.
CAS Registry No. 1902756-28-8 (May 3, 2016). "Urea, N-(2-cyclohexylethyl)-N'-[(4-methoxyphenyl)methyl]-," 1 page.
CAS Registry No. 1902756-85-7 (May 3, 2016). "Urea, N-(2-cyclohexylethyl)-N'-[[4-(hydroxymethyl)phenyl]methyl]-," 2 pages.
CAS Registry No. 1904704-52-4 (May 6, 2016). "Urea, N-[(4-chlorophenyl)methyl]-N'-(cyclohexylmethyl)-," 1 page.
CAS Registry No. 1906033-26-8 (May 8, 2016). "Urea, N-[(4-fluorophenyl)methyl]-N'-[4-(1H-pyrrol-1-yl)phenyl]-," 1 page.
CAS Registry No. 1906636-09-6 (May 9, 2016). "Urea, N-(2-cyclohexylethyl)-N'-(4-pyridinylmethyl)-," 1 page.
CAS Registry No. 1906934-57-3 (May 9, 2016). "Urea, N-(cyclohexylmethyl)-N'-(4-pyridinylmethyl)-," 1 page.
CAS registry No. 1906939-32-9 (May 9, 2016). "Urea, N-[(4-chlorophenyl)methyl]-N'-[4-(4-methyl-1-piperazinyl)phenyl]-," 2 pages.
CAS Registry No. 1908093-29-7 (May 11, 2016). "Urea, N-[(4-chlorophenyl)methyl]-N'-(2-cyclohexylethyl)-," 1 page.
CAS Registry No. 1908404-55-6 (May 11, 2016). Urea, N-(cyclohexylmethyl)-N'-[(4-fluorophenyl)methyl]-, 2 pages.
CAS Registry No. 1908596-70-2 (May 12, 2016). "Benzamide, 4-[[[(cyclohexylamino) carbonyl]amino]methyl)-," 1 page.
CAS Registry No. 1908872-93-4 (May 12, 2016). "Urea, N-(2-cyclohexylethyl)-N'-[(4-fluorophenyl)methyl]-," 2 pages.
CAS Registry No. 1909101-62-7 (May 12, 2016). "Urea, N-(cyclohexylmethyl)-N'-[[4-(hydroxymethyl)phenyl]methyl]-," 1 page.
CAS Registry No. 1909213-71-3 (May 12, 2016). "Urea, N-cyclohexyl-N'-[[4-(hydroxymethyl)phenyl]methyl] ," 1 Page.
CAS Registry No. 2427208-21-5 (Jun. 17, 2020) "Urea, N-[(4-methoxyphenyl)methyl]-N'-[4-(2-oxo-3-oxazolidinyl)phenyl]-," 1 page.
CAS Registry No. 313386-80-0 (Jan. 10, 2001). "Urea, N-cyclohexyl-N'-[(4-fluorophenyl)methyl]-," 1 page.
CAS Registry No. 951617-35-9 (Oct. 26, 2007). "Urea, N-[4-(2-benzothiazolyl)-3-chlorophenyl]-N'-[(4-fluorophenyl) methyl]-," 1 page.
Gaina, V. et al. (Jan. 1, 2003). "AB Monomers. I. Synthesis and Polymerization of Furyl-Maleimide Monomers", XP093156487, Database Accession No. 2004:464480, Database Caplus [Online] Chemical Abstract Service, Columbus, Ohio, 2 pages.
International Preliminary Report on Patentability issued on Jun. 24, 2025, for PCT Application No. PCT/ US2023/085420, filed Dec. 21, 2023, 10 pages.
International Search Report and Written Opinion of the International Searching Authority mailed May 8, 2024, for International Application No. PCT/US2023/085420, filed Dec. 21, 2023, 14 pages.
Pubchem (Jan. 15, 2016). CID: 108988951. "1-[(4-Chlorophenyl)methyl]-3-(4-phenylmethoxyphenyl)urea," 8 pages.
Pubchem (Jan. 15, 2016). CID: 108988965. "1-[(4-Methoxyphenyl)methyl]-3-(4-phenylmethoxyphenyl)urea," 8 pages.
Pubchem (May 29, 2009). CID: 38209383. "1-[(4-Fluorophenyl)methyl]-3-(4-phenylmethoxyphenyl)urea," 7 pages.
STN Registry Database Record Report. (Jan. 7, 2025). 124 STN records. 67 pages.
STN Registry No. 1388613-78-2. (Aug. 9, 2012). "N-[(4-Fluorophenyl)methyl]-N'-[4-(2-oxo-3-oxazolidinyl)phenyl]urea", 1 page.
Bennett, J. C. ed et al. (1997). "154. Introduction" Part 14, Oncology in Cecil Textbook of Medicine, 20th Ed, vol. 1. W. B. Saunders, pp. 1004-1110.
Wu, Q. et al. (Oct. 8, 2022). "Small-molecule Inhibitors, Immune Checkpoint Inhibitors, and More: FDA-approved Novel Therapeutic Drugs For Solid Tumors From 1991 to 2021," J Hematol Oncol. 15(1): 143, 63 pages.

* cited by examiner

PYRAZOLE DERIVATIVES USEFUL AS NAMPT MODULATORS

CROSS REFERENCE TO RELATED APPLICATIONS

This application is a national stage application under 35 U.S.C. § 371 of International Application No. PCT/US2021/064422, filed internationally on Dec. 20, 2021, which claims priority to and the benefit of U.S. Provisional Application No. 63/128,756, filed on Dec. 21, 2020, the disclosures of which are incorporated herein by reference in their entirety.

FIELD

Provided herein are compounds, pharmaceutical compositions comprising such compounds, and methods of treating various diseases and conditions mediated by nicotinamide adenine dinucleotide (NAD+) modulation via nicotinamide phosphoribosyltransferase (NAMPT) with such compounds.

BACKGROUND

The present disclosure relates to the use of modulators of nicotinamide phosphoribosyltransferase (NAMPT) and derivatives thereof, as well as enhancers or inducers of NAMPT expression, NAMPT activity or NAMPT-mediated signaling for preventing or treating a variety of pathological conditions.

Nicotinamide adenine dinucleotide (NAD+) is an essential coenzyme (enzyme cofactor) involved in fundamental biological processes of both catabolic and anabolic metabolism. As a coenzyme, NAD is associated with many oxidative enzymes (typically dehydrogenases) involved in energy metabolism, serving as a universal electron carrier. NAD exists in cells in the oxidized state (NAD+ and NADP+), and the reduced state (NADH and NADPH), acting as a chemical means to capture and transfer free energy from oxidative processes in catabolism, or to provide small packets of energy to build macromolecules in anabolism. NADH produced from the oxidation of carbohydrates, lipids, and amino acids provides reducing equivalents to the electron transport chain of mitochondria, ultimately driving the synthesis of ATP in oxidative phosphorylation.

More than 200 enzymes use either NAD+ or NADP+ as a coenzyme, and the enzymatic functions are not limited to energy metabolism. It is now appreciated that NAD+ plays a role in regulating diverse functions, including mitochondrial function, respiratory capacity, and biogenesis, mitochondrial-nuclear signaling. Further, it controls cell signaling, gene expression, DNA repair, hematopoiesis, immune function, the unfolded protein response, and autophagy. Furthermore, NAD is anti-inflammatory and is the precursor for NADPH, which is the primary source of reducing power for combating oxidative stress. A large body of literature indicates that boosting NAD levels is an effective strategy to either prevent or ameliorate a wide variety of disease states (Stromland et al., *Biochem Soc Trans.* 2019, 47(1):119-130; Ralto et al., *Nat Rev Nephrol.* 2019; Fang et al., *Trends Mol Med.* 2017, 23(10):899-916; Yoshino et al., *Cell Metab.* 2011, 14(4):528-36; Yang and Sauve, *Biochim Biophys Acta.* 2016, 1864:1787-1800; Verdin, *Science.* 2015, 350(6265): 1208-13).

Levels of NAD+ and NADP+-associated enzymes play important roles in normal physiology and are altered under various disease and stress conditions including aging. Cellular NAD+ levels decrease during aging, metabolic disease, inflammatory diseases, during ischemia/reperfusion injury, and in other conditions in humans (Massudi et al., *PLoS ONE.* 2012, 7(7): e42357) and animals (Yang et al., *Cell.* 2007, 130(6):1095-107; Braidy et al. *PLoS One.* 2011, 26;6(4):e19194; Peek et al. *Science.* 2013, 342(6158): 1243417; Ghosh et al., *J Neurosci.* 2012, 32(17):5821-32), suggesting that modulation of cellular NAD+ level affects the speed and severity of the decline and deterioration of bodily functions. Therefore, an increase in cellular NAD+ concentration could be beneficial in the context of aging and age-related diseases.

The cellular NAD+ pool is controlled by a balance between the activity of NAD+-synthesizing and consuming enzymes. In mammals, NAD+ is synthesized from a variety of dietary sources, including one or more of its major precursors that include: tryptophan (Trp), nicotinic acid (NA), nicotinamide riboside (NR), nicotinamide mononucleotide (NMN), and nicotinamide (NAM). Based upon the bioavailability of its precursors, there are three pathways for the synthesis of NAD+ in cells: (i) from Trp by the de novo biosynthesis pathway or kynurenine pathway (ii) from NA in the Preiss-Handler pathway and (iii) from NAM, NR, and NMN in the salvage pathway (Verdin et al., *Science.* 2015, 350(6265):1208-13). Of these, the predominant NAD+ biosynthetic pathway involves the step of synthesis of nicotinamide mononucleotide (NMN) using nicotinamide and 5'-phosphoribosyl-pyrophosphate by the rate-limiting enzyme nicotinamide phosphoribosyl-transferase (NAMPT) that is critical to determination of longevity and responses to a variety of stresses (Fulco et al, *Dev Cell.* 2008, 14(5):661-73; Imai, *Curr Pharm Des.* 2009, 15(1):20-8; Revollo et al., *J Biol Chem.* 2004, 279(49):50754-63; Revollo et al., *Cell Metab.* 2007, November; 6(5):363-75; van der Veer et al., *J Biol Chem.* 2007, 282(15):10841-5; Yang et al., Cell. 2007, 130(6):1095-107). Thus, increasing the rate of NAMPT catalysis by a small molecule activator would be an effective strategy to boost NAD levels and thereby address a broad spectrum of disease states. These include cardiac diseases, chemotherapy induced tissue damage, renal diseases, metabolic diseases, muscular diseases, neurological diseases and injuries, diseases caused by impaired stem cell function, and DNA damage and primary mitochondrial disorders.

SUMMARY

In one aspect, provided herein is a compound of formula (A):

(A)

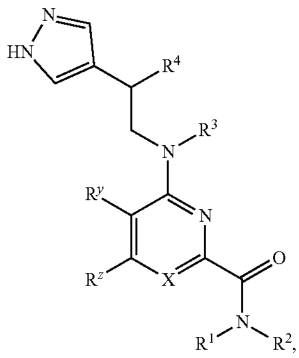

or a pharmaceutically acceptable salt thereof, wherein:

X is N or CH;

$R^1$ and $R^2$ are each independently H, optionally substituted $C_{1-6}$alkyl, optionally substituted $C_{3-10}$cycloalkyl, optionally substituted $C_{6-20}$aryl, optionally substituted 3-15 membered heterocyclyl, or optionally substituted 5-20 membered heteroaryl, or $R^1$ and $R^2$ are taken together with the nitrogen to which they are attached to form an optionally substituted 3-15 membered heterocyclyl;

$R^3$ is H or optionally substituted $C_{1-6}$alkyl, and $R^4$ is H;

or $R^3$ and $R^4$ taken together are —$CH_2CH_2$—; and $R^y$ and $R^z$ are each independently H, halo, or optionally substituted $C_{1-6}$alkyl;

or $R^y$ and $R^z$ are taken together with the carbon atoms to which they are attached to form an optionally substituted non-aromatic cyclic ring containing 3 to 10 carbon atoms.

In another aspect, provided herein is a compound of formula (I):

(I)

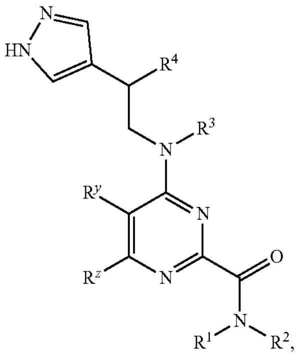

or a stereoisomer or tautomer thereof, or a pharmaceutically acceptable salt of any of the foregoing, wherein $R^1$, $R^2$, $R^3$, $R^4$, $R^y$, and $R^z$, are as defined above for the compound of formula (A).

In another aspect, provided herein is a compound of formula (I):

(I)

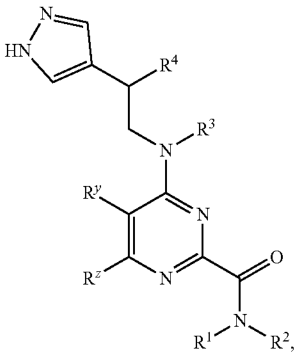

or a pharmaceutically acceptable salt thereof, wherein:

$R^1$ and $R^2$ are each independently H, optionally substituted $C_{1-6}$alkyl, optionally substituted $C_{3-10}$cycloalkyl, optionally substituted $C_{6-20}$aryl, optionally substituted 3-15 membered heterocyclyl, or optionally substituted 5-20 membered heteroaryl, or $R^1$ and $R^2$ are taken together with the nitrogen to which they are attached to form an optionally substituted 3-15 membered heterocyclyl;

$R^3$ is H or optionally substituted $C_{1-6}$alkyl, and $R^4$ is H; or $R^3$ and $R^4$ taken together are —$CH_2CH_2$—; and $R^y$ and $R^z$ are each independently optionally substituted $C_{1-6}$alkyl.

In another aspect, provided herein is a compound of formula (I-A):

(I-A)

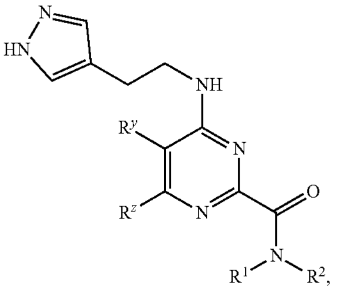

or a stereoisomer or tautomer thereof, or a pharmaceutically acceptable salt of any of the foregoing, wherein $R^1$, $R^2$, $R^y$, and $R^z$ are as defined above for the compound of formula (I).

In a further aspect, provided herein is a compound of formula (I-A1):

(I-A1)

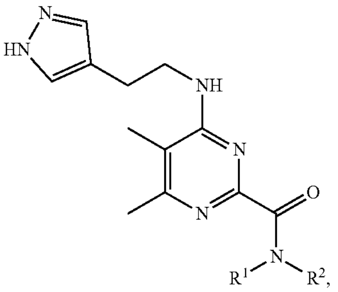

or a stereoisomer or tautomer thereof, or a pharmaceutically acceptable salt of any of the foregoing, wherein $R^1$ and $R^2$ are as defined above for the compound of formula (I).

In a further aspect, provided herein is a compound of formula (I-A2):

(I-A2)

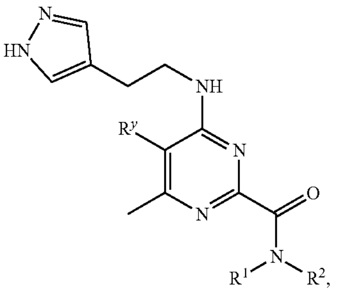

or a stereoisomer or tautomer thereof, or a pharmaceutically acceptable salt of any of the foregoing, wherein $R^1$ and $R^2$ are as defined above for the compound of formula (I) and wherein $R^y$ is halo.

In a further aspect, provided herein is a compound of formula (I-A3):

(I-A3)

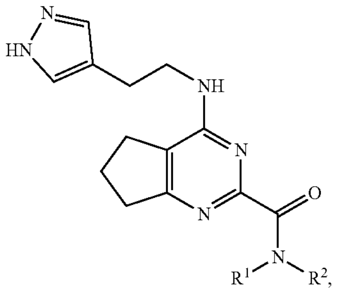

or a stereoisomer or tautomer thereof, or a pharmaceutically acceptable salt of any of the foregoing, wherein $R^1$ and $R^2$ are as defined above for the compound of formula (I).

In yet another aspect, provided herein is a compound of formula (I-B):

(I-B)

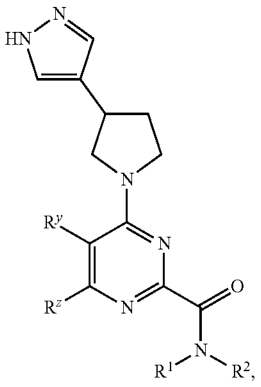

or a stereoisomer or tautomer thereof, or a pharmaceutically acceptable salt of any of the foregoing, wherein $R^1$, $R^2$, $R^y$, and $R^z$ are as defined above for the compound of formula (I).

In another aspect, provided herein is a compound of formula (I-B1):

(I-B1)

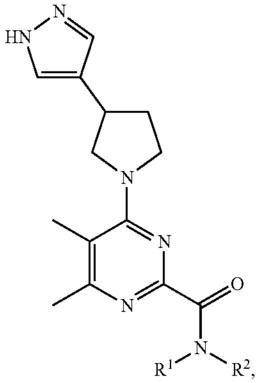

or a stereoisomer or tautomer thereof, or a pharmaceutically acceptable salt of any of the foregoing, wherein $R^1$ and $R^2$ are as defined above for the compound of formula (I).

In another aspect, provided herein is a compound of formula (II):

(II)

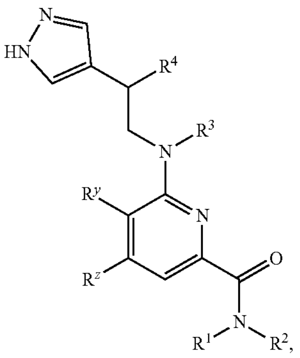

or a stereoisomer or tautomer thereof, or a pharmaceutically acceptable salt of any of the foregoing, wherein $R^1$, $R^2$, $R^3$, $R^4$, $R^y$, and $R^z$ are as defined above for the compound of formula (A).

In another aspect, provided herein is a compound of formula (II-A):

(II-A)

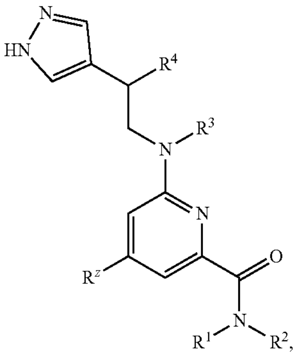

or a stereoisomer or tautomer thereof, or a pharmaceutically acceptable salt of any of the foregoing, wherein $R^1$, $R^2$, $R^3$, $R^4$, and $R^z$ are as defined above for the compound of formula (II).

In another aspect, provided herein is a compound of formula (II-A1):

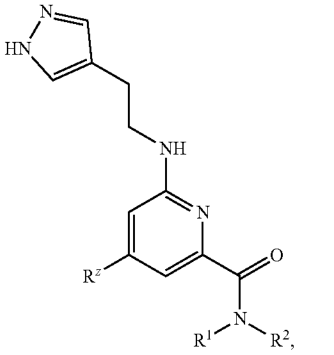

(II-A1)

or a stereoisomer or tautomer thereof, or a pharmaceutically acceptable salt of any of the foregoing, wherein $R^1$, $R^2$, and $R^z$ are as defined above for the compound of formula (II).

In a further aspect, provided herein are pharmaceutical compositions comprising a compound of formula (A) such as a compound of Table 1, or a pharmaceutically acceptable salt of any of the foregoing, optionally further comprising a pharmaceutically acceptable excipient. In some embodiments, provided herein are pharmaceutical compositions comprising a compound of formula (A), (I), (I-A), (I-A1), (I-A2), (I-A3), (I-B), (I-B1), (II), (II-A), or (II-A1), such as a compound of Table 1, or a pharmaceutically acceptable salt of any of the foregoing, optionally further comprising a pharmaceutically acceptable excipient. In some embodiments, provided herein are pharmaceutical compositions comprising a compound of formula (I), (I-A), (I-A1), (I-B), or (I-B1), such as a compound of Table 1, or a pharmaceutically acceptable salt of any of the foregoing, optionally further comprising a pharmaceutically acceptable excipient.

In another aspect, provided herein is a method of treating a disease or condition mediated by NAMPT activity in a subject in need thereof, comprising administering to the subject an effective amount of a compound of formula (A), (I), (I-A), (I-A1), (I-A2), (I-A3), (I-B), (I-B1), (II), (II-A), or (II-A1), such as a compound of Table 1, or a pharmaceutically acceptable salt thereof, or a pharmaceutical composition comprising a compound of formula (A), (I), (I-A), (I-A1), (I-A2), (I-A3), (I-B), (I-B1), (II), (II-A), or (II-A1), such as a compound of Table 1, or a pharmaceutically acceptable salt thereof. In some embodiments, provided herein is a method of treating a disease or condition mediated by NAMPT activity in a subject in need thereof, comprising administering to the subject an effective amount of a compound formula (I), (I-A), (I-A1), (I-B), or (I-B1), such as a compound of Table 1, or a pharmaceutically acceptable salt thereof, or a pharmaceutical composition comprising a compound of formula (I), (I-A), (I-A1), (I-B), or (I-B1), or a pharmaceutically acceptable salt thereof. In some embodiments, the disease or condition is selected from the group consisting of cancer, a hyperproliferative disease or condition, an inflammatory disease or condition, a metabolic disorder, a cardiac disease or condition, chemotherapy induced tissue damage, a renal disease, a metabolic disease, a neurological disease or injury, a neurodegenerative disorder or disease, diseases caused by impaired stem cell function, diseases caused by DNA damage, primary mitochondrial disorders, or a muscule disease or muscle wasting disorder. In some embodiments, the disease or condition is selected from the group consisting of obesity, atherosclerosis, insulin resistance, type 2 diabetes, cardiovascular disease, Alzheimer's disease, Huntington's disease, Parkinson's disease, amyotrophic lateral sclerosis, depression, Down syndrome, neonatal nerve injury, aging, axonal degeneration, carpal tunnel syndrome, Guillain-Barre syndrome, nerve damage, polio (poliomyelitis), and spinal cord injury.

Additional embodiments, features, and advantages of the present disclosure will be apparent from the following detailed description and through practice of the present disclosure.

For the sake of brevity, the disclosures of publications cited in this specification, including patents, are herein incorporated by reference.

DETAILED DESCRIPTION

Definitions

As used in the present specification, the following words and phrases are generally intended to have the meanings as set forth below, except to the extent that the context in which they are used indicates otherwise.

Throughout this application, unless the context indicates otherwise, references to a compound of formula (A) includes all subgroups of formula (A) defined herein, including all substructures, subgenera, preferences, embodiments, examples and particular compounds defined and/or described herein, in particular compounds of formula (I), (I-A), (I-A1), (I-A2), (I-A3), (I-B), (I-B1), (II), (II-A), or (II-A1), such as a compound of Table 1. References to a compound of formula (A) and subgroups thereof, include ionic forms, polymorphs, pseudopolymorphs, amorphous forms, solvates, co-crystals, chelates, isomers, tautomers, oxides (e.g., N-oxides, S-oxides), esters, prodrugs, isotopes and/or protected forms thereof. In some embodiments, references to a compound of formula (A) and subgroups thereof, include polymorphs, solvates, co-crystals, isomers, tautomers and/or oxides thereof. In some embodiments, references to a compound of formula (A) and subgroups thereof, include polymorphs, solvates, and/or co-crystals thereof. In some embodiments, references to a compound of formula (A) and subgroups thereof, include isomers, tautomers and/or oxides thereof. In some embodiments, references to a compound of formula (A) and subgroups thereof, include solvates thereof. Similarly, the term "salts" includes solvates of salts of compounds. In particular, throughout this application, unless the context indicates otherwise, references to a compound of formula (I) includes all subgroups of formula (I) defined herein, including all substructures, subgenera, preferences, embodiments, examples and particular compounds defined and/or described herein. References to a compound of formula (I) and subgroups thereof, include ionic forms, polymorphs, pseudopolymorphs, amorphous forms, solvates, co-crystals, chelates, isomers, tautomers, oxides (e.g., N-oxides, S-oxides), esters, prodrugs, isotopes and/or protected forms thereof. In some embodiments, references to a compound of formula (I) and subgroups thereof, include polymorphs, solvates, co-crystals, isomers, tautomers and/or oxides thereof. In some embodiments, references to a compound of formula (I) and subgroups thereof, include polymorphs, solvates, and/or co-crystals thereof. In some embodiments, references to a compound of formula (I) and subgroups thereof, include isomers, tautomers and/or oxides thereof. In some embodiments, references to a compound of formula (I) and subgroups thereof, include solvates thereof. Similarly, the term "salts" includes solvates of salts of compounds.

"Alkyl" encompasses straight and branched carbon chains having the indicated number of carbon atoms; for example, from 1 to 20 carbon atoms, or 1 to 12 carbon atoms, or 1 to 8 carbon atoms, or 1 to 6 carbon atoms. For example, $C_{1-6}$alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "propyl" includes n-propyl and isopropyl; and "butyl" includes n-butyl, sec-butyl, isobutyl, and t-butyl. Examples of alkyl groups include, but are not limited to, methyl, ethyl, propyl, isopropyl, n-butyl, sec-butyl, tert-butyl, pentyl, 2-pentyl, 3-pentyl, isopentyl, neopentyl, hexyl, 2-hexyl, 3-hexyl, and 3-methylpentyl.

As used herein, the term "alkylene" refers to divalent alkyl group as defined herein above having 1 to 20 carbon atoms. Unless otherwise provided, alkylene refers to moieties having 1 to 20 carbon atoms, 1 to 16 carbon atoms, 1 to 12 carbon atoms, 1 to 10 carbon atoms, 1 to 7 carbon atoms, or 1 to 4 carbon atoms. Alkylene groups include, but are not limited to, methylene, ethylene, n-propylene, isopropylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, and n-decylene.

When a range of values is given (e.g., $C_{1-6}$ alkyl), each value within the range as well as all intervening ranges are included. For example, "$C_{1-6}$ alkyl" includes $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1-4}$, $C_{2-4}$, $C_{3-4}$, $C_{1-3}$, $C_{2-3}$, and $C_{1-2}$ alkyl.

"Alkenyl" refers to an unsaturated branched or straight-chain alkyl group having the indicated number of carbon atoms (e.g., 2 to 8, or 2 to 6 carbon atoms) and at least one carbon-carbon double bond. The group may be in either the cis or trans configuration (Z or E configuration) about the double bond(s). Alkenyl groups include, but are not limited to, ethenyl, propenyl (e.g., prop-1-en-1-yl, prop-1-en-2-yl, prop-2-en-1-yl (allyl), prop-2-en-2-yl), and butenyl (e.g., but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl).

"Alkynyl" refers to an unsaturated branched or straight-chain alkyl group having the indicated number of carbon atoms (e.g., 2 to 8 or 2 to 6 carbon atoms) and at least one carbon-carbon triple bond. Alkynyl groups include, but are not limited to, ethynyl, propynyl (e.g., prop-1-yn-1-yl, prop-2-yn-1-yl) and butynyl (e.g., but-1-yn-1-yl, but-1-yn-3-yl, but-3-yn-1-yl).

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, and cyclohexyl, as well as bridged, caged, and spirocyclic ring groups (e.g., norbornane, bicyclo[2.2.2]octane, spiro[3.3]heptane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group. Examples of polycyclic cycloalkyl groups consisting of a cycloalkyl group fused to an aromatic ring are described below.

"Cycloalkenyl" indicates a non-aromatic carbocyclic ring, containing the indicated number of carbon atoms (e.g., 3 to 10, or 3 to 8, or 3 to 6 ring carbon atoms) and at least one carbon-carbon double bond. Cycloalkenyl groups may be monocyclic or polycyclic (e.g., bicyclic, tricyclic). Examples of cycloalkenyl groups include cyclopropenyl, cyclobutenyl, cyclopentenyl, cyclopentadienyl, and cyclohexenyl, as well as bridged, caged (e.g., bicyclo[2.2.2]octene), and spirocyclic ring groups. In addition, one ring of a polycyclic cycloalkenyl group may be aromatic, provided the polycyclic alkenyl group is bound to the parent structure via a non-aromatic carbon atom. For example, inden-1-yl (wherein the moiety is bound to the parent structure via a non-aromatic carbon atom) is considered a cycloalkenyl group, while inden-4-yl (wherein the moiety is bound to the parent structure via an aromatic carbon atom) is not considered a cycloalkenyl group. Examples of polycyclic cycloalkenyl groups consisting of a cycloalkenyl group fused to an aromatic ring are described below.

"Aryl" indicates an aromatic carbocyclic ring having the indicated number of carbon atoms, for example, 6 to 20, or 6 to 12, or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl", as defined herein, regardless of the point of attachment (e.g., both quinolin-5-yl and quinolin-2-yl are heteroaryl groups). In some instances, aryl is phenyl or naphthyl. In certain instances, aryl is phenyl. Additional examples of aryl groups comprising an aromatic carbon ring fused to a non-aromatic ring are described below.

"Heteroaryl" indicates an aromatic ring containing the indicated number of atoms (e.g., 5 to 20, 5 to 12, or 5 to 10 membered heteroaryl) made up of one or more heteroatoms (e.g., 1, 2, 3 or 4 heteroatoms) selected from N, O, and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups.

In some instances, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine), and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, is othiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole, and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group. Examples of polycyclic heteroaryl groups consisting of a heteroaryl ring fused to a non-aromatic ring are described below.

As defined herein, "heterocyclyl" encompasses "heterocycloalkyl" and "heterocycloalkenyl," as defined below.

"Heterocycloalkyl" indicates a non-aromatic, fully saturated ring having the indicated number of atoms (e.g., 3 to 15, 3 to 10, or 3 to 7 membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic). Examples of heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl. Examples include thiomorpholine S-oxide and thiomorpholine S,S-dioxide. Examples of spirocyclic heterocycloalkyl groups include azaspiro[3.3]heptane, diazaspiro[3.3]heptane, diazaspiro[3.4]octane, and diazaspiro[3.5]nonane. In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group. Examples of polycyclic heterocycloalkyl groups consisting of a heterocycloalkyl group fused to an aromatic ring are described below.

"Heterocycloalkenyl" indicates a non-aromatic ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group. Examples of polycyclic heterocycloalkenyl groups consisting of a heterocycloalkenyl group fused to an aromatic ring are described below.

Examples of polycyclic rings consisting of an aromatic ring (e.g., aryl or heteroaryl) fused to a non-aromatic ring (e.g., cycloalkyl, cycloalkenyl, heterocycloalkyl, heterocycloalkenyl) include indenyl, 2,3-dihydro-1H-indenyl, 1,2,3,4-tetrahydronaphthalenyl, benzo[1,3]dioxolyl, tetrahydroquinolinyl, 2,3-dihydrobenzo[1,4]dioxinyl, indolinyl, isoindolinyl, 2,3-dihydro-1H-indazolyl, 2,3-dihydro-1H-benzo[d]imidazolyl, 2,3-dihydrobenzofuranyl, 1,3-dihydroisobenzofuranyl, 1,3-dihydrobenzo[c]isoxazolyl, 2,3-dihydrobenzo[d]isoxazolyl, 2,3-dihydrobenzo[d]oxazolyl, 2,3-dihydrobenzo[b]thiophenyl, 1,3-dihydrobenzo[c]thiophenyl, 1,3-dihydrobenzo[c]isothiazolyl, 2,3-dihydrobenzo[d]isothiazolyl, 2,3-dihydrobenzo[d]thiazolyl, 5,6-dihydro-4H-cyclopenta[d]thiazolyl, 4,5,6,7-tetrahydrobenzo[d]thiazolyl, 5,6-dihydro-4H-pyrrolo[3,4-d]thiazolyl, 4,5,6,7-tetrahydrothiazolo[5,4-c]pyridinyl, indolin-2-one, indolin-3-one, isoindolin-1-one, 1,2-dihydroindazol-3-one, 1H-benzo[d]imidazol-2(3H)-one, benzofuran-2(3H)-one, benzofuran-3(2H)-one, isobenzofuran-1(3H)-one, benzo[c]isoxazol-3(1H)-one, benzo[d]isoxazol-3(2H)-one, benzo[d]

oxazol-2(3H)-one, benzo[b]thiophen-2(3H)-one, benzo[b]thiophen-3(2H)-one, benzo[c]thiophen-1(3H)-one, benzo[c]isothiazol-3(1H)-one, benzo[d]isothiazol-3(2H)-one, benzo[d]thiazol-2(3H)-one, 4,5-dihydropyrrolo[3,4-d]thiazol-6-one, 1,2-dihydropyrazolo[3,4-d]thiazol-3-one, quinolin-4(3H)-one, quinazolin-4(3H)-one, quinazoline-2,4(1H,3H)-dione, quinoxalin-2(1H)-one, quinoxaline-2,3(1H,4H)-dione, cinnolin-4(3H)-one, pyridin-2(1H)-one, pyrimidin-2(1H)-one, pyrimidin-4(3H)-one, pyridazin-3(2H)-one, 1H-pyrrolo[3,2-b]pyridin-2(3H)-one, 1H-pyrrolo[3,2-c]pyridin-2(3H)-one, 1H-pyrrolo[2,3-c]pyridin-2(3H)-one, 1H-pyrrolo[2,3-b]pyridin-2(3H)-one, 1,2-dihydropyrazolo[3,4-d]thiazol-3-one and 4,5-dihydropyrrolo[3,4-d]thiazol-6-one. As discussed herein, whether each ring is considered an aryl, heteroaryl, cycloalkyl, cycloalkenyl, heterocycloalkyl or heterocycloalkenyl group is determined by the atom through which the moiety is bound to the parent structure.

"Halogen" or "halo" refers to fluorine, chlorine, bromine or iodine.

"Sulfonyl" refers to a $—S(O)_2H$ moiety. In some instances, the sulfonyl moiety is substituted, such that the H of the $—S(O)_2H$ moiety is replaced by a non-H moiety. For example, "sulfonyl substituted with methyl" refers to a $—S(O)_2—CH_3$ moiety.

Unless otherwise indicated, compounds disclosed and/or described herein include all possible enantiomers, diastereomers, meso isomers and other stereoisomeric forms, including racemic mixtures, optically pure forms and intermediate mixtures thereof. Enantiomers, diastereomers, meso isomers and other stereoisomeric forms can be prepared using chiral synthons or chiral reagents, or resolved using conventional techniques. Unless specified otherwise, when the compounds disclosed and/or described herein contain olefinic double bonds or other centers of geometric asymmetry, it is intended that the compounds include both E and Z isomers. When the compounds described herein contain moieties capable of tautomerization, and unless specified otherwise, it is intended that the compounds include all possible tautomers.

"Protecting group" has the meaning conventionally associated with it in organic synthesis, i.e., a group that selectively blocks one or more reactive sites in a multifunctional compound such that a chemical reaction can be carried out selectively on another unprotected reactive site, and such that the group can readily be removed after the selective reaction is complete. A variety of protecting groups are disclosed, for example, in T. H. Greene and P. G. M. Wuts, *Protective Groups in Organic Synthesis*, Third Edition, John Wiley & Sons, New York (1999). For example, a "hydroxy protected form" contains at least one hydroxy group protected with a hydroxy protecting group. Likewise, amines and other reactive groups may similarly be protected.

The term "pharmaceutically acceptable salt" refers to a salt of any of the compounds herein that are known to be non-toxic and are commonly used in the pharmaceutical literature. In some embodiments, the pharmaceutically acceptable salt of a compound retains the biological effectiveness of the compounds described herein and are not biologically or otherwise undesirable. Examples of pharmaceutically acceptable salts can be found in Berge et al., Pharmaceutical Salts, *J. Pharmaceutical Sciences*, January 1977, 66(1), 1-19. Pharmaceutically acceptable acid addition salts can be formed with inorganic acids and organic acids. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, pyruvic acid, lactic acid, oxalic acid, malic acid, maleic acid, malonic acid, succinic acid, fumaric acid, tartaric acid, citric acid, benzoic acid, cinnamic acid, mandelic acid, methanesulfonic acid, ethanesulfonic acid, 2-hydroxyethylsulfonic acid, p-toluenesulfonic acid, stearic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, and aluminum. Organic bases from which salts can be derived include, for example, primary, secondary, and tertiary amines; substituted amines including naturally occurring substituted amines; cyclic amines; and basic ion exchange resins. Examples of organic bases include isopropylamine, trimethylamine, diethylamine, triethylamine, tripropylamine, and ethanolamine. In some embodiments, the pharmaceutically acceptable base addition salt is selected from ammonium, potassium, sodium, calcium, and magnesium salts.

If the compound described herein is obtained as an acid addition salt, the free base can be obtained by basifying a solution of the acid salt. Conversely, if the compound is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds (see, e.g., Berge et al., Pharmaceutical Salts, *J. Pharmaceutical Sciences*, January 1977, 66(1), 1-19). Those skilled in the art will recognize various synthetic methodologies that may be used to prepare pharmaceutically acceptable addition salts.

A "solvate" is formed by the interaction of a solvent and a compound. Suitable solvents include, for example, water and alcohols (e.g., ethanol). Solvates include hydrates having any ratio of compound to water, such as monohydrates, dihydrates and hemi-hydrates.

The term "substituted" means that the specified group or moiety bears one or more substituents including, but not limited to, substituents such as alkoxy, acyl, acyloxy, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, cycloalkyl, cycloalkenyl, alkyl, alkenyl, alkynyl, heterocycloalkyl, heterocycloalkenyl, aralkyl, aminosulfonyl, sulfonylamino, sulfonyl, oxo, carbonylalkylenealkoxy and the like. The term "unsubstituted" means that the specified group bears no substituents. Where the term "substituted" is used to describe a structural system, the substitution is meant to occur at any valency-allowed position on the system. When a group or moiety bears more than one substituent, it is understood that the substituents may be the same or different from one another. In some embodiments, a substituted group or moiety bears from one to five substituents. In some embodiments, a substituted group or moiety bears one substituent. In some embodiments, a substituted group or moiety bears two substituents. In some embodiments, a substituted group or moiety bears three substituents. In some embodiments, a substituted group or moiety bears four substituents. In some embodiments, a substituted group or moiety bears five substituents.

By "optional" or "optionally," it is meant that the subsequently described event or circumstance may or may not occur, and that the description includes instances where the event or circumstance occurs and instances in which it does not. For example, "optionally substituted alkyl" encompasses both "alkyl" and "substituted alkyl," as defined herein. It will be understood by those skilled in the art, with respect to any group containing one or more substituents, that such groups are not intended to introduce any substitution or substitution patterns that are sterically impractical, synthetically non-feasible, and/or inherently unstable. It will also be understood that where a group or moiety is optionally substituted, the disclosure includes both embodiments in which the group or moiety is substituted and embodiments in which the group or moiety is unsubstituted.

The compounds disclosed and/or described herein can be enriched isotopic forms, e.g., enriched in the content of $^2H$, $^3H$, $^{11}C$, $^{13}C$, and/or $^{14}C$. In one embodiment, the compound contains at least one deuterium atom. Such deuterated forms can be made, for example, by the procedure described in U.S. Pat. Nos. 5,846,514 and 6,334,997. Such deuterated compounds may improve the efficacy and increase the duration of action of compounds disclosed and/or described herein. Deuterium substituted compounds can be synthesized using various methods, such as those described in: Dean, D., Recent Advances in the Synthesis and Applications of Radiolabeled Compounds for Drug Discovery and Development, *Curr. Pharm. Des.,* 2000; 6(10); Kabalka, G. et al., The Synthesis of Radiolabeled Compounds via Organometallic Intermediates, *Tetrahedron,* 1989, 45(21), 6601-21; and Evans, E., Synthesis of radiolabeled compounds, *J. Radioanal. Chem.,* 1981, 64(1-2), 9-32.

The term "pharmaceutically acceptable carrier" or "pharmaceutically acceptable excipient" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active ingredient, its use in pharmaceutical compositions is contemplated. Supplementary active ingredients can also be incorporated into the pharmaceutical compositions.

The terms "patient," "individual," and "subject" refer to an animal, such as a mammal, bird, or fish. In some embodiments, the patient or subject is a mammal. Mammals include, for example, mice, rats, dogs, cats, pigs, sheep, horses, cows and humans. In some embodiments, the patient or subject is a human, for example a human that has been or will be the object of treatment, observation or experiment. The compounds, compositions and methods described herein can be useful in both human therapy and veterinary applications.

As used herein, the term "therapeutic" refers to the ability to modulate nicotinamide phosphoribosyltransferase (NAMPT). As used herein, "modulation" refers to a change in activity as a direct or indirect response to the presence of a chemical entity as described herein, relative to the activity of in the absence of the chemical entity. The change may be an increase in activity or a decrease in activity, and may be due to the direct interaction of the chemical entity with the a target or due to the interaction of the chemical entity with one or more other factors that in turn affect the target's activity. For example, the presence of the chemical entity may, for example, increase or decrease the target activity by directly binding to the target, by causing (directly or indirectly) another factor to increase or decrease the target activity, or by (directly or indirectly) increasing or decreasing the amount of target present in the cell or organism.

The term "therapeutically effective amount" or "effective amount" refers to that amount of a compound disclosed and/or described herein that is sufficient to affect treatment, as defined herein, when administered to a patient in need of such treatment. A therapeutically effective amount of a compound may be an amount sufficient to treat a disease responsive to modulation of nicotinamide phosphoribosyltransferase (NAMPT). The therapeutically effective amount will vary depending upon, for example, the subject and disease condition being treated, the weight and age of the subject, the severity of the disease condition, the particular compound, the dosing regimen to be followed, timing of administration, the manner of administration, all of which can readily be determined by one of ordinary skill in the art. The therapeutically effective amount may be ascertained experimentally, for example by assaying blood concentration of the chemical entity, or theoretically, by calculating bioavailability.

"Treatment" (and related terms, such as "treat", "treated", "treating") includes one or more of: inhibiting a disease or disorder; slowing or arresting the development of clinical symptoms of a disease or disorder; and/or relieving a disease or disorder (i.e., causing relief from or regression of clinical symptoms). The term covers both complete and partial reduction of the condition or disorder, and complete or partial reduction of clinical symptoms of a disease or disorder. Thus, compounds described and/or disclosed herein may prevent an existing disease or disorder from worsening, assist in the management of the disease or disorder, or reduce or eliminate the disease or disorder.

"Prevention" (and related terms, such as "prevent", "prevented", "preventing") includes causing the clinical symptoms of a disease or disorder not to develop. The term encompasses situations where the disease or disorder is not currently being experienced but is expected to arise. When used in a prophylactic manner, the compounds disclosed and/or described herein may prevent a disease or disorder from developing or lessen the extent of a disease or disorder that may develop.

Compounds

Compounds and salts thereof (such as pharmaceutically acceptable salts) are detailed herein, including in the Brief Summary and in the appended claims. Also provided are the use of all of the compounds described herein, including any and all stereoisomers, including geometric isomers (cis/trans), E/Z isomers, enantiomers, diastereomers, and mixtures thereof in any ratio including racemic mixtures, salts and solvates of the compounds described herein, as well as methods of making such compounds. Any compound described herein may also be referred to as a drug.

In one aspect, provided herein is a compound of formula (A):

(A)

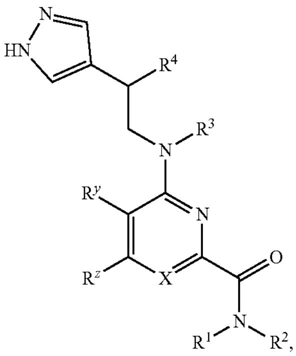
, or a pharmaceutically acceptable salt thereof, wherein:

X is N or CH;

$R^1$ and $R^2$ are each independently H, optionally substituted $C_{1-6}$alkyl, optionally substituted $C_{3-10}$cycloalkyl, optionally substituted $C_{6-20}$aryl, optionally substituted 3-15 membered heterocyclyl, or optionally substituted 5-20 membered heteroaryl, or $R^1$ and $R^2$ are taken together with the nitrogen to which they are attached to form an optionally substituted 3-15 membered heterocyclyl;

$R^3$ is H or optionally substituted $C_{1-6}$alkyl, and $R^4$ is H; or $R^3$ and $R^4$ taken together are $-CH_2CH_2-$; and $R^y$ and $R^z$ are each independently H, halo, or optionally substituted $C_{1-6}$alkyl; or $R^y$ and $R^z$ are taken together with the carbon atoms to which they are attached to form an optionally substituted non-aromatic cyclic ring containing 3 to 10 carbon atoms.

In some embodiments, provided is a compound of formula (A), or a stereoisomer or tautomer thereof, or a pharmaceutically acceptable salt of any of the foregoing, wherein X is N. In some embodiments, X is CH.

In some embodiments, provided herein is a compound of formula (I):

(I)

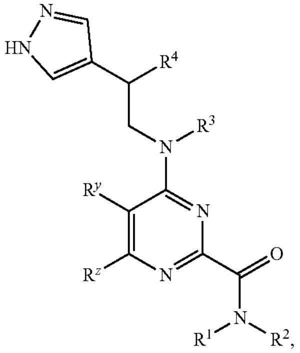

or a stereoisomer or tautomer thereof, or a pharmaceutically acceptable salt of any of the foregoing, wherein $R^1$, $R^2$, $R^3$, $R^4$, $R^y$, and $R^z$, are as defined elsewhere herein.

In some embodiments, provided herein is a compound of formula (I):

(I)

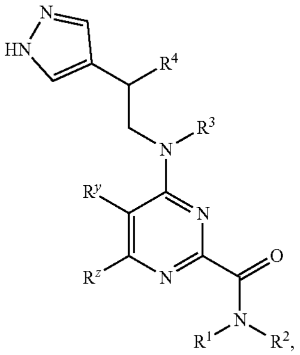

or a pharmaceutically acceptable salt thereof, wherein: $R^1$ and $R^2$ are each independently H, optionally substituted $C_{1-6}$alkyl, optionally substituted $C_{3-10}$cycloalkyl, optionally substituted $C_{6-20}$aryl, optionally substituted 3-15 membered heterocyclyl, or optionally substituted 5-20 membered heteroaryl, or $R^1$ and $R^2$ are taken together with the nitrogen to which they are attached to form an optionally substituted 3-15 membered heterocyclyl; $R^3$ is H or optionally substituted $C_{1-6}$alkyl and $R^4$ is H; or $R^3$ and $R^4$ taken together are $-CH_2CH_2-$; and $R^y$ and $R^z$ are each independently optionally substituted $C_{1-6}$alkyl.

In some embodiments, provided herein is a compound of formula (I), or a stereoisomer or tautomer thereof, or a pharmaceutically acceptable salt of any of the foregoing, wherein $R^3$ is H and $R^4$ is H, such that the compound of formula (I) is a compound of formula (I A):

(I-A)

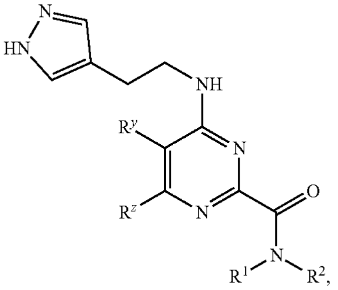

or a stereoisomer or tautomer thereof, or a pharmaceutically acceptable salt of any of the foregoing, wherein $R^1$, $R^2$, $R^y$, and $R^z$ are as defined elsewhere herein.

In some embodiments, provided is a compound of formula (I), or a stereoisomer or tautomer thereof, or a pharmaceutically acceptable salt of any of the foregoing, wherein $R^3$ is optionally substituted $C_{1-6}$alkyl and $R^4$ is H. In some embodiments, $R^3$ is unsubstituted $C_{1-6}$alkyl and $R^4$ is H. In some embodiments, $R^3$ is unsubstituted n-propyl and $R^4$ is H. In some embodiments, $R^3$ is $C_{1-6}$alkyl, wherein the $C_{1-6}$alkyl of $R^3$ is substituted with one or more $C_{6-20}$aryl, and $R^4$ is H. In some embodiments, $R^3$ is $C_{1-6}$alkyl, wherein the $C_{1-6}$alkyl of $R^3$ is substituted with one or more phenyl, and $R^4$ is H. In some embodiments, $R^3$ is optionally substituted ethyl and $R^4$ is H. In some embodiments, $R^3$ is ethyl, wherein the ethyl of $R^3$ is substituted with one or more $C_{6-20}$aryl, and $R^4$ is H. In some embodiments, $R^3$ is ethyl, wherein the ethyl of $R^3$ is substituted with one or more phenyl, and $R^4$ is H. In some embodiments, $R^3$ is

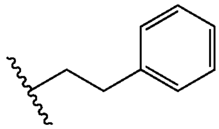 [SMILES: *CCc1ccccc1]

and $R^4$ is H.

In some embodiments, provided herein is a compound of formula (I), such as a compound of formula (I-A), or a stereoisomer or tautomer thereof, or a pharmaceutically acceptable salt of any of the foregoing, wherein $R^y$ and $R^z$ are each independently unsubstituted $C_{1-6}$alkyl. In some embodiments, $R^y$ and $R^z$ are each independently unsubstituted $C_{1-3}$alkyl. In certain embodiments, $R^y$ and $R^z$ are each independently unsubstituted methyl.

In some embodiments, provided herein is a compound of formula (I-A), or a stereoisomer or tautomer thereof, or a pharmaceutically acceptable salt of any of the foregoing, wherein $R^y$ and $R^z$ are each independently unsubstituted methyl, such that the compound of formula (I-A) is a compound of formula (I-A1):

(I-A1)

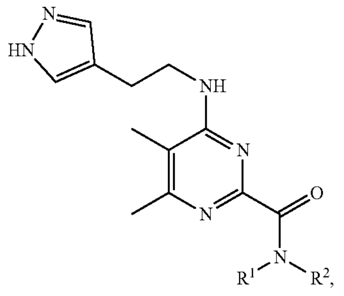

or a stereoisomer or tautomer thereof, or a pharmaceutically acceptable salt of any of the foregoing, wherein $R^1$ and $R^2$ are as defined elsewhere herein.

In some embodiments, provided herein is a compound of formula (I), such as a compound of formula (I-A), or a stereoisomer or tautomer thereof, or a pharmaceutically acceptable salt of any of the foregoing, wherein $R^y$ is halo and $R^z$ is unsubstituted $C_{1-6}$alkyl. In some embodiments, $R^y$ is halo and $R^z$ is unsubstituted $C_{1-3}$alkyl. In certain embodiments, $R^y$ is halo and $R^z$ is unsubstituted methyl.

In some embodiments, provided herein is a compound of formula (I-A), or a stereoisomer or tautomer thereof, or a pharmaceutically acceptable salt of any of the foregoing, wherein $R^y$ is halo and $R^z$ is unsubstituted methyl, such that the compound of formula (I-A) is a compound of formula (I-A2):

(I-A2)

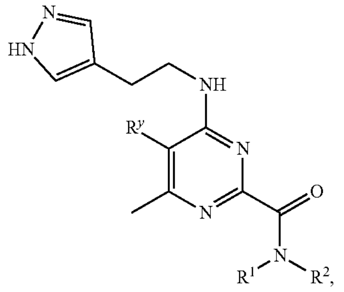

or a stereoisomer or tautomer thereof, or a pharmaceutically acceptable salt of any of the foregoing, wherein $R^1$ and $R^2$ are as defined elsewhere herein. In some embodiments, $R^y$ is fluoro, chloro, or bromo. In some embodiments, $R^y$ is fluoro or chloro. In some embodiments, $R^y$ is fluoro. In some embodiments, $R^y$ is chloro.

In some embodiments, provided herein is a compound of formula (I), such as a compound of formula (I-A), or a stereoisomer or tautomer thereof, or a pharmaceutically acceptable salt of any of the foregoing, wherein $R^y$ and $R^z$ are taken together with the carbon atoms to which they are attached to form an optionally substituted non-aromatic cyclic ring containing 3 to 10 carbon atoms. In some embodiments, $R^y$ and $R^z$ are taken together with the carbon atoms to which they are attached to form an optionally substituted non-aromatic cyclic ring containing 3 to 6 carbon atoms. In certain embodiments, $R^y$ and $R^z$ are taken together with the carbon atoms to which they are attached to form an optionally substituted non-aromatic cyclic ring containing 5 carbon atoms. In some embodiments, $R^y$ and $R^z$ are taken together with the carbon atoms to which they are attached to form an unsubstituted non-aromatic cyclic ring containing 3 to 10 carbon atoms, or an unsubstituted non-aromatic cyclic ring containing 3 to 6 carbon atoms. In some embodiments, $R^y$ and $R^z$ are taken together with the carbon atoms to which they are attached to form an optionally substituted non-aromatic cyclic ring containing 3 to 10 carbon atoms. In some embodiments, $R^y$ and $R^z$ are taken together with the carbon atoms to which they are attached to form an optionally substituted non-aromatic cyclic ring containing 3 to 6 carbon atoms. In certain embodiments, $R^y$ and $R^z$ are taken together with the carbon atoms to which they are attached to form an unsubstituted non-aromatic cyclic ring containing 5 carbon atoms.

In some embodiments, provided herein is a compound of formula (I-A), or a stereoisomer or tautomer thereof, or a pharmaceutically acceptable salt of any of the foregoing, having the formula (I-A3):

(I-A3)

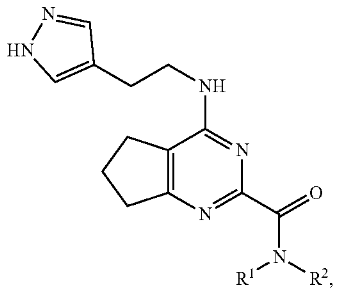

or a stereoisomer or tautomer thereof, or a pharmaceutically acceptable salt of any of the foregoing, wherein $R^1$ and $R^2$ are as defined above for the compound of formula (I).

In some embodiments, provided herein is a compound of formula (I), or a stereoisomer or tautomer thereof, or a pharmaceutically acceptable salt of any of the foregoing, wherein $R^3$ and $R^4$ taken together are —$CH_2CH_2$—, such that the compound of formula (I) is a compound of formula (I-B):

(I-B)

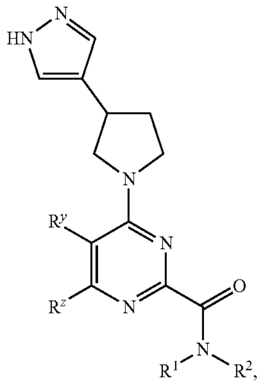

or a stereoisomer or tautomer thereof, or a pharmaceutically acceptable salt of any of the foregoing, wherein $R^1$, $R^2$, $R^y$, and $R^z$ are as defined elsewhere herein.

In some embodiments, provided herein is a compound of formula (I), such as a compound of formula (I-B), or a stereoisomer or tautomer thereof, or a pharmaceutically acceptable salt of any of the foregoing, wherein $R^y$ and $R^z$ are each independently unsubstituted $C_{1-6}$alkyl. In some embodiments, $R^y$ and $R^z$ are each independently unsubstituted $C_{1-3}$alkyl. In certain embodiments, $R^y$ and $R^z$ are each independently unsubstituted methyl.

In some embodiments, provided herein is a compound of formula (I-B), or a stereoisomer or tautomer thereof, or a pharmaceutically acceptable salt of any of the foregoing, wherein $R^y$ and $R^z$ are each independently unsubstituted methyl, such that the compound of formula (I-B) is a compound of formula (I-B1):

(I-B1)

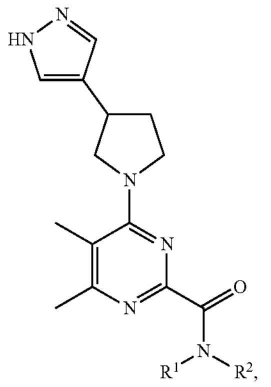

or a stereoisomer or tautomer thereof, or a pharmaceutically acceptable salt of any of the foregoing, wherein $R^1$ and $R^2$ are as defined elsewhere herein.

In some embodiments, provided is a compound of formula (A), (I), (I-A), or (I-B), or a stereoisomer or tautomer thereof, or a pharmaceutically acceptable salt of any of the foregoing, wherein $R^y$ and $R^z$ are each independently H, halo, or optionally substituted $C_{1-6}$alkyl. In some embodiments, $R^y$ and $R^z$ are each independently optionally substituted $C_{1-6}$alkyl. In some embodiments, $R^y$ and $R^z$ are each independently unsubstituted $C_{1-6}$alkyl. In some embodiments, $R^y$ and $R^z$ are each independently unsubstituted $C_{1-3}$alkyl. In certain embodiments, $R^y$ and $R^z$ are each independently unsubstituted methyl. In some embodiments, $R^y$ is halo and $R^z$ is optionally substituted $C_{1-6}$alkyl. In some embodiments, $R^y$ is halo and $R^z$ is unsubstituted $C_{1-6}$alkyl. In some embodiments, $R^y$ is halo and $R^z$ is unsubstituted $C_{1-3}$alkyl. In certain embodiments, $R^y$ is halo and $R^z$ is unsubstituted methyl. In some embodiments, $R^y$ is chloro or fluoro, and $R^z$ is optionally substituted $C_{1-6}$alkyl. In some embodiments, $R^y$ is chloro or fluoro, and $R^z$ is unsubstituted $C_{1-6}$alkyl. In some embodiments, $R^y$ is chloro or fluoro, and $R^z$ is unsubstituted $C_{1-3}$alkyl. In certain embodiments, $R^y$ is chloro or fluoro, and $R^z$ is unsubstituted methyl. In some embodiments, $R^y$ is chloro and $R^z$ is optionally substituted $C_{1-6}$alkyl. In some embodiments, $R^y$ is chloro and $R^z$ is unsubstituted $C_{1-6}$alkyl. In some embodiments, $R^y$ is chloro and $R^z$ is unsubstituted $C_{1-3}$alkyl. In certain embodiments, $R^y$ is chloro and $R^z$ is unsubstituted methyl. In some embodiments, $R^y$ is fluoro and $R^z$ is optionally substituted $C_{1-6}$alkyl. In some embodiments, $R^y$ is fluoro and $R^z$ is unsubstituted $C_{1-6}$alkyl. In some embodiments, $R^y$ is fluoro and $R^z$ is unsubstituted $C_{1-3}$alkyl. In certain embodiments, $R^y$ is fluoro and $R^z$ is unsubstituted methyl. In some embodiments, $R^y$ is H and $R^z$ is halo or optionally substituted $C_{1-6}$alkyl. In some embodiments, $R^y$ is H and $R^z$ is optionally substituted $C_{1-6}$alkyl. In some embodiments, $R^y$ is H and $R^z$ is unsubstituted $C_{1-6}$alkyl. In some embodiments, $R^y$ is H and $R^z$ is unsubstituted $C_{1-3}$alkyl. In certain embodiments, $R^y$ is H and $R^z$ is unsubstituted methyl. In some embodiments, $R^y$ is H and $R^z$ is halo. In some embodiments, $R^y$ is H and $R^z$ is bromo. In some embodiments, $R^y$ and $R^z$ are taken together with the carbon atoms to which they are attached to form an optionally substituted non-aromatic cyclic ring containing 3 to 10 carbon atoms. In some embodiments, $R^y$ and $R^z$ are taken together with the carbon atoms to which they are attached to form an optionally substituted non-aromatic cyclic ring containing 3 to 6 carbon atoms. In certain embodiments, $R^y$ and $R^z$ are taken together with the carbon atoms to which they are attached to form an optionally substituted non-aromatic cyclic ring containing 5 carbon atoms. In certain embodiments, $R^y$ and $R^z$ are taken together with the carbon atoms to which they are attached to form an unsubstituted non-aromatic cyclic ring containing 5 carbon atoms.

In some embodiments, provided herein is a compound of formula (II):

(II)

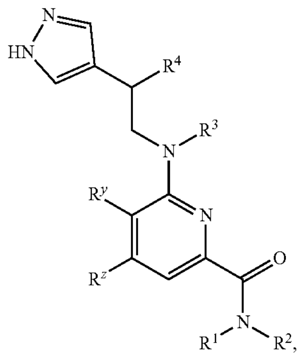

or a stereoisomer or tautomer thereof, or a pharmaceutically acceptable salt of any of the foregoing, wherein $R^1$, $R^2$, $R^3$, $R^4$, $R^y$, and $R^z$ are as defined above for the compound of formula (A).

In some embodiments, provided is a compound of formula (A) or (II), or a stereoisomer or tautomer thereof, or a pharmaceutically acceptable salt of any of the foregoing, wherein $R^y$ and $R^z$ are each independently H, halo, or optionally substituted $C_{1-6}$alkyl. In some embodiments, $R^y$ and $R^z$ are each independently optionally substituted $C_{1-6}$alkyl. In some embodiments, $R^y$ and $R^z$ are each independently unsubstituted $C_{1-6}$alkyl. In some embodiments, $R^y$ and $R^z$ are each independently unsubstituted $C_{1-3}$alkyl. In certain embodiments, $R^y$ and $R^z$ are each independently unsubstituted methyl. In some embodiments, $R^y$ is halo and $R^z$ is optionally substituted $C_{1-6}$alkyl. In some embodiments, $R^y$ is halo and $R^z$ is unsubstituted $C_{1-6}$alkyl. In some embodiments, $R^y$ is halo and $R^z$ is unsubstituted $C_{1-3}$alkyl. In certain embodiments, $R^y$ is halo and $R^z$ is unsubstituted methyl. In some embodiments, $R^y$ is chloro or fluoro, and $R^z$ is optionally substituted $C_{1-6}$alkyl. In some embodiments, $R^y$ is chloro or fluoro, and $R^z$ is unsubstituted $C_{1-6}$alkyl. In some embodiments, $R^y$ is chloro or fluoro, and $R^z$ is unsubstituted $C_{1-3}$alkyl. In certain embodiments, $R^y$ is chloro or fluoro, and $R^z$ is unsubstituted methyl. In some embodiments, $R^y$ is chloro and $R^z$ is optionally substituted $C_{1-6}$alkyl. In some embodiments, $R^y$ is chloro and $R^z$ is unsubstituted $C_{1-6}$alkyl. In some embodiments, $R^y$ is chloro and $R^z$ is unsubstituted $C_{1-3}$alkyl. In certain embodiments, $R^y$ is chloro and $R^z$ is unsubstituted methyl. In some embodiments, $R^y$ is fluoro and $R^z$ is optionally substituted $C_{1-6}$alkyl. In some embodiments, $R^y$ is fluoro and $R^z$ is unsubstituted $C_{1-6}$alkyl. In some embodiments, $R^y$ is fluoro and $R^z$ is unsubstituted $C_{1-3}$alkyl. In certain embodiments, $R^y$ is fluoro and $R^z$ is unsubstituted methyl. In some embodiments, $R^y$ is H and $R^z$ is halo or optionally substituted $C_{1-6}$alkyl. In some embodiments, $R^y$ is H and $R^z$ is optionally substituted $C_{1-6}$alkyl. In some embodiments, $R^y$ is H and $R^z$ is unsubstituted $C_{1-6}$alkyl. In some embodiments, $R^y$ is H and $R^z$ is unsubstituted $C_{1-3}$alkyl. In certain embodiments, $R^y$ is H and $R^z$ is unsubstituted methyl. In some embodiments, $R^y$ is H and $R^z$ is halo. In some embodiments, $R^y$ is H and $R^z$ is bromo. In some embodiments, $R^y$ and $R^z$ are taken together with the carbon atoms to which they are attached to form an optionally substituted non-aromatic cyclic ring containing 3 to 10 carbon atoms. In some embodiments, $R^y$ and $R^z$ are taken together with the carbon atoms to which they are attached to form an optionally substituted non-aromatic cyclic ring containing 3 to 6 carbon atoms. In certain embodiments, $R^y$ and $R^z$ are taken together with the carbon atoms to which they are attached to form an optionally substituted non-aromatic cyclic ring containing 5 carbon atoms. In certain embodiments, $R^y$ and $R^z$ are taken together with the carbon atoms to which they are attached to form an unsubstituted non-aromatic cyclic ring containing 5 carbon atoms.

In some embodiments, provided herein is a compound of formula (II), or a stereoisomer or tautomer thereof, or a pharmaceutically acceptable salt of any of the foregoing, wherein $R^y$ is H, such that the compound of formula (II) is a compound of formula (II-A):

(II-A)

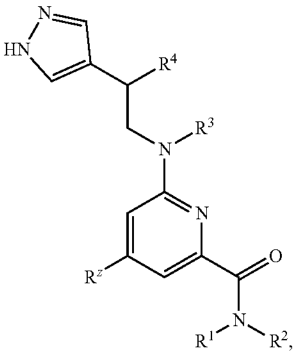

or a stereoisomer or tautomer thereof, or a pharmaceutically acceptable salt of any of the foregoing, wherein $R^1$, $R^2$, $R^3$, $R^4$, and $R^z$ are as defined above for the compound of formula (II).

In some embodiments, provided herein is a compound of formula (II-A), or a stereoisomer or tautomer thereof, or a pharmaceutically acceptable salt of any of the foregoing, wherein $R^3$ is H and $R^4$ is H, such that the compound of formula (II-A) is a compound of formula (II-A1):

(II-A1)

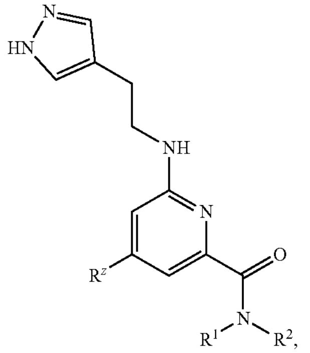

or a stereoisomer or tautomer thereof, or a pharmaceutically acceptable salt of any of the foregoing, wherein $R^1$, $R^2$, and $R^z$ are as defined above for the compound of formula (II-A).

In some embodiments, provided is a compound of formula (II), (II-A), or (II-A1), or a stereoisomer or tautomer thereof, or a pharmaceutically acceptable salt of any of the foregoing, wherein $R^z$ is halo or optionally substituted $C_{1-6}$alkyl. In some embodiments, $R^z$ is optionally substituted $C_{1-6}$alkyl. In some embodiments, $R^z$ is unsubstituted $C_{1-6}$alkyl. In some embodiments, $R^z$ is unsubstituted $C_{1-3}$alkyl. In certain embodiments, $R^z$ is unsubstituted methyl. In some embodiments, $R^z$ is halo. In some embodiments, $R^z$ is bromo.

In some embodiments, provided is a compound of formula (A), (I), (II), or (II-A), or a stereoisomer or tautomer thereof, or a pharmaceutically acceptable salt of any of the foregoing, wherein $R^3$ is optionally substituted $C_{1-6}$alkyl and $R^4$ is H. In some embodiments, $R^3$ is unsubstituted $C_{1-6}$alkyl and $R^4$ is H. In some embodiments, $R^3$ is unsubstituted n-propyl and $R^4$ is H. In some embodiments, $R^3$ is $C_{1-6}$alkyl, wherein the $C_{1-6}$alkyl of $R^3$ is substituted with one or more $C_{6-20}$aryl, and $R^4$ is H. In some embodiments, $R^3$ is $C_{1-6}$alkyl, wherein the $C_{1-6}$alkyl of $R^3$ is substituted with one or more phenyl, and $R^4$ is H. In some embodiments, $R^3$ is optionally substituted ethyl and $R^4$ is H. In some embodiments, $R^3$ is ethyl, wherein the ethyl of $R^3$ is substituted with one or more $C_{6-20}$aryl, and $R^4$ is H. In some embodiments, $R^3$ is ethyl, wherein the ethyl of $R^3$ is substituted with one or more phenyl, and $R^4$ is H. In some embodiments, $R^3$ is

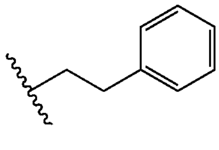 [SMILES: *CCc1ccccc1]

and $R^4$ is H. In some embodiments, $R^3$ is H and $R^4$ is H. In some embodiments, $R^3$ and $R^4$ taken together are $-CH_2CH_2-$.

In some embodiments, provided herein is a compound of formula (A), such as a compound of formula (I), (I-A), (I-A1), (I-A2), (I-A3), (I-B), (I-B1), (II), (II-A), or (II-A1), or a stereoisomer or tautomer thereof, or a pharmaceutically acceptable salt of any of the foregoing, wherein $R^1$ and $R^2$ are each independently H, optionally substituted $C_{1-6}$alkyl, optionally substituted $C_{3-10}$cycloalkyl, optionally substituted $C_{6-20}$aryl, optionally substituted 3-15 membered heterocyclyl, or optionally substituted 5-20 membered heteroaryl. In some embodiments, one of $R^1$ and $R^2$ is H and the other of $R^1$ and $R^2$ is optionally substituted $C_{1-6}$alkyl, optionally substituted $C_{3-10}$cycloalkyl, optionally substituted $C_{6-20}$aryl, optionally substituted 3-15 membered heterocyclyl, or optionally substituted 5-20 membered heteroaryl.

In some embodiments, provided herein is a compound of formula (I), such as a compound of formula (I-A), (I-A1), (I-B), or (I-B1), or a stereoisomer or tautomer thereof, or a pharmaceutically acceptable salt of any of the foregoing, wherein $R^1$ and $R^2$ are each independently H, optionally substituted $C_{1-6}$alkyl, optionally substituted $C_{3-10}$cycloalkyl, optionally substituted $C_{6-20}$aryl, optionally substituted 3-15 membered heterocyclyl, or optionally substituted 5-20 membered heteroaryl. In some embodiments, one of $R^1$ and $R^2$ is H and the other of $R^1$ and $R^2$ is optionally substituted $C_{1-6}$alkyl, optionally substituted $C_{3-10}$cycloalkyl, optionally substituted $C_{6-20}$aryl, optionally substituted 3-15 membered heterocyclyl, or optionally substituted 5-20 membered heteroaryl.

In some embodiments, provided herein is a compound of formula (A), such as a compound of formula (I), (I-A), (I-A1), (I-A2), (I-A3), (I-B), (I-B1), (II), (II-A), or (II-A1), or a stereoisomer or tautomer thereof, or a pharmaceutically acceptable salt of any of the foregoing, wherein $R^1$ and $R^2$ are each independently H. In some embodiments, provided herein is a compound of formula (I), such as a compound of formula (I-A), (I-A1), (I-B), or (I-B1), or a stereoisomer or tautomer thereof, or a pharmaceutically acceptable salt of any of the foregoing, wherein $R^1$ and $R^2$ are each independently H. In some embodiments, provided herein is a compound of formula (A), such as a compound of formula (I), (I-A), (I-A1), (I-A2), (I-A3), (I-B), (I-B1), (II), (II-A), or (II-A1), or a stereoisomer or tautomer thereof, or a pharmaceutically acceptable salt of any of the foregoing, wherein one of $R^1$ and $R^2$ is H and the other of $R^1$ and $R^2$ is optionally substituted $C_{1-6}$alkyl. In other embodiments, provided herein is a compound of formula (I), such as a compound of formula (I-A), (I-A1), (I-B), or (I-B1), or a stereoisomer or tautomer thereof, or a pharmaceutically acceptable salt of any of the foregoing, wherein one of $R^1$ and $R^2$ is H and the other of $R^1$ and $R^2$ is optionally substituted $C_{1-6}$alkyl. In some embodiments, provided herein is a compound of formula (A), such as a compound of formula (I), (I-A), (I-A1), (I-A2), (I-A3), (I-B), (I-B1), (II), (II-A), or (II-A1), or a stereoisomer or tautomer thereof, or a pharmaceutically acceptable salt of any of the foregoing, wherein $R^1$ and $R^2$ are each independently optionally substituted $C_{1-6}$alkyl. In other embodiments, provided herein is a compound of formula (I), such as a compound of formula (I-A), (I-A1), (I-B), or (I-B1), or a stereoisomer or tautomer thereof, or a pharmaceutically acceptable salt of any of the foregoing, wherein $R^1$ and $R^2$ are each independently optionally substituted $C_{1-6}$alkyl. In some embodiments of the foregoing, wherein one or both of $R^1$ and $R^2$ is optionally substituted $C_{1-6}$alkyl, the $C_{1-6}$alkyl of $R^1$ and/or $R^2$ is, independently at each occurrence, unsubstituted or is substituted with one or more $R'''$, wherein $R'''$ is, independently at each occurrence, —OH, halo, optionally substituted $C_{1-6}$alkoxy, optionally substituted sulfonyl, optionally substituted $C_{3-10}$cycloalkyl, optionally substituted 3-15 membered heterocyclyl, optionally substituted $C_{6-20}$aryl, or optionally substituted 5-20 membered heteroaryl. In some embodiments, wherein one or both of $R^1$ and $R^2$ is optionally substituted $C_{1-6}$alkyl, the $C_{1-6}$alkyl of $R^1$ and/or $R^2$ is, independently at each occurrence, unsubstituted or is substituted with one $R'''$. In other embodiments, wherein one or both of $R^1$ and $R^2$ is optionally substituted $C_{1-6}$alkyl, the $C_{1-6}$alkyl of $R^1$ and/or $R^2$ is, independently at each occurrence, unsubstituted or is substituted with two $R'''$. In other embodiments, wherein one or both of $R^1$ and $R^2$ is optionally substituted $C_{1-6}$alkyl, the $C_{1-6}$alkyl of $R^1$ and/or $R^2$ is, independently at each occurrence, unsubstituted or is substituted with three or more $R'''$.

In some embodiments, the $C_{1-6}$alkoxy, sulfonyl, $C_{3-20}$cycloalkyl, 3-15 membered heterocyclyl, $C_{6-20}$aryl, or 5-20 membered heteroaryl of $R'''$ is, independently at each occurrence, unsubstituted or is substituted with one or more $R''$, wherein $R''$ is, independently at each occurrence, halo, —OH, $C_{1-6}$alkyl, $C_{1-6}$alkoxy, —C(O)—$C_{6-20}$aryl, —$C_{1-6}$alkyl-$C_{6-20}$aryl, or $C_{6-20}$aryl, wherein the $C_{6-20}$aryl of $R''$ is, independently at each occurrence, optionally substituted with one or more halo. In some embodiments, the $C_{1-6}$alkoxy, sulfonyl, $C_{3-10}$cycloalkyl, 3-15 membered heterocyclyl, $C_{6-20}$aryl, or 5-20 membered heteroaryl of $R'''$ is, independently at each occurrence, unsubstituted or is substituted with one $R''$. In some embodiments, the $C_{1-6}$alkoxy, sulfonyl, $C_{3-10}$cycloalkyl, 3-15 membered heterocyclyl, $C_{6-20}$aryl, or 5-20 membered heteroaryl of $R'''$ is, independently at each occurrence, unsubstituted or is substituted with two $R''$. In some embodiments, the $C_{1-6}$alkoxy, sulfonyl, $C_{3-10}$cycloalkyl, 3-15 membered heterocyclyl, $C_{6-20}$aryl, or 5-20 membered heteroaryl of $R'''$ is, independently at each occurrence, unsubstituted or is substituted with three or more $R''$. In some embodiments, the $C_{1-6}$alkoxy, sulfonyl, $C_{3-10}$cycloalkyl, 3-15 membered heterocyclyl, $C_{6-20}$aryl, or 5-20 membered heteroaryl of $R'''$ is, independently at each occurrence, unsubstituted or is substituted with one to five $R''$.

In some embodiments, provided herein is a compound of formula (A), such as a compound of formula (I), (I-A), (I-A1), (I-A2), (I-A3), (I-B), (I-B1), (II), (II-A), or (II-A1), or a stereoisomer or tautomer thereof, or a pharmaceutically acceptable salt of any of the foregoing, wherein one of $R^1$ and $R^2$ is H and the other of $R^1$ and $R^2$ is unsubstituted $C_{1-6}$alkyl. In some embodiments, one of $R^1$ and $R^2$ is H and the other of $R^1$ and $R^2$ is unsubstituted methyl. In some embodiments, provided herein is a compound of formula (I), such as a compound of formula (I A), (I-A1), (I-B), or (I-B1), or a stereoisomer or tautomer thereof, or a pharmaceutically acceptable salt of any of the foregoing, wherein one of $R^1$ and $R^2$ is H and the other of $R^1$ and $R^2$ is unsubstituted $C_{1-6}$alkyl. In some embodiments, one of $R^1$ and $R^2$ is H and the other of $R^1$ and $R^2$ is unsubstituted methyl.

In some embodiments, one of $R^1$ and $R^2$ is H and the other of $R^1$ and $R^2$ is $C_{1-6}$alkyl, wherein the $C_{1-6}$alkyl of $R^1$ or $R^2$ is optionally substituted with one or more $R'''$, wherein each $R'''$ is independently 5-20 membered heteroaryl or $C_{6-20}$aryl, wherein the 5-20 membered heteroaryl or $C_{6-20}$aryl of $R'''$ is independently optionally substituted with one or more halo, $C_{1-6}$alkyl, or $C_{1-6}$alkoxy. In some embodiments, $R^1$ and $R^2$ are both independently optionally substituted $C_{1-6}$alkyl, wherein the optionally substituted $C_{1-6}$alkyl of $R^1$ and $R^2$ is independently optionally substituted with one or more $R'''$, wherein $R'''$ is 5-20 membered heteroaryl or $C_{6-20}$aryl, wherein the 5-20 membered heteroaryl or $C_{6-20}$aryl or $R'''$ is independently optionally substituted with one or more halo, $C_{1-6}$alkyl, or $C_{1-6}$alkoxy.

In some embodiments, one of $R^1$ and $R^2$ is H and the other of $R^1$ and $R^2$ is $C_{1-6}$alkyl, wherein the $C_{1-6}$alkyl of $R^1$ or $R^2$ is optionally substituted with one or more $R'''$, wherein each $R'''$ is independently —OH, halo, or $C_{1-6}$alkoxy. In some embodiments, each of $R^1$ and $R^2$ is $C_{1-6}$alkyl, wherein the $C_{1-6}$alkyl of $R^1$ or $R^2$ is optionally substituted with one or more $R'''$, wherein each $R'''$ is independently —OH, halo, or $C_{1-6}$alkoxy.

In some embodiments, one of $R^1$ and $R^2$ is H and the other of $R^1$ and $R^2$ is $C_{1-6}$alkyl, wherein the $C_{1-6}$alkyl of $R^1$ or $R^2$ is optionally substituted with one or more $R'''$, wherein each $R'''$ is independently 5-20 membered heteroaryl or $C_{6-20}$aryl, wherein the 5-20 membered heteroaryl or $C_{6-20}$aryl of $R'''$ is optionally substituted with one or more halo. In some embodiments, each of $R^1$ and $R^2$ is independently $C_{1-6}$alkyl, wherein the $C_{1-6}$alkyl of $R^1$ or $R^2$ is optionally substituted with one or more $R'''$, wherein each $R'''$ is independently 5-20 membered heteroaryl or $C_{6-20}$aryl, wherein the 5-20 membered heteroaryl or $C_{6-20}$aryl of $R'''$ is optionally substituted with one or more halo. In some embodiments, the halo is independently chloro or fluoro.

In some embodiments, one of $R^1$ and $R^2$ is H and the other of $R^1$ and $R^2$ is $C_{1-6}$alkyl, wherein the $C_{1-6}$alkyl of $R^1$ or $R^2$ is optionally substituted with one or more $R'''$, wherein each $R'''$ is independently 5-20 membered heteroaryl, wherein the 5-20 membered heteroaryl of $R'''$ is optionally substituted with one or more $C_{1-6}$alkyl, $C_{1-6}$alkoxy, or halo. In some embodiments, each of $R^1$ and $R^2$ is independently $C_{1-6}$alkyl, wherein the $C_{1-6}$alkyl of $R^1$ or $R^2$ is optionally substituted with one or more $R'''$, wherein each $R'''$ is independently 5-20 membered heteroaryl, wherein the 5-20 membered heteroaryl of $R'''$ is optionally substituted with one or more $C_{1-6}$alkyl, $C_{1-6}$alkoxy, or halo. In some embodiments, the halo is independently chloro or fluoro. In some embodiments, the 5-20 membered heteroaryl is benzofuranyl, indazolyl, pyridinyl, imidazolyl, oxazolyl, isoxazolyl, pyrazolyl, furanyl, thiazolyl, or thiophenyl.

In some embodiments, one of $R^1$ and $R^2$ is H and the other of $R^1$ and $R^2$ is $C_{1-6}$alkyl, wherein the $C_{1-6}$alkyl of $R^1$ or $R^2$ is optionally substituted with one or more $R'''$, wherein each $R'''$ is independently $C_{6-20}$aryl, wherein the $C_{6-20}$aryl of $R'''$ is optionally substituted with one or more $C_{1-6}$alkyl, $C_{1-6}$alkoxy, or halo. In some embodiments, each of $R^1$ and $R^2$ is independently $C_{1-6}$alkyl, wherein the $C_{1-6}$alkyl of $R^1$ or $R^2$ is optionally substituted with one or more $R'''$, wherein each $R'''$ is independently $C_{6-20}$aryl, wherein the $C_{6-20}$aryl of $R'''$ is optionally substituted with one or more $C_{1-6}$alkyl, $C_{1-6}$alkoxy, or halo. In some embodiments, the halo is independently chloro or fluoro.

In some embodiments, one of $R^1$ and $R^2$ is H and the other of $R^1$ and $R^2$ is $C_{1-6}$alkyl, wherein the $C_{1-6}$alkyl of $R^1$ or $R^2$ is optionally substituted with one or more $R'''$, wherein each $R'''$ is independently phenyl, wherein the phenyl of $R'''$ is optionally substituted with one or more $C_{1-6}$alkyl, $C_{1-6}$alkoxy, or halo. In some embodiments, each of $R^1$ and $R^2$ is independently $C_{1-6}$alkyl, wherein the $C_{1-6}$alkyl of $R^1$ or $R^2$ is optionally substituted with one or more $R'''$, wherein each $R'''$ is independently phenyl, wherein the phenyl of $R'''$ is optionally substituted with one or more $C_{1-6}$alkyl, $C_{1-6}$alkoxy, or halo. In some embodiments, the halo is independently chloro or fluoro.

In some embodiments, one of $R^1$ and $R^2$ is H and the other of $R^1$ and $R^2$ is $C_{1-6}$alkyl, wherein the $C_{1-6}$alkyl of $R^1$ or $R^2$ is optionally substituted with one or more $R'''$, wherein each $R'''$ is independently 5-6 membered heteroaryl, wherein the 5-6 membered heteroaryl of $R'''$ is optionally substituted with one or more $C_{1-6}$alkyl, $C_{1-6}$alkoxy, or halo. In some embodiments, one of $R^1$ and $R^2$ is H and the other of $R^1$ and $R^2$ is $C_{1-6}$alkyl, wherein the $C_{1-6}$alkyl of $R^1$ or $R^2$ is optionally substituted with one or more $R'''$, wherein each $R'''$ is independently 5-6 membered heteroaryl, wherein the 5-6 membered heteroaryl of $R'''$ is optionally substituted with one or more halo. In some embodiments, each of $R^1$ and $R^2$ is independently $C_{1-6}$alkyl, wherein the $C_{1-6}$alkyl of $R^1$ or $R^2$ is optionally substituted with one or more $R'''$, wherein each $R'''$ is independently 5-6 membered heteroaryl, wherein the 5-6 membered heteroaryl of $R'''$ is optionally substituted with one or more $C_{1-6}$alkyl, $C_{1-6}$alkoxy, or halo. In some embodiments, each of $R^1$ and $R^2$ is independently $C_{1-6}$alkyl, wherein the $C_{1-6}$alkyl of $R^1$ or $R^2$ is optionally substituted with one or more $R'''$, wherein each $R'''$ is independently 5-6 membered heteroaryl, wherein the 5-6 membered heteroaryl of $R'''$ is optionally substituted with one or more halo. In some embodiments of the foregoing, the 5-6 membered heteroaryl is pyridinyl. In some embodiments, the 5-6 heteroaryl is imidazolyl, oxazolyl, isoxazolyl, pyrazolyl, furanyl, thiazolyl, or thiophenyl. In some embodiments of the foregoing, the 5-6 membered heteroaryl of $R'''$ is optionally substituted with one or more halo, wherein the halo is independently chloro or fluoro. In some embodiments, the halo is fluoro. In some embodiments, provided herein is a compound of formula (A), such as a compound of formula (I), (I-A), (I-A1), (I-A2), (I-A3), (I-B), (I-B1), (II), (II-A), or (II-A1), or a stereoisomer or tautomer thereof, or a pharmaceutically acceptable salt of any of the foregoing, wherein one of $R^1$ and $R^2$ is H and the other of $R^1$ and $R^2$ is $C_1$-6alkyl, wherein the $C_{1-6}$alkyl of $R^1$ or $R^2$ is optionally substituted with one $R'''$, wherein $R'''$ is pyridinyl, wherein the pyridinyl of $R'''$ is optionally substituted with one or more fluoro. In some embodiments, one of $R^1$ and $R^2$ is H and the other of $R^1$ and $R^2$ is

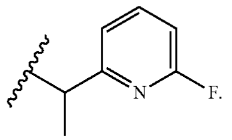 [SMILES: *C(C)c1cccc(F)n1]

In some embodiments, one of $R^1$ and $R^2$ is H and the other of $R^1$ and $R^2$ is

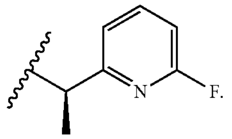 [SMILES: *[C@H](C)c1cccc(F)n1]

In some embodiments, provided herein is a compound of formula (I), such as a compound of formula (I-A), (I-A1), (I-B), or (I-B1), or a stereoisomer or tautomer thereof, or a pharmaceutically acceptable salt of any of the foregoing, wherein one of $R^1$ and $R^2$ is H and the other of $R^1$ and $R^2$ is $C_{1-6}$alkyl, wherein the $C_{1-6}$alkyl of $R^1$ or $R^2$ is optionally substituted with one $R'''$, wherein $R'''$ is pyridinyl, wherein the pyridinyl of $R'''$ is optionally substituted with one or more fluoro. In some embodiments, one of $R^1$ and $R^2$ is H and the other of $R^1$ and $R^2$ is

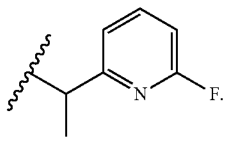 [SMILES: *C(C)c1cccc(F)n1]

In some embodiments, one of $R^1$ and $R^2$ is H and the other of $R^1$ and $R^2$ is

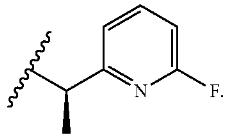 [SMILES: *[C@H](C)c1cccc(F)n1]

In some embodiments, one of $R^1$ and $R^2$ is H and the other of $R^1$ and $R^2$ is $C_{1-6}$alkyl, wherein the $C_{1-6}$alkyl of $R^1$ or $R^2$ is optionally substituted with one or more $R'''$, wherein each $R'''$ is $C_{3-10}$cycloalkyl. In some embodiments, $R'''$ is $C_{3-6}$cycloalkyl. In some embodiments, $R'''$ is cyclohexyl. In some embodiments, one of $R^1$ and $R^2$ is H and the other of $R^1$ and $R^2$ is $C_{1-6}$alkyl, wherein the $C_{1-6}$alkyl of $R^1$ or $R^2$ is optionally substituted with one or more $R'''$, wherein each $R'''$ is $C_{3-10}$cycloalkyl or 5-20 membered heteroaryl. In some embodiments, the $C_{3-10}$cycloalkyl of $R'''$ is spiro.

In some embodiments, one of $R^1$ and $R^2$ is H and the other of $R^1$ and $R^2$ is $C_{1-6}$alkyl, wherein the $C_{1-6}$alkyl of $R^1$ or $R^2$ is optionally substituted with one or more $R'''$, wherein each $R'''$ is sulfonyl, wherein the sulfonyl of $R'''$ is independently optionally substituted with one or more —$C_{1-6}$alkyl-$C_{6-20}$aryl. In some embodiments, each of $R^1$ and $R^2$ is $C_{1-6}$alkyl, wherein the $C_{1-6}$alkyl of $R^1$ or $R^2$ is independently optionally substituted with one or more $R'''$, wherein each $R'''$ is sulfonyl, wherein the sulfonyl of $R'''$ is independently optionally substituted with one or more —$C_{1-6}$alkyl-$C_{6-20}$aryl. in some embodiments, one of $R^1$ and $R^2$ is H and the other of $R^1$ and $R^2$ is

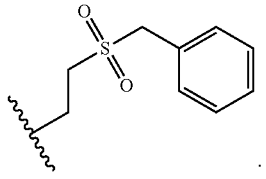 [SMILES: *CCS(=O)(=O)Cc1ccccc1]

In some embodiments, one of $R^1$ and $R^2$ is H and the other of $R^1$ and $R^2$ is $C_{1-6}$alkyl, wherein the $C_{1-6}$alkyl of $R^1$ or $R^2$ is optionally substituted with one or more $R'''$, wherein $R'''$ is 3-15 membered heterocyclyl, wherein the 3-15 membered heterocyclyl of $R'''$ is independently optionally substituted with one or more $R''$, wherein $R''$ is $C_{6-20}$aryl, wherein the $C_{6-20}$aryl of $R''$ is optionally substituted with one or more halo. In some embodiments, each of $R^1$ and $R^2$ is $C_{1-6}$alkyl, wherein the $C_{1-6}$alkyl of $R^1$ or $R^2$ is optionally substituted with one or more $R'''$, wherein $R'''$ is 3-15 membered heterocyclyl, wherein the 3-15 membered heterocyclyl of $R'''$ is independently optionally substituted with one or more $R''$, wherein $R''$ is $C_{6-20}$aryl, wherein the $C_{6-20}$aryl of $R''$ is optionally substituted with one or more halo. In some embodiments, the halo is independently chloro or fluoro. In some embodiments, one of $R^1$ and $R^2$ is H and the other of $R^1$ and $R^2$ is $C_{1-6}$alkyl, wherein the $C_{1-6}$alkyl of $R^1$ or $R^2$ is optionally substituted with one or more $R'''$, wherein $R'''$ is oxetanyl, wherein the oxetanyl of $R'''$ is independently optionally substituted with one or more $R''$, wherein $R''$ is phenyl, wherein the phenyl of $R''$ is optionally substituted with one or more halo. In some embodiments, the halo is independently fluoro or chloro. In some embodiments, the 3-15 membered heterocyclyl of $R'''$ is spiro.

In some embodiments, one of $R^1$ and $R^2$ is H and the other of $R^1$ and $R^2$ is $C_{1-6}$alkyl, wherein the $C_{1-6}$alkyl of $R^1$ or $R^2$ is optionally substituted with one or more $R'''$, wherein $R'''$ is 3-15 membered heterocyclyl or $C_{6-20}$aryl, wherein the $C_{6-20}$aryl of $R'''$ is optionally substituted with one or more halo. In some embodiments, the halo is independently fluoro or chloro. In some embodiments, one of $R^1$ and $R^2$ is H and the other of $R^1$ and $R^2$ is $C_{1-6}$alkyl, wherein the $C_{1-6}$alkyl of $R^1$ or $R^2$ is optionally substituted with one or more $R'''$, wherein $R'''$ is 3-15 membered heterocyclyl or unsubstituted $C_{6-20}$aryl. In some embodiments, one of $R^1$ and $R^2$ is H and the other of $R^1$ and $R^2$ is $C_{1-6}$alkyl, wherein the $C_{1-6}$alkyl of $R^1$ or $R^2$ is optionally substituted with one or more $R'''$, wherein $R'''$ is 3-15 membered heterocyclyl or $C_{6-20}$aryl, wherein the $C_{6-20}$aryl of $R'''$ is substituted with one or more halo. In some embodiments, the halo is independently fluoro or chloro.

In some embodiments, one of $R^1$ and $R^2$ is H and the other of $R^1$ and $R^2$ is optionally substituted $C_{3-10}$cycloalkyl. In some embodiments, one of $R^1$ and $R^2$ is H and the other of $R^1$ and $R^2$ is unsubstituted $C_{3-10}$cycloalkyl. In some embodiments, one of $R^1$ and $R^2$ is H and the other of $R^1$ and $R^2$ is $C_{3-10}$cycloalkyl, wherein the $C_{3-10}$cycloalkyl of $R^1$ or $R^2$ is substituted with one or more halo or $C_{6-20}$aryl. In some embodiments, one of $R^1$ and $R^2$ is H and the other of $R^1$ and $R^2$ is cyclobutyl, wherein the cyclobutyl of $R^1$ or $R^2$ is optionally substituted with one or more halo or $C_{6-20}$aryl. In some embodiments, one of $R^1$ and $R^2$ is H and the other of $R^1$ and $R^2$ is cyclobutyl, wherein the cyclobutyl of $R^1$ or $R^2$ is optionally substituted with one or more phenyl. In some embodiments, one of $R^1$ and $R^2$ is H and the other of $R^1$ and $R^2$ is dihydroindenyl, wherein the dihydroindenyl of $R^1$ or $R^2$ is optionally substituted with one or more halo or $C_{6-20}$aryl. In some embodiments, one of $R^1$ and $R^2$ is H and the other of $R^1$ and $R^2$ is dihydroindenyl, wherein the dihydroindenyl of $R^1$ or $R^2$ is optionally substituted with one or more halo. In some embodiments of the foregoing, the halo is independently chloro or fluoro. In some embodiments, the halo is fluoro.

In some embodiments, one of $R^1$ and $R^2$ is H and the other of $R^1$ and $R^2$ is optionally substituted 3-15 membered heterocyclyl. In some embodiments, one of $R^1$ and $R^2$ is H and the other of $R^1$ and $R^2$ is optionally substituted 3-8 membered heterocyclyl. In some embodiments, one of $R^1$ and $R^2$ is H and the other of $R^1$ and $R^2$ is optionally substituted 3-6 membered heterocyclyl. In some embodiments, one of $R^1$ and $R^2$ is H and the other of $R^1$ and $R^2$ is unsubstituted 3-15 membered heterocyclyl. In some embodiments, one of $R^1$ and $R^2$ is H and the other of $R^1$ and $R^2$ is 3-15 membered heterocyclyl, wherein the 3-15 membered heterocyclyl of $R^1$ or $R^2$ is substituted with one or more $R^p$, wherein $R^p$ is, independently at each occurrence, $C_{1-6}$alkyl or $C_{6-20}$aryl, wherein the $C_{1-6}$alkyl of $R^p$ is, independently at each occurrence, optionally substituted with one or more $R^p$, wherein $R^p$ is, independently at each occurrence, $C_{6-20}$aryl, wherein the $C_{6-20}$aryl of $R^p$ is, independently at each occurrence, optionally substituted with one or more halo. In some embodiments, one of $R^1$ and $R^2$ is H and the other of $R^1$ and $R^2$ is 3-15 membered heterocyclyl, wherein the 3-15 membered heterocyclyl of $R^1$ or $R^2$ is substituted with one $R^p$, wherein $R^p$ is $C_{6-20}$aryl. In some embodiments, one of $R^1$ and $R^2$ is H and the other of $R^1$ and $R^2$ is oxetanyl, wherein the oxetanyl of $R^1$ or $R^2$ is substituted with one $R^p$, wherein $R^p$ is phenyl. In some embodiments, one of $R^1$ and $R^2$ is H and the other of $R^1$ and $R^2$ is 3-15 membered heterocyclyl, wherein the 3-15 membered heterocyclyl of $R^1$ or $R^2$ is substituted with one or more $R^p$, wherein $R^p$ is, independently at each occurrence, $C_{1-6}$alkyl, wherein the $C_{1-6}$alkyl of $R^p$ is, independently at each occurrence, optionally substituted with one or more $R^p$, wherein $R^p$ is, independently at each occurrence, $C_{6-20}$aryl, wherein the $C_{6-20}$aryl of $R^p$ is, independently at each occurrence, optionally substituted with one or more halo. In some embodiments, one of $R^1$ and $R^2$ is H and the other of $R^1$ and $R^2$ is tetrahydropyranyl, wherein the tetrahydropyranyl of $R^1$ or $R^2$ is substituted with one or more $R^p$, wherein $R^p$ is, independently at each occurrence, $C_{1-6}$alkyl, wherein the $C_{1-6}$alkyl of $R^p$ is, independently at each occurrence, optionally substituted with one or more $R^p$, wherein $R^p$ is, independently at each occurrence, phenyl, wherein the phenyl of $R^p$ is, independently at each occurrence, optionally substituted with one or more halo. In some embodiments, each halo is independently chloro or fluoro.

In some embodiments, one of $R^1$ and $R^2$ is H and the other of $R^1$ and $R^2$ is optionally substituted $C_{6-20}$aryl. In some embodiments, one of $R^1$ and $R^2$ is H and the other of $R^1$ and $R^2$ is unsubstituted $C_{6-20}$aryl. In some embodiments, one of $R^1$ and $R^2$ is H and the other of $R^1$ and $R^2$ is $C_{6-20}$aryl, wherein the $C_{6-20}$aryl of $R^1$ or $R^2$ is substituted with one or more halo or $C_{1-6}$alkyl. In some embodiments, one of $R^1$ and $R^2$ is H and the other of $R^1$ and $R^2$ is phenyl, wherein the phenyl of $R^1$ or $R^2$ is optionally substituted with one or more halo or $C_{1-6}$alkyl. In some embodiments of the foregoing, the halo is independently chloro or fluoro. In some embodiments, the $C_{1-6}$alkyl is methyl.

In some embodiments, one of $R^1$ and $R^2$ is H and the other of $R^1$ and $R^2$ is optionally substituted 5-20 membered heteroaryl. In some embodiments, one of $R^1$ and $R^2$ is H and the other of $R^1$ and $R^2$ is unsubstituted 5-20 membered heteroaryl. In some embodiments, one of $R^1$ and $R^2$ is H and the other of $R^1$ and $R^2$ is 5-20 membered heteroaryl, wherein the 5-20 membered heteroaryl of $R^1$ or $R^2$ is substituted with one or more halo. In some embodiments, one of $R^1$ and $R^2$ is H and the other of $R^1$ and $R^2$ is 5-6 membered heteroaryl, wherein the 5-6 membered heteroaryl of $R^1$ or $R^2$ is optionally substituted with one or more halo. In some embodiments, one of $R^1$ and $R^2$ is H and the other of $R^1$ and $R^2$ is pyridinyl, wherein the pyridinyl of $R^1$ or $R^2$ is optionally substituted with one or more halo. In some embodiments of the foregoing, the halo is independently chloro or fluoro.

In some embodiments, provided herein is a compound of formula (A), such as a compound of formula (I), (I-A), (I-A1), (I-A2), (I-A3), (I-B), (I-B1), (II), (II-A), or (II-A1), or a stereoisomer or tautomer thereof, or a pharmaceutically acceptable salt of any of the foregoing, wherein $R^1$ and $R^2$ are taken together with the nitrogen to which they are attached to form an optionally substituted 3-15 membered heterocyclyl. In some embodiments, $R^1$ and $R^2$ are taken together with the nitrogen to which they are attached to form an optionally substituted 3-12 membered heterocyclyl. In other embodiments, $R^1$ and $R^2$ are taken together with the nitrogen to which they are attached to form an optionally substituted 3-10 membered heterocyclyl. In some embodiments, $R^1$ and $R^2$ are taken together with the nitrogen to which they are attached to form an optionally substituted 3-8 membered heterocyclyl. In other embodiments, $R^1$ and $R^2$ are taken together with the nitrogen to which they are attached to form an optionally substituted 3-6 membered heterocyclyl. In some embodiments, $R^1$ and $R^2$ are taken together with the nitrogen to which they are attached to form an optionally substituted 5-6 membered heterocyclyl. In some embodiments, provided herein is a compound of formula (I), such as a compound of formula (I A), (I-A1), (I-B), or (I-B1), or a stereoisomer or tautomer thereof, or a pharmaceutically acceptable salt of any of the foregoing, wherein $R^1$ and $R^2$ are taken together with the nitrogen to which they are attached to form an optionally substituted 3-15 membered heterocyclyl. In some embodiments, $R^1$ and $R^2$ are taken together with the nitrogen to which they are attached to form an optionally substituted 3-12 membered heterocyclyl. In other embodiments, $R^1$ and $R^2$ are taken together with the nitrogen to which they are attached to form an optionally substituted 3-10 membered heterocyclyl. In some embodiments, $R^1$ and $R^2$ are taken together with the nitrogen to which they are attached to form an optionally substituted 3-8 membered heterocyclyl. In other embodiments, $R^1$ and $R^2$ are taken together with the nitrogen to which they are attached to form an optionally substituted 3-6 membered heterocyclyl. In some embodiments, $R^1$ and $R^2$ are taken together with the nitrogen to which they are attached to form an optionally substituted 5-6 membered heterocyclyl.

In some embodiments, wherein $R^1$ and $R^2$ are taken together with the nitrogen to which they are attached to form an optionally substituted 3-15 membered heterocyclyl, the optionally substituted 3-15 membered heterocyclyl is monocyclic. In other embodiments, the optionally substituted 3-15 membered heterocyclyl is bicyclic. In still other embodiments, the optionally substituted 3-15 membered heterocyclyl is tricyclic. In some embodiments, optionally substituted 3-15 membered heterocyclyl is spiro. In other embodiments, optionally substituted 3-15 membered heterocyclyl is bridged.

In some embodiments, provided herein is a compound of formula (A), such as a compound of formula (I), (I-A), (I-A1), (I-A2), (I-A3), (I-B), (I-B1), (II), (II-A), or (II-A1), or a stereoisomer or tautomer thereof, or a pharmaceutically acceptable salt of any of the foregoing, wherein $R^1$ and $R^2$ are taken together with the nitrogen to which they are attached to form an optionally substituted azetidinyl, an optionally substituted pyrrolidinyl, an optionally substituted piperidinyl, an optionally substituted piperazinyl, an optionally substituted morpholinyl, an optionally substituted spiro[azetidine-3,3'-indolin]-2'-on-yl, or an optionally substituted 2-azaspiro[3.3]heptanyl. In some embodiments, $R^1$ and $R^2$ are taken together with the nitrogen to which they are attached to form an optionally substituted azetidinyl, an optionally substituted pyrrolidinyl, an optionally substituted piperidinyl, an optionally substituted piperazinyl, or an optionally substituted morpholinyl. In some embodiments, $R^1$ and $R^2$ are taken together with the nitrogen to which they are attached to form an optionally substituted azetidinyl. In some embodiments, $R^1$ and $R^2$ are taken together with the nitrogen to which they are attached to form an optionally substituted pyrrolidinyl, an optionally substituted piperidinyl, or an optionally substituted piperazinyl. In some embodiments, $R^1$ and $R^2$ are taken together with the nitrogen to which they are attached to form an optionally substituted pyrrolidinyl. In some embodiments, $R^1$ and $R^2$ are taken together with the nitrogen to which they are attached to form an optionally substituted morpholinyl. In some embodiments, provided herein is a compound of formula (I), such as a compound of formula (I-A), (I-A1), (I-B), or (I-B1), or a stereoisomer or tautomer thereof, or a pharmaceutically acceptable salt of any of the foregoing, wherein $R^1$ and $R^2$ are taken together with the nitrogen to which they are attached to form an optionally substituted azetidinyl, an optionally substituted pyrrolidinyl, an optionally substituted piperidinyl, an optionally substituted piperazinyl, an optionally substituted morpholinyl, an optionally substituted spiro[azetidine-3,3'-indolin]-2'-on-yl, or an optionally substituted 2-azaspiro[3.3]heptanyl. In some embodiments, $R^1$ and $R^2$ are taken together with the nitrogen to which they are attached to form an optionally substituted azetidinyl, an optionally substituted pyrrolidinyl, an optionally substituted piperidinyl, an optionally substituted piperazinyl, or an optionally substituted morpholinyl. In some embodiments, $R^1$ and $R^2$ are taken together with the nitrogen to which they are attached to form an optionally substituted azetidinyl. In some embodiments, $R^1$ and $R^2$ are taken together with the nitrogen to which they are attached to form an optionally substituted pyrrolidinyl, an optionally substituted piperidinyl, or an optionally substituted piperazinyl. In some embodiments, $R^1$ and $R^2$ are taken together with the nitrogen to which they are attached to form an optionally substituted pyrrolidinyl. In some embodiments, $R^1$ and $R^2$ are taken together with the nitrogen to which they are attached to form an optionally substituted morpholinyl.

In some embodiments, the 3-15 membered heterocyclyl formed by $R^1$ and $R^2$ is unsubstituted or is substituted with one or more $R^s$, wherein $R^s$ is, independently at each occurrence, halo, —OH, —CN, oxo, optionally substituted $C_{1-6}$alkyl, optionally substituted optionally substituted $C_{1-6}$alkoxy, optionally substituted $C_{3-10}$cycloalkyl, optionally substituted 3-15 membered heterocyclyl, optionally substituted $C_{6-20}$aryl, or optionally substituted 5-20 membered heteroaryl. In some embodiments, the 3-15 membered heterocyclyl formed by $R^1$ and $R^2$ is unsubstituted or is substituted with one $R^s$. In some embodiments, the 3-15 membered heterocyclyl formed by $R^1$ and $R^2$ is unsubstituted or is substituted with two $R^s$. In other embodiments, the 3-15 membered heterocyclyl formed by $R^1$ and $R^2$ is unsubstituted or is substituted with three or more $R^s$.

In some embodiments, the 3-15 membered heterocyclyl formed by $R^1$ and $R^2$ is unsubstituted or is substituted with one or more $R^s$, wherein $R^s$ is, independently at each occurrence, halo, —OH, —CN, oxo, $C_{1-6}$alkyl, $C_{1-6}$alkoxy, $C_{3-10}$cycloalkyl, 3-15 membered heterocyclyl, $C_{6-20}$aryl, or 5-20 membered heteroaryl, wherein the $C_{1-6}$alkyl, $C_{1-6}$alkoxy, $C_{3-10}$cycloalkyl, 3-15 membered heterocyclyl, $C_{6-20}$aryl, or 5-20 membered heteroaryl of $R^s$ is, independently at each occurrence, optionally substituted with one or more halo, —OH, $C_{1-6}$alkyl, or $C_{6-20}$aryl. In some embodiments of the foregoing, the $C_{1-6}$alkyl, $C_{1-6}$alkoxy, $C_{3-10}$cycloalkyl, 3-15 membered heterocyclyl, $C_{6-20}$aryl, or 5-20 membered heteroaryl of $R^s$ is, independently at each occurrence, optionally substituted with one or more halo, —OH, methyl, or phenyl. In some embodiments, the 3-15 membered heterocyclyl formed by $R^1$ and $R^2$ is substituted with one or more $R^s$, wherein $R^s$ is, independently at each occurrence, —OH, —CN, halo, $C_{1-6}$alkyl, $C_{1-6}$alkoxy, or phenyl, wherein the phenyl of $R^s$ is, independently at each occurrence, optionally substituted with one or more halo. In some embodiments, the halo is independently chloro or fluoro.

In some embodiments, the 3-15 membered heterocyclyl formed by $R^1$ and $R^2$ is unsubstituted. In other embodiments, the 3-15 membered heterocyclyl formed by $R^1$ and $R^2$ is substituted with one or more $R^s$, wherein $R^s$ is, independently at each occurrence, halo, —OH, —CN, oxo, $C_{1-6}$alkyl, $C_{1-6}$alkoxy, $C_{3-10}$cycloalkyl, 3-15 membered heterocyclyl, $C_{6-20}$aryl, or 5-20 membered heteroaryl, wherein the $C_{1-6}$alkyl, $C_{1-6}$alkoxy, $C_{3-10}$cycloalkyl, 3-15 membered heterocyclyl, $C_{6-20}$aryl, or 5-20 membered heteroaryl of $R^s$ is, independently at each occurrence, optionally substituted with one or more halo, —OH, $C_{1-6}$alkyl, or $C_{6-20}$aryl. In some embodiments, the 3-15 membered heterocyclyl formed by $R^1$ and $R^2$ is substituted with one or more $R^s$, wherein $R^s$ is, independently at each occurrence, halo, —OH, —CN, oxo, $C_{1-6}$alkyl, or $C_{1-6}$alkoxy, wherein the $C_{1-6}$alkyl or $C_{1-6}$alkoxy, of $R^s$ is, independently at each occurrence, optionally substituted with one or more halo, —OH, $C_{1-6}$alkyl, or $C_{6-20}$aryl. In some embodiments, the 3-15 membered heterocyclyl formed by $R^1$ and $R^2$ is unsubstituted or is substituted with one or more $R^s$, wherein $R^s$ is, independently at each occurrence, $C_{3-10}$cycloalkyl, 3-15 membered heterocyclyl, $C_{6-20}$aryl, or 5-20 membered heteroaryl, wherein the $C_{3-10}$cycloalkyl, 3-15 membered heterocyclyl, $C_{6-20}$aryl, or 5-20 membered heteroaryl of $R^s$ is, independently at each occurrence, optionally substituted with one or more halo, —OH, $C_{1-6}$alkyl, or $C_{6-20}$aryl. In some embodiments, the 3-15 membered heterocyclyl formed by $R^1$ and $R^2$ is unsubstituted or is substituted with one or more $R^s$, wherein $R^s$ is, independently at each occurrence, $C_{6-20}$aryl, wherein the $C_{6-20}$aryl of $R^s$ is, independently at each occurrence, optionally substituted with one or more halo. In some embodiments, the 3-15 membered heterocyclyl formed by $R^1$ and $R^2$ is unsubstituted or is substituted with one or more $R^s$, wherein $R^s$ is, independently at each occurrence, phenyl, wherein the phenyl of $R^s$ is, independently at each occurrence, optionally substituted with one or more halo. In some embodiments of the foregoing, the halo is independently chloro or fluoro.

In some embodiments, provided herein is a compound of formula (A), such as a compound of formula (I), (I-A), (I-A1), (I-A2), (I-A3), (I-B), (I-B1), (II), (II-A), or (II-A1), or a stereoisomer or tautomer thereof, or a pharmaceutically acceptable salt of any of the foregoing, wherein $R^1$ and $R^2$ are taken together with the nitrogen to which they are attached to form a pyrrolidinyl, wherein the pyrrolidinyl formed by $R^1$ and $R^2$ is substituted with one $R^s$, wherein $R^s$ is phenyl, wherein the phenyl of $R^s$ is substituted with one or more fluoro. In some embodiments, $R^1$ and $R^2$ are taken together with the nitrogen to which they are attached to form

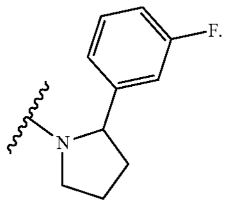 [SMILES: *N1CCCC1c1cccc(F)c1]

In some embodiments, $R^1$ and $R^2$ are taken together with the nitrogen to which they are attached to form

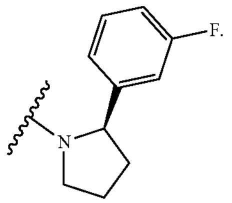 [SMILES: *N1CCC[C@@H]1c1cccc(F)c1]

In some embodiments, provided herein is a compound of formula (I), such as a compound of formula (I-A), (I-A1), (I-B), or (I-B1), or a stereoisomer or tautomer thereof, or a pharmaceutically acceptable salt of any of the foregoing, wherein $R^1$ and $R^2$ are taken together with the nitrogen to which they are attached to form a pyrrolidinyl, wherein the pyrrolidinyl formed by $R^1$ and $R^2$ is substituted with one $R^s$, wherein $R^5$ is phenyl, wherein the phenyl of $R^5$ is substituted with one or more fluoro. In some embodiments, $R^1$ and $R^2$ are taken together with the nitrogen to which they are attached to form

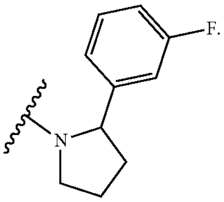 [SMILES: *N1CCCC1c1cccc(F)c1]

In some embodiments, $R^1$ and $R^2$ are taken together with the nitrogen to which they are attached to form

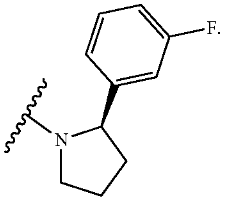 [SMILES: *N1CCC[C@@H]1c1cccc(F)c1]

In some embodiments, provided herein are compounds, and salts thereof, as described in Table 1.

TABLE 1

| No. | Structure | Name |
|---|---|---|
| 1 | 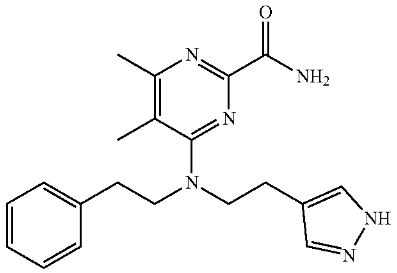 [SMILES: Cc1nc(C(N)=O)nc(N(CCc2ccccc2)CCc2cn[nH]c2)c1C] | 4-((2-(1H-pyrazol-4-yl)ethyl)(phenethyl)amino)-5,6-dimethylpyrimidine-2-carboxamide |
| 2 | 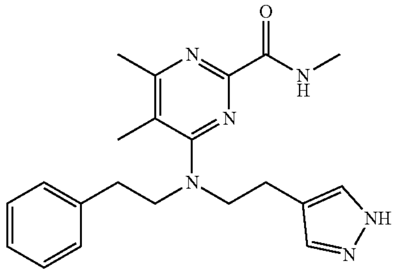 [SMILES: CNC(=O)c1nc(C)c(C)c(N(CCc2ccccc2)CCc2cn[nH]c2)n1] | 4-((2-(1H-pyrazol-4-yl)ethyl)(phenethyl)amino)-N,5,6-trimethylpyrimidine-2-carboxamide |
| 3 | 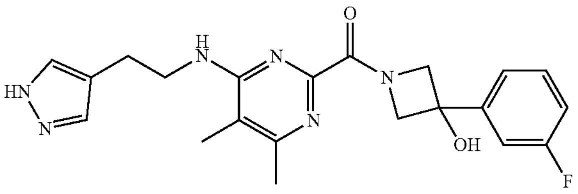 [SMILES: Cc1nc(C(=O)N2CC(O)(c3cccc(F)c3)C2)nc(NCCc2cn[nH]c2)c1C] | (4-((2-(1H-pyrazol-4-yl)ethyl)amino)-5,6-dimethylpyrimidin-2-yl)(3-(3-fluorophenyl)-3-hydroxyazetidin-1-yl)methanone |
| 4 | 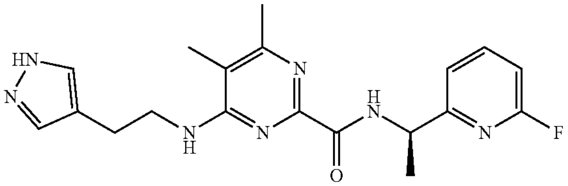 [SMILES: Cc1nc(C(=O)N[C@H](C)c2cccc(F)n2)nc(NCCc2cn[nH]c2)c1C] | (R)-4-((2-(1H-pyrazol-4-yl)ethyl)amino)-N-(1-(6-fluoropyridin-2-yl)ethyl)-5,6-dimethylpyrimidine-2-carboxamide |

TABLE 1-continued

| No. | Structure | Name |
| --- | --- | --- |
| 5 | 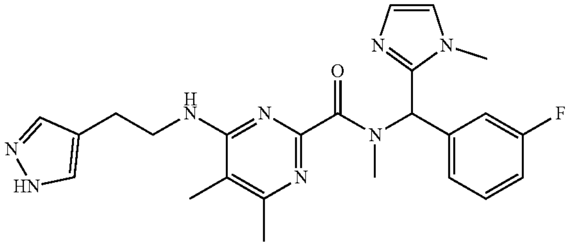 [SMILES: Cc1nc(C(=O)N(C)C(c2cccc(F)c2)c2nccn2C)nc(NCCc2cn[nH]c2)c1C] | 4-((2-(1H-pyrazol-4-yl)ethyl)amino)-N-((3-flurophenyl)(1-methyl-1H-imidazol-2-yl)methyl)-N,5,6-trimethylpyrimidine-2-carboxamide |
| 6 | 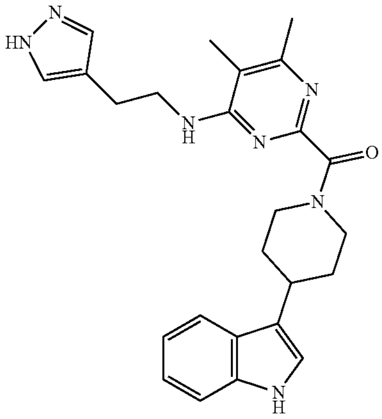 [SMILES: Cc1nc(C(=O)N2CCC(c3c[nH]c4ccccc34)CC2)nc(NCCc2cn[nH]c2)c1C] | (4-(1H-indol-3-yl)piperidin-1-yl)(4-((2-(1H-pyrazol-4-yl)ethyl)amino)-5,6-dimethylpyrimidin-2-yl)methanone |
| 7 | 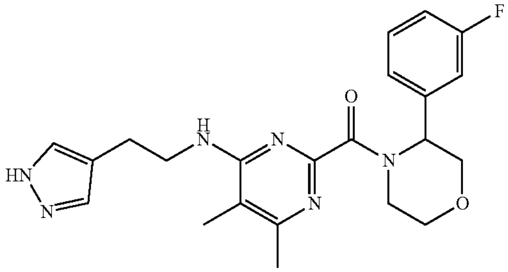 [SMILES: Cc1nc(C(=O)N2CCOCC2c2cccc(F)c2)nc(NCCc2cn[nH]c2)c1C] | (4-((2-(1H-pyrazol-4-yl)ethyl)amino)-5,6-dimethylpyrimidin-2-yl)(3-(3-fluorophenyl)morpholino)methanone |
| 8 | 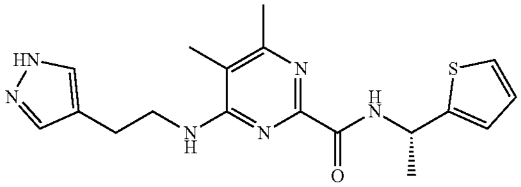 [SMILES: Cc1nc(C(=O)N[C@@H](C)c2cccs2)nc(NCCc2cn[nH]c2)c1C] | (S)-4-((2-(1H-pyrazol-4-yl)ethyl)amino)-5,6-dimethyl-N-(1-(thiophen-2-yl)ethyl)pyrimidine-2-carboxamide |
| 9 | 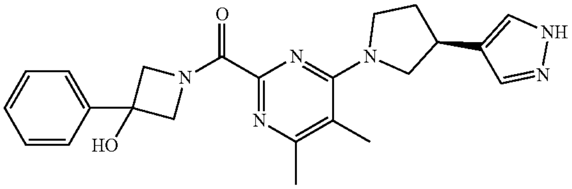 [SMILES: Cc1nc(C(=O)N2CC(O)(c3ccccc3)C2)nc(N2CC[C@@H](c3cn[nH]c3)C2)c1C] | (S)-(4-(3-(1H-pyrazol-4-yl)pyrrolidin-1-yl)-5,6-dimethylpyrimidin-2-yl)(3-hydroxy-3-phenylazeitidin-1-yl)methanone |
| 10 | 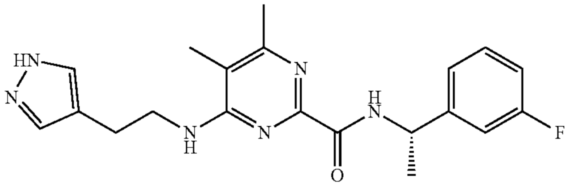 [SMILES: Cc1nc(C(=O)N[C@@H](C)c2cccc(F)c2)nc(NCCc2cn[nH]c2)c1C] | (S)-4-((2-(1H-pyrazol-4-yl)ethyl)amino)-N-(1-(3-fluorophenyl)ethyl)-5,6-dimethylpyrimidine-2-carboxamide |

TABLE 1-continued

| No. | Structure | Name |
| --- | --- | --- |
| 11 | 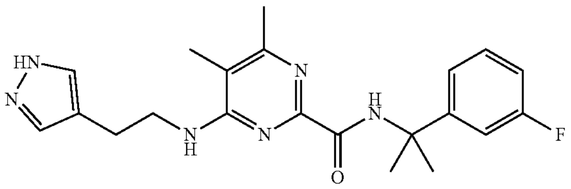 [SMILES: Cc1nc(C(=O)NC(C)(C)c2cccc(F)c2)nc(NCCc2cn[nH]c2)c1C] | 4-((2-(1H-pyrazol-4-yl)ethyl)amino)-N-(2-(3-fluorophenyl)propan-2-yl)-5,6-dimethylpyrimidine-2-carboxamide |
| 12 | 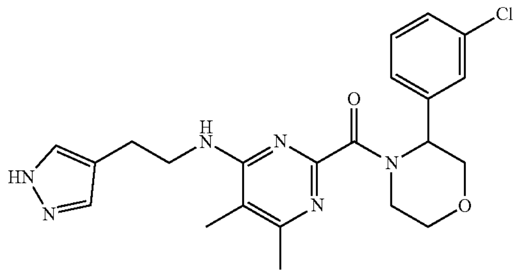 [SMILES: Cc1nc(C(=O)N2CCOCC2c2cccc(Cl)c2)nc(NCCc2cn[nH]c2)c1C] | (4-((2-(1H-pyrazol-4-yl)ethyl)amino)-5,6-dimethylpyrimidin-2-yl)(3-(3-chlorophenyl)morpholino)meth-anone |
| 13 | 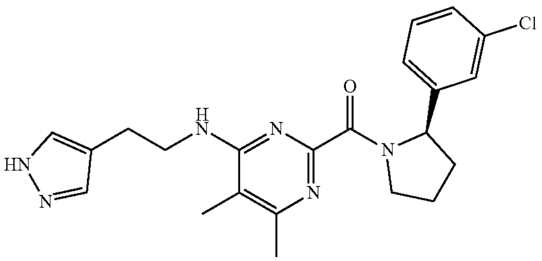 [SMILES: Cc1nc(C(=O)N2CCC[C@@H]2c2cccc(Cl)c2)nc(NCCc2cn[nH]c2)c1C] | (R)-(4-((2-(1H-pyrazol-4-yl)ethyl)amino)-5,6-dimethylpyrimidin-2-yl)(2-(3-chlorophenyl)pyrrolidin-1-yl)methanone |
| 14 | 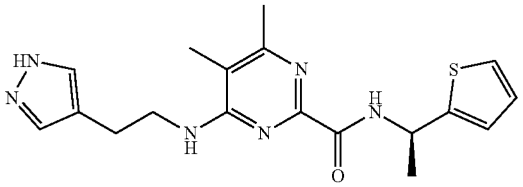 [SMILES: Cc1nc(C(=O)N[C@H](C)c2cccs2)nc(NCCc2cn[nH]c2)c1C] | (R)-4-((2-(1H-pyrazol-4-yl)ethyl)amino)-5,6-dimethyl-N-(1-(thiophen-2-yl)ethyl)pyrimidine-2-carboxamide |
| 15 | 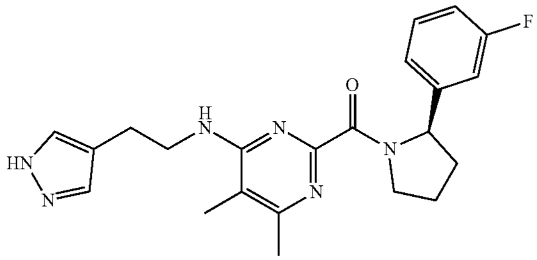 [SMILES: Cc1nc(C(=O)N2CCC[C@@H]2c2cccc(F)c2)nc(NCCc2cn[nH]c2)c1C] | (R)-(4-((2-(1H-pyrazol-4-yl)ethyl)amino)-5,6-dimethylpyrimidin-2-yl)(2-(3-fluorophenyl)pyrrolidin-1-yl)methanone |
| 16 | 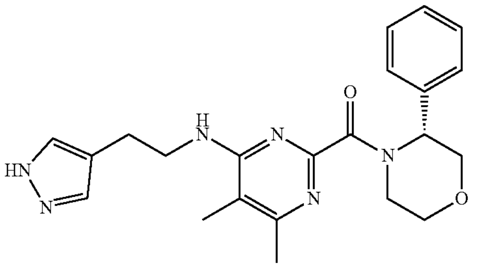 [SMILES: Cc1nc(C(=O)N2CCOC[C@H]2c2ccccc2)nc(NCCc2cn[nH]c2)c1C] | (R)-(4-((2-(1H-pyrazol-4-yl)ethyl)amino)-5,6-dimethylpyrimidin-2-yl)(3-phenylmorpholino)methanone |

TABLE 1-continued

| No. | Structure | Name |
|---|---|---|
| 17 | 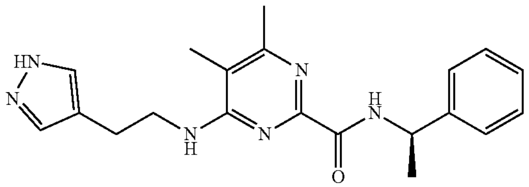 [SMILES: Cc1nc(C(=O)N[C@H](C)c2ccccc2)nc(NCCc2cn[nH]c2)c1C] | (R)-4-((2-(1H-pyrazol-4-yl)ethyl)amino)-5,6-dimethyl-N-(1-phenylethyl)pyrimidine-2-carboxamide |
| 18 | 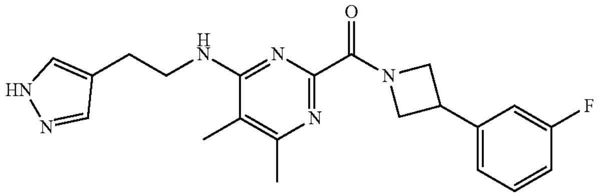 [SMILES: Cc1nc(C(=O)N2CC(c3cccc(F)c3)C2)nc(NCCc2cn[nH]c2)c1C] | (4-((2-(1H-pyrazol-4-yl)ethyl)amino)-5,6-dimethylpyrimidin-2-yl)(3-(3-fluorophenyl)azetidin-1-yl)methanone |
| 19 | 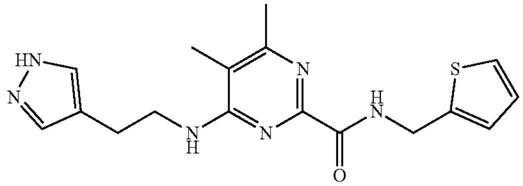 [SMILES: Cc1nc(C(=O)NCc2cccs2)nc(NCCc2cn[nH]c2)c1C] | 4-((2-(1H-pyrazol-4-yl)ethyl)amino)-5,6-dimethyl-N-(thiophen-2-ylmethyl)pyrimidine-2-carboxamide |
| 20 | 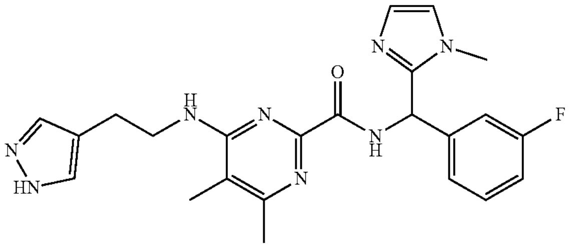 [SMILES: Cc1nc(C(=O)NC(c2cccc(F)c2)c2nccn2C)nc(NCCc2cn[nH]c2)c1C] | 4-((2-(1H-pyrazol-4-yl)ethyl)amino)-N-((3-fluorophenyl)(1-methyl-1H-imidazol-2-yl)methyl)-5,6-dimethylpyrimidine-2-carboxamide |
| 21 | 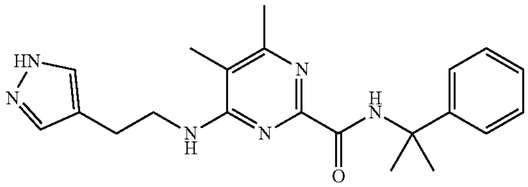 [SMILES: Cc1nc(C(=O)NC(C)(C)c2ccccc2)nc(NCCc2cn[nH]c2)c1C] | 4-((2-(1H-pyrazol-4-yl)ethyl)amino)-5,6-dimethyl-N-(2-phenylpropan-2-yl)pyrimidine-2-carboxamide |
| 22 | 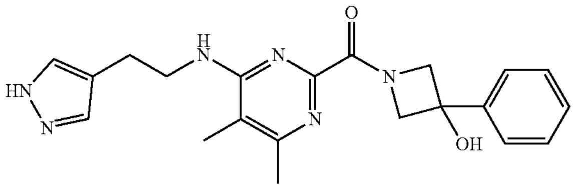 [SMILES: Cc1nc(C(=O)N2CC(O)(c3ccccc3)C2)nc(NCCc2cn[nH]c2)c1C] | (4-((2-(1H-pyrazol-4-yl)ethyl)amino)-5,6-dimethylpyrimidin-2-yl)(3-hydroxy-3-phenylazetidin-1-yl)methanone |
| 23 | 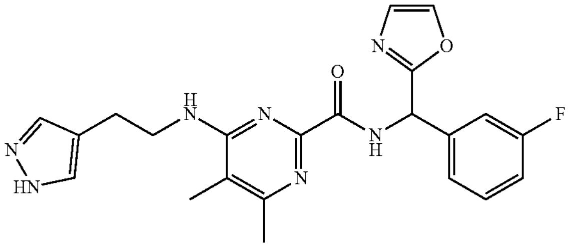 [SMILES: Cc1nc(C(=O)NC(c2cccc(F)c2)c2ncco2)nc(NCCc2cn[nH]c2)c1C] | 4-((2-(1H-pyrazol-4-yl)ethyl)amino)-N-((3-fluorophenyl)(oxazol-2-yl)methyl)-5,6-dimethylpyrimidine-2-carboxamide |

TABLE 1-continued

| No. | Structure | Name |
|---|---|---|
| 24 | 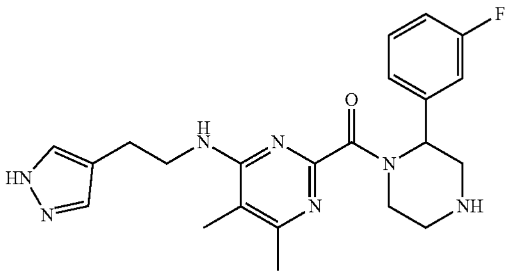 [SMILES: Cc1nc(C(=O)N2CCNCC2c2cccc(F)c2)nc(NCCc2cn[nH]c2)c1C] | (4-((2-(1H-pyrazol-4-yl)ethyl)amino)-5,6-dimethylpyrimidin-2-yl)(2-(3-fluorophenyl)piperazin-1-yl)methanone |
| 25 | 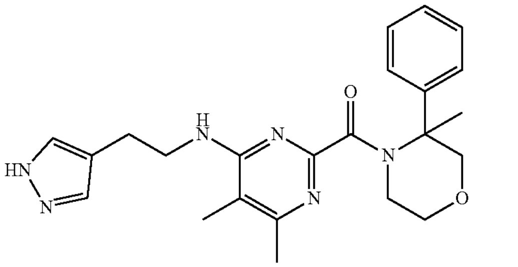 [SMILES: Cc1nc(C(=O)N2CCOCC2(C)c2ccccc2)nc(NCCc2cn[nH]c2)c1C] | (4-((2-(1H-pyrazol-4-yl)ethyl)amino)-5,6-dimethylpyrimidin-2-yl)(3-methyl-3-phenylmorpholino)methanone |
| 26 | 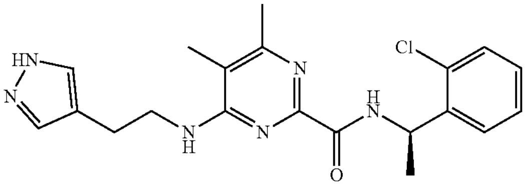 [SMILES: Cc1nc(C(=O)N[C@H](C)c2ccccc2Cl)nc(NCCc2cn[nH]c2)c1C] | (R)-4-((2-(1H-pyrazol-4-yl)ethyl)amino)-N-(1-(2-chlorophenyl)ethyl)-5,6-dimethylpyrimidine-2-carboxamide |
| 27 | 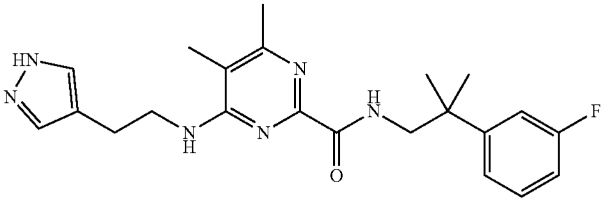 [SMILES: Cc1nc(C(=O)NCC(C)(C)c2cccc(F)c2)nc(NCCc2cn[nH]c2)c1C] | 4-((2-(1H-pyrazol-4-yl)ethyl)amino)-N-(2-(3-fluorophenyl)-2-methylpropyl)-5,6-dimethylpyrimidine-2-carboxamide |
| 28 | 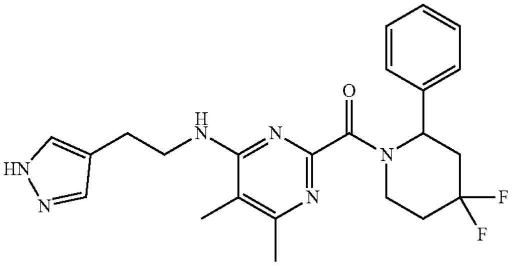 [SMILES: Cc1nc(C(=O)N2CCC(F)(F)CC2c2ccccc2)nc(NCCc2cn[nH]c2)c1C] | (4-((2-(1H-pyrazol-4-yl)ethyl)amino)-5,6-dimethylpyrimidin-2-yl)(4,4-difluoro-2-phenylpiperidin-1-yl)methanone |
| 29 | 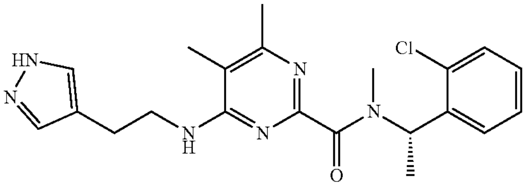 [SMILES: Cc1nc(C(=O)N(C)[C@@H](C)c2ccccc2Cl)nc(NCCc2cn[nH]c2)c1C] | (S)-4-((2-(1H-pyrazol-4-yl)ethyl)amino)-N-(1-(2-chlorophenyl)ethyl)-N,5,6-trimethylpyrimidine-2-carboxamide |

TABLE 1-continued

| No. | Structure | Name |
| --- | --- | --- |
| 30 | 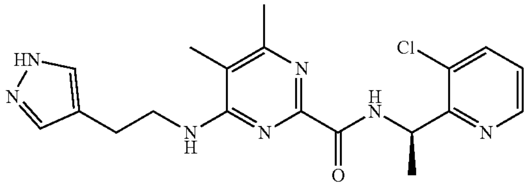 [SMILES: Cc1nc(C(=O)N[C@H](C)c2ncccc2Cl)nc(NCCc2cn[nH]c2)c1C] | (R)-4-((2-(1H-pyrazol-4-yl)ethyl)amino)-N-(1-(3-chloropyridin-2-yl)ethyl)-5,6-dimethylpyrimidine-2-carboxamide |
| 31 | 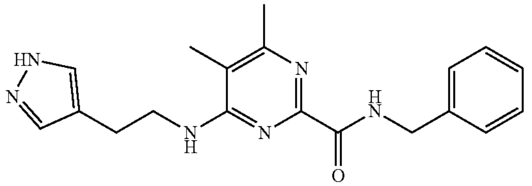 [SMILES: Cc1nc(C(=O)NCc2ccccc2)nc(NCCc2cn[nH]c2)c1C] | 4-((2-(1H-pyrazol-4-yl)ethyl)amino)-N-benzyl-5,6-dimethylpyrimidine-2-carboxamide |
| 32 | 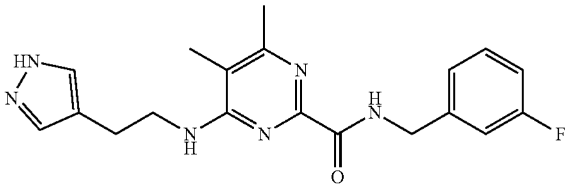 [SMILES: Cc1nc(C(=O)NCc2cccc(F)c2)nc(NCCc2cn[nH]c2)c1C] | 4-((2-(1H-pyrazol-4-yl)ethyl)amino)-N-(3-fluorobenzyl)-5,6-dimethylpyrimidine-2-carboxamide |
| 33 | 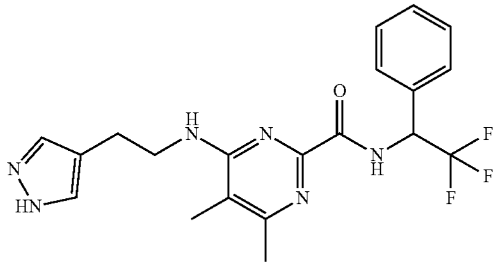 [SMILES: Cc1nc(C(=O)NC(c2ccccc2)C(F)(F)F)nc(NCCc2cn[nH]c2)c1C] | 4-((2-(1H-pyrazol-4-yl)ethyl)amino)-5,6-dimethyl-N-(2,2,2-trifluoro-1-phenylethyl)pyrimidine-2-carboxamide |
| 34 | 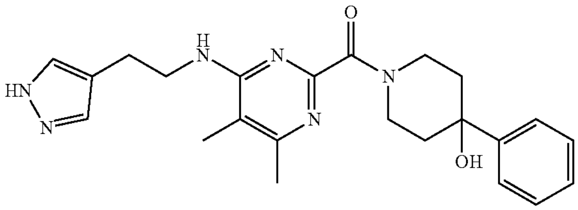 [SMILES: Cc1nc(C(=O)N2CCC(O)(c3ccccc3)CC2)nc(NCCc2cn[nH]c2)c1C] | (4-((2-(1H-pyrazol-4-yl)ethyl)amino)-5,6-dimethylpyrimidin-2-yl)(4-hydroxy-4-phenylpiperidin-1-yl)methanone |
| 35 | 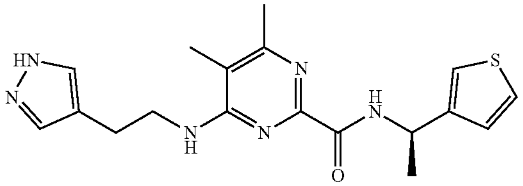 [SMILES: Cc1nc(C(=O)N[C@H](C)c2ccsc2)nc(NCCc2cn[nH]c2)c1C] | (R)-4-((2-(1H-pyrazol-4-yl)ethyl)amino)-5,6-dimethyl-N-(2-(thiophen-3-yl)ethyl)pyrimidine-2-carboxamide |
| 36 | 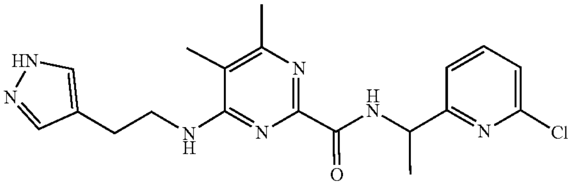 [SMILES: Cc1nc(C(=O)NC(C)c2cccc(Cl)n2)nc(NCCc2cn[nH]c2)c1C] | 4-((2-(1H-pyrazol-4-yl)ethyl)amino)-N-(1-(6-chloropyridin-2-yl)ethyl)-5,6-dimethylpyrimidine-2-carboxamide |

TABLE 1-continued

| No. | Structure | Name |
| --- | --- | --- |
| 37 | 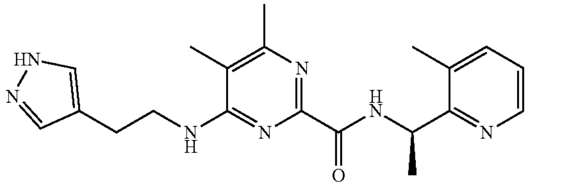 | (R)-4-((2-(1H-pyrazol-4-yl)ethyl)amino)-5,6-dimethyl-N-(1-(3-methylpyridin-2-yl)ethyl)pyrimidine-2-carboxamide |
| 38 | 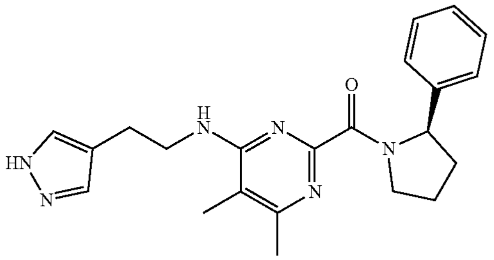 [SMILES: Cc1nc(C(=O)N2CCC[C@@H]2c2ccccc2)nc(NCCc2cn[nH]c2)c1C] | (R)-(4-((2-(1H-pyrazol-4-yl)ethyl)amino)-5,6-dimethylpyrimidin-2-yl)(2-phenylpyrrolidin-1-yl)methanone |
| 39 | 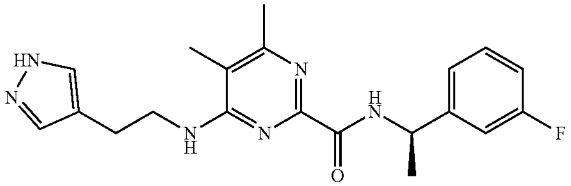 [SMILES: Cc1nc(C(=O)N[C@H](C)c2cccc(F)c2)nc(NCCc2cn[nH]c2)c1C] | (R)-4-((2-(1H-pyrazol-4-yl)ethyl)amino)-N-(1-(3-fluorophenyl)ethyl)-5,6-dimethylpyrimidine-2-carboxamide |
| 40 | 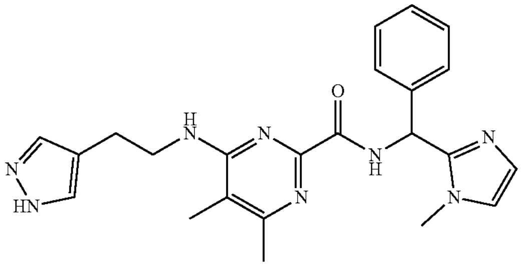 [SMILES: Cc1nc(C(=O)NC(c2ccccc2)c2nccn2C)nc(NCCc2cn[nH]c2)c1C] | 4-((2-(1H-pyrazol-4-yl)ethyl)amino)-5,6-dimethyl-N-((1-methyl-1H-imidazol-2-yl)(phenyl)methyl)pyrimidine-2-carboxamide |
| 41 | 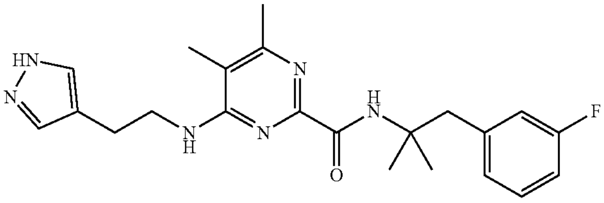 [SMILES: Cc1nc(C(=O)NC(C)(C)Cc2cccc(F)c2)nc(NCCc2cn[nH]c2)c1C] | 4-((2-(1H-pyrazol-4-yl)ethyl)amino)-N-(1-(3-fluorophenyl)-2-methylpropan-2-yl)-5,6-dimethylpyrimidine-2-carboxamide |
| 42 | 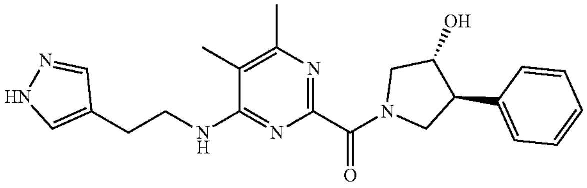 [SMILES: Cc1nc(C(=O)N2C[C@H](c3ccccc3)[C@@H](O)C2)nc(NCCc2cn[nH]c2)c1C] | (4-((2-(1H-pyraazol-4-yl)ethyl)amino)-5,6-dimethylpyrimidin-2-yl)((3R,4S)-3-hydroxy-4-phenylpyrrolidin-1-yl)methanone |
| 43 | 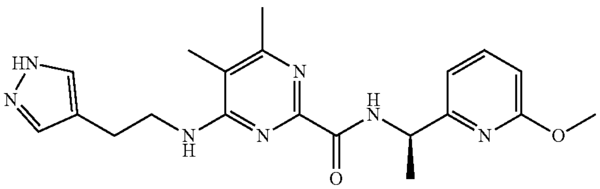 [SMILES: COc1cccc([C@@H](C)NC(=O)c2nc(C)c(C)c(NCCc3cn[nH]c3)n2)n1] | (R)-4-((2-(1H-pyrazol-4-yl)ethyl)amino)-N-(1-(6-methoxypyridin-2-yl)ethyl)-5,6-dimethylpyrimidine-2-carboxamide |

TABLE 1-continued

| No. | Structure | Name |
|---|---|---|
| 44 | 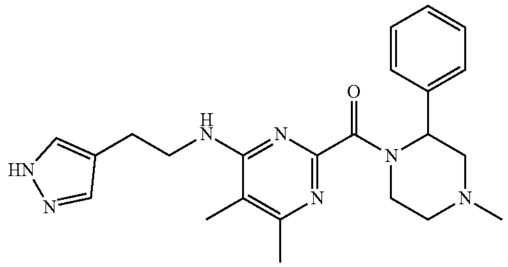 [SMILES: Cc1nc(C(=O)N2CCN(C)CC2c2ccccc2)nc(NCCc2cn[nH]c2)c1C] | (4-((2-(1H-pyrazol-4-yl)ethyl)amino)-5,6-dimethylpyrimidin-2-yl)(4-methyl-2-phenylpiperazin-1-yl)methanone |
| 45 | 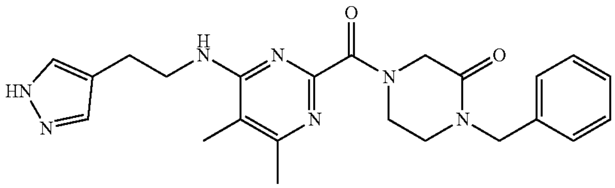 [SMILES: Cc1nc(C(=O)N2CCN(Cc3ccccc3)C(=O)C2)nc(NCCc2cn[nH]c2)c1C] | 4-(4-((2-(1H-pyrazol-4-yl)ethyl)amino)-5,6-dimethylpyrimidine-2-carbonyl)-1-benzoylpiperazin-2-one |
| 46 | 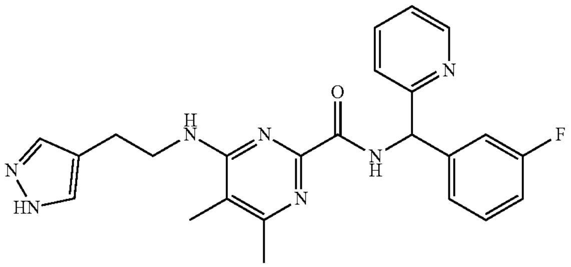 [SMILES: Cc1nc(C(=O)NC(c2cccc(F)c2)c2ccccn2)nc(NCCc2cn[nH]c2)c1C] | 4-((2-(1H-pyrazol-4-yl)ethyl)amino)-N-((3-fluorophenyl)(pyridin-2-yl)methyl)-5,6-dimethylpyrimidine-2-carboxamide |
| 47 | 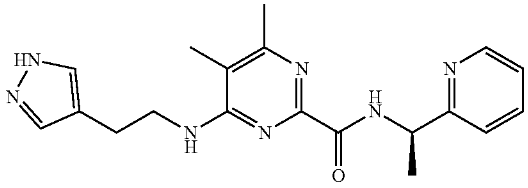 [SMILES: Cc1nc(C(=O)N[C@H](C)c2ccccn2)nc(NCCc2cn[nH]c2)c1C] | (R)-4-((2-(1H-pyrazol-4-yl)ethyl)amino)-5,6-dimethyl-N-(1-(pyridin-2-yl)ethyl)pyrimidine-2-carboxamide |
| 48 | 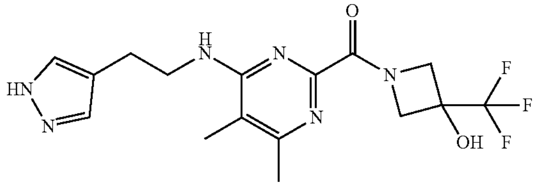 [SMILES: Cc1nc(C(=O)N2CC(O)(C(F)(F)F)C2)nc(NCCc2cn[nH]c2)c1C] | (4-((2-(1H-pyrazol-4-yl)ethyl)amino)-5,6-dimethylpyrimidin-2-yl)(3-hydroxy-3-(trifluoromethyl)azetidin-1-yl)methanone |
| 49 | 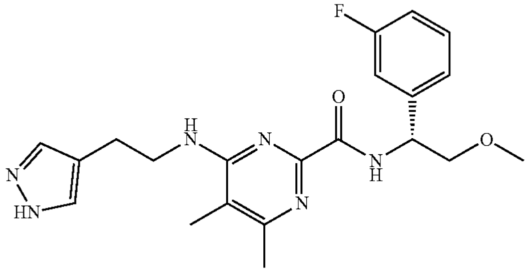 [SMILES: COC[C@H](NC(=O)c1nc(C)c(C)c(NCCc2cn[nH]c2)n1)c1cccc(F)c1] | (R)-4-((2-(1H-pyrazol-4-yl)ethyl)amino)-N-(1-(3-fluorophenyl)-2-methoxyethyl)-5,6-dimethylpyrimidine-2-carboxamide |

TABLE 1-continued

| No. | Structure | Name |
| --- | --- | --- |
| 50 | 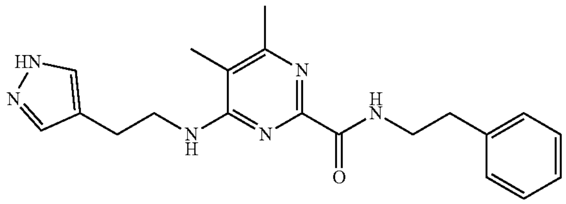 [SMILES: Cc1nc(C(=O)NCCc2ccccc2)nc(NCCc2cn[nH]c2)c1C] | 4-((2-(1H-pyrazol-4-yl)ethyl)amino)-5,6-dimethyl-N-phenethylpyrimidine-2-carboxamide |
| 51 | 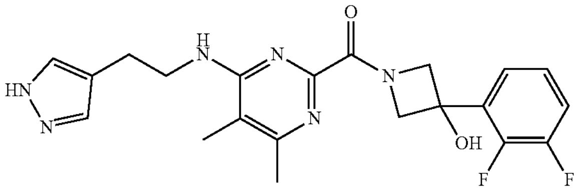 [SMILES: Cc1nc(C(=O)N2CC(O)(c3cccc(F)c3F)C2)nc(NCCc2cn[nH]c2)c1C] | (4-((2-(1H-pyrazol-4-yl)ethyl)amino)-5,6-dimethylpyrimidin-2-yl)(3-(2,3-difluorophenyl)-3-hydroxyazetidin-1-yl)methanone |
| 52 | 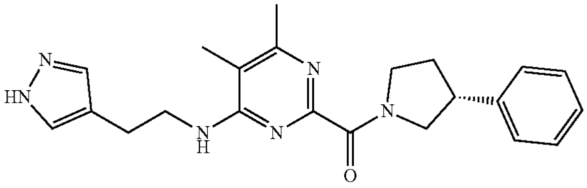 [SMILES: Cc1nc(C(=O)N2CC[C@H](c3ccccc3)C2)nc(NCCc2cn[nH]c2)c1C] | (R)-(4-((2-(1H-pyrazol-4-yl)ethyl)amino)-5,6-dimethylpyrimidin-2-yl)(3-phenylpyrrolidin-1-yl)methanone |
| 53 | 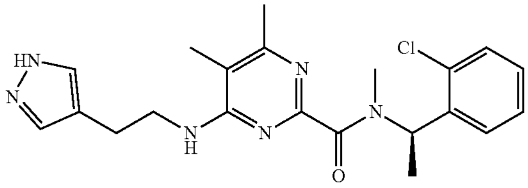 [SMILES: Cc1nc(C(=O)N(C)[C@H](C)c2ccccc2Cl)nc(NCCc2cn[nH]c2)c1C] | (R)-4-((2-(1H-pyrazol-4-yl)ethyl)amino)-N-(1-(2-chlorophenyl)ethyl)-N,5,6-trimethylpyrimidine-2-carboxamide |
| 54 | 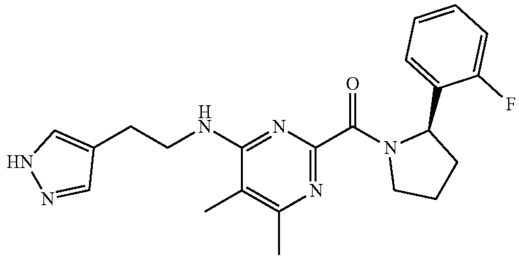 [SMILES: Cc1nc(C(=O)N2CCC[C@@H]2c2ccccc2F)nc(NCCc2cn[nH]c2)c1C] | (R)-(4-((2-(1H-pyrazol-4-yl)ethyl)amino)-5,6-dimethylpyrimidin-2-yl)(2-(2-fluorophenyl)pyrrolidin-1-yl)methanone |
| 55 | 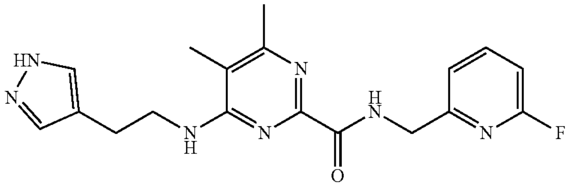 [SMILES: Cc1nc(C(=O)NCc2cccc(F)n2)nc(NCCc2cn[nH]c2)c1C] | 4-((2-(1H-pyrazol-4-yl)ethyl)amino)-N-((6-fluoropyridin-2-yl)methyl)-5,6-dimethylpyrimidine-2-carboxamide |
| 56 | 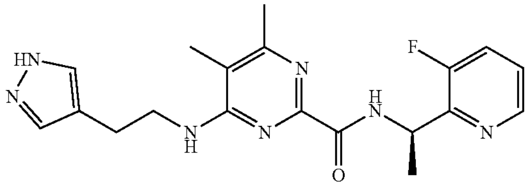 | (R)-4-((2-(1H-pyrazol-4-yl)ethyl)amino)-N-(1-(3-fluoropyridin-2-yl)ethyl)-5,6-dimethylpyrimidine-2-carboxamide |

TABLE 1-continued

| No. | Structure | Name |
| --- | --- | --- |
| 57 | 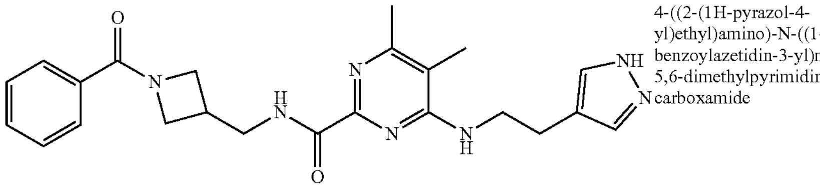 | 4-((2-(1H-pyrazol-4-yl)ethyl)amino)-N-((1-benzoylazetidin-3-yl)methyl)-5,6-dimethylpyrimidine-2-carboxamide |
| 58 | 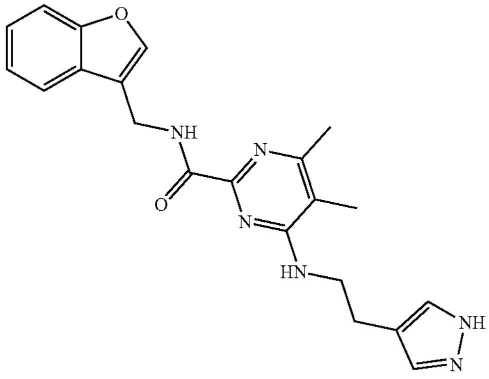 [SMILES: Cc1nc(C(=O)NCc2coc3ccccc23)nc(NCCc2cn[nH]c2)c1C] | 4-((2-(1H-pyrazol-4-yl)ethyl)amino)-N-(benzofuran-3-ylmethyl)-5,6-dimethylpyrimidine-2-carboxamide |
| 59 | 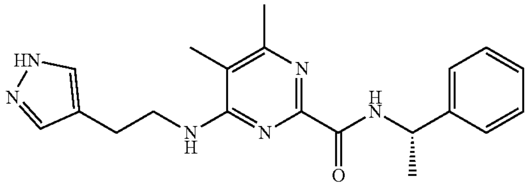 [SMILES: Cc1nc(C(=O)N[C@@H](C)c2ccccc2)nc(NCCc2cn[nH]c2)c1C] | (S)-4-((2-(1H-pyrazol-4-yl)ethyl)amino)-5,6-dimethyl-N-(1-phenylethyl)pyrimidine-2-carboxamide |
| 60 | 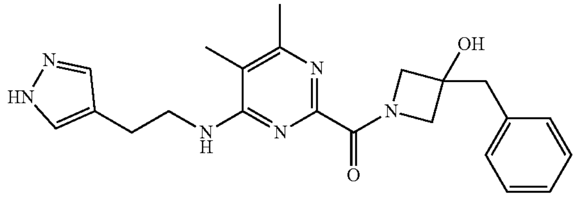 [SMILES: Cc1nc(C(=O)N2CC(O)(Cc3ccccc3)C2)nc(NCCc2cn[nH]c2)c1C] | (4-((2-(1H-pyrazol-4-yl)ethyl)amino)-5,6-dimethylpyrimidin-2-yl)(3-benzyl)-3-hydroxyazetidin-1-yl)methanone |
| 61 | 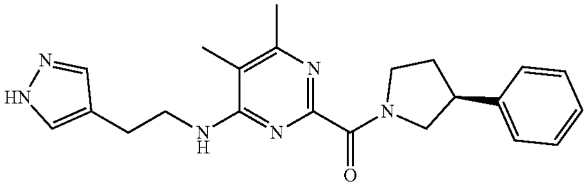 [SMILES: Cc1nc(C(=O)N2CC[C@@H](c3ccccc3)C2)nc(NCCc2cn[nH]c2)c1C] | (S)-(4-((2-(1H-pyrazol-4-yl)ethyl)amino)-5,6-dimethylpyrimidin-2-yl)(3-phenylpyrrolidin-1-yl)methanone |
| 62 | 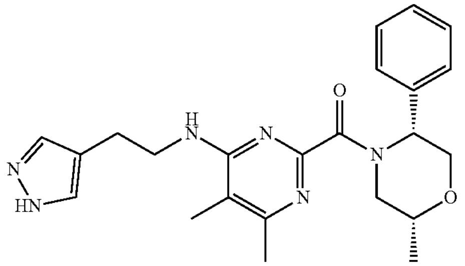 [SMILES: Cc1nc(C(=O)N2C[C@@H](C)OC[C@H]2c2ccccc2)nc(NCCc2cn[nH]c2)c1C] | (4-((2-(1H-pyrazol-4-yl)ethyl)amino)-5,6-dimethylpyrimidin-2-yl)((2R,5R)-2-methyl-5-phenylmorpholino)methanone |

TABLE 1-continued

| No. | Structure | Name |
|---|---|---|
| 63 | 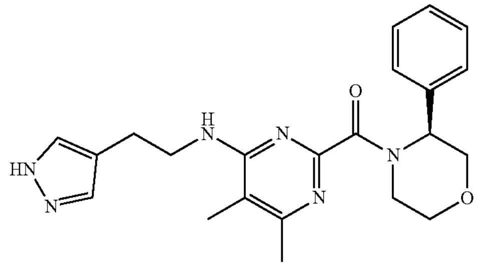 [SMILES: Cc1nc(C(=O)N2CCOC[C@@H]2c2ccccc2)nc(NCCc2cn[nH]c2)c1C] | (S)-(4-((2-(1H-pyrazol-4-yl)ethyl)amino)-5,6-dimethylpyrimidin-2-yl)(3-phenylmorpholino)methanone |
| 64 | 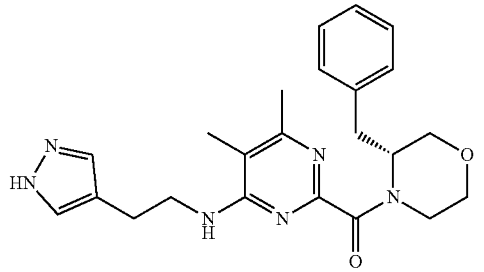 [SMILES: Cc1nc(C(=O)N2CCOC[C@H]2Cc2ccccc2)nc(NCCc2cn[nH]c2)c1C] | (R)-(4-((2-(1H-pyrazol-4-yl)ethyl)amino)-5,6-dimethylpyrimidin-2-yl)(3-benzylmorpholino)methanone |
| 65 | 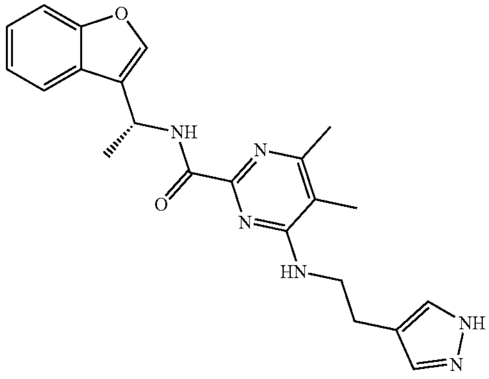 [SMILES: Cc1nc(C(=O)N[C@H](C)c2coc3ccccc23)nc(NCCc2cn[nH]c2)c1C] | (R)-4-((2-(1H-pyrazol-4-yl)ethyl)amino)-N-(1-(benzofuran-3-yl)ethyl)-5,6-dimethylpyrimidine-2-carboxamide |
| 66 | 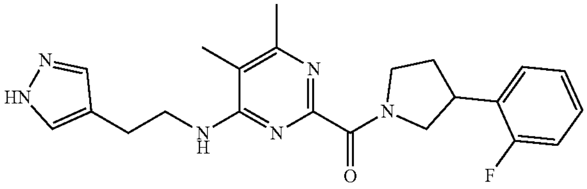 [SMILES: Cc1nc(C(=O)N2CCC(c3ccccc3F)C2)nc(NCCc2cn[nH]c2)c1C] | (4-((2-(1H-pyrazol-4-yl)ethyl)amino)-5,6-dimethylpyrimidin-2-yl)(3-(2-fluorophenyl)pyrrolidin-1-yl)methanone |
| 67 | 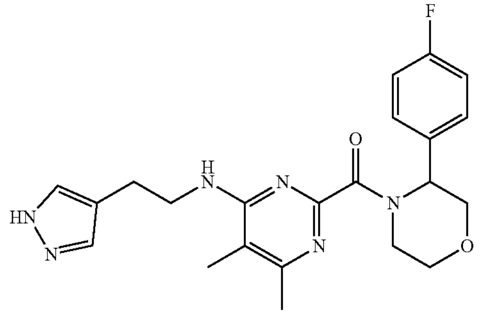 [SMILES: Cc1nc(C(=O)N2CCOCC2c2ccc(F)cc2)nc(NCCc2cn[nH]c2)c1C] | (4-((2-(1H-pyrazol-4-yl)ethyl)amino)-5,6-dimethylpyrimidin-2-yl)(3-(4-fluorophenyl)morpholino)methanone |

TABLE 1-continued

| No. | Structure | Name |
| --- | --- | --- |
| 68 | 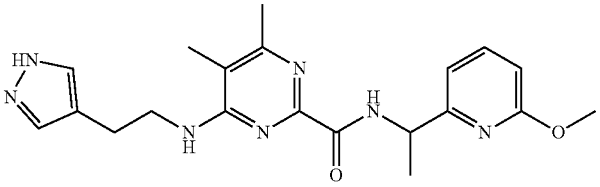 [SMILES: COc1cccc(C(C)NC(=O)c2nc(C)c(C)c(NCCc3cn[nH]c3)n2)n1] | 4-((2-(1H-pyrazol-4-yl)ethyl)amino)-N-(1-(6-methoxypyridin-2-yl)ethyl)-5,6-dimethylpyrimidine-2-carboxamide |
| 69 | 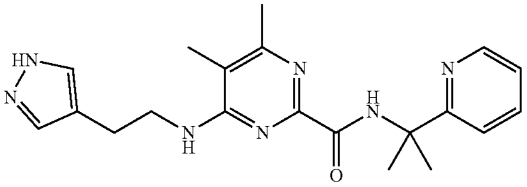 [SMILES: Cc1nc(C(=O)NC(C)(C)c2ccccn2)nc(NCCc2cn[nH]c2)c1C] | 4-((2-(1H-pyrazol-4-yl)ethyl)amino)-5,6-dimethyl-N-(2-(pyridin-2-yl)propan-2-yl)pyrimidine-2-carboxamide |
| 70 | 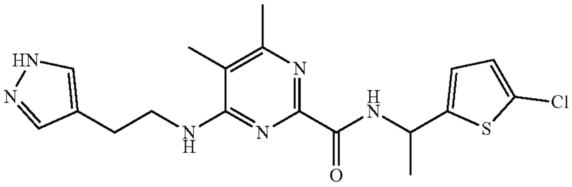 [SMILES: Cc1nc(C(=O)NC(C)c2ccc(Cl)s2)nc(NCCc2cn[nH]c2)c1C] | 4-((2-(1H-pyrazol-4-yl)ethyl)amino)-N-(1-(5-chlorothiophen-2-yl)ethyl)-5,6-dimethylpyrimidine-2-carboxamide |
| 71 | 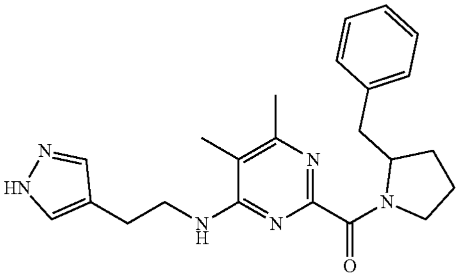 [SMILES: Cc1nc(C(=O)N2CCCC2Cc2ccccc2)nc(NCCc2cn[nH]c2)c1C] | (4-((2-(1H-pyrazol-4-yl)ethyl)amino)-5,6-dimethylpyrimidin-2-yl)(2-benzylpyrrolidin-1-yl)methanone |
| 72 | 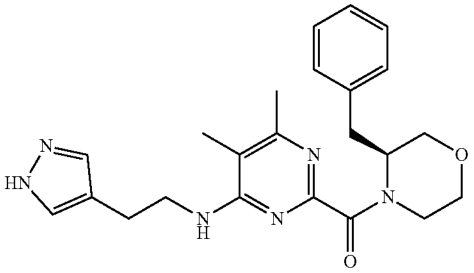 [SMILES: Cc1nc(C(=O)N2CCOC[C@@H]2Cc2ccccc2)nc(NCCc2cn[nH]c2)c1C] | (S)-(4-((2-(1H-pyrazol-4-yl)ethyl)amino)-5,6-dimethylpyrimidin-2-yl)(3-benzylmorpholino)methanone |
| 73 | 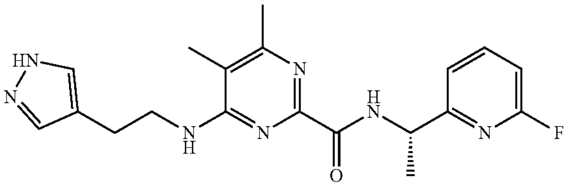 [SMILES: Cc1nc(C(=O)N[C@@H](C)c2cccc(F)n2)nc(NCCc2cn[nH]c2)c1C] | (S)-4-((2-(1H-pyrazol-4-yl)ethyl)amino)-N-(1-(6-fluoropyridin-2-yl)ethyl)-5,6-dimethylpyrimidine-2-carboxamide |
| 74 | 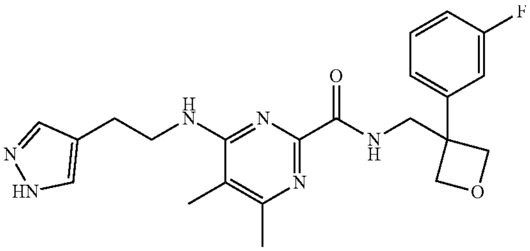 [SMILES: Cc1nc(C(=O)NCC2(c3cccc(F)c3)COC2)nc(NCCc2cn[nH]c2)c1C] | 4-((2-(1H-pyrazol-4-yl)ethyl)amino)-N-((3-(3-fluorophenyl)oxetan-3-yl)methyl)-5,6-dimethylpyrimidine-2-carboxamide |

TABLE 1-continued

| No. | Structure | Name |
| --- | --- | --- |
| 75 | 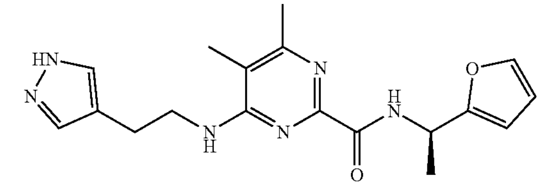 | (R)-4-((2-(1H-pyrazol-4-yl)ethyl)amino)-N-(1-(furan-2-yl)ethyl)-5,6-dimethylpyrimidine-2-carboxamide |
| 76 | 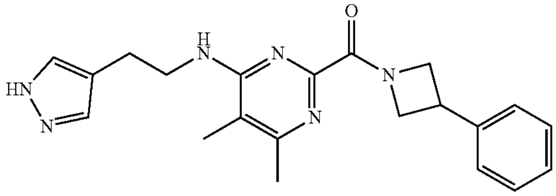 [SMILES: Cc1nc(C(=O)N2CC(c3ccccc3)C2)nc(NCCc2cn[nH]c2)c1C] | (4-((2-(1H-pyrazol-4-yl)ethyl)amino)-5,6-dimethylpyrimidin-2-yl)(3-phenylazetidin-1-yl)methanone |
| 77 | 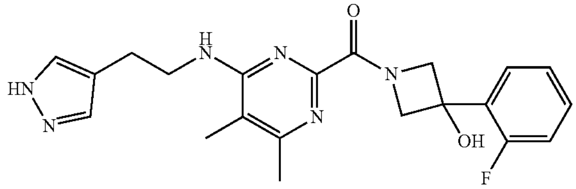 [SMILES: Cc1nc(C(=O)N2CC(O)(c3ccccc3F)C2)nc(NCCc2cn[nH]c2)c1C] | (4-((2-(1H-pyrazol-4-yl)ethyl)amino)-5,6-dimethylpyrimidin-2-yl)(3-(2-fluorophenyl)-3-hydroxyazetidin-1-yl)methanone |
| 78 | 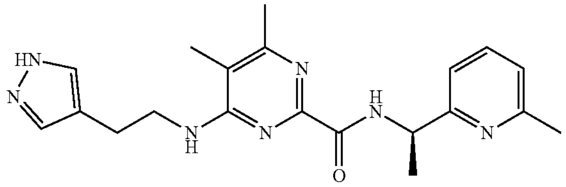 [SMILES: Cc1cccc([C@@H](C)NC(=O)c2nc(C)c(C)c(NCCc3cn[nH]c3)n2)n1] | (R)-4-((2-(1H-pyrazol-4-yl)ethyl)amino)-5,6-dimethyl-N-(1-(6-methylpyridin-2-yl)ethyl)pyrimidine-2-carboxamide |
| 79 | 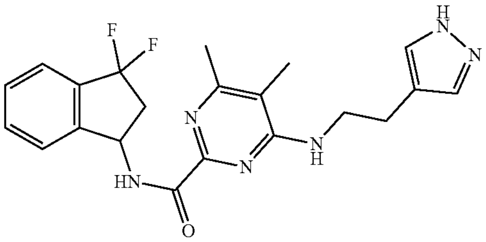 [SMILES: Cc1nc(C(=O)NC2CC(F)(F)c3ccccc32)nc(NCCc2cn[nH]c2)c1C] | 4-((2-(1H-pyrazol-4-yl)ethyl)amino)-N-(3,3-difluoro-2,3-dihydro-1H-inden-1-yl)-5,6-dimethylpyrimidine-2-carboxmaide |
| 80 | 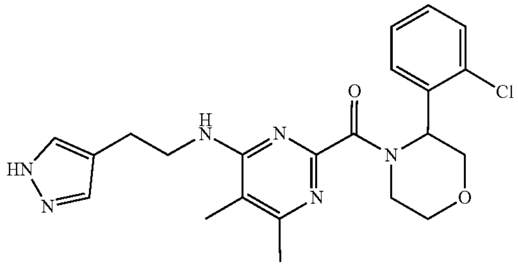 [SMILES: Cc1nc(C(=O)N2CCOCC2c2ccccc2Cl)nc(NCCc2cn[nH]c2)c1C] | (4-((2-(1H-pyrazol-4-yl)ethyl)amino)-5,6-dimethylpyrimidin-2-yl)(3-(2-chlorophenyl)morpholino)methanone |
| 81 | 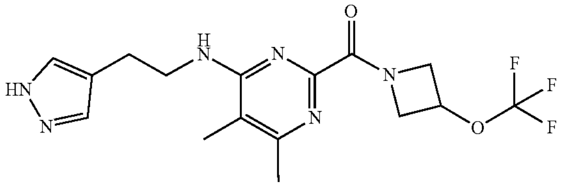 [SMILES: Cc1nc(C(=O)N2CC(OC(F)(F)F)C2)nc(NCCc2cn[nH]c2)c1C] | (4-((2-(1H-pyrazol-4-yl)ethyl)amino)-5,6-dimethylpyrimidin-2-yl)(3-(trifluoromethoxy)azetidin-1-yl)methanone |

TABLE 1-continued

| No. | Structure | Name |
|---|---|---|
| 82 | 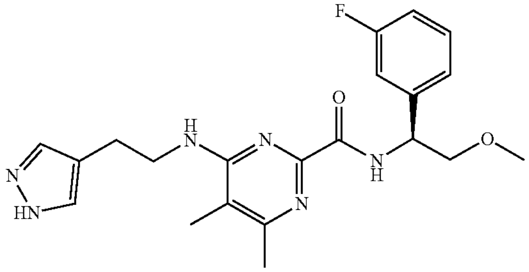 [SMILES: COC[C@@H](NC(=O)c1nc(C)c(C)c(NCCc2cn[nH]c2)n1)c1cccc(F)c1] | (S)-4-((2-(1H-pyrazol-4-yl)ethyl)amino)-N-(1-(3-fluorophenyl)-2-methoxyethyl)-5,6-dimethylpyrimidine-2-carboxamide |
| 83 | 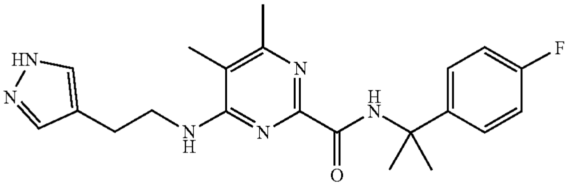 [SMILES: Cc1nc(C(=O)NC(C)(C)c2ccc(F)cc2)nc(NCCc2cn[nH]c2)c1C] | 4-((2-(1H-pyrazol-4-yl)ethyl)amino)-N-(2-(4-fluorophenyl)propan-2-yl)-5,6-dimethylpyrimidine-2-carboxamide |
| 84 | 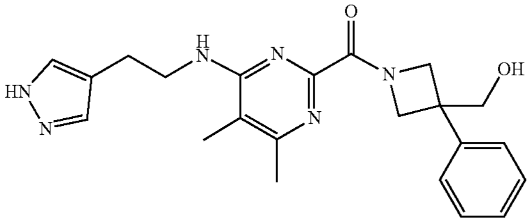 [SMILES: Cc1nc(C(=O)N2CC(CO)(c3ccccc3)C2)nc(NCCc2cn[nH]c2)c1C] | (4-((2-(1H-pyrazol-4-yl)ethyl)amino)-5,6-dimethylpyrimidin-2-yl)(3-(hydroxymethyl)-3-phenylazetidin-1-yl)methanone |
| 85 | 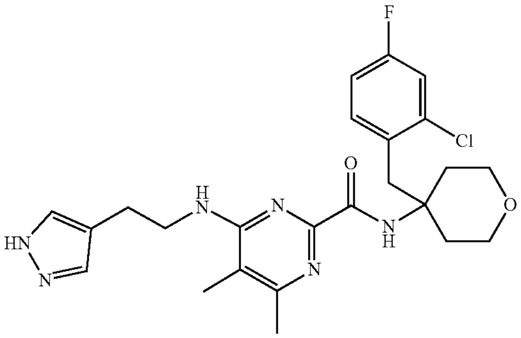 [SMILES: Cc1nc(C(=O)NC2(Cc3ccc(F)cc3Cl)CCOCC2)nc(NCCc2cn[nH]c2)c1C] | 4-((2-(1H-pyrazol-4-yl)ethyl)amino)-N-(4-(2-chloro-4-fluorobenzyl)tetrahydro-2H-pyran-4-yl)-5,6-dimethylpyrimidine-2-carboxamide |
| 86 | 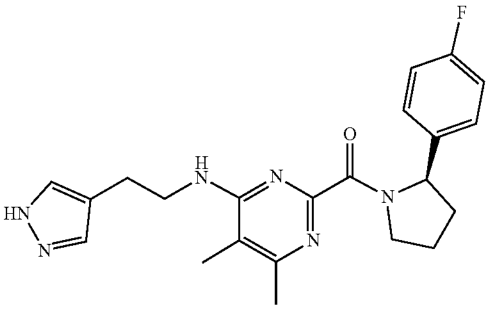 [SMILES: Cc1nc(C(=O)N2CCC[C@@H]2c2ccc(F)cc2)nc(NCCc2cn[nH]c2)c1C] | (R)-(4-((2-(1H-pyrazol-4-yl)ethyl)amino)-5,6-dimethylpyrimidin-2-yl)(2-(4-flurophenyl)pyrrolidin-1-yl)methanone |
| 87 | 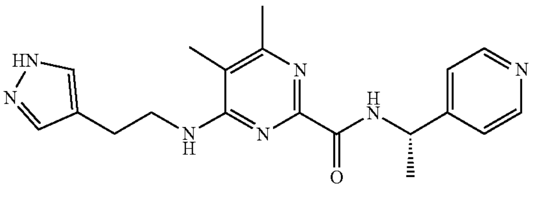 [SMILES: Cc1nc(C(=O)N[C@@H](C)c2ccncc2)nc(NCCc2cn[nH]c2)c1C] | (S)-4-((2-(1H-pyrazol-4-yl)ethyl)amino)-5,6-dimethyl-N-(1-(pyridin-4-yl)ethyl)pyrimidine-2-carboxamide |

TABLE 1-continued

| No. | Structure | Name |
| --- | --- | --- |
| 88 | 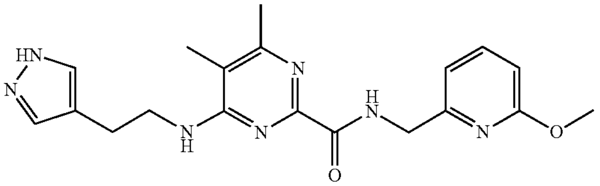 [SMILES: COc1cccc(CNC(=O)c2nc(C)c(C)c(NCCc3cn[nH]c3)n2)n1] | 4-((2-(1H-pyrazol-4-yl)ethyl)amino)-N-((6-methoxypyridin-2-yl)methyl)-5,6-dimethylpyrimidine-2-carboxamide |
| 89 | 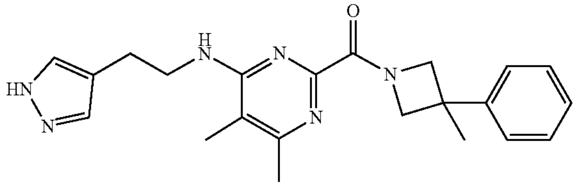 [SMILES: Cc1nc(C(=O)N2CC(C)(c3ccccc3)C2)nc(NCCc2cn[nH]c2)c1C] | (4-((2-(1H-pyrazol-4-yl)ethyl)amino)-5,6-dimethylpyrimidin-2-yl)(3-methyl-3-phenylazetidin-1-yl)methanone |
| 90 | 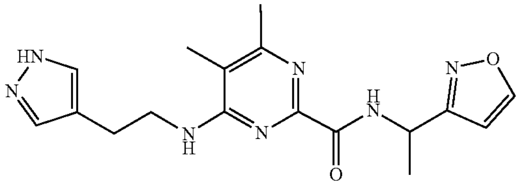 [SMILES: Cc1nc(C(=O)NC(C)c2ccon2)nc(NCCc2cn[nH]c2)c1C] | 4-((2-(1H-pyrazol-4-yl)ethyl)amino)-N-(1-(isoxazol-3-yl)ethyl)-5,6-dimethylpyrimidine-2-carboxamide |
| 91 | 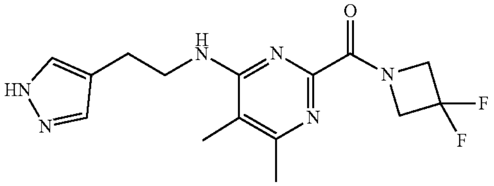 [SMILES: Cc1nc(C(=O)N2CC(F)(F)C2)nc(NCCc2cn[nH]c2)c1C] | (4-((2-(1H-pyrazol-4-yl)ethyl)amino)-5,6-dimethylpyrimidin-2-yl)(3,3-difluoroazetidin-1-yl)methanone |
| 92 | 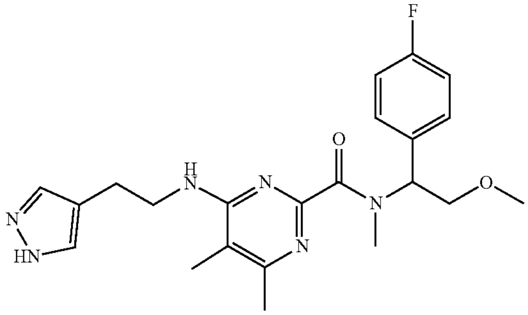 [SMILES: COCC(c1ccc(F)cc1)N(C)C(=O)c1nc(C)c(C)c(NCCc2cn[nH]c2)n1] | 4-((2-(1H-pyrazol-4-yl)ethyl)amino)-N-(1-(4-fluorophenyl)-2-methoxyethyl)-N,5,6-trimethylpyrimidine-2-carboxamide |
| 93 | 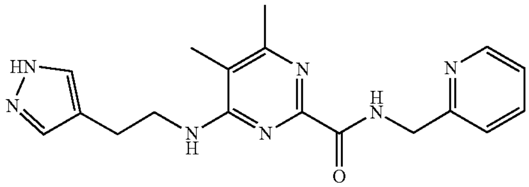 [SMILES: Cc1nc(C(=O)NCc2ccccn2)nc(NCCc2cn[nH]c2)c1C] | 4-((2-(1H-pyrazol-4-yl)ethyl)amino)-5,6-dimethyl-N-(pyridin-2-ylmethyl)pyrimidine-2-carboxamide |
| 94 | 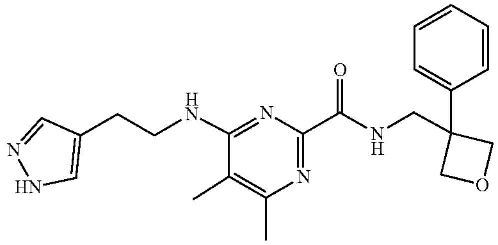 [SMILES: Cc1nc(C(=O)NCC2(c3ccccc3)COC2)nc(NCCc2cn[nH]c2)c1C] | 4-((2-(1H-pyrazol-4-yl)ethyl)amino)-5,6-dimethyl-N-((3-phenyloxetan-3-yl)methyl)pyrimidine-2-carboxamide |

TABLE 1-continued

| No. | Structure | Name |
|---|---|---|
| 95 | 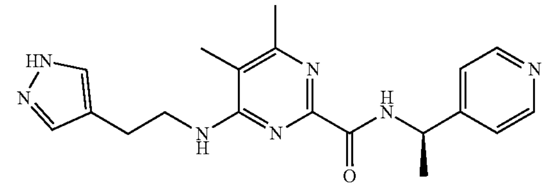 [SMILES: Cc1nc(C(=O)N[C@H](C)c2ccncc2)nc(NCCc2cn[nH]c2)c1C] | (R)-4-((2-(1H-pyrazol-4-yl)ethyl)amino)-5,6-dimethyl-N-(1-(pyridin-4-yl)ethyl)pyrimidine-2-carboxamide |
| 96 | 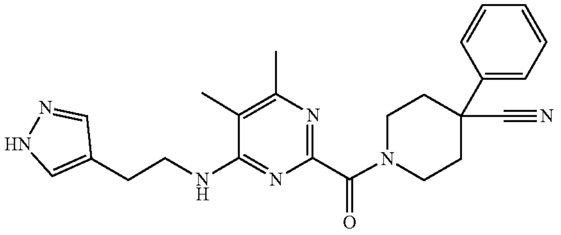 | 1-(4-((2-(1H-pyrazol-4-yl)ethyl)amino)-5,6-dimethylpyrimidine-2-carbonyl)-4-phenylpiperidine-4-carbonitrile |
| 97 | 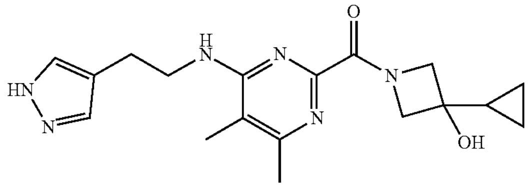 [SMILES: Cc1nc(C(=O)N2CC(O)(C3CC3)C2)nc(NCCc2cn[nH]c2)c1C] | (4-((2-(1H-pyrazol-4 yl)ethyl)amino)-5,6-dimethylpyrimidin-2-yl)(3-cyclopropyl-3-hydroxyazetidin-1-yl)methanone |
| 98 | 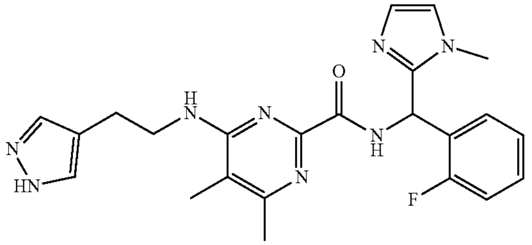 [SMILES: Cc1nc(C(=O)NC(c2ccccc2F)c2nccn2C)nc(NCCc2cn[nH]c2)c1C] | 4-((2-(1H-pyrazol-4-yl)ethyl)amino)-N-((2-fluorophenyl)(1-methyl-1H-imidazol-2-yl)methyl)-5,6-dimethylpyrimidine-2-carboxamide |
| 99 | 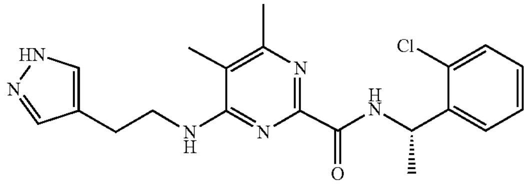 [SMILES: Cc1nc(C(=O)N[C@@H](C)c2ccccc2Cl)nc(NCCc2cn[nH]c2)c1C] | (S)-4-((2-(1H-pyrazol-4-yl)ethyl)amino)-N-(1-(2-chlorophenyl)ethyl)-5,6-dimethylpyrimidine-2-carboxamide |
| 100 | 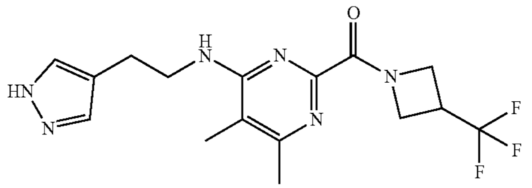 [SMILES: Cc1nc(C(=O)N2CC(C(F)(F)F)C2)nc(NCCc2cn[nH]c2)c1C] | (4-((2-(1H-pyrazol-4-yl)ethyl)amino)-5,6-dimethylpyrimidin-2-yl)(3-(trifluoromethyl)azetidin-1-yl)methanone |
| 101 | 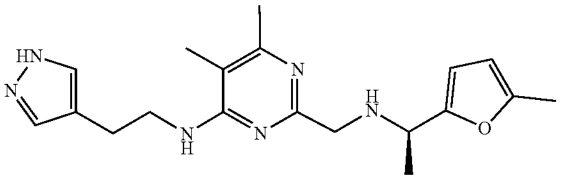 [SMILES: Cc1ccc([C@@H](C)NCc2nc(C)c(C)c(NCCc3cn[nH]c3)n2)o1] | (R)-4-((2-(1H-pyrazol-4-ylethyl)amino)-5,6-dimethyl-N-(2-(5-methylfuran-2-yl)ethyl)pyrimidine-2-carboxamide |

TABLE 1-continued

| No. | Structure | Name |
|---|---|---|
| 102 | 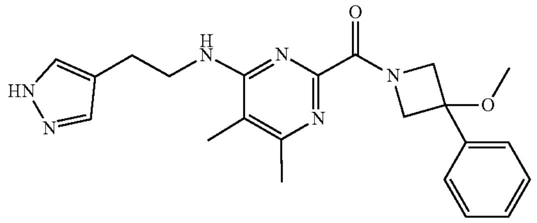 [SMILES: COC1(c2ccccc2)CN(C(=O)c2nc(C)c(C)c(NCCc3cn[nH]c3)n2)C1] | (4-((2-(1H-pyrazol-4-yl)ethyl)amino)-5,6-dimethylpyrimidin-2-yl)(3-methoxy-3-phenylazetidin-1-yl)methanone |
| 103 | 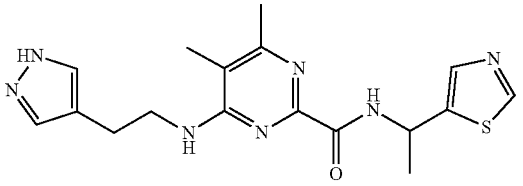 [SMILES: Cc1nc(C(=O)NC(C)c2cncs2)nc(NCCc2cn[nH]c2)c1C] | 4-((2-(1H-pyrazol-4-yl)ethyl)amino)-5,6-dimethyl-N-(1-(thiazol-5-yl)ethyl)pyrimidine-2-carboxamide |
| 104 | 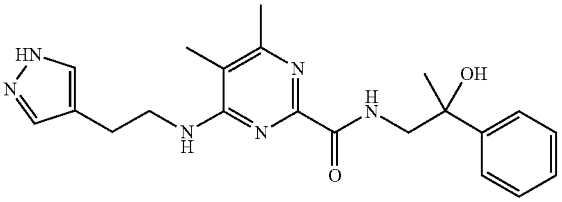 [SMILES: Cc1nc(C(=O)NCC(C)(O)c2ccccc2)nc(NCCc2cn[nH]c2)c1C] | 4-((2-(1H-pyrazol-4-yl)ethyl)amino)-N-(2-hydroxy-2-phenylpropyl)-5,6-dimethylpyrimidine-2-carboxamide |
| 105 | 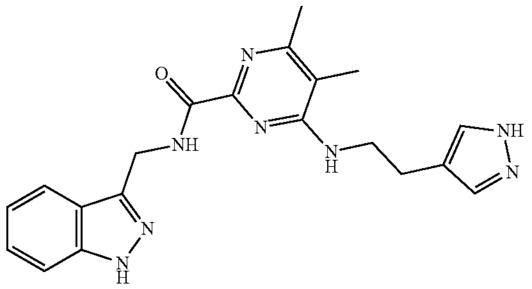 [SMILES: Cc1nc(C(=O)NCc2n[nH]c3ccccc23)nc(NCCc2cn[nH]c2)c1C] | N-((1H-indazol-3-yl)methyl)-4-((2-(1H-pyrazol-4-yl)ethyl)amino)-5,6-dimethylpyrimidine-2-carboxamide |
| 106 | 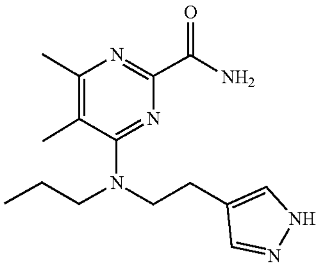 [SMILES: CCCN(CCc1cn[nH]c1)c1nc(C(N)=O)nc(C)c1C] | 4-((2-(1H-pyrazol-4-yl)ethyl)(propyl)amino)-5,6-dimethylpyrimidine-2-carboxamide |
| 107 | 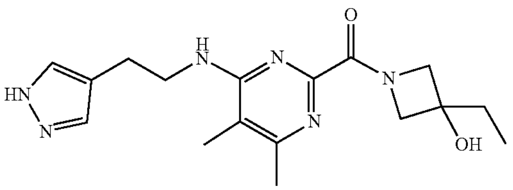 [SMILES: CCC1(O)CN(C(=O)c2nc(C)c(C)c(NCCc3cn[nH]c3)n2)C1] | (4-((2-(1H-pyrazol-4-yl)ethyl)amino)-5,6-dimethylpyrimidin-2-yl)(3-ethyl-3-hydroxyazetidin-1-yl)methanone |
| 108 | 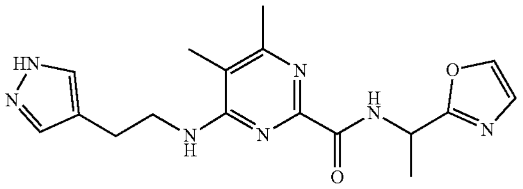 [SMILES: Cc1nc(C(=O)NC(C)c2ncco2)nc(NCCc2cn[nH]c2)c1C] | 4-((2-(1H-pyrazol-4-yl)ethyl)amino)-5,6-dimethyl-N-(1-(oxazol-2-yl)ethyl)pyrimidine-2-carboxamide |

TABLE 1-continued

| No. | Structure | Name |
| --- | --- | --- |
| 109 | 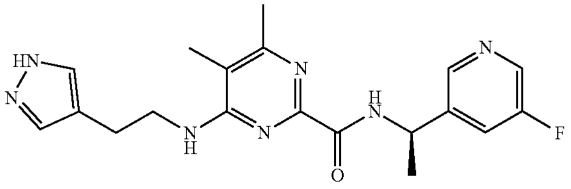 [SMILES: Cc1nc(C(=O)N[C@H](C)c2cncc(F)c2)nc(NCCc2cn[nH]c2)c1C] | (R)-4-((2-(1H-pyrazol-4-yl)ethyl)amino)-N-(1-(5-fluoropyridin-3-yl)ethyl)-5,6-dimethylpyrimidine-2-carboxamide |
| 110 | 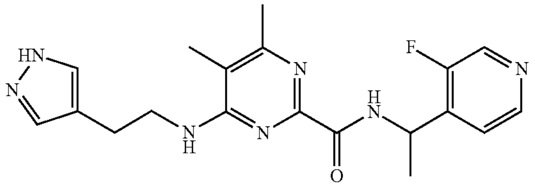 [SMILES: Cc1nc(C(=O)NC(C)c2ccncc2F)nc(NCCc2cn[nH]c2)c1C] | 4-((2-(1H-pyrazol-4-yl)ethyl)amino)-N-(1-(3-fluoropyridin-4-yl)ethyl)-5,6-dimethylpyrimidine-2-carboxamide |
| 111 | 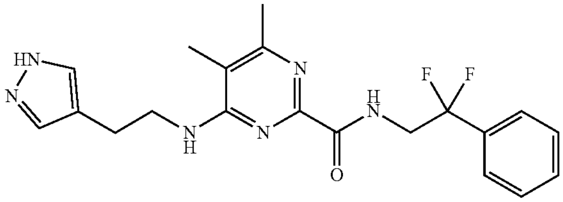 [SMILES: Cc1nc(C(=O)NCC(F)(F)c2ccccc2)nc(NCCc2cn[nH]c2)c1C] | 4-((2-(1H-pyrazol-4-yl)ethyl)amino)-N-(2,2-difluoro-2-phenylethyl)-5,6-dimethylpyrimidine-2-carboxamide |
| 112 | 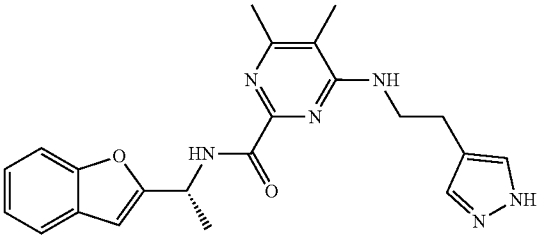 [SMILES: Cc1nc(C(=O)N[C@H](C)c2cc3ccccc3o2)nc(NCCc2cn[nH]c2)c1C] | (R)-4-((2-(1H-pyrazol-4-yl)ethyl)amino)-N-(1-(benzofuran-2-yl)ethyl)-5,6-dimethylpyrimidine-2-carboxamide |
| 113 | 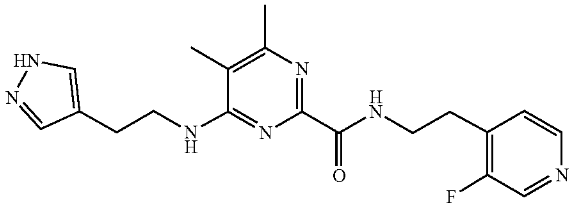 [SMILES: Cc1nc(C(=O)NCCc2ccncc2F)nc(NCCc2cn[nH]c2)c1C] | 4-((2-(1H-pyrazol-4-yl)ethyl)amino)-N-(2-(3-fluoropyridin-4-yl)ethyl)-5,6-dimethylpyrimidine-2-carboxamide |
| 114 | 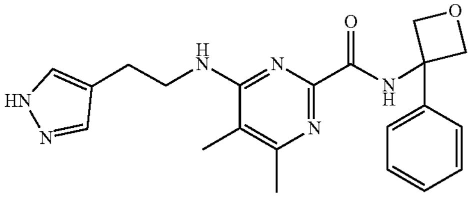 [SMILES: Cc1nc(C(=O)NC2(c3ccccc3)COC2)nc(NCCc2cn[nH]c2)c1C] | 4-((2-(1H-pyrazol-4-yl)ethyl)amino)-5,6-dimethyl-N-(3-phenyloxetan-3-yl)pyrimidine-2-carboxamide |
| 115 | 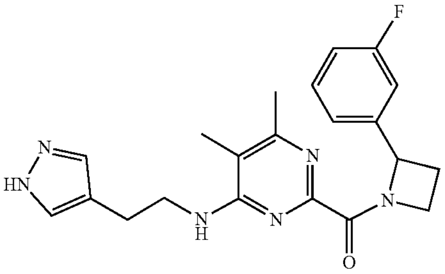 [SMILES: Cc1nc(C(=O)N2CCC2c2cccc(F)c2)nc(NCCc2cn[nH]c2)c1C] | (4-((2-(1H-pyrazol-4-yl)ethyl)amino)-5,6-dimethylpyrimidin-2-yl)(2-(3-fluorophenyl)azetidin-1-yl)methanone |

TABLE 1-continued

| No. | Structure | Name |
| --- | --- | --- |
| 116 | 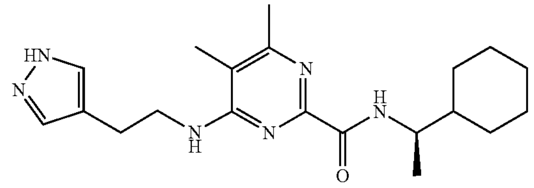 [SMILES: Cc1nc(C(=O)N[C@H](C)C2CCCCC2)nc(NCCc2cn[nH]c2)c1C] | (R)-4-((2-(1H-pyrazol-4-yl)ethyl)amino)-N-(1-cyclohexylethyl)-5,6-dimethylpyrimidine-2-carboxamide |
| 117 | 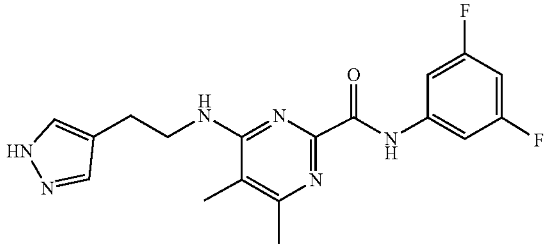 [SMILES: Cc1nc(C(=O)Nc2cc(F)cc(F)c2)nc(NCCc2cn[nH]c2)c1C] | 4-((2-(1H-pyrazol-4-yl)ethyl)amino)-N-(3,5-difluorophenyl)-5,6-dimethylpyrimidine-2-carboxamide |
| 118 | 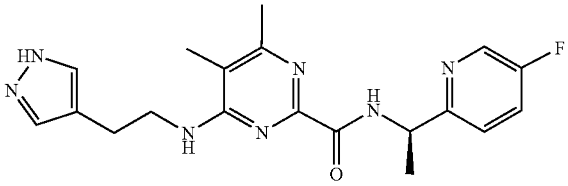 [SMILES: Cc1nc(C(=O)N[C@H](C)c2ccc(F)cn2)nc(NCCc2cn[nH]c2)c1C] | (R)-4-((2-(1H-pyrazol-4-yl)ethyl)amino)-N-(1-(5-fluoropyridin-2-yl)ethyl)-5,6-dimethylpyrimidine-2-carboxamide |
| 119 | 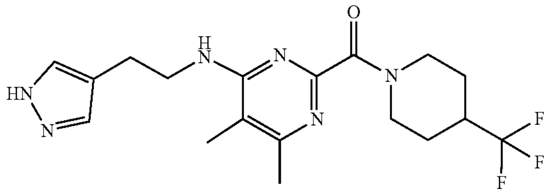 [SMILES: Cc1nc(C(=O)N2CCC(C(F)(F)F)CC2)nc(NCCc2cn[nH]c2)c1C] | (4-((2-(1H-pyrazol-4-yl)ethyl)amino)-5,6-dimethylpyrimidin-2-yl)(4-(trifluoromethyl)piperidin-1-yl)methanone |
| 120 | 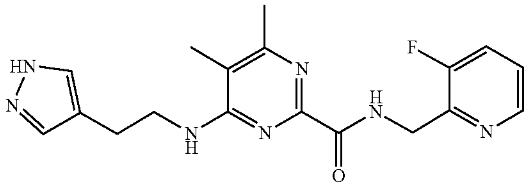 [SMILES: Cc1nc(C(=O)NCc2ncccc2F)nc(NCCc2cn[nH]c2)c1C] | 4-((2-(1H-pyrazol-4-yl)ethyl)amino)-N-((3-fluoropyridin-2-yl)methyl)-5,6-dimethylpyrimidine-2-carboxamide |
| 121 | 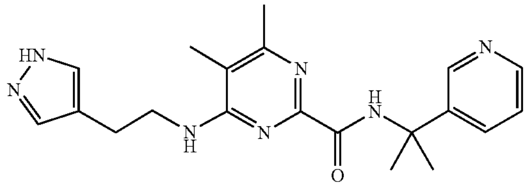 [SMILES: Cc1nc(C(=O)NC(C)(C)c2cccnc2)nc(NCCc2cn[nH]c2)c1C] | 4-((2-(1H-pyrazol-4-yl)ethyl)amino)-5,6-dimethyl-N-(2-(pyridin-3-yl)propan-2-yl)pyrimidine-2-carboxamide |
| 122 | 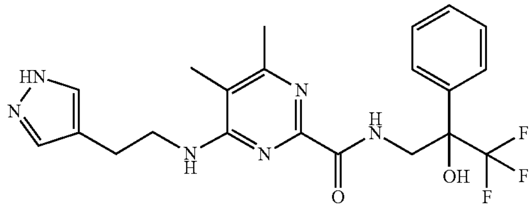 [SMILES: Cc1nc(C(=O)NCC(O)(c2ccccc2)C(F)(F)F)nc(NCCc2cn[nH]c2)c1C] | 4-((2-(1H-pyrazol-4-yl)ethyl)amino)-5,6-dimethyl-N-(3,3,3-trifluoro-2-hydroxy-2-phenylpropyl)pyrimidine-2-carboxamide |

TABLE 1-continued

| No. | Structure | Name |
| --- | --- | --- |
| 123 | 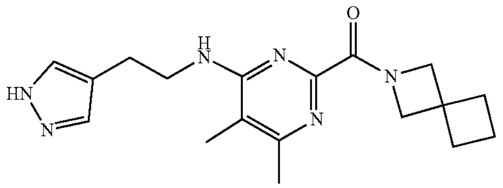 [SMILES: Cc1nc(C(=O)N2CC3(CCC3)C2)nc(NCCc2cn[nH]c2)c1C] | (4-((2-(1H-pyrazol-4-yl)ethyl)amino)-5,6-dimethylpyrimidin-2-yl)(2-azaspiro[3.3]heptan-2-yl)methanone |
| 124 | 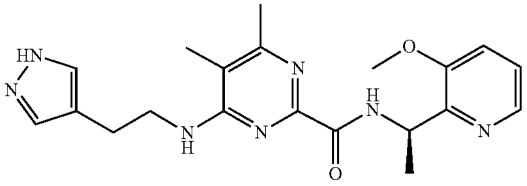 [SMILES: COc1cccnc1[C@@H](C)NC(=O)c1nc(C)c(C)c(NCCc2cn[nH]c2)n1] | (R)-4-((2-(1H-pyrazol-4-yl)ethyl)amino)-N-(1-(3-methoxypyridin-2-yl)ethyl)-5,6-dimethylpyrimidine-2-carboxamide |
| 125 | 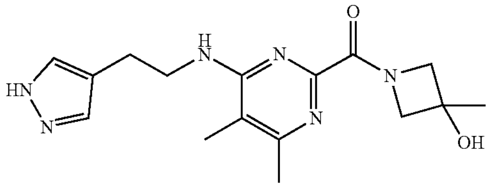 [SMILES: Cc1nc(C(=O)N2CC(C)(O)C2)nc(NCCc2cn[nH]c2)c1C] | (4-((2-(1H-pyrazol-4-yl)ethyl)amino)-5,6-dimethylpyrimidin-2-yl)(3-hydroxy-3-methylazetidin-1-yl)methanone |
| 126 | 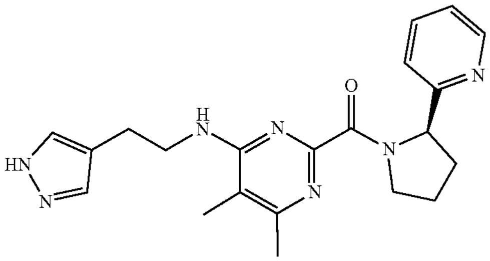 [SMILES: Cc1nc(C(=O)N2CCC[C@@H]2c2ccccn2)nc(NCCc2cn[nH]c2)c1C] | (R)-(4-((2-(1H-pyrazol-4-yl)ethyl)amino)-5,6-dimethylpyrimidin-2-yl)(2-(pyridin-2-yl)pyrrolidin-1-yl)methanone |
| 127 | 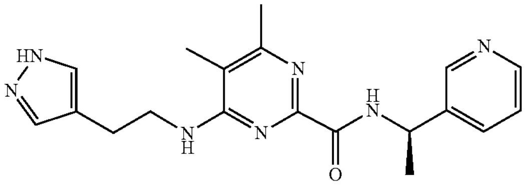 [SMILES: Cc1nc(C(=O)N[C@H](C)c2cccnc2)nc(NCCc2cn[nH]c2)c1C] | (R)-4-((2-(1H-pyrazol-4-yl)ethyl)amino)-5,6-dimethyl-N-(1-(pyridin-3-yl)ethyl)pyrimidine-2-carboxamide |
| 128 | 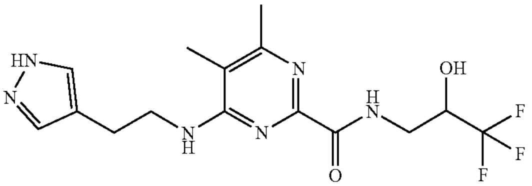 [SMILES: Cc1nc(C(=O)NCC(O)C(F)(F)F)nc(NCCc2cn[nH]c2)c1C] | 4-((2-(1H-pyrazol-4-yl)ethyl)amino)-5,6-dimethyl-N-(3,3,3-trifluoro-2-hydroxypropyl)pyrimidine-2-carboxamide |
| 129 | 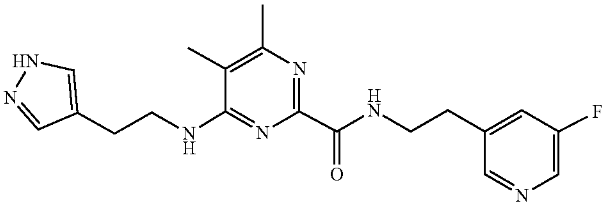 [SMILES: Cc1nc(C(=O)NCCc2cncc(F)c2)nc(NCCc2cn[nH]c2)c1C] | 4-((2-(1H-pyrazol-4-yl)ethyl)amino)-N-(2-(5-fluoropyridin-3-yl)ethyl)-5,6-dimethylpyrimidine-2-carboxamide |

TABLE 1-continued

| No. | Structure | Name |
|---|---|---|
| 130 | 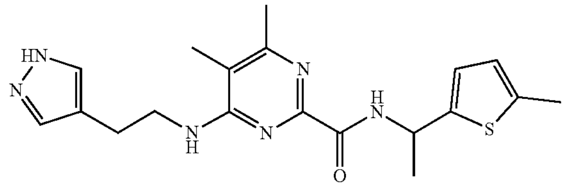 [SMILES: Cc1ccc(C(C)NC(=O)c2nc(C)c(C)c(NCCc3cn[nH]c3)n2)s1] | 4-((2-(1H-pyrazol-4-yl)ethyl)amino)-5,6-dimethyl-N-(1-(5-methylthiophen-2-yl)ethyl)pyrimidine-2-carboxamide |
| 131 | 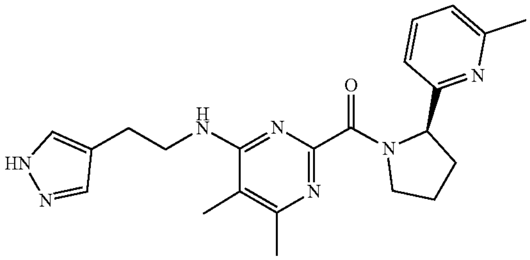 [SMILES: Cc1cccc([C@H]2CCCN2C(=O)c2nc(C)c(C)c(NCCc3cn[nH]c3)n2)n1] | (R)-(4-((2-(1H-pyrazol-4-yl)ethyl)amino)-5,6-dimethylpyrimidin-2-yl)(2-(6-methylpyridin-2-yl)pyrrolidin-1-yl)methanone |
| 132 | 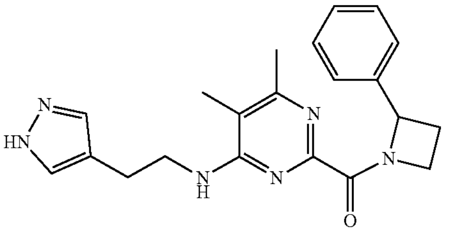 [SMILES: Cc1nc(C(=O)N2CCC2c2ccccc2)nc(NCCc2cn[nH]c2)c1C] | (4-((2-(1H-pyrazol-4-yl)ethyl)amino)-5,6-dimethylpyrimidin-2-yl)(2-phenylazetidin-1-yl)methanone |
| 133 | 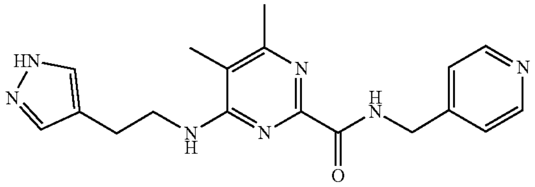 [SMILES: Cc1nc(C(=O)NCc2ccncc2)nc(NCCc2cn[nH]c2)c1C] | 4-((2-(1H-pyrazol-4-yl)ethyl)amino)-5,6-dimethyl-N-(pyridin-4-ylmethyl)pyrimidine-2-carboxamide |
| 134 | 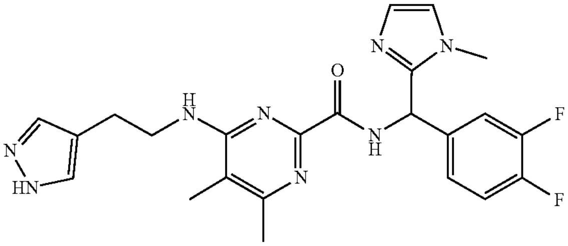 [SMILES: Cc1nc(C(=O)NC(c2ccc(F)c(F)c2)c2nccn2C)nc(NCCc2cn[nH]c2)c1C] | 4-((2-(1H-pyrazol-4-yl)ethyl)amino)-N-((3,4-difluorophenyl)(1-methyl-1H-imidazol-2-yl)methyl)-5,6-dimethylpyrimidine-2-carboxamide |
| 135 | 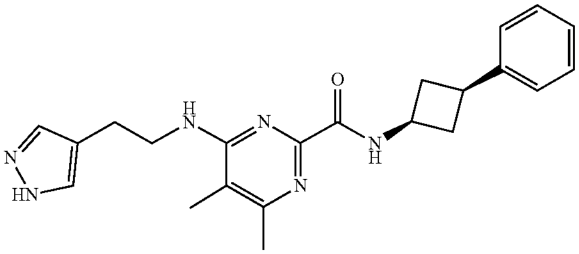 [SMILES: Cc1nc(C(=O)N[C@H]2C[C@@H](c3ccccc3)C2)nc(NCCc2cn[nH]c2)c1C] | 4-((2-(1H-pyrazol-4-yl)ethyl)amino)-5,6-dimethyl-N-((1s,3s)-3-phenylcyclobutyl)pyrimidine-2-carboxamide |

TABLE 1-continued

| No. | Structure | Name |
|---|---|---|
| 136 | 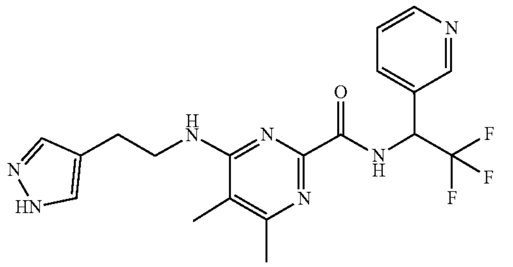 [SMILES: Cc1nc(C(=O)NC(c2cccnc2)C(F)(F)F)nc(NCCc2cn[nH]c2)c1C] | 4-((2-(1H-pyrazol-4-yl)ethyl)amino)-5,6-dimethyl-N-(2,2,2-trifluoro-1-(pyridin-3-yl)ethyl)pyrimidine-2-carboxamide |
| 137 | 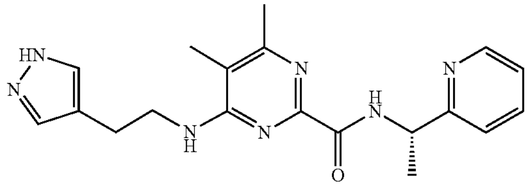 [SMILES: Cc1nc(C(=O)N[C@@H](C)c2ccccn2)nc(NCCc2cn[nH]c2)c1C] | (S)-4-((2-(1H-pyrazol-4-yl)ethyl)amino)-5,6-dimethyl-N-(1-(pyridin-2-yl)ethyl)pyrimidine-2-carboxamide |
| 138 | 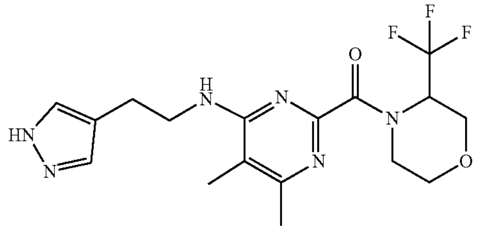 [SMILES: Cc1nc(C(=O)N2CCOCC2C(F)(F)F)nc(NCCc2cn[nH]c2)c1C] | (4-((2-(1H-pyrazol-4-y)ethyl)amino)-5,6-dimethylpyrimidin-2-yl)(3-(trifluoromethyl)morpholino)methanone |
| 139 | 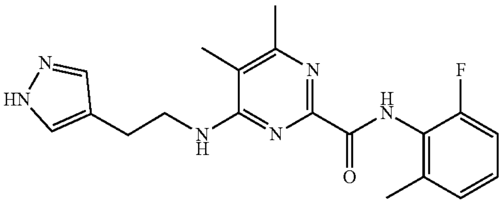 [SMILES: Cc1cccc(F)c1NC(=O)c1nc(C)c(C)c(NCCc2cn[nH]c2)n1] | 4-((2-(1H-pyrazol-4-yl)ethyl)amino)-N-(2-fluoro-6-methylphenyl)-5,6-dimethylpyrimidine-2-carboxamide |
| 140 | 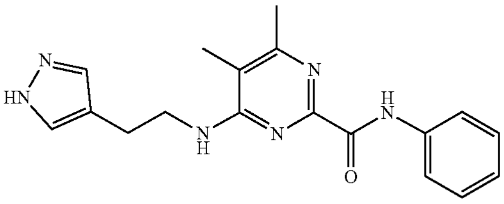 [SMILES: Cc1nc(C(=O)Nc2ccccc2)nc(NCCc2cn[nH]c2)c1C] | 4-((2-(1H-pyrazol-4-yl)ethyl)amino)-5,6-dimethyl-N-phenylpyrimidine-2-carboxamide |
| 141 | 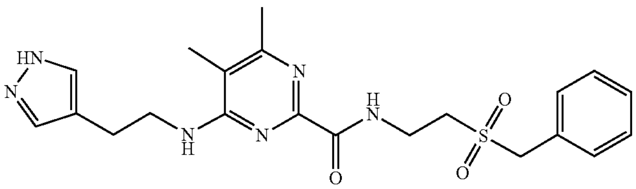 [SMILES: Cc1nc(C(=O)NCCS(=O)(=O)Cc2ccccc2)nc(NCCc2cn[nH]c2)c1C] | 4-((2-(1H-pyrazol-4-yl)ethyl)amino)-N-(2-(benzylsulfonyl)ethyl)-5,6-dimethylpyrimidine-2-carboxamide |

TABLE 1-continued

| No. | Structure | Name |
|---|---|---|
| 142 | 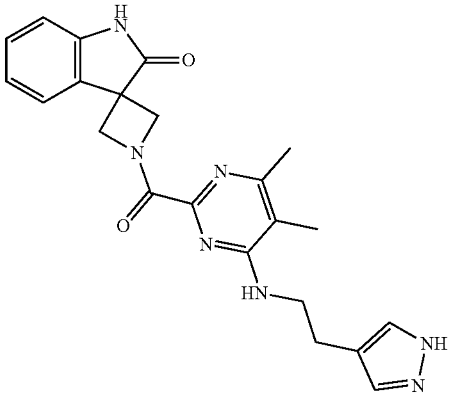 [SMILES: Cc1nc(C(=O)N2CC3(C2)C(=O)Nc2ccccc23)nc(NCCc2cn[nH]c2)c1C] | 1-(4-((2-(1H-pyrazol-4-yl)ethyl)amino)-5,6-dimethylpyrimidine-2-carbonyl)spiro[azetidine-3,3'-indolin]-2'-one |
| 143 | 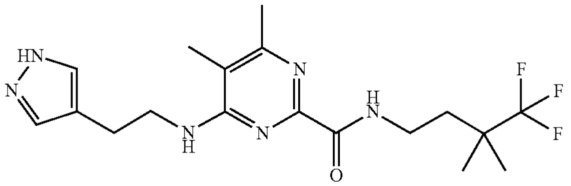 [SMILES: Cc1nc(C(=O)NCCC(C)(C)C(F)(F)F)nc(NCCc2cn[nH]c2)c1C] | 4-((2-(1H-pyrazol-4-yl)ethyl)amino)-5,6-dimethyl-N-(4,4,4-trifluoro-3,3-dimethylbutyl)pyrimidine-2-carboxamide |
| 144 | 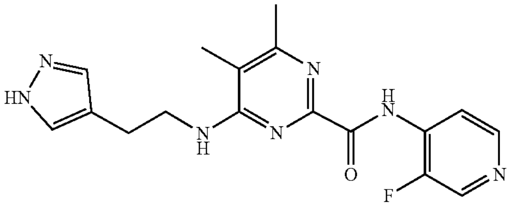 [SMILES: Cc1nc(C(=O)Nc2ccncc2F)nc(NCCc2cn[nH]c2)c1C] | 4-((2-(1H-pyrazol-4-yl)ethyl)amino)-N-(3-fluoropyridin-4-yl)-5,6-dimethylpyrimidine-2-carboxamide |
| 145 | 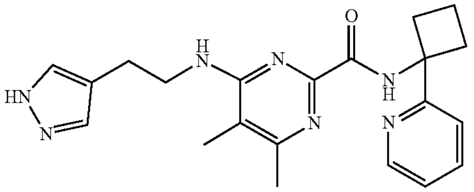 [SMILES: Cc1nc(C(=O)NC2(c3ccccn3)CCC2)nc(NCCc2cn[nH]c2)c1C] | 4-((2-(1H-pyrazol-4-yl)ethyl)amino)-5,6-dimethyl-N-(1-(pyridin-2-yl)cyclobutyl)pyrimidine-2-carboxamide |
| 146 | 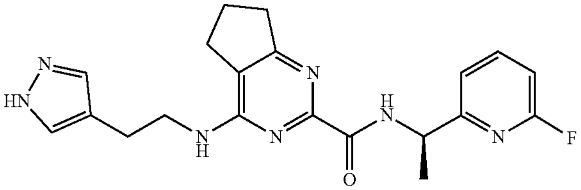 [SMILES: C[C@@H](NC(=O)c1nc2c(c(NCCc3cn[nH]c3)n1)CCC2)c1cccc(F)n1] | (R)-4-((2-(1H-pyrazol-4-yl)ethyl)amino)-N-(1-(6-fluoropyridin-2-yl)ethyl)-6,7-dihydro-5H-cyclopenta[d]pyrimidine-2-carboxamide |
| 147 | 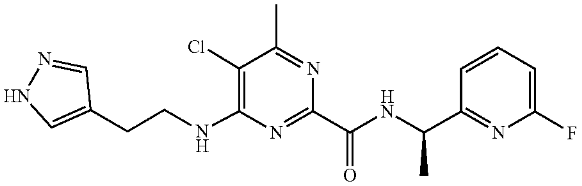 [SMILES: Cc1nc(C(=O)N[C@H](C)c2cccc(F)n2)nc(NCCc2cn[nH]c2)c1Cl] | (R)-4-((2-(1H-pyrazol-4-yl)ethyl)amino)-5-chloro-N-(1-(6-fluoropyridin-2-yl)ethyl)-6-methylpyrimidine-2-carboxamide |

TABLE 1-continued

| No. | Structure | Name |
|---|---|---|
| 148 | 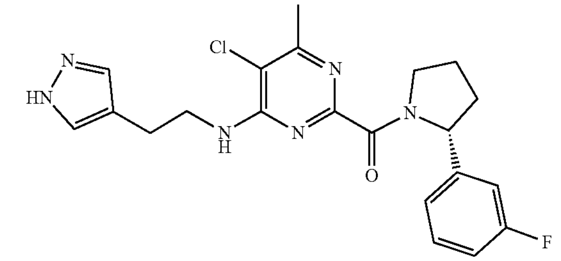 [SMILES: Cc1nc(C(=O)N2CCC[C@@H]2c2cccc(F)c2)nc(NCCc2cn[nH]c2)c1Cl] | (R)-(4-((2-(1H-pyrazol-4-yl)ethyl)amino)-5-chloro-6-methylpyrimidin-2-yl)(2-(3-fluorophenyl)pyrrolidin-1-yl)methanone |
| 149 | 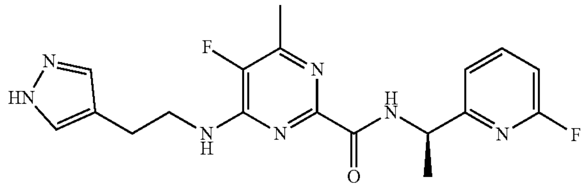 [SMILES: Cc1nc(C(=O)N[C@H](C)c2cccc(F)n2)nc(NCCc2cn[nH]c2)c1F] | (R)-4-((2-(1H-pyrazol-4-yl)ethyl)amino)-5-fluoro-N-(1-(6-fluoropyridin-2-yl)ethyl)-6-methylpyrimidine-2-carboxamide |
| 150 | 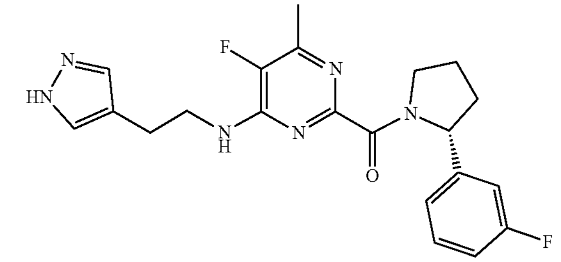 [SMILES: Cc1nc(C(=O)N2CCC[C@@H]2c2cccc(F)c2)nc(NCCc2cn[nH]c2)c1F] | (R)-(4-((2-(1H-pyrazol-4-yl)ethyl)amino)-5-fluoro-6-methylpyrimidin-2-yl)(2-(3-fluorophenyl)pyrrolidin-1-yl)methanone |
| 151 | 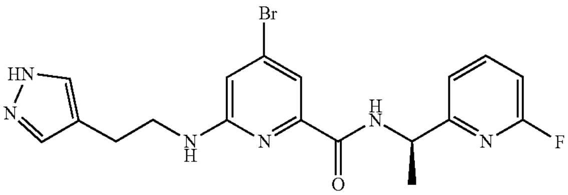 [SMILES: C[C@@H](NC(=O)c1cc(Br)cc(NCCc2cn[nH]c2)n1)c1cccc(F)n1] | (R)-6-((2-(1H-pyrazol-4-yl)ethyl)amino)-4-bromo-N-(1-(6-fluoropyridin-2-yl)ethyl)picolinamide |
| 152 | 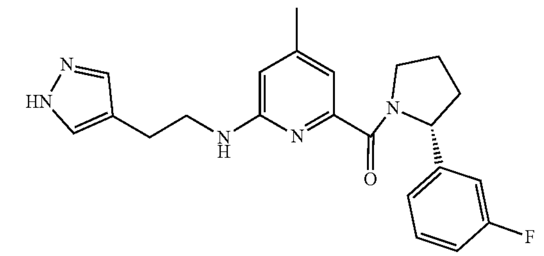 | (R)-6-((2-(1H-pyrazol-4-yl)ethyl)amino)-4-methylpyridin-2-yl)(2-(3-fluorophenyl)pyrrolidin-1-yl)methanone |

In some embodiments, provided herein is a compound, or a stereoisomer or tautomer thereof, or a pharmaceutically acceptable salt of any of the foregoing, wherein the compound is selected from the group consisting of:

4-((2-(1H-pyrazol-4-yl)ethyl)(phenethyl)amino)-5,6-dimethylpyrimidine-2-carboxamide;

4-((2-(1H-pyrazol-4-yl)ethyl)(phenethyl)amino)-N,5,6-trimethylpyrimidine-2-carboxamide;

(4-((2-(1H-pyrazol-4-yl)ethyl)amino)-5,6-dimethylpyrimidin-2-yl)(3-(3-fluorophenyl)-3-hydroxyazetidin-1-yl)methanone;

4-((2-(1H-pyrazol-4-yl)ethyl)amino)-N-(1-(6-fluoropyridin-2-yl)ethyl)-5,6-dimethylpyrimidine-2-carboxamide;

4-((2-(1H-pyrazol-4-yl)ethyl)amino)-N-((3-fluorophenyl)(1-methyl-1H-imidazol-2-yl)methyl)-N,5,6-trimethylpyrimidine-2-carboxamide;

(4-(1H-indol-3-yl)piperidin-1-yl)(4-((2-(1H-pyrazol-4-yl)ethyl)amino)-5,6-dimethylpyrimidin-2-yl)methanone;

(4-((2-(1H-pyrazol-4-yl)ethyl)amino)-5,6-dimethylpyrimidin-2-yl)(3-(3-fluorophenyl) morpholino)methanone;

4-((2-(1H-pyrazol-4-yl)ethyl)amino)-5,6-dimethyl-N-(1-(thiophen-2-yl)ethyl)pyrimidine-2-carboxamide;

(4-(3-(1H-pyrazol-4-yl)pyrrolidin-1-yl)-5,6-dimethylpyrimidin-2-yl)(3-hydroxy-3-phenylazetidin-1-yl)methanone;

4-((2-(1H-pyrazol-4-yl)ethyl)amino)-N-(1-(3-fluorophenyl)ethyl)-5,6-dimethylpyrimidine-2-carboxamide;

4-((2-(1H-pyrazol-4-yl)ethyl)amino)-N-(2-(3-fluorophenyl)propan-2-yl)-5,6-dimethylpyrimidine-2-carboxamide;

(4-((2-(1H-pyrazol-4-yl)ethyl)amino)-5,6-dimethylpyrimidin-2-yl)(3-(3-chlorophenyl)morpholino)methanone;

(4-((2-(1H-pyrazol-4-yl)ethyl)amino)-5,6-dimethylpyrimidin-2-yl)(2-(3-chlorophenyl)pyrrolidin-1-yl)methanone;

4-((2-(1H-pyrazol-4-yl)ethyl)amino)-5,6-dimethyl-N-(1-(thiophen-2-yl)ethyl)pyrimidine-2-carboxamide;

(4-((2-(1H-pyrazol-4-yl)ethyl)amino)-5,6-dimethylpyrimidin-2-yl)(2-(3-fluorophenyl)pyrrolidin-1-yl)methanone;

(4-((2-(1H-pyrazol-4-yl)ethyl)amino)-5,6-dimethylpyrimidin-2-yl)(3-phenylmorpholino)methanone;

4-((2-(1H-pyrazol-4-yl)ethyl)amino)-5,6-dimethyl-N-(1-phenylethyl)pyrimidine-2-carboxamide;

(4-((2-(1H-pyrazol-4-yl)ethyl)amino)-5,6-dimethylpyrimidin-2-yl)(3-(3-fluorophenyl)azetidin-1-yl)methanone;

4-((2-(1H-pyrazol-4-yl)ethyl)amino)-5,6-dimethyl-N-(thiophen-2-ylmethyl)pyrimidine-2-carboxamide;

4-((2-(1H-pyrazol-4-yl)ethyl)amino)-N-((3-fluorophenyl)(1-methyl-1H-imidazol-2-yl)methyl)-,6-dimethylpyrimidine-2-carboxamide;

4-((2-(1H-pyrazol-4-yl)ethyl)amino)-5,6-dimethyl-N-(2-phenylpropan-2-yl)pyrimidine-2-carboxamide;

(4-((2-(1H-pyrazol-4-yl)ethyl)amino)-5,6-dimethylpyrimidin-2-yl)(3-hydroxy-3-phenylazetidin-1-yl)methanone;

4-((2-(1H-pyrazol-4-yl)ethyl)amino)-N-((3-fluorophenyl)(oxazol-2-yl)methyl)-5,6-dimethylpyrimidine-2-carboxamide;

(4-((2-(1H-pyrazol-4-yl)ethyl)amino)-5,6-dimethylpyrimidin-2-yl)(2-(3-fluorophenyl)piperazin-1-yl)methanone;

(4-((2-(1H-pyrazol-4-yl)ethyl)amino)-5,6-dimethylpyrimidin-2-yl)(3-methyl-3-phenylmorpholino)methanone;

4-((2-(1H-pyrazol-4-yl)ethyl)amino)-N-(1-(2-chlorophenyl)ethyl)-5,6-dimethylpyrimidine-2-carboxamide;

4-((2-(1H-pyrazol-4-yl)ethyl)amino)-N-(2-(3-fluorophenyl)-2-methylpropyl)-5,6-dimethylpyrimidine-2-carboxamide;

(4-((2-(1H-pyrazol-4-yl)ethyl)amino)-5,6-dimethylpyrimidin-2-yl)(4,4-difluoro-2-phenylpiperidin-1-yl)methanone;

4-((2-(1H-pyrazol-4-yl)ethyl)amino)-N-(1-(2-chlorophenyl)ethyl)-N,5,6-trimethylpyrimidine-2-carboxamide;

4-((2-(1H-pyrazol-4-yl)ethyl)amino)-N-(1-(3-chloropyridin-2-yl)ethyl)-5,6-dimethylpyrimidine-2-carboxamide;

4-((2-(1H-pyrazol-4-yl)ethyl)amino)-N-benzyl-5,6-dimethylpyrimidine-2-carboxamide;

4-((2-(1H-pyrazol-4-yl)ethyl)amino)-N-(3-fluoropenzyl)-5,6-dimethylpyrimidine-2-carboxamide;

4-((2-(1H-pyrazol-4-yl)ethyl)amino)-5,6-dimethyl-N-(2,2,2-trifluoro-1-phenylethyl)pyrimidine-2-carboxamide;

(4-((2-(1H-pyrazol-4-yl)ethyl)amino)-5,6-dimethylpyrimidin-2-yl)(4-hydroxy-4-phenylpiperidin-1-yl)methanone;

4-((2-(1H-pyrazol-4-yl)ethyl)amino)-5,6-dimethyl-N-(1-(thiophen-3-yl)ethyl)pyrimidine-2-carboxamide;

4-((2-(1H-pyrazol-4-yl)ethyl)amino)-N-(1-(6-chloropyridin-2-yl)ethyl)-5,6-dimethylpyrimidine-2-carboxamide;

4-((2-(1H-pyrazol-4-yl)ethyl)amino)-5,6-dimethyl-N-(1-(3-methylpyridin-2-yl)ethyl)pyrimidine-2-carboxamide;

(4-((2-(1H-pyrazol-4-yl)ethyl)amino)-5,6-dimethylpyrimidin-2-yl)(2-phenylpyrrolidin-1-yl)methanone;

4-((2-(1H-pyrazol-4-yl)ethyl)amino)-N-(1-(3-fluorophenyl)ethyl)-5,6-dimethylpyrimidine-2-carboxamide;

4-((2-(1H-pyrazol-4-yl)ethyl)amino)-5,6-dimethyl-N-((1-methyl-1H-imidazol-2-yl)(phenyl)methyl)pyrimidine-2-carboxamide;

4-((2-(1H-pyrazol-4-yl)ethyl)amino)-N-(1-(3-fluorophenyl)-2-methylpropan-2-yl)-5,6-dimethylpyrimidine-2-carboxamide;

(4-((2-(1H-pyrazol-4-yl)ethyl)amino)-5,6-dimethylpyrimidin-2-yl)(3-hydroxy-4-phenylpyrrolidin-1-yl)methanone;

4-((2-(1H-pyrazol-4-yl)ethyl)amino)-N-(1-(6-methoxypyridin-2-yl)ethyl)-5,6-dimethylpyrimidine-2-carboxamide;

(4-((2-(1H-pyrazol-4-yl)ethyl)amino)-5,6-dimethylpyrimidin-2-yl)(4-methyl-2-phenylpiperazin-1-yl)methanone;

4-(4-((2-(1H-pyrazol-4-yl)ethyl)amino)-5,6-dimethylpyrimidine-2-carbonyl)-1-benzylpiperazin-2-one;

4-((2-(1H-pyrazol-4-yl)ethyl)amino)-N-((3-fluorophenyl)(pyridin-2-yl)methyl)-5,6-dimethylpyrimidine-2-carboxamide;

4-((2-(1H-pyrazol-4-yl)ethyl)amino)-5,6-dimethyl-N-(1-(pyridin-2-yl)ethyl)pyrimidine-2-carboxamide;

(4-((2-(1H-pyrazol-4-yl)ethyl)amino)-5,6-dimethylpyrimidin-2-yl)(3-hydroxy-3-(trifluoromethyl)azetidin-1-yl)methanone;

4-((2-(1H-pyrazol-4-yl)ethyl)amino)-N-(1-(3-fluorophenyl)-2-methoxyethyl)-5,6-dimethylpyrimidine-2-carboxamide;

4-((2-(1H-pyrazol-4-yl)ethyl)amino)-5,6-dimethyl-N-phenethylpyrimidine-2-carboxamide;

(4-((2-(1H-pyrazol-4-yl)ethyl)amino)-5,6-dimethylpyrimidin-2-yl)(3-(2,3-difluorophenyl)-3-hydroxyazetidin-1-yl)methanone;

(4-((2-(1H-pyrazol-4-yl)ethyl)amino)-5,6-dimethylpyrimidin-2-yl)(3-phenylpyrrolidin-1-yl)methanone;

4-((2-(1H-pyrazol-4-yl)ethyl)amino)-N-(1-(2-chlorophenyl)ethyl)-N,5,6-trimethylpyrimidine-2-carboxamide;

(4-((2-(1H-pyrazol-4-yl)ethyl)amino)-5,6-dimethylpyrimidin-2-yl)(2-(2-fluorophenyl)pyrrolidin-1-yl)methanone;

4-((2-(1H-pyrazol-4-yl)ethyl)amino)-N-((6-fluoropyridin-2-yl)methyl)-5,6-dimethylpyrimidine-2-carboxamide;

4-((2-(1H-pyrazol-4-yl)ethyl)amino)-N-(1-(3-fluoropyridin-2-yl)ethyl)-5,6-dimethylpyrimidine-2-carboxamide;

4-((2-(1H-pyrazol-4-yl)ethyl)amino)-N-((1-benzoylazetidin-3-yl)methyl)-5,6-dimethylpyrimidine-2-carboxamide;

4-((2-(1H-pyrazol-4-yl)ethyl)amino)-N-(benzofuran-3-ylmethyl)-5,6-dimethylpyrimidine-2-carboxamide;

4-((2-(1H-pyrazol-4-yl)ethyl)amino)-5,6-dimethyl-N-(1-phenylethyl)pyrimidine-2-carboxamide;

(4-((2-(1H-pyrazol-4-yl)ethyl)amino)-5,6-dimethylpyrimidin-2-yl)(3-benzyl-3-hydroxyazetidin-1-yl)methanone;

(4-((2-(1H-pyrazol-4-yl)ethyl)amino)-5,6-dimethylpyrimidin-2-yl)(3-phenylpyrrolidin-1-yl)methanone;

(4-((2-(1H-pyrazol-4-yl)ethyl)amino)-5,6-dimethylpyrimidin-2-yl)(2-methyl-5-phenylmorpholino)methanone;

(4-((2-(1H-pyrazol-4-yl)ethyl)amino)-5,6-dimethylpyrimidin-2-yl)(3-phenylmorpholino)methanone;

(4-((2-(1H-pyrazol-4-yl)ethyl)amino)-5,6-dimethylpyrimidin-2-yl)(3-benzylmorpholino)methanone;

4-((2-(1H-pyrazol-4-yl)ethyl)amino)-N-(1-(benzofuran-3-yl)ethyl)-5,6-dimethylpyrimidine-2-carboxamide;

(4-((2-(1H-pyrazol-4-yl)ethyl)amino)-5,6-dimethylpyrimidin-2-yl)(3-(2-fluorophenyl)pyrrolidin-1-yl)methanone;

(4-((2-(1H-pyrazol-4-yl)ethyl)amino)-5,6-dimethylpyrimidin-2-yl)(3-(4-fluorophenyl) morpholino)methanone;

4-((2-(1H-pyrazol-4-yl)ethyl)amino)-N-(1-(6-methoxypyridin-2-yl)ethyl)-5,6-dimethylpyrimidine-2-carboxamide;

4-((2-(1H-pyrazol-4-yl)ethyl)amino)-5,6-dimethyl-N-(2-(pyridin-2-yl)propan-2-yl)pyrimidine-2-carboxamide;

4-((2-(1H-pyrazol-4-yl)ethyl)amino)-N-(1-(5-chlorothiophen-2-yl)ethyl)-5,6-dimethylpyrimidine-2-carboxamide;

(4-((2-(1H-pyrazol-4-yl)ethyl)amino)-5,6-dimethylpyrimidin-2-yl)(2-benzylpyrrolidin-1-yl)methanone;
(4-((2-(1H-pyrazol-4-yl)ethyl)amino)-5,6-dimethylpyrimidin-2-yl)(3-benzylmorpholino)methanone;
4-((2-(1H-pyrazol-4-yl)ethyl)amino)-N-(1-(6-fluoropyridin-2-yl)ethyl)-5,6-dimethylpyrimidine-2-carboxamide;
4-((2-(1H-pyrazol-4-yl)ethyl)amino)-N-((3-(3-fluorophenyl)oxetan-3-yl)methyl)-5,6-dimethylpyrimidine-2-carboxamide;
4-((2-(1H-pyrazol-4-yl)ethyl)amino)-N-(1-(furan-2-yl)ethyl)-5,6-dimethylpyrimidine-2-carboxamide;
(4-((2-(1H-pyrazol-4-yl)ethyl)amino)-5,6-dimethylpyrimidin-2-yl)(3-phenylazetidin-1-yl)methanone;
(4-((2-(1H-pyrazol-4-yl)ethyl)amino)-5,6-dimethylpyrimidin-2-yl)(3-(2-fluorophenyl)-3-hydroxyazetidin-1-yl)methanone;
4-((2-(1H-pyrazol-4-yl)ethyl)amino)-5,6-dimethyl-N-(1-(6-methylpyridin-2-yl)ethyl)pyrimidine-2-carboxamide;
4-((2-(1H-pyrazol-4-yl)ethyl)amino)-N-(3,3-difluoro-2,3-dihydro-1H-inden-1-yl)-5,6-dimethylpyrimidine-2-carboxamide;
(4-((2-(1H-pyrazol-4-yl)ethyl)amino)-5,6-dimethylpyrimidin-2-yl)(3-(2-chlorophenyl)morpholino)methanone;
(4-((2-(1H-pyrazol-4-yl)ethyl)amino)-5,6-dimethylpyrimidin-2-yl)(3-(trifluoromethoxy)azetidin-1-yl)methanone;
4-((2-(1H-pyrazol-4-yl)ethyl)amino)-N-(1-(3-fluorophenyl)-2-methoxyethyl)-5,6-dimethylpyrimidine-2-carboxamide;
4-((2-(1H-pyrazol-4-yl)ethyl)amino)-N-(2-(4-fluorophenyl)propan-2-yl)-5,6-dimethylpyrimidine-2-carboxamide;
(4-((2-(1H-pyrazol-4-yl)ethyl)amino)-5,6-dimethylpyrimidin-2-yl)(3-(hydroxymethyl)-3-phenylazetidin-1-yl)methanone;
4-((2-(1H-pyrazol-4-yl)ethyl)amino)-N-(4-(2-chloro-4-fluoropenzyl)tetrahydro-2H-pyran-4-yl)-5,6-dimethylpyrimidine-2-carboxamide;
(4-((2-(1H-pyrazol-4-yl)ethyl)amino)-5,6-dimethylpyrimidin-2-yl)(2-(4-fluorophenyl)pyrrolidin-1-yl)methanone;
4-((2-(1H-pyrazol-4-yl)ethyl)amino)-5,6-dimethyl-N-(1-(pyridin-4-yl)ethyl)pyrimidine-2-carboxamide;
4-((2-(1H-pyrazol-4-yl)ethyl)amino)-N-((6-methoxypyridin-2-yl)methyl)-5,6-dimethylpyrimidine-2-carboxamide;
(4-((2-(1H-pyrazol-4-yl)ethyl)amino)-5,6-dimethylpyrimidin-2-yl)(3-methyl-3-phenylazetidin-1-yl)methanone;
4-((2-(1H-pyrazol-4-yl)ethyl)amino)-N-(1-(isoxazol-3-yl)ethyl)-5,6-dimethylpyrimidine-2-carboxamide;
(4-((2-(1H-pyrazol-4-yl)ethyl)amino)-5,6-dimethylpyrimidin-2-yl)(3,3-difluoroazetidin-1-yl)methanone;
4-((2-(1H-pyrazol-4-yl)ethyl)amino)-N-(1-(4-fluorophenyl)-2-methoxyethyl)-N,5,6-trimethylpyrimidine-2-carboxamide;
4-((2-(1H-pyrazol-4-yl)ethyl)amino)-5,6-dimethyl-N-(pyridin-2-ylmethyl)pyrimidine-2-carboxamide;
4-((2-(1H-pyrazol-4-yl)ethyl)amino)-5,6-dimethyl-N-((3-phenyloxetan-3-yl)methyl)pyrimidine-2-carboxamide;
4-((2-(1H-pyrazol-4-yl)ethyl)amino)-5,6-dimethyl-N-(1-(pyridin-4-yl)ethyl)pyrimidine-2-carboxamide;
1-(4-((2-(1H-pyrazol-4-yl)ethyl)amino)-5,6-dimethylpyrimidine-2-carbonyl)-4-phenylpiperidine-4-carbonitrile;
(4-((2-(1H-pyrazol-4-yl)ethyl)amino)-5,6-dimethylpyrimidin-2-yl)(3-cyclopropyl-3-hydroxyazetidin-1-yl)methanone;
4-((2-(1H-pyrazol-4-yl)ethyl)amino)-N-((2-fluorophenyl)(1-methyl-1H-imidazol-2-yl)methyl)-,6-dimethylpyrimidine-2-carboxamide;
4-((2-(1H-pyrazol-4-yl)ethyl)amino)-N-(1-(2-chlorophenyl)ethyl)-5,6-dimethylpyrimidine-2-carboxamide;
(4-((2-(1H-pyrazol-4-yl)ethyl)amino)-5,6-dimethylpyrimidin-2-yl)(3-(trifluoromethyl)azetidin-1-yl)methanone;
4-((2-(1H-pyrazol-4-yl)ethyl)amino)-5,6-dimethyl-N-(1-(5-methylfuran-2-yl)ethyl)pyrimidine-2-carboxamide;
(4-((2-(1H-pyrazol-4-yl)ethyl)amino)-5,6-dimethylpyrimidin-2-yl)(3-methoxy-3-phenylazetidin-1-yl)methanone;
4-((2-(1H-pyrazol-4-yl)ethyl)amino)-5,6-dimethyl-N-(1-(thiazol-5-yl)ethyl)pyrimidine-2-carboxamide;
4-((2-(1H-pyrazol-4-yl)ethyl)amino)-N-(2-hydroxy-2-phenylpropyl)-5,6-dimethylpyrimidine-2-carboxamide;
N-((1H-indazol-3-yl)methyl)-4-((2-(1H-pyrazol-4-yl)ethyl)amino)-5,6-dimethylpyrimidine-2-carboxamide;
4-((2-(1H-pyrazol-4-yl)ethyl)(propyl)amino)-5,6-dimethylpyrimidine-2-carboxamide;
(4-((2-(1H-pyrazol-4-yl)ethyl)amino)-5,6-dimethylpyrimidin-2-yl)(3-ethyl-3-hydroxyazetidin-1-yl)methanone;
4-((2-(1H-pyrazol-4-yl)ethyl)amino)-5,6-dimethyl-N-(1-(oxazol-2-yl)ethyl)pyrimidine-2-carboxamide;
4-((2-(1H-pyrazol-4-yl)ethyl)amino)-N-(1-(5-fluoropyridin-3-yl)ethyl)-5,6-dimethylpyrimidine-2-carboxamide;
4-((2-(1H-pyrazol-4-yl)ethyl)amino)-N-(1-(3-fluoropyridin-4-yl)ethyl)-5,6-dimethylpyrimidine-2-carboxamide;
4-((2-(1H-pyrazol-4-yl)ethyl)amino)-N-(2,2-difluoro-2-phenylethyl)-5,6-dimethylpyrimidine-2-carboxamide;
4-((2-(1H-pyrazol-4-yl)ethyl)amino)-N-(1-(benzofuran-2-yl)ethyl)-5,6-dimethylpyrimidine-2-carboxamide;
4-((2-(1H-pyrazol-4-yl)ethyl)amino)-N-(2-(3-fluoropyridin-4-yl)ethyl)-5,6-dimethylpyrimidine-2-carboxamide;
4-((2-(1H-pyrazol-4-yl)ethyl)amino)-5,6-dimethyl-N-(3-phenyloxetan-3-yl)pyrimidine-2-carboxamide;
(4-((2-(1H-pyrazol-4-yl)ethyl)amino)-5,6-dimethylpyrimidin-2-yl)(2-(3-fluorophenyl)azetidin-1-yl)methanone;
4-((2-(1H-pyrazol-4-yl)ethyl)amino)-N-(1-cyclohexylethyl)-5,6-dimethylpyrimidine-2-carboxamide;
4-((2-(1H-pyrazol-4-yl)ethyl)amino)-N-(3,5-difluorophenyl)-5,6-dimethylpyrimidine-2-carboxamide;
4-((2-(1H-pyrazol-4-yl)ethyl)amino)-N-(1-(5-fluoropyridin-2-yl)ethyl)-5,6-dimethylpyrimidine-2-carboxamide;
(4-((2-(1H-pyrazol-4-yl)ethyl)amino)-5,6-dimethylpyrimidin-2-yl)(4-(trifluoromethyl)piperidin-1-yl)methanone;
4-((2-(1H-pyrazol-4-yl)ethyl)amino)-N-((3-fluoropyridin-2-yl)methyl)-5,6-dimethylpyrimidine-2-carboxamide;
4-((2-(1H-pyrazol-4-yl)ethyl)amino)-5,6-dimethyl-N-(2-(pyridin-3-yl)propan-2-yl)pyrimidine-2-carboxamide;
4-((2-(1H-pyrazol-4-yl)ethyl)amino)-5,6-dimethyl-N-(3,3,3-trifluoro-2-hydroxy-2-phenylpropyl)pyrimidine-2-carboxamide;
(4-((2-(1H-pyrazol-4-yl)ethyl)amino)-5,6-dimethylpyrimidin-2-yl)(2-azaspiro[3.3]heptan-2-yl)methanone;
4-((2-(1H-pyrazol-4-yl)ethyl)amino)-N-(1-(3-methoxypyridin-2-yl)ethyl)-5,6-dimethylpyrimidine-2-carboxamide;
(4-((2-(1H-pyrazol-4-yl)ethyl)amino)-5,6-dimethylpyrimidin-2-yl)(3-hydroxy-3-methylazetidin-1-yl)methanone;
(4-((2-(1H-pyrazol-4-yl)ethyl)amino)-5,6-dimethylpyrimidin-2-yl)(2-(pyridin-2-yl)pyrrolidin-1-yl)methanone;
4-((2-(1H-pyrazol-4-yl)ethyl)amino)-5,6-dimethyl-N-(1-(pyridin-3-yl)ethyl)pyrimidine-2-carboxamide;
4-((2-(1H-pyrazol-4-yl)ethyl)amino)-5,6-dimethyl-N-(3,3,3-trifluoro-2-hydroxypropyl)pyrimidine-2-carboxamide;
4-((2-(1H-pyrazol-4-yl)ethyl)amino)-N-(2-(5-fluoropyridin-3-yl)ethyl)-5,6-dimethylpyrimidine-2-carboxamide;
4-((2-(1H-pyrazol-4-yl)ethyl)amino)-5,6-dimethyl-N-(1-(5-methylthiophen-2-yl)ethyl)pyrimidine-2-carboxamide;

(4-((2-(1H-pyrazol-4-yl)ethyl)amino)-5,6-dimethylpyrimidin-2-yl)(2-(6-methylpyridin-2-yl)pyrrolidin-1-yl)methanone;

(4-((2-(1H-pyrazol-4-yl)ethyl)amino)-5,6-dimethylpyrimidin-2-yl)(2-phenylazetidin-1-yl)methanone;

4-((2-(1H-pyrazol-4-yl)ethyl)amino)-5,6-dimethyl-N-(pyridin-4-ylmethyl)pyrimidine-2-carboxamide;

4-((2-(1H-pyrazol-4-yl)ethyl)amino)-N-((3,4-difluorophenyl)(1-methyl-1H-imidazol-2-yl)methyl)-5,6-dimethylpyrimidine-2-carboxamide;

4-((2-(1H-pyrazol-4-yl)ethyl)amino)-5,6-dimethyl-N-(3-phenylcyclobutyl)pyrimidine-2-carboxamide;

4-((2-(1H-pyrazol-4-yl)ethyl)amino)-5,6-dimethyl-N-(2,2,2-trifluoro-1-(pyridin-3-yl)ethyl)pyrimidine-2-carboxamide;

4-((2-(1H-pyrazol-4-yl)ethyl)amino)-5,6-dimethyl-N-(1-(pyridin-2-yl)ethyl)pyrimidine-2-carboxamide;

(4-((2-(1H-pyrazol-4-yl)ethyl)amino)-5,6-dimethylpyrimidin-2-yl)(3-(trifluoromethyl)morpholino)methanone;

4-((2-(1H-pyrazol-4-yl)ethyl)amino)-N-(2-fluoro-6-methylphenyl)-5,6-dimethylpyrimidine-2-carboxamide;

4-((2-(1H-pyrazol-4-yl)ethyl)amino)-5,6-dimethyl-N-phenylpyrimidine-2-carboxamide;

4-((2-(1H-pyrazol-4-yl)ethyl)amino)-N-(2-(benzylsulfonyl)ethyl)-5,6-dimethylpyrimidine-2-carboxamide;

1-(4-((2-(1H-pyrazol-4-yl)ethyl)amino)-5,6-dimethylpyrimidine-2-carbonyl)spiro[azetidine-3,3'-indolin]-2'-one;

4-((2-(1H-pyrazol-4-yl)ethyl)amino)-5,6-dimethyl-N-(4,4,4-trifluoro-3,3-dimethylbutyl)pyrimidine-2-carboxamide;

4-((2-(1H-pyrazol-4-yl)ethyl)amino)-N-(3-fluoropyridin-4-yl)-5,6-dimethylpyrimidine-2-carboxamide;

4-((2-(1H-pyrazol-4-yl)ethyl)amino)-5,6-dimethyl-N-(1-(pyridin-2-yl)cyclobutyl)pyrimidine-2-carboxamide;

4-((2-(1H-pyrazol-4-yl)ethyl)amino)-N-(1-(6-fluoropyridin-2-yl)ethyl)-6,7-dihydro-5H-cyclopenta[d]pyrimidine-2-carboxamide;

4-((2-(1H-pyrazol-4-yl)ethyl)amino)-5-chloro-N-(1-(6-fluoropyridin-2-yl)ethyl)-6-methylpyrimidine-2-carboxamide;

(4-((2-(1H-pyrazol-4-yl)ethyl)amino)-5-chloro-6-methylpyrimidin-2-yl)(2-(3-fluorophenyl)pyrrolidin-1-yl)methanone;

4-((2-(1H-pyrazol-4-yl)ethyl)amino)-5-fluoro-N-(1-(6-fluoropyridin-2-yl)ethyl)-6-methylpyrimidine-2-carboxamide;

(4-((2-(1H-pyrazol-4-yl)ethyl)amino)-5-fluoro-6-methylpyrimidin-2-yl)(2-(3-fluorophenyl)pyrrolidin-1-yl)methanone;

6-((2-(1H-pyrazol-4-yl)ethyl)amino)-4-bromo-N-(1-(6-fluoropyridin-2-yl)ethyl)picolinamide;

and (6-((2-(1H-pyrazol-4-yl)ethyl)amino)-4-methylpyridin-2-yl)(2-(3-fluorophenyl)pyrrolidin-1-yl)methanone, or a stereoisomer or tautomer thereof, or a pharmaceutically acceptable salt of any of the foregoing.

In some embodiments, provided herein is a compound, or a stereoisomer or tautomer thereof, or a pharmaceutically acceptable salt of any of the foregoing, wherein the compound is selected from the group consisting of:

4-((2-(1H-pyrazol-4-yl)ethyl)(phenethyl)amino)-5,6-dimethylpyrimidine-2-carboxamide;

4-((2-(1H-pyrazol-4-yl)ethyl)(phenethyl)amino)-N,5,6-trimethylpyrimidine-2-carboxamide;

(4-((2-(1H-pyrazol-4-yl)ethyl)amino)-5,6-dimethylpyrimidin-2-yl)(3-(3-fluorophenyl)-3-hydroxyazetidin-1-yl)methanone;

4-((2-(1H-pyrazol-4-yl)ethyl)amino)-N-(1-(6-fluoropyridin-2-yl)ethyl)-5,6-dimethylpyrimidine-2-carboxamide;

4-((2-(1H-pyrazol-4-yl)ethyl)amino)-N-((3-fluorophenyl)(1-methyl-1H-imidazol-2-yl)methyl)-N,5,6-trimethylpyrimidine-2-carboxamide;

(4-(1H-indol-3-yl)piperidin-1-yl)(4-((2-(1H-pyrazol-4-yl)ethyl)amino)-5,6-dimethylpyrimidin-2-yl)methanone;

(4-((2-(1H-pyrazol-4-yl)ethyl)amino)-5,6-dimethylpyrimidin-2-yl)(3-(3-fluorophenyl) morpholino)methanone;

4-((2-(1H-pyrazol-4-yl)ethyl)amino)-5,6-dimethyl-N-(1-(thiophen-2-yl)ethyl)pyrimidine-2-carboxamide;

(4-(3-(1H-pyrazol-4-yl)pyrrolidin-1-yl)-5,6-dimethylpyrimidin-2-yl)(3-hydroxy-3-phenylazetidin-1-yl)methanone;

4-((2-(1H-pyrazol-4-yl)ethyl)amino)-N-(1-(3-fluorophenyl)ethyl)-5,6-dimethylpyrimidine-2-carboxamide;

4-((2-(1H-pyrazol-4-yl)ethyl)amino)-N-(2-(3-fluorophenyl)propan-2-yl)-5,6-dimethylpyrimidine-2-carboxamide;

(4-((2-(1H-pyrazol-4-yl)ethyl)amino)-5,6-dimethylpyrimidin-2-yl)(3-(3-chlorophenyl)morpholino)methanone;

(4-((2-(1H-pyrazol-4-yl)ethyl)amino)-5,6-dimethylpyrimidin-2-yl)(2-(3-chlorophenyl)pyrrolidin-1-yl)methanone;

4-((2-(1H-pyrazol-4-yl)ethyl)amino)-5,6-dimethyl-N-(1-(thiophen-2-yl)ethyl)pyrimidine-2-carboxamide;

(4-((2-(1H-pyrazol-4-yl)ethyl)amino)-5,6-dimethylpyrimidin-2-yl)(2-(3-fluorophenyl)pyrrolidin-1-yl)methanone;

(4-((2-(1H-pyrazol-4-yl)ethyl)amino)-5,6-dimethylpyrimidin-2-yl)(3-phenylmorpholino)methanone;

4-((2-(1H-pyrazol-4-yl)ethyl)amino)-5,6-dimethyl-N-(1-phenylethyl)pyrimidine-2-carboxamide;

(4-((2-(1H-pyrazol-4-yl)ethyl)amino)-5,6-dimethylpyrimidin-2-yl)(3-(3-fluorophenyl)azetidin-1-yl)methanone;

4-((2-(1H-pyrazol-4-yl)ethyl)amino)-5,6-dimethyl-N-(thiophen-2-ylmethyl)pyrimidine-2-carboxamide;

4-((2-(1H-pyrazol-4-yl)ethyl)amino)-N-((3-fluorophenyl)(1-methyl-1H-imidazol-2-yl)methyl)-,6-dimethylpyrimidine-2-carboxamide;

4-((2-(1H-pyrazol-4-yl)ethyl)amino)-5,6-dimethyl-N-(2-phenylpropan-2-yl)pyrimidine-2-carboxamide;

(4-((2-(1H-pyrazol-4-yl)ethyl)amino)-5,6-dimethylpyrimidin-2-yl)(3-hydroxy-3-phenylazetidin-1-yl)methanone;

4-((2-(1H-pyrazol-4-yl)ethyl)amino)-N-((3-fluorophenyl)(oxazol-2-yl)methyl)-5,6-dimethylpyrimidine-2-carboxamide;

(4-((2-(1H-pyrazol-4-yl)ethyl)amino)-5,6-dimethylpyrimidin-2-yl)(2-(3-fluorophenyl)piperazin-1-yl)methanone;

(4-((2-(1H-pyrazol-4-yl)ethyl)amino)-5,6-dimethylpyrimidin-2-yl)(3-methyl-3-phenylmorpholino)methanone;

4-((2-(1H-pyrazol-4-yl)ethyl)amino)-N-(1-(2-chlorophenyl)ethyl)-5,6-dimethylpyrimidine-2-carboxamide;

4-((2-(1H-pyrazol-4-yl)ethyl)amino)-N-(2-(3-fluorophenyl)-2-methylpropyl)-5,6-dimethylpyrimidine-2-carboxamide;

(4-((2-(1H-pyrazol-4-yl)ethyl)amino)-5,6-dimethylpyrimidin-2-yl)(4,4-difluoro-2-phenylpiperidin-1-yl)methanone;

4-((2-(1H-pyrazol-4-yl)ethyl)amino)-N-(1-(2-chlorophenyl)ethyl)-N,5,6-trimethylpyrimidine-2-carboxamide;

4-((2-(1H-pyrazol-4-yl)ethyl)amino)-N-(1-(3-chloropyridin-2-yl)ethyl)-5,6-dimethylpyrimidine-2-carboxamide;

4-((2-(1H-pyrazol-4-yl)ethyl)amino)-N-benzyl-5,6-dimethylpyrimidine-2-carboxamide;

4-((2-(1H-pyrazol-4-yl)ethyl)amino)-N-(3-fluoropenzyl)-5,6-dimethylpyrimidine-2-carboxamide;

4-((2-(1H-pyrazol-4-yl)ethyl)amino)-5,6-dimethyl-N-(2,2,2-trifluoro-1-phenylethyl)pyrimidine-2-carboxamide;

(4-((2-(1H-pyrazol-4-yl)ethyl)amino)-5,6-dimethylpyrimidin-2-yl)(4-hydroxy-4-phenylpiperidin-1-yl)methanone;
4-((2-(1H-pyrazol-4-yl)ethyl)amino)-5,6-dimethyl-N-(1-(thiophen-3-yl)ethyl)pyrimidine-2-carboxamide;
4-((2-(1H-pyrazol-4-yl)ethyl)amino)-N-(1-(6-chloropyridin-2-yl)ethyl)-5,6-dimethylpyrimidine-2-carboxamide;
4-((2-(1H-pyrazol-4-yl)ethyl)amino)-5,6-dimethyl-N-(1-(3-methylpyridin-2-yl)ethyl)pyrimidine-2-carboxamide;
(4-((2-(1H-pyrazol-4-yl)ethyl)amino)-5,6-dimethylpyrimidin-2-yl)(2-phenylpyrrolidin-1-yl)methanone;
4-((2-(1H-pyrazol-4-yl)ethyl)amino)-N-(1-(3-fluorophenyl)ethyl)-5,6-dimethylpyrimidine-2-carboxamide;
4-((2-(1H-pyrazol-4-yl)ethyl)amino)-5,6-dimethyl-N-((1-methyl-1H-imidazol-2-yl)(phenyl)methyl)pyrimidine-2-carboxamide;
4-((2-(1H-pyrazol-4-yl)ethyl)amino)-N-(1-(3-fluorophenyl)-2-methylpropan-2-yl)-5,6-dimethylpyrimidine-2-carboxamide;
(4-((2-(1H-pyrazol-4-yl)ethyl)amino)-5,6-dimethylpyrimidin-2-yl)(3-hydroxy-4-phenylpyrrolidin-1-yl)methanone;
4-((2-(1H-pyrazol-4-yl)ethyl)amino)-N-(1-(6-methoxypyridin-2-yl)ethyl)-5,6-dimethylpyrimidine-2-carboxamide;
(4-((2-(1H-pyrazol-4-yl)ethyl)amino)-5,6-dimethylpyrimidin-2-yl)(4-methyl-2-phenylpiperazin-1-yl)methanone;
4-(4-((2-(1H-pyrazol-4-yl)ethyl)amino)-5,6-dimethylpyrimidine-2-carbonyl)-1-benzylpiperazin-2-one;
4-((2-(1H-pyrazol-4-yl)ethyl)amino)-N-((3-fluorophenyl)(pyridin-2-yl)methyl)-5,6-dimethylpyrimidine-2-carboxamide;
4-((2-(1H-pyrazol-4-yl)ethyl)amino)-5,6-dimethyl-N-(1-(pyridin-2-yl)ethyl)pyrimidine-2-carboxamide;
(4-((2-(1H-pyrazol-4-yl)ethyl)amino)-5,6-dimethylpyrimidin-2-yl)(3-hydroxy-3-(trifluoromethyl)azetidin-1-yl)methanone;
4-((2-(1H-pyrazol-4-yl)ethyl)amino)-N-(1-(3-fluorophenyl)-2-methoxyethyl)-5,6-dimethylpyrimidine-2-carboxamide;
4-((2-(1H-pyrazol-4-yl)ethyl)amino)-5,6-dimethyl-N-phenethylpyrimidine-2-carboxamide;
(4-((2-(1H-pyrazol-4-yl)ethyl)amino)-5,6-dimethylpyrimidin-2-yl)(3-(2,3-difluorophenyl)-3-hydroxyazetidin-1-yl)methanone;
(4-((2-(1H-pyrazol-4-yl)ethyl)amino)-5,6-dimethylpyrimidin-2-yl)(3-phenylpyrrolidin-1-yl)methanone;
4-((2-(1H-pyrazol-4-yl)ethyl)amino)-N-(1-(2-chlorophenyl)ethyl)-N,5,6-trimethylpyrimidine-2-carboxamide;
(4-((2-(1H-pyrazol-4-yl)ethyl)amino)-5,6-dimethylpyrimidin-2-yl)(2-(2-fluorophenyl)pyrrolidin-1-yl)methanone;
4-((2-(1H-pyrazol-4-yl)ethyl)amino)-N-((6-fluoropyridin-2-yl)methyl)-5,6-dimethylpyrimidine-2-carboxamide;
4-((2-(1H-pyrazol-4-yl)ethyl)amino)-N-(1-(3-fluoropyridin-2-yl)ethyl)-5,6-dimethylpyrimidine-2-carboxamide;
4-((2-(1H-pyrazol-4-yl)ethyl)amino)-N-((1-benzoylazetidin-3-yl)methyl)-5,6-dimethylpyrimidine-2-carboxamide;
4-((2-(1H-pyrazol-4-yl)ethyl)amino)-N-(benzofuran-3-ylmethyl)-5,6-dimethylpyrimidine-2-carboxamide;
4-((2-(1H-pyrazol-4-yl)ethyl)amino)-5,6-dimethyl-N-(1-phenylethyl)pyrimidine-2-carboxamide;
(4-((2-(1H-pyrazol-4-yl)ethyl)amino)-5,6-dimethylpyrimidin-2-yl)(3-benzyl-3-hydroxyazetidin-1-yl)methanone;
(4-((2-(1H-pyrazol-4-yl)ethyl)amino)-5,6-dimethylpyrimidin-2-yl)(3-phenylpyrrolidin-1-yl)methanone;
(4-((2-(1H-pyrazol-4-yl)ethyl)amino)-5,6-dimethylpyrimidin-2-yl)(2-methyl-5-phenylmorpholino)methanone;
(4-((2-(1H-pyrazol-4-yl)ethyl)amino)-5,6-dimethylpyrimidin-2-yl)(3-phenylmorpholino)methanone;
(4-((2-(1H-pyrazol-4-yl)ethyl)amino)-5,6-dimethylpyrimidin-2-yl)(3-benzylmorpholino)methanone;
4-((2-(1H-pyrazol-4-yl)ethyl)amino)-N-(1-(benzofuran-3-yl)ethyl)-5,6-dimethylpyrimidine-2-carboxamide;
(4-((2-(1H-pyrazol-4-yl)ethyl)amino)-5,6-dimethylpyrimidin-2-yl)(3-(2-fluorophenyl)pyrrolidin-1-yl)methanone;
(4-((2-(1H-pyrazol-4-yl)ethyl)amino)-5,6-dimethylpyrimidin-2-yl)(3-(4-fluorophenyl) morpholino)methanone;
4-((2-(1H-pyrazol-4-yl)ethyl)amino)-N-(1-(6-methoxypyridin-2-yl)ethyl)-5,6-dimethylpyrimidine-2-carboxamide;
4-((2-(1H-pyrazol-4-yl)ethyl)amino)-5,6-dimethyl-N-(2-(pyridin-2-yl)propan-2-yl)pyrimidine-2-carboxamide;
4-((2-(1H-pyrazol-4-yl)ethyl)amino)-N-(1-(5-chlorothiophen-2-yl)ethyl)-5,6-dimethylpyrimidine-2-carboxamide;
(4-((2-(1H-pyrazol-4-yl)ethyl)amino)-5,6-dimethylpyrimidin-2-yl)(2-benzylpyrrolidin-1-yl)methanone;
(4-((2-(1H-pyrazol-4-yl)ethyl)amino)-5,6-dimethylpyrimidin-2-yl)(3-benzylmorpholino)methanone;
4-((2-(1H-pyrazol-4-yl)ethyl)amino)-N-(1-(6-fluoropyridin-2-yl)ethyl)-5,6-dimethylpyrimidine-2-carboxamide;
4-((2-(1H-pyrazol-4-yl)ethyl)amino)-N-((3-(3-fluorophenyl)oxetan-3-yl)methyl)-5,6-dimethylpyrimidine-2-carboxamide;
4-((2-(1H-pyrazol-4-yl)ethyl)amino)-N-(1-(furan-2-yl)ethyl)-5,6-dimethylpyrimidine-2-carboxamide;
(4-((2-(1H-pyrazol-4-yl)ethyl)amino)-5,6-dimethylpyrimidin-2-yl)(3-phenylazetidin-1-yl)methanone;
(4-((2-(1H-pyrazol-4-yl)ethyl)amino)-5,6-dimethylpyrimidin-2-yl)(3-(2-fluorophenyl)-3-hydroxyazetidin-1-yl)methanone;
4-((2-(1H-pyrazol-4-yl)ethyl)amino)-5,6-dimethyl-N-(1-(6-methylpyridin-2-yl)ethyl)pyrimidine-2-carboxamide;
4-((2-(1H-pyrazol-4-yl)ethyl)amino)-N-(3,3-difluoro-2,3-dihydro-1H-inden-1-yl)-5,6-dimethylpyrimidine-2-carboxamide;
(4-((2-(1H-pyrazol-4-yl)ethyl)amino)-5,6-dimethylpyrimidin-2-yl)(3-(2-chlorophenyl)morpholino)methanone;
(4-((2-(1H-pyrazol-4-yl)ethyl)amino)-5,6-dimethylpyrimidin-2-yl)(3-(trifluoromethoxy)azetidin-1-yl)methanone;
4-((2-(1H-pyrazol-4-yl)ethyl)amino)-N-(1-(3-fluorophenyl)-2-methoxyethyl)-5,6-dimethylpyrimidine-2-carboxamide;
4-((2-(1H-pyrazol-4-yl)ethyl)amino)-N-(2-(4-fluorophenyl)propan-2-yl)-5,6-dimethylpyrimidine-2-carboxamide;
(4-((2-(1H-pyrazol-4-yl)ethyl)amino)-5,6-dimethylpyrimidin-2-yl)(3-(hydroxymethyl)-3-phenylazetidin-1-yl)methanone;
4-((2-(1H-pyrazol-4-yl)ethyl)amino)-N-(4-(2-chloro-4-fluoropenzyl)tetrahydro-2H-pyran-4-yl)-5,6-dimethylpyrimidine-2-carboxamide;
(4-((2-(1H-pyrazol-4-yl)ethyl)amino)-5,6-dimethylpyrimidin-2-yl)(2-(4-fluorophenyl)pyrrolidin-1-yl)methanone;
4-((2-(1H-pyrazol-4-yl)ethyl)amino)-5,6-dimethyl-N-(1-(pyridin-4-yl)ethyl)pyrimidine-2-carboxamide;
4-((2-(1H-pyrazol-4-yl)ethyl)amino)-N-((6-methoxypyridin-2-yl)methyl)-5,6-dimethylpyrimidine-2-carboxamide;
(4-((2-(1H-pyrazol-4-yl)ethyl)amino)-5,6-dimethylpyrimidin-2-yl)(3-methyl-3-phenylazetidin-1-yl)methanone;
4-((2-(1H-pyrazol-4-yl)ethyl)amino)-N-(1-(isoxazol-3-yl)ethyl)-5,6-dimethylpyrimidine-2-carboxamide;
(4-((2-(1H-pyrazol-4-yl)ethyl)amino)-5,6-dimethylpyrimidin-2-yl)(3,3-difluoroazetidin-1-yl)methanone;
4-((2-(1H-pyrazol-4-yl)ethyl)amino)-N-(1-(4-fluorophenyl)-2-methoxyethyl)-N,5,6-trimethylpyrimidine-2-carboxamide;

4-((2-(1H-pyrazol-4-yl)ethyl)amino)-5,6-dimethyl-N-(pyridin-2-ylmethyl)pyrimidine-2-carboxamide;
4-((2-(1H-pyrazol-4-yl)ethyl)amino)-5,6-dimethyl-N-((3-phenyloxetan-3-yl)methyl)pyrimidine-2-carboxamide;
4-((2-(1H-pyrazol-4-yl)ethyl)amino)-5,6-dimethyl-N-(1-(pyridin-4-yl)ethyl)pyrimidine-2-carboxamide;
1-(4-((2-(1H-pyrazol-4-yl)ethyl)amino)-5,6-dimethylpyrimidine-2-carbonyl)-4-phenylpiperidine-4-carbonitrile;
(4-((2-(1H-pyrazol-4-yl)ethyl)amino)-5,6-dimethylpyrimidin-2-yl)(3-cyclopropyl-3-hydroxyazetidin-1-yl)methanone;
4-((2-(1H-pyrazol-4-yl)ethyl)amino)-N-((2-fluorophenyl)(1-methyl-1H-imidazol-2-yl)methyl)-,6-dimethylpyrimidine-2-carboxamide;
4-((2-(1H-pyrazol-4-yl)ethyl)amino)-N-(1-(2-chlorophenyl)ethyl)-5,6-dimethylpyrimidine-2-carboxamide;
(4-((2-(1H-pyrazol-4-yl)ethyl)amino)-5,6-dimethylpyrimidin-2-yl)(3-(trifluoromethyl)azetidin-1-yl)methanone;
4-((2-(1H-pyrazol-4-yl)ethyl)amino)-5,6-dimethyl-N-(1-(5-methylfuran-2-yl)ethyl)pyrimidine-2-carboxamide;
(4-((2-(1H-pyrazol-4-yl)ethyl)amino)-5,6-dimethylpyrimidin-2-yl)(3-methoxy-3-phenylazetidin-1-yl)methanone;
4-((2-(1H-pyrazol-4-yl)ethyl)amino)-5,6-dimethyl-N-(1-(thiazol-5-yl)ethyl)pyrimidine-2-carboxamide;
4-((2-(1H-pyrazol-4-yl)ethyl)amino)-N-(2-hydroxy-2-phenylpropyl)-5,6-dimethylpyrimidine-2-carboxamide;
N-((1H-indazol-3-yl)methyl)-4-((2-(1H-pyrazol-4-yl)ethyl)amino)-5,6-dimethylpyrimidine-2-carboxamide;
4-((2-(1H-pyrazol-4-yl)ethyl)(propyl)amino)-5,6-dimethylpyrimidine-2-carboxamide;
(4-((2-(1H-pyrazol-4-yl)ethyl)amino)-5,6-dimethylpyrimidin-2-yl)(3-ethyl-3-hydroxyazetidin-1-yl)methanone;
4-((2-(1H-pyrazol-4-yl)ethyl)amino)-5,6-dimethyl-N-(1-(oxazol-2-yl)ethyl)pyrimidine-2-carboxamide;
4-((2-(1H-pyrazol-4-yl)ethyl)amino)-N-(1-(5-fluoropyridin-3-yl)ethyl)-5,6-dimethylpyrimidine-2-carboxamide;
4-((2-(1H-pyrazol-4-yl)ethyl)amino)-N-(1-(3-fluoropyridin-4-yl)ethyl)-5,6-dimethylpyrimidine-2-carboxamide;
4-((2-(1H-pyrazol-4-yl)ethyl)amino)-N-(2,2-difluoro-2-phenylethyl)-5,6-dimethylpyrimidine-2-carboxamide;
4-((2-(1H-pyrazol-4-yl)ethyl)amino)-N-(1-(benzofuran-2-yl)ethyl)-5,6-dimethylpyrimidine-2-carboxamide;
4-((2-(1H-pyrazol-4-yl)ethyl)amino)-N-(2-(3-fluoropyridin-4-yl)ethyl)-5,6-dimethylpyrimidine-2-carboxamide;
4-((2-(1H-pyrazol-4-yl)ethyl)amino)-5,6-dimethyl-N-(3-phenyloxetan-3-yl)pyrimidine-2-carboxamide;
(4-((2-(1H-pyrazol-4-yl)ethyl)amino)-5,6-dimethylpyrimidin-2-yl)(2-(3-fluorophenyl)azetidin-1-yl)methanone;
4-((2-(1H-pyrazol-4-yl)ethyl)amino)-N-(1-cyclohexylethyl)-5,6-dimethylpyrimidine-2-carboxamide;
4-((2-(1H-pyrazol-4-yl)ethyl)amino)-N-(3,5-difluorophenyl)-5,6-dimethylpyrimidine-2-carboxamide;
4-((2-(1H-pyrazol-4-yl)ethyl)amino)-N-(1-(5-fluoropyridin-2-yl)ethyl)-5,6-dimethylpyrimidine-2-carboxamide;
(4-((2-(1H-pyrazol-4-yl)ethyl)amino)-5,6-dimethylpyrimidin-2-yl)(4-(trifluoromethyl)piperidin-1-yl)methanone;
4-((2-(1H-pyrazol-4-yl)ethyl)amino)-N-((3-fluoropyridin-2-yl)methyl)-5,6-dimethylpyrimidine-2-carboxamide;
4-((2-(1H-pyrazol-4-yl)ethyl)amino)-5,6-dimethyl-N-(2-(pyridin-3-yl)propan-2-yl)pyrimidine-2-carboxamide;
4-((2-(1H-pyrazol-4-yl)ethyl)amino)-5,6-dimethyl-N-(3,3,3-trifluoro-2-hydroxy-2-phenylpropyl)pyrimidine-2-carboxamide;
(4-((2-(1H-pyrazol-4-yl)ethyl)amino)-5,6-dimethylpyrimidin-2-yl)(2-azaspiro[3.3]heptan-2-yl)methanone;
4-((2-(1H-pyrazol-4-yl)ethyl)amino)-N-(1-(3-methoxypyridin-2-yl)ethyl)-5,6-dimethylpyrimidine-2-carboxamide;
(4-((2-(1H-pyrazol-4-yl)ethyl)amino)-5,6-dimethylpyrimidin-2-yl)(3-hydroxy-3-methylazetidin-1-yl)methanone;
(4-((2-(1H-pyrazol-4-yl)ethyl)amino)-5,6-dimethylpyrimidin-2-yl)(2-(pyridin-2-yl)pyrrolidin-1-yl)methanone;
4-((2-(1H-pyrazol-4-yl)ethyl)amino)-5,6-dimethyl-N-(1-(pyridin-3-yl)ethyl)pyrimidine-2-carboxamide;
4-((2-(1H-pyrazol-4-yl)ethyl)amino)-5,6-dimethyl-N-(3,3,3-trifluoro-2-hydroxypropyl)pyrimidine-2-carboxamide;
4-((2-(1H-pyrazol-4-yl)ethyl)amino)-N-(2-(5-fluoropyridin-3-yl)ethyl)-5,6-dimethylpyrimidine-2-carboxamide;
4-((2-(1H-pyrazol-4-yl)ethyl)amino)-5,6-dimethyl-N-(1-(5-methylthiophen-2-yl)ethyl)pyrimidine-2-carboxamide;
(4-((2-(1H-pyrazol-4-yl)ethyl)amino)-5,6-dimethylpyrimidin-2-yl)(2-(6-methylpyridin-2-yl)pyrrolidin-1-yl)methanone;
(4-((2-(1H-pyrazol-4-yl)ethyl)amino)-5,6-dimethylpyrimidin-2-yl)(2-phenylazetidin-1-yl)methanone;
4-((2-(1H-pyrazol-4-yl)ethyl)amino)-5,6-dimethyl-N-(pyridin-4-ylmethyl)pyrimidine-2-carboxamide;
4-((2-(1H-pyrazol-4-yl)ethyl)amino)-N-((3,4-difluorophenyl)(1-methyl-1H-imidazol-2-yl)methyl)-5,6-dimethylpyrimidine-2-carboxamide;
4-((2-(1H-pyrazol-4-yl)ethyl)amino)-5,6-dimethyl-N-(3-phenylcyclobutyl)pyrimidine-2-carboxamide;
4-((2-(1H-pyrazol-4-yl)ethyl)amino)-5,6-dimethyl-N-(2,2,2-trifluoro-1-(pyridin-3-yl)ethyl)pyrimidine-2-carboxamide;
4-((2-(1H-pyrazol-4-yl)ethyl)amino)-5,6-dimethyl-N-(1-(pyridin-2-yl)ethyl)pyrimidine-2-carboxamide;
(4-((2-(1H-pyrazol-4-yl)ethyl)amino)-5,6-dimethylpyrimidin-2-yl)(3-(trifluoromethyl)morpholino)methanone;
4-((2-(1H-pyrazol-4-yl)ethyl)amino)-N-(2-fluoro-6-methylphenyl)-5,6-dimethylpyrimidine-2-carboxamide;
4-((2-(1H-pyrazol-4-yl)ethyl)amino)-5,6-dimethyl-N-phenylpyrimidine-2-carboxamide;
4-((2-(1H-pyrazol-4-yl)ethyl)amino)-N-(2-(benzylsulfonyl)ethyl)-5,6-dimethylpyrimidine-2-carboxamide;
1-(4-((2-(1H-pyrazol-4-yl)ethyl)amino)-5,6-dimethylpyrimidine-2-carbonyl)spiro[azetidine-3,3'-indolin]-2'-one;
4-((2-(1H-pyrazol-4-yl)ethyl)amino)-5,6-dimethyl-N-(4,4,4-trifluoro-3,3-dimethylbutyl)pyrimidine-2-carboxamide;
4-((2-(1H-pyrazol-4-yl)ethyl)amino)-N-(3-fluoropyridin-4-yl)-5,6-dimethylpyrimidine-2-carboxamide; and
4-((2-(1H-pyrazol-4-yl)ethyl)amino)-5,6-dimethyl-N-(1-(pyridin-2-yl)cyclobutyl)pyrimidine-2-carboxamide, or a stereoisomer or tautomer thereof, or a pharmaceutically acceptable salt of any of the foregoing.

In some variations, any of the compounds described herein, such as a compound of formula (A), or any variation thereof, such as a compound of formula (I), (I-A), (I-A1), (I-A2), (I-A3), (I-B), (I-B1), (II), (II-A), or (II-A1), or a compound of Table 1 may be deuterated (e.g., a hydrogen atom is replaced by a deuterium atom). In some variations, any of the compounds described herein, such as a compound of formula (I), or any variation thereof, or a compound of Table 1 may be deuterated (e.g., a hydrogen atom is replaced by a deuterium atom). In some of these variations, the compound is deuterated at a single site. In other variations, the compound is deuterated at multiple sites. Deuterated compounds can be prepared from deuterated starting materials in a manner similar to the preparation of the corresponding non-deuterated compounds. Hydrogen atoms may also be replaced with deuterium atoms using other method known in the art.

Any formula given herein, such as formula (A), or formula (I), (I-A), (I-A1), (I-A2), (I-A3), (I-B), (I-B1), (II), (II-A), or (II-A1), is intended to represent compounds having structures depicted by the structural formula as well as certain variations or forms. Any formula given herein, such as formula (I), or formula (I-A), (I-A1), (I-B), or (I-B1), is intended to represent compounds having structures depicted by the structural formula as well as certain variations or forms. In particular, compounds of any formula given herein may have asymmetric centers and therefore exist in different enantiomeric or diastereomeric forms. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms, and mixtures thereof in any ratio. Where a compound of Table 1 is depicted with a particular stereochemical configuration, also provided herein is any alternative stereochemical configuration of the compound, as well as a mixture of stereoisomers of the compound in any ratio. For example, where a compound of Table 1 has a stereocenter that is in an "S" stereochemical configuration, also provided herein is enantiomer of the compound wherein that stereocenter is in an "R" stereochemical configuration. Likewise, when a compound of Table 1 has a stereocenter that is in an "R" configuration, also provided herein is enantiomer of the compound in an "S" stereochemical configuration. Also provided are mixtures of the compound with both the "S" and the "R" stereochemical configuration. Additionally, if a compound of Table 1 has two or more stereocenters, also provided are any enantiomer or diastereomer of the compound. For example, if a compound of Table 1 contains a first stereocenter and a second stereocenter with "R" and "R" stereochemical configurations, respectively, also provided are stereoisomers of the compound having first and second stereocenters with "S" and "S" stereochemical configurations, respectively, "S" and "R" stereochemical configurations, respectively, and "R" and "S" stereochemical configurations, respectively. If a compound of Table 1 contains a first stereocenter and a second stereocenter with "S" and "S" stereochemical configurations, respectively, also provided are stereoisomers of the compound having first and second stereocenters with "R" and "R" stereochemical configurations, respectively, "S" and "R" stereochemical configurations, respectively, and "R" and "S" stereochemical configurations, respectively. If a compound of Table 1 contains a first stereocenter and a second stereocenter with "S" and "R" stereochemical configurations, respectively, also provided are stereoisomers of the compound having first and second stereocenters with "R" and "S" stereochemical configurations, respectively, "R" and "R" stereochemical configurations, respectively, and "S" and "S" stereochemical configurations, respectively. Similarly, if a compound of Table 1 contains a first stereocenter and a second stereocenter with "R" and "S" stereochemical configurations, respectively, also provided are stereoisomers of the compound having first and second stereocenters with "S" and "R" stereochemical configurations, respectively, "R" and "R" stereochemical configurations, respectively, and "S" and "S" stereochemical configurations, respectively. Furthermore, certain structures may exist as geometric isomers (i.e., cis and trans isomers), as tautomers, or as atropisomers. Additionally, any formula given herein is intended to refer also to any one of hydrates, solvates, and amorphous and polymorphic forms of such compounds, and mixtures thereof, even if such forms are not listed explicitly. In some embodiments, the solvent is water and the solvates are hydrates.

Representative examples of compounds detailed herein, including intermediates and final compounds, are depicted in the tables and elsewhere herein. It is understood that in one aspect, any of the compounds may be used in the methods detailed herein, including, where applicable, intermediate compounds that may be isolated and administered to an individual or subject.

The compounds depicted herein may be present as salts even if salts are not depicted, and it is understood that the compositions and methods provided herein embrace all salts and solvates of the compounds depicted here, as well as the non-salt and non-solvate form of the compound, as is well understood by the skilled artisan. In some embodiments, the salts of the compounds provided herein are pharmaceutically acceptable salts.

In one variation, the compounds herein are synthetic compounds prepared for administration to an individual or subject. In another variation, compositions are provided containing a compound in substantially pure form. In another variation, provided are pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Any variation or embodiment of $R^1$, $R^2$, $R^3$, $R^4$, $R^y$, $R^z$, $R^m$, $R^n$, $R^p$, $R^p$, and $R^s$ is provided herein can be combined with every other variation or embodiment of $R^1$, $R^2$, $R^3$, $R^4$, $R^y$, $R^z$, $R^m$, $R^n$, $R^p$, $R^q$, and $R^s$, the same as if each combination had been individually and specifically described.

Other embodiments will be apparent to those skilled in the art from the following detailed description.

As used herein, when any variable occurs more than one time in a chemical formula, its definition on each occurrence is independent of its definition at every other occurrence.

Formula (A) includes all subformulae thereof. Formula (I) includes all subformulae thereof. Formula (II) includes all subformulae thereof.

The compound names provided herein, including in Table 1, are provided by ChemBioDraw Professional 15.0. One of skilled in the art would understand that the compounds may be named or identified using various commonly recognized nomenclature systems and symbols. By way of example, the compounds may be named or identified with common names, systematic or non-systematic names. The nomenclature systems and symbols that are commonly recognized in the art of chemistry include, for example, Chemical Abstract Service (CAS), ChemBioDraw Ultra, and International Union of Pure and Applied Chemistry (IUPAC).

Compositions

Also provided are compositions, such as pharmaceutical compositions, that include a compound disclosed and/or described herein and one or more additional medicinal agents, pharmaceutical agents, adjuvants, carriers, excipients, and the like. Suitable medicinal and pharmaceutical agents include those described herein. In some embodiments, the pharmaceutical composition includes a pharmaceutically acceptable excipient or adjuvant and at least one chemical entity as described herein. Examples of pharmaceutically acceptable excipients include, but are not limited to, mannitol, lactose, starch, magnesium stearate, sodium saccharine, talcum, cellulose, sodium crosscarmellose, glucose, gelatin, sucrose, and magnesium carbonate. In some embodiments, provided are compositions, such as pharmaceutical compositions that contain one or more compounds described herein, or a pharmaceutically acceptable salt thereof.

In some embodiments, provided is a pharmaceutically acceptable composition comprising a compound of formula (A), or formula (I), (I-A), (I-A1), (I-A2), (I-A3), (I-B), (I-B1), (II), (II-A), or (II-A1), or a compound of Table 1, or a pharmaceutically acceptable salt thereof. In some aspects, a composition may contain a synthetic intermediate that may be used in the preparation of a compound described herein. In some embodiments, provided is a pharmaceutically acceptable composition comprising a compound of formula (I), or a compound of formula (I-A), (I-A1), (I-B), or (I-B1), or a compound of Table 1, or a pharmaceutically acceptable salt thereof. In some aspects, a composition may contain a synthetic intermediate that may be used in the preparation of a compound described herein. The compositions described herein may contain any other suitable active or inactive agents.

Any of the compositions described herein may be sterile or contain components that are sterile. Sterilization can be achieved by methods known in the art. Any of the compositions described herein may contain one or more compounds or conjugates that are substantially pure.

Also provided are packaged pharmaceutical compositions, comprising a pharmaceutical composition as described herein and instructions for using the composition to treat a patient suffering from a disease or condition described herein.

Methods of Use

Compounds and compositions detailed herein, such as a pharmaceutical composition comprising a compound of any formula provided herein, or a pharmaceutically acceptable salt thereof, and a pharmaceutically acceptable carrier or excipient, may be used in methods of administration and treatment as provided herein.

Without being bound by theory, the compounds and pharmaceutical compositions disclosed herein are believed to act by modulating nicotinamide phosphoribosyltransferase (NAMPT). In some embodiments, the compounds and pharmaceutical compositions disclosed herein are activators of NAMPT. In some embodiments, provided are methods of treating a disease or condition mediated by NAMPT activity in an individual or subject, comprising administering to the individual or subject in need thereof a compound of formula (A), (I), (I-A), (I-A1), (I-A2), (I-A3), (I-B), (I-B1), (II), (II-A), or (II-A1), such as a compound of Table 1, or a pharmaceutically acceptable salt thereof. In some embodiments, provided are methods of treating a disease or condition mediated by NAMPT activity in an individual or subject, comprising administering to the individual or subject in need thereof a compound of formula (I), (I-A), (I-A1), (I-B), or (I-B1), or a compound of Table 1, or a pharmaceutically acceptable salt thereof. In some embodiments, provided are methods of treating cancer, a hyperproliferative disease or condition, an inflammatory disease or condition, a metabolic disorder, a cardiac disease or condition, chemotherapy induced tissue damage, a renal disease, a metabolic disease, a neurological disease or injury, a neurodegenerative disorder or disease, diseases caused by impaired stem cell function, diseases caused by DNA damage, primary mitochondrial disorders, or a muscule disease or muscle wasting disorder in an individual or subject, comprising administering to the individual or subject in need thereof a compound of formula (A), (I), (I-A), (I-A1), (I-A2), (I-A3), (I-B), (I-B1), (II), (II-A), or (II-A1), such as a compound of Table 1, or a pharmaceutically acceptable salt thereof. In some embodiments, provided are methods of treating cancer, a hyperproliferative disease or condition, an inflammatory disease or condition, a metabolic disorder, a cardiac disease or condition, chemotherapy induced tissue damage, a renal disease, a metabolic disease, a neurological disease or injury, a neurodegenerative disorder or disease, diseases caused by impaired stem cell function, diseases caused by DNA damage, primary mitochondrial disorders, or a muscule disease or muscle wasting disorder in an individual or subject, comprising administering to the individual or subject in need thereof a compound of formula (I), (I-A), (I-A1), (I-B), or (I-B1), or a compound of Table 1, or a pharmaceutically acceptable salt thereof.

Also provided herein is the use of a compound of formula (A), (I), (I-A), (I-A1), (I-A2), (I-A3), (I-B), (I-B1), (II), (II-A), or (II-A1), such as a compound of Table 1, or a pharmaceutically acceptable salt thereof in the manufacture of a medicament for treatment of a disease or condition mediated by NAMPT activity in a subject. In some aspects, provided is a compound or composition as described herein for use in a method of treatment of the human or animal body by therapy. Also provided herein is the use of a compound of formula (I), (I-A), (I-A1), (I-B), or (I-B1), or a compound of Table 1, or a pharmaceutically acceptable salt thereof in the manufacture of a medicament for treatment of a disease or condition mediated by NAMPT activity in a subject. In some aspects, provided is a compound or composition as described herein for use in a method of treatment of the human or animal body by therapy. In some embodiments, provided herein are compounds of formula (A), (I), (I-A), (I-A1), (I-A2), (I-A3), (I-B), (I-B1), (II), (II-A), or (II-A1), such as a compound of Table 1, or a pharmaceutically acceptable salt thereof, for use in a method of treatment of the human or animal body by therapy. In some embodiments, provided herein are compounds of formula (I), (I-A), (I-A1), (I-B), or (I-B1), or a compound of Table 1, or a pharmaceutically acceptable salt thereof, for use in a method of treatment of the human or animal body by therapy. In some embodiments, provided herein are compounds of formula (A), (I), (I-A), (I-A1), (I-A2), (I-A3), (I-B), (I-B1), (II), (II-A), or (II-A1), such as a compound of Table 1, or a pharmaceutically acceptable salt thereof, for use in treating a disease or condition mediated by NAMPT activity. In some embodiments, provided herein are compounds of formula (I), (I-A), (I-A1), (I-B), or (I-B1), or a compound of Table 1, or a pharmaceutically acceptable salt thereof, for use in treating a disease or condition mediated by NAMPT activity. In some embodiments, the disease or condition is selected from the group consisting of cancer, a hyperproliferative disease or condition, an inflammatory disease or condition, a metabolic disorder, a cardiac disease or condition, chemotherapy induced tissue damage, a renal disease, a metabolic disease, a neurological disease or injury, a neurodegenerative disorder or disease, diseases caused by impaired stem cell function, diseases caused by DNA damage, primary mitochondrial disorders, or a muscule disease or muscle wasting disorder.

Also provided herein are compositions (including pharmaceutical compositions) as described herein for the use in treating, preventing, and/or delaying the onset and/or development of a disease described herein and other methods described herein. In certain embodiments, the composition comprises a pharmaceutical formulation which is present in a unit dosage form.

In some embodiments, the subject is a mammal. In some embodiments, the subject is a mouse, rat, dog, cat, rabbit, pig, sheep, horse, cow, or human. In some embodiments, the subject is a human.

There are numerous conditions in which small molecule-mediated stimulation of NAMPT activity that boosts NAD+ levels would potentially be clinically beneficial (Stromland et al., *Biochem Soc Trans.* 2019, 47(1):119-130; Ralto et al., *Nat Rev Nephrol.* 2019; Fang et al., *Trends Mol Med.* 2017, 23(10):899-916; Yoshino et al., *Cell Metab.* 2011, 14(4): 528-36; Yang and Sauve, *Biochim Biophys Acta.* 2016, 1864:1787-1800; Verdin, *Science.* 2015, 350(6265):1208-13). These conditions include, but are not limited to, cardiac diseases, chemotherapy induced tissue damage, renal diseases, metabolic diseases, muscular diseases, neurological diseases and injuries, diseases caused by impaired stem cell function, and DNA damage and primary mitochondrial disorders. In some embodiments, the disease or condition mediated by NAMPT activity is a cardiac disease, chemotherapy induced tissue damage, a renal disease, a metabolic disease, a muscular disease, a neurological disease or injury, a disease caused by impaired stem cell function, or DNA damage and primary mitochondrial disorder.

Cardiac diseases. In various preclinical models of heart failure NAD as well as NAMPT levels are decreased. In these models, cardiac function can be rescued, either by restoring NAD via oral supplementation or overexpression of NAMPT (Diguet et al, *Circulation.* 2018, 137:2256-2273; Zheng et al., *Clin Sci* (*Lond*). 2019, 133(13):1505-1521; Smyrnias et al., *J Am Coll Cardiol.* 2019, 73(14):1795-1806). Thus, increasing the catalytic efficiency of NAMPT with a small molecule activator to compensate for the decreased protein levels is a promising strategy to treat various forms of heart failure.

Chemotherapy induced tissue damage. Use of chemotherapy regimens frequently is limited by toxicity to healthy tissues and severe oxidative stress is thought to play a major role. NAD boosting has been shown to trigger a strong anti-oxidant response. Therefore, NAMPT activators are considered broadly useful in various settings of chemotherapy to prevent reversible and irreversible secondary pathologies. Examples are anthracycline and trastuzumab cardiotoxicity, cisplatin induced kidney injury, peripheral neuropathies induced by cisplatin, paclitaxel, vincristine and other agents. Neuroprotection by NAMPT activation is also useful in treating/preventing chemotherapy associated cognitive ("chemo brain"), which is caused by destruction of healthy nerve tissue, both during active treatment and long after treatment has been halted. For instance, see Zheng et al., *Clin Sci* (*Lond*). 2019, 133(13):1505-1521.

Renal diseases. Renal diseases are highly prevalent and an area of urgent unmet medical need. In approximately 3% of hospitalized patients, acute kidney injury (AKI) is diagnosed. A subset of patients will progress to chronic kidney disease that may require long term dialysis or kidney transplantation. A key feature of kidney dysfunction is a decrease in the activities of SIRT1 and SIRT3, characterized by a reduction of the sirtuin substrate NAD, primarily due to impairment of de novo NAD+ synthesis. NAMPT is robustly expressed during kidney injury, thus small molecule activation with NAMPT is considered an effective measure to prevent AKI. Similarly, kidney mesangial cell hypertrophy exhibits depletion of NAD+, and restoration of intracellular NAD+ levels is considered efficacious. For instance, see Poyan Mehr et al., *Nat Med.* 2018, September; 24(9): 1351-9.

Metabolic disease. NAD+ boosting improves insulin sensitivity, dyslipidemia, mitochondrial function in metabolic disease and protects from/improves non-alcoholic and alcoholic steatohepatitis in preclinical models. More than 3 million people per year in the U.S. alone are diagnosed with non-alcoholic steatohepatitis and it is one of the leading causes of liver transplantation. See Guarino and Dufour, *Metabolites.* 2019, Sep. 10; 9(9), pii: E180; Yoshino et al., *Cell Metab.* 2011, 14(4):528-36.

Muscular diseases. Preclinical data has suggested that NAD+ boosting strategies could alleviate skeletal muscle dysfunction in a number of conditions, including Duchenne's muscular dystrophy, and age-related sarcopenia. See Zhang et al., *Clin Sci* (*Lond*). 2019, 133(13):1505-1521; Mohamed et al., *Aging* (*Albany NY*). 2014, 6(10):820-34; Ryu et al., *Sci Transl Med.* 2016, 8(361):361ra139.

Neurological diseases and injuries. Repletion of NAD by means of NAMPT activation is neuroprotective and of therapeutic benefit in a wide range of preclinical models of neurological diseases and injuries, including age-related cognitive decline, glaucoma, ischemic stroke, and ALS. See Johnson et al., *NPJ Aging Mech Dis.* 2018, 4:10; Harlan et al., *J Biol Chem.* 2016, 291(20):10836-46; Zhao et al., *Stroke.* 2015, July; 46(7):1966-74; Williams et al., *Front Neurosci.* 2017, Apr. 25; 11:232.

Diseases caused by impaired stem cell function. NAD boosting promotes stem cell activation and hematopoiesis and is useful in accelerating the expansion of stem cell populations following a stem cell transplant. See Pi et al., *Aging* (*Albany NY*). 2019, 11(11):3505-3522.

DNA damage disorders and primary mitochondrial disorders. NAMPT activators will also be useful in the treatment of DNA damage disorders which are associated with an accelerated aging phenotype, such as Xeroderma pigmentosum, Cockayne syndrome, and Ataxia telangiectasia. Similarly, there are several primary mitochondrial disorders with shared symptoms and manifestations for which NAD boosting via NAMPT activation may be a suitable therapeutic intervention. See Fang et al, *Cell.* 2014, 157(4):882-896; Khan et al, *EMBO Mol Med.* 2014, June; 6(6):721-31; Cerutti et al., *Cell Metab.* 2014, 19(6):1042-9.

Provided in some embodiments are methods of treating a disease or condition mediated by NAMPT activity in a subject in need thereof, comprising administering to the individual or subject in need thereof a compound of formula (A), (I), (I-A), (I-A1), (I-A2), (I-A3), (I-B), (I-B1), (II), (II-A), or (II-A1), such as a compound of Table 1, or a pharmaceutically acceptable salt thereof, wherein the disease or condition is selected from the group consisting of cardiac diseases, chemotherapy induced tissue damage, renal diseases, metabolic diseases, muscular diseases, neurological diseases and injuries, diseases caused by impaired stem cell function, and DNA damage and primary mitochondrial disorders. Provided in some embodiments are methods of treating a disease or condition mediated by NAMPT activity in a subject in need thereof, comprising administering to the individual or subject in need thereof a compound of formula (I), (I-A), (I-A1), (I-B), or (I-B1), or a compound of Table 1, or a pharmaceutically acceptable salt thereof, wherein the disease or condition is selected from the group consisting of cardiac diseases, chemotherapy induced tissue damage, renal diseases, metabolic diseases, muscular diseases, neurological diseases and injuries, diseases caused by impaired stem cell function, and DNA damage and primary mitochondrial disorders.

Additional applications of small molecule NAMPT activators are provided in Table 2.

TABLE 2

| | |
|---|---|
| Cancer and Chemotherapy induced tissue damage | Anthracycline and trastuzumab cardiotoxicity<br>Proteasome inhibitor cardiotoxicity<br>Cisplatin induced kidney injury<br>Prevention/treatment of cognitive dysfunction resulting from chemotherapy ("chemo brain")<br>Chemotherapy induced impairment of hematopoiesis and myelosuppression<br>Cachexia of cancer<br>Chemoprevention of non-melanoma skin cancer in high risk patients<br>chemoprevention of hepatocellular carcinoma |
| Cardiovascular diseases | Heart failure with reduced ejection fraction<br>Heart failure with preserved ejection fraction<br>Hypertrophic cardiomyopathy<br>Cardiac arrhythmias<br>Duchenne Muscular Dystrophy-related cardiac dysfunction<br>Cardiac dysfunction associated with Scleroderma, Lupus, Mitochondrial Disorders, Kawasaki Disease<br>Hypertension<br>Myocardial Infarction<br>Kinase-inhibitor cardiotoxicity |
| Renal diseases | Acute kidney injury including nephropathy following major surgeries including cardiac and vascular surgeries<br>Acute kidney injury following hypotension, hemorrhagic shock, or cardiac arrest<br>Acute kidney injury following exposure to contrast imaging agents used for MRI, CT scans, or other imaging modalities, particularly in the context of diabetes<br>Chronic kidney disease<br>Glomerular nephritis<br>Kidney mesangial cell hypertrophy<br>Arterial venous fistula maturation |
| Chronic inflammatory and fibrotic diseases | Chronic obstructive pulmonary disease<br>Asthma<br>Scleroderma<br>Dermatomyositis<br>Lupus erythematosus<br>Rheumatoid arthritis and spondyloarthropathy<br>Juvenile idiopathic arthritis<br>Crohn's disease<br>Inflammatory Bowel Disease<br>Eczema<br>Psoriasis and psoriatic arthritis<br>Idiopathic pulmonary fibrosis |
| Vascular diseases | Arterial and venous thrombosis<br>Ischemic Stroke<br>Arteriosclerosis |
| Metabolic dysfunction | Obesity<br>Diabetes<br>Metabolic Syndrome<br>Alcoholic steatohepatitis<br>Non-alcoholic steatohepatitis<br>Dyslipidemia<br>Diabetic neuropathy<br>Diabetic gastroparesis |
| Muscular diseases | Muscular dystrophies, including: Duchenne, Becker's, Congenital, Distal, Emery-Dreifuss', Facio-scapulo-humeral, Limb-girdle, myotonic, and oculopharyngeal Sarcopenia<br>Frailty<br>Polymyositis<br>Muscle stem cell senescence developed in the context of nutritional deficiencies<br>Non-mitochondrial myopathies such as inherited myopathies, myotonia, congenital myopathies selected from nemaline myopathy, multi/minicore myopathy, centronuclear myopathy and metabolic myopathies, inflammatory myopathies |
| Neurological diseases and injuries | Depression<br>Frontotemporal dementia<br>Multiple sclerosis<br>Amyotrophic lateral sclerosis<br>Peripheral neuropathy due to diabetes, chemotherapy<br>Alzheimer's disease<br>Parkinson's disease<br>Huntington's Disease<br>Spinal muscular atrophy<br>Spinocerebellar ataxias<br>Spastic paraplegias<br>Glaucoma<br>Age-related macular degeneration<br>Age-related cognitive decline |

TABLE 2-continued

| | |
|---|---|
| | Noise induced and age-related hearing loss<br>Ischemic stroke<br>Traumatic brain injury<br>Neonatal nerve damage<br>Optic nerve injury<br>Spinal cord injuries<br>Peripheral neuropathies or tissue inflammation induced by cisplatin, paclitaxel, vincristine, other chemotherapeutic agents, or radiation.<br>Peripheral neuropathies (length and non-length dependent) affecting motor, sensory, or autonomic nerves, arising from: diabetes, impaired glucose tolerance, hypertension, infection, trauma, autoimmune disorders, vasculitis, arteriosclerosis, vitamin deficiencies (particularly B6 and B12), alcoholism, liver or kidney disease, or exposure to toxins |
| DNA damage disorders and Primary Mitochondrial Disorders | Xeroderma pigmentosum<br>Cockayne syndrome<br>Ataxia telangiectasia<br>MEGDEL syndrome<br>Charcot-Marie-Tooth type 2<br>Primary Mitochondrial Diseases (Disorders) including NARP, MELAS, Chronic Progressive External Ophthalmoplegia, Leigh's disease, Leber's Hereditary Optic Neuropathy, MERRF, Barth Syndrome, Luft Disease, Kearns Sayre Syndrome, Autosomal dominant optic atrophy<br>Friedreich's ataxia<br>Werner syndrome |
| General | Tissue repair following physical trauma, hemorrhagic shock, tissue grafting, organ transplant including heart, lung, liver, and kidney<br>Stem cell therapies, including hematopoietic stem cell transfer, allogenic mesenchymal stem therapy for acute graft-vs-host disease, limbal stem cell deficiency due to genetic or acquired conditions that compromise normal turnover of the corneal epithelium |

In some embodiments, the disease or condition mediated by NAMPT activity is cancer and chemotherapy-induced tissue damage, a cardiovascular disease, a renal disease, chronic inflammatory and fibrotic disease, a vascular disease, metabolic dysfunction, a muscular disease, a neurological disease or injury, or a DNA damage disorder or primary mitochondrial disorder. Provided in some embodiments are methods of treating a disease or condition mediated by NAMPT activity in a subject in need thereof, comprising administering to the individual or subject in need thereof a compound of formula (A), (I), (I-A), (I-A1), (I-A2), (I-A3), (I-B), (I-B1), (II), (II-A), or (II-A1), such as a compound of Table 1, or a pharmaceutically acceptable salt thereof. Provided in some embodiments are methods of treating a disease or condition mediated by NAMPT activity in a subject in need thereof, comprising administering to the individual or subject in need thereof a compound of formula (I), (I-A), (I-A1), (I-B), or (I-B1), or a compound of Table 1, or a pharmaceutically acceptable salt thereof. In some embodiments, the disease or condition is cancer or chemotherapy induced tissue damage, a cardiovascular disease, a renal disease, a chronic inflammatory or fibrotic disease, a vascular disease, metabolic dysfunction, a muscular disease, a neurological disease or injury, a DNA damage disorder or Primary Mitochondrial Disorder, including any of the diseases listed in Table 2.

Dosages

The compounds and compositions disclosed and/or described herein are administered at a therapeutically effective dosage, e.g., a dosage sufficient to provide treatment for the disease state. While human dosage levels have yet to be optimized for the chemical entities described herein, generally, a daily dose ranges from about 0.01 to 100 mg/kg of body weight; in some embodiments, from about 0.05 to 10.0 mg/kg of body weight, and in some embodiments, from about 0.10 to 1.4 mg/kg of body weight. Thus, for administration to a 70 kg person, in some embodiments, the dosage range would be about from 0.7 to 7000 mg per day; in some embodiments, about from 3.5 to 700.0 mg per day, and in some embodiments, about from 7 to 100.0 mg per day. The amount of the chemical entity administered will be dependent, for example, on the subject and disease state being treated, the severity of the affliction, the manner and schedule of administration and the judgment of the prescribing physician. For example, an exemplary dosage range for oral administration is from about 5 mg to about 500 mg per day, and an exemplary intravenous administration dosage is from about 5 mg to about 500 mg per day, each depending upon the compound pharmacokinetics.

A daily dose is the total amount administered in a day. A daily dose may be, but is not limited to be, administered each day, every other day, each week, every 2 weeks, every month, or at a varied interval. In some embodiments, the daily dose is administered for a period ranging from a single day to the life of the subject. In some embodiments, the daily dose is administered once a day. In some embodiments, the daily dose is administered in multiple divided doses, such as in 2, 3, or 4 divided doses. In some embodiments, the daily dose is administered in 2 divided doses.

Administration of the compounds and compositions disclosed and/or described herein can be via any accepted mode of administration for therapeutic agents including, but not limited to, oral, sublingual, subcutaneous, parenteral, intravenous, intranasal, topical, transdermal, intraperitoneal, intramuscular, intrapulmonary, vaginal, rectal, or intraocular administration. In some embodiments, the compound or composition is administered orally or intravenously. In some embodiments, the compound or composition disclosed and/or described herein is administered orally.

Pharmaceutically acceptable compositions include solid, semi-solid, liquid and aerosol dosage forms, such as tablet, capsule, powder, liquid, suspension, suppository, and aerosol forms. The compounds disclosed and/or described herein can also be administered in sustained or controlled release dosage forms (e.g., controlled/sustained release pill, depot injection, osmotic pump, or transdermal (including electrotransport) patch forms) for prolonged timed, and/or pulsed administration at a predetermined rate. In some embodiments, the compositions are provided in unit dosage forms suitable for single administration of a precise dose.

The compounds disclosed and/or described herein can be administered either alone or in combination with one or more conventional pharmaceutical carriers or excipients (e.g., mannitol, lactose, starch, magnesium stearate, sodium saccharine, talcum, cellulose, sodium crosscarmellose, glucose, gelatin, sucrose, magnesium carbonate). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate). Generally, depending on the intended mode of administration, the pharmaceutical composition will contain about 0.005% to 95%, or about 0.5% to 50%, by weight of a compound disclosed and/or described herein. Actual methods of preparing such dosage forms are known, or will be apparent, to those skilled in this art; for example, see *Remington's Pharmaceutical Sciences*, Mack Publishing Company, Easton, Pennsylvania.

In some embodiments, the compositions will take the form of a pill or tablet and thus the composition may contain, along with a compounds disclosed and/or described herein, one or more of a diluent (e.g., lactose, sucrose, dicalcium phosphate), a lubricant (e.g., magnesium stearate), and/or a binder (e.g., starch, gum acacia, polyvinylpyrrolidine, gelatin, cellulose, cellulose derivatives). Other solid dosage forms include a powder, marume, solution or suspension (e.g., in propylene carbonate, vegetable oils or triglycerides) encapsulated in a gelatin capsule.

Liquid pharmaceutically administrable compositions can, for example, be prepared by dissolving, dispersing or suspending etc. a compound disclosed and/or described herein and optional pharmaceutical additives in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of the compound contained in such parenteral compositions depends, for example, on the physical nature of the compound, the activity of the compound and the needs of the subject. However, percentages of active ingredient of 0.01% to 10% in solution are employable, and may be higher if the composition is a solid which will be subsequently diluted to another concentration. In some embodiments, the composition will comprise from about 0.2 to 2% of a compound disclosed and/or described herein in solution.

Pharmaceutical compositions of the compounds disclosed and/or described herein may also be administered to the respiratory tract as an aerosol or solution for a nebulizer, or as a microfine powder for insufflation, alone or in combination with an inert carrier such as lactose. In such a case, the particles of the pharmaceutical composition may have diameters of less than 50 microns, or in some embodiments, less than 10 microns.

In addition, pharmaceutical compositions can include a compound disclosed and/or described herein and one or more additional medicinal agents, pharmaceutical agents, adjuvants, and the like. Suitable medicinal and pharmaceutical agents include those described herein.

Kits

Also provided are articles of manufacture and kits containing any of the compounds or pharmaceutical compositions provided herein. The article of manufacture may comprise a container with a label. Suitable containers include, for example, bottles, vials, and test tubes. The containers may be formed from a variety of materials such as glass or plastic. The container may hold a pharmaceutical composition provided herein. The label on the container may indicate that the pharmaceutical composition is used for preventing, treating or suppressing a condition described herein, and may also indicate directions for either in vivo or in vitro use.

In one aspect, provided herein are kits containing a compound or composition described herein and instructions for use. The kits may contain instructions for use in the treatment of a heart disease in an individual or subject in need thereof. A kit may additionally contain any materials or equipment that may be used in the administration of the compound or composition, such as vials, syringes, or IV bags. A kit may also contain sterile packaging.

Combinations

The compounds and compositions described and/or disclosed herein may be administered alone or in combination with other therapies and/or therapeutic agents useful in the treatment of the aforementioned disorders, diseases, or conditions.

General Synthetic Methods

Compounds of formula (A), (I), (I-A), (I-A1), (I-A2), (I-A3), (I-B), (I-B1), (II), (II-A), or (II-A1) will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. In addition, one of skill in the art will recognize that protecting groups may be used to protect certain functional groups (amino, carboxy, or side chain groups) from reaction conditions, and that such groups are removed under standard conditions when appropriate. Unless otherwise specified, the variables are as defined above in reference to formula (A), (I), (I-A), (I-A1), (I-A2), (I-A3), (I-B), (I-B1), (II), (II-A), or (II-A1).

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography.

Alternatively, if desired a particular enantiomer may be obtained by using an appropriate chiral intermediate in one of the processes described.

Chromatography, recrystallization, and other conventional separation procedures may also be used with intermediates or final products where it is desired to obtain a particular isomer of a compound or to otherwise purify a product of a reaction.

General Scheme 1, shown below, may be used to prepare a compound as described herein, such as a compound of formula (A), such as a compound of formula (I), (I-A), (I-A1), (I-A2), (I-A3), (I-B), (I-B1), (II), (II-A), or (II-A1), or a stereoisomer or tautomer thereof, or a pharmaceutically acceptable salt of any of the foregoing. In General Scheme 1, $R^1$, $R^2$, $R^3$, $R^4$, $R^y$, and $R^z$ are as defined else wherein herein for a compound of formula (A), such as a compound of formula (I), (I-A), (I-A1), (I-A2), (I-A3), (I-B), (I-B1), (II), (II-A), or (II-A1), or a stereoisomer or tautomer thereof, or a pharmaceutically acceptable salt of any of the foregoing.

General Scheme 1

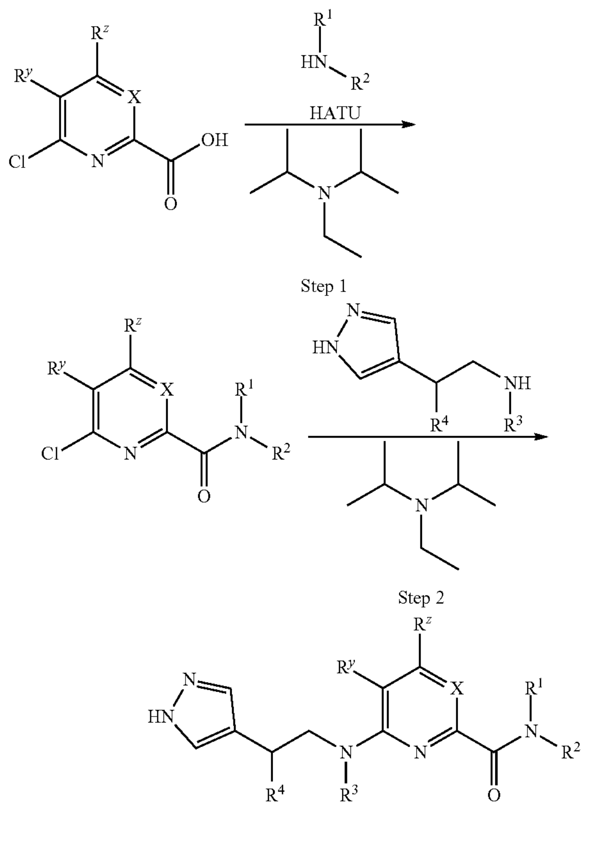

General Scheme A, shown below, may be used to prepare a compound as described herein, such as a compound of formula (I), such as a compound of formula (I-A), (I-A1), (I-A2), (I-A3), (I-B), or (I-B1), or a stereoisomer or tautomer thereof, or a pharmaceutically acceptable salt of any of the foregoing. In General Scheme A, $R^1$, $R^2$, $R^3$, $R^4$, $R^y$, and $R^z$ are as defined else wherein herein for a compound of formula (I), such as a compound of formula (I-A), (I-A1), (I-A2), (I-A3), (I-B), or (I-B1), or a stereoisomer or tautomer thereof, or a pharmaceutically acceptable salt of any of the foregoing. General Scheme A, shown below, may be used to prepare a compound as described herein, such as a compound of formula (I), such as a compound of formula (I-A), (I-A1), (I-B), or (I-B1), or a stereoisomer or tautomer thereof, or a pharmaceutically acceptable salt of any of the foregoing. In General Scheme A, $R^1$, $R^2$, $R^3$, $R^4$, $R^y$, and $R^z$ are as defined else wherein herein for a compound of formula (I), such as a compound of formula (I-A), (I-A1), (I-B), or (I-B1), or a stereoisomer or tautomer thereof, or a pharmaceutically acceptable salt of any of the foregoing.

General Scheme A

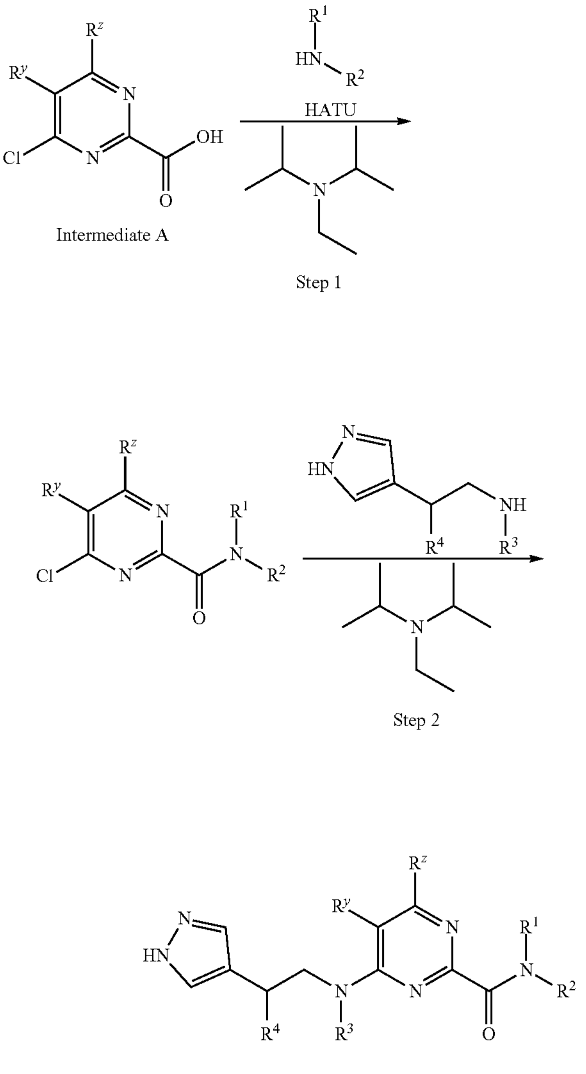

General Scheme B, shown below, may be used to prepare a compound as described herein, such as a compound of formula (II), such as a compound of formula (II-A) or (II-A1), or a stereoisomer or tautomer thereof, or a pharmaceutically acceptable salt of any of the foregoing. In General Scheme B, $R^1$, $R^2$, $R^3$, $R^4$, $R^y$, and $R^z$ are as defined else wherein herein for a compound of formula (II), such as a compound of formula (II-A) or (II-A1), or a stereoisomer or tautomer thereof, or a pharmaceutically acceptable salt of any of the foregoing.

General Scheme B

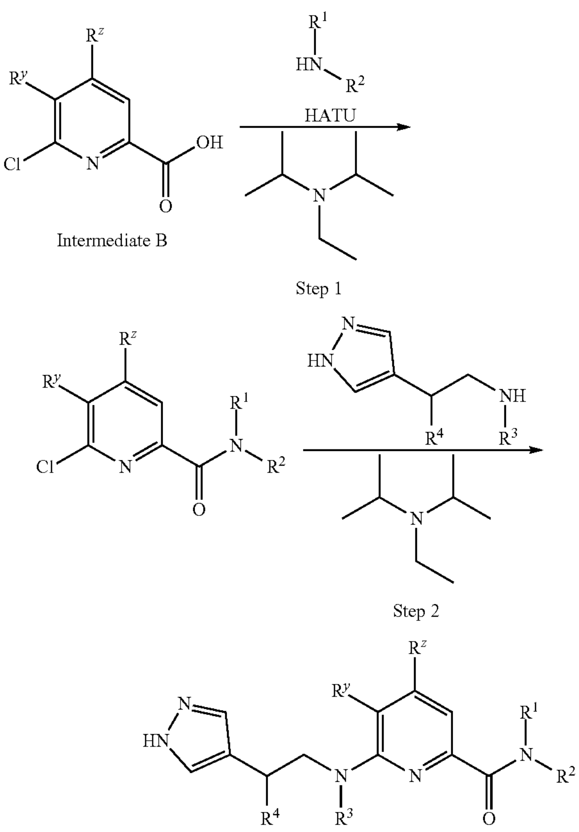

General Scheme 2, shown below, may be used to prepare a compound as described herein, such as a compound of formula (A), such as a compound of formula (I), (I-A), (I-A1), (I-A2), (I-A3), (I-B), (I-B1), (II), (II-A), or (II-A1), or a stereoisomer or tautomer thereof, or a pharmaceutically acceptable salt of any of the foregoing. In General Scheme 2, $R^1$, $R^2$, $R^3$, $R^4$, $R^y$, and $R^z$ are as defined else wherein herein for a compound of formula (A), such as a compound of formula (I), (I-A), (I-A1), (I-A2), (I-A3), (I-B), (I-B1), (II), (II-A), or (II-A1), or a stereoisomer or tautomer thereof, or a pharmaceutically acceptable salt of any of the foregoing.

General Scheme 2

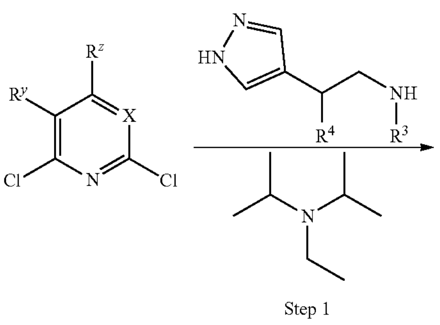

-continued

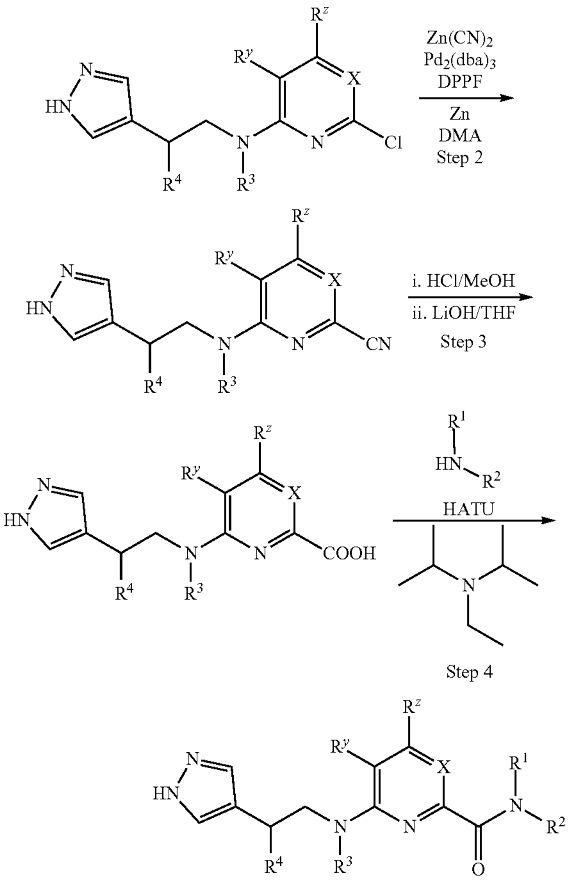

General Scheme C, shown below, may be used to prepare a compound as described herein, such as a compound of formula (I), such as a compound of formula (I-A), (I-A1), (I-A2), (I-A3), (I-B), or (I-B1), or a stereoisomer or tautomer thereof, or a pharmaceutically acceptable salt of any of the foregoing. In General Scheme C, $R^1$, $R^2$, $R^3$, $R^4$, $R^y$, and $R^z$ are as defined else wherein herein for a compound of formula (I), such as a compound of formula (I-A), (I-A1), (I-A2), (I-A3), (I-B), or (I-B1), or a stereoisomer or tautomer thereof, or a pharmaceutically acceptable salt of any of the foregoing.

General Scheme C

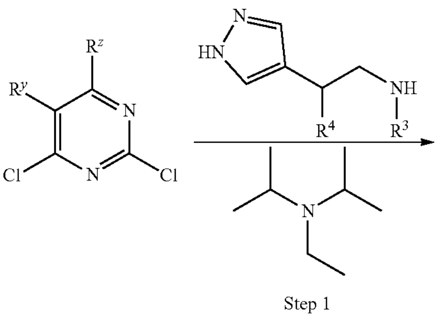

-continued

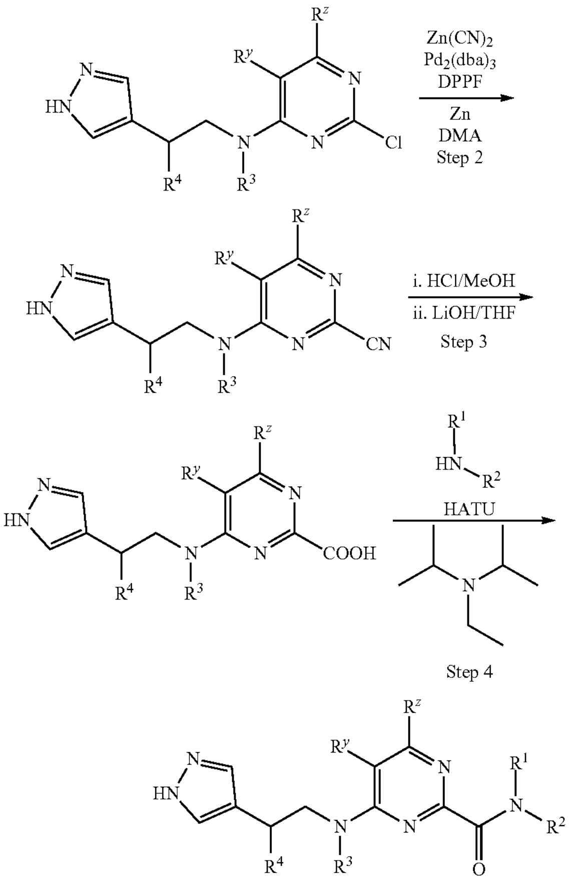

General Scheme D, shown below, may be used to prepare a compound as described herein, such as a compound of formula (II), such as a compound of formula (II-A) or (II-A1), or a stereoisomer or tautomer thereof, or a pharmaceutically acceptable salt of any of the foregoing. In General Scheme D, $R^1$, $R^2$, $R^3$, $R^4$, $R^y$, and $R^z$ are as defined else wherein herein for a compound of formula (II), such as a compound of formula (II-A) or (II-A1), or a stereoisomer or tautomer thereof, or a pharmaceutically acceptable salt of any of the foregoing.

General Scheme D

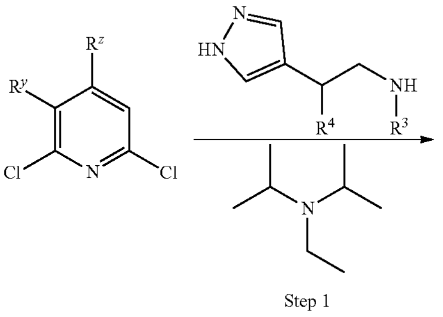

-continued

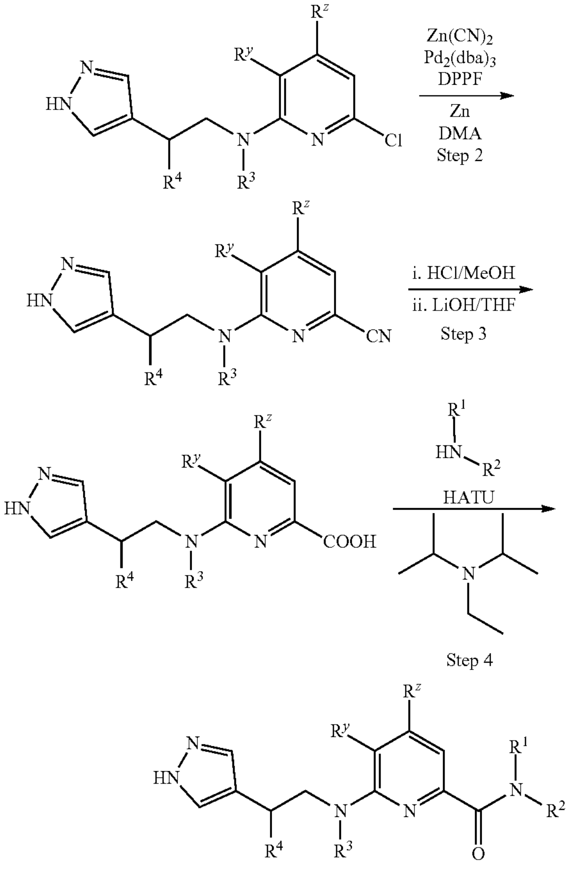

Particular non-limiting examples are provided in the Example section below.

EXAMPLES

The following general schemes and examples are offered to illustrate but not to limit the compositions, uses, and methods provided herein. The compounds are prepared using the general methods described above.

The following abbreviations are used throughout the Examples: TEA (triethylamine), DCM (dichloromethane), $(Boc)_2O$ (di-tert-butyl dicarbonate), EA (Ethyl acetate), PE (Petroleum ether), DMF (N,N-dimethylformamide), DIEA (N-ethyl-N-isopropylpropan-2-amine), HATU (1-[Bis(dimethylamino)methylene]-1H-1,2,3-triazolo[4,5-b]pyridinium 3-oxid hexafluorophosphate), HOAt (1-Hydroxy-7-azabenzotriazole), HOBt (Hydroxybenzotriazole), EDCI (1-Ethyl-3-(3-dimethylaminopropyl)carbodiimide), McOH (methanol), EtOH (ethanol), iPrOH (propan-2-ol), ACN (acetonitrile), TFA (trifluoroacetic acid), DPPA (Diphenylphosphoryl azide), DBU (1,8-Diazabicyclo(5.4.0)undec-7-ene), THE (tetrahydrofuran), $PPh_3$ (triphenylphosphane), SM (starting material), Hex (hexane), NCS (N-chlorosuccinimide), r.t. (room temperature), DCE (dichloroethane), FA (formic acid), $CHCl_3$ (Chloroform), BnBr (benzyl bromide), HCl (hydrogen chloride), equiv (equivalent), and DSC (bis(2,5-dioxopyrrolidin-1-yl) carbonate), HBTU (O-(benzotriazol-1-yl)-N,N,N',N'-tetramethyluronium hexafluorophosphate).

Example A

Preparation of 4-chloro-5,6-dimethylpyrimidine-2-carboxylic acid (Intermediate 1)

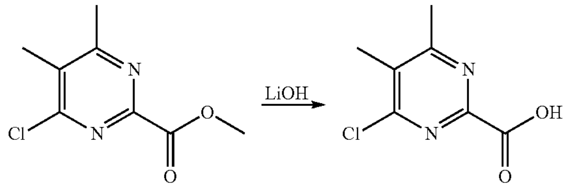

intermediate 1

To a solution of methyl 4-chloro-5,6-dimethylpyrimidine-2-carboxylate (3.1 g, 15.0 mmol, 1.0 equiv) in THE (45 mL) was added a solution of LiOH (15 mL, 2 M in $H_2O$, 30.0 mmol, 2.0 equiv) slowly at 0° C. The reaction was then allowed to stir at 23° C. for 3 hours. Upon completion, 4 N HCl solution (8 mL) was added and pH was monitored to be lower than 2. EtOAc (50 mL) and $H_2O$ (30 mL) were added and the aqueous phase was extracted by EtOAc (10 mL). The combined organic phase was dried ($MgSO_4$), filtered, and concentrated to yield the desired acid (2.5 g, 90%) as a brownish solid. LRMS (APCI+) calcd for $C_7H_8ClN_2O_2^+$ [M+H$^+$] 187, found 187. $^1$H NMR (400 MHz, Methanol-$d_4$) δ 2.66 (s, 3H), 2.48 (s, 3H).

Example A-1

Preparation of 4-chloro-6,7-dihydro-5H-cyclopenta[d]pyrimidine-2-carboxylic acid (Intermediate 1-1)

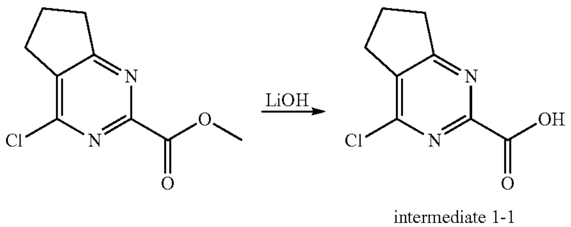

intermediate 1-1

To a solution of methyl 4-chloro-6,7-dihydro-5H-cyclopenta[d]pyrimidine-2-carboxylate (638 mg, 3.00 mmol) in THE (10 mL) was added LiOH solution (2 M in $H_2O$, 1.8 mL, 3.60 mmol) dropwise at 0° C. The resulting solution was stirred at rt for 30 min. LC-MS showed complete consumption of starting material. 4 M HCl was then added to acidify the reaction media till pH=3. This mixture was extracted by EtOAc (10 mL×3). The combined organic phase was dried over $MgSO_4$, filtered, and concentrated to yield the desired product as a solid (596 mg, 83%). LRMS (APCI+) 199.00 [M+H$^+$]. This intermediate is directly used in the next step without purification.

Example A-2

Preparation of 4-bromo-6-chloropicolinic acid (Intermediate 1-2)

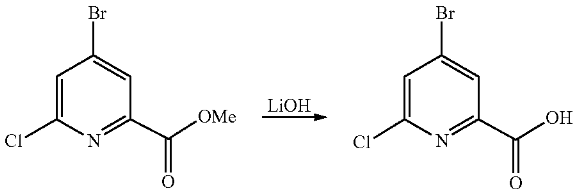

Intermediate 1-2

4-bromo-6-chloropicolinic acid (Intermediate 1-2) was prepared according to Example A-1.

Example A-3

Preparation of 4-methyl-6-chloropicolinic acid (Intermediate 1-3)

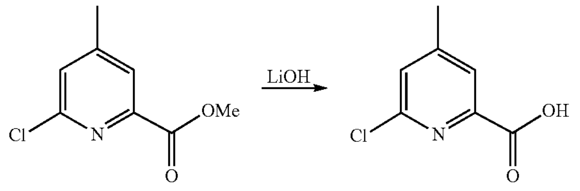

Intermediate 1-3

4-methyl-6-chloropicolinic acid (Intermediate 1-3) was prepared according to Example A-1.

Example B

Preparation of N-(2-(1H-pyrazol-4-yl)ethyl)-2-chloro-5,6-dimethylpyrimidin-4-amine (Intermediate 2)

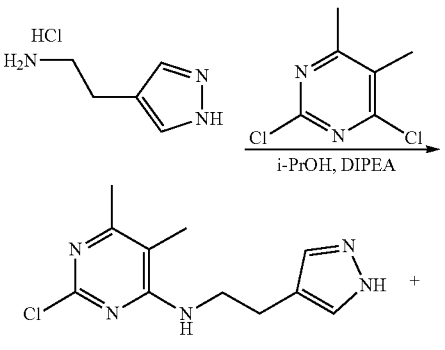

Intermediate 2

-continued

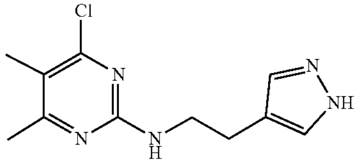

To a solution of 2,4-dichloro-5,6-dimethylpyrimidine (7.0 g, 38.0 mmol, 1.0 equiv) in i-PrOH (150 mL) was added 2-(1H-pyrazol-4-yl)ethanamine hydrochloride (6.73 g, 38.0 mmol, 1.01 equiv) and diisopropylethylamine (29.4 g, 228 mmol, 6.0 equiv). The resulting mixture was stirred at 90° C. for 15 h. The mixture was directly concentrated and purified by reverse-phase column chromatography ($H_2O$ (0.05% $NH_4HCO_3$)/MeCN, 3:2) to afford the desired product Intermediate 2 (4.4 g, 46%) as a white solid and regio-isomer N-(2-(1H-pyrazol-4-yl)ethyl)-4-chloro-5,6-dimethylpyrimidin-2-amine (600 mg).

Intermediate 2: $^1H$ NMR (400 MHz, DMSO-$d_6$) δ 12.61-12.56 (m, 1H), 7.45 (s, 2H), 7.17 (t, J=5.6 Hz, 1H), 3.49 (td, J=7.6, 5.7 Hz, 2H), 2.71 (t, J=7.4 Hz, 2H), 2.22 (s, 3 H), 1.93 (s, 3H).

Regio-isomer: $^1H$ NMR (400 MHz, DMSO-$d_6$) δ 12.64-12.53 (m, 1H), 7.45 (s, 2H), 7.29 (t, J=5.8 Hz, 1H), 3.38 (t, J=7.0 Hz, 2H), 2.67 (t, J=7.4 Hz, 2H), 2.30 (s, 3H), 2.11 (d, J=1.5 Hz, 3H).

Example C

Preparation of 1-(3-fluorophenyl)-N-methyl-1-(1-methyl-1H-imidazol-2-yl)methanamine (Amine 1)

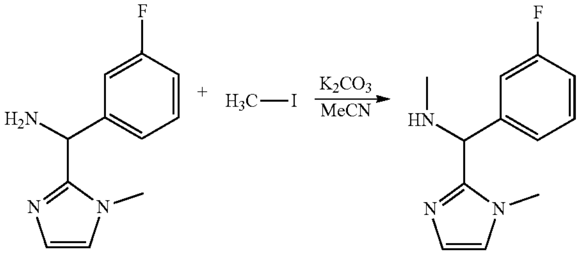

Amine 1

To a solution of (3-fluorophenyl)(1-methyl-1H-imidazol-2-yl)methanamine (205 mg, 1.0 mmol, 1.0 equiv) in MeCN (5 mL) was added $K_2CO_3$ (345 mg, 2.5 mmol, 2.5 equiv) and MeI (149 mg, 1.05 mmol, 1.05 equiv) at 23° C. The resulting mixture was vigorously stirred at this temperature for 14 hours. LC-MS monitoring indicated that a mixture of starting material, desired product, and bis-methylated product was formed. EtOAc (10 mL) and half-saturated $NH_4Cl$ solution (10 mL) were added and the aqueous phase was extracted by EtOAc (5 mL). The combined organic phase was dried ($MgSO_4$), filtered, concentrated, and purified by reverse-phase HPLC (formic acid in $H_2O$/formic acid in MeCN, 100% to 70%) to yield a sample of mono-methylated product (30 mg, 14%). LRMS (APCI+) calcd for $C_{10}H_{15}FN_3^+$ [M+H$^+$] 220, found 220.

Example D

Preparation of (3-fluorophenyl)(oxazol-2-yl)methanamine (Amine 2)

Step 1: Synthesis of (3-fluorophenyl)(oxazol-2-yl)methanol

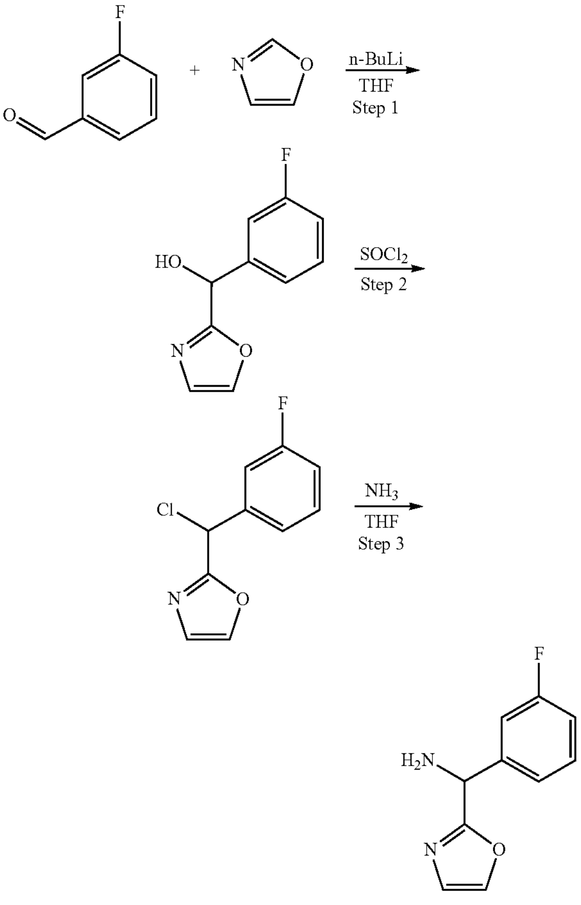

Amine 2

To a solution of oxazole (138 mg, 2.0 mmol, 1.0 equiv) in THF (10 mL) was added n-BuLi (1.6 M in hexanes, 1.3 mL, 2.1 mmol, 1.05 equiv) dropwise over 5 min at −78° C. The resulting solution was stirred at this temperature for 1 hour before 3-fluorobenzaldehyde (260 mg, 2.1 mmol, 1.05 equiv) was added at −78° C. The reaction was maintained at −78° C. for 2 hours and was then allowed to warm up to 23° C. over 2 hours. After stirring at 23° C. for 10 hours, the reaction was quenched by the addition of half-saturated $NH_4Cl$ solution (15 mL). The aqueous phase was extracted by EtOAc (10 mL×2) and the combined organic phase was dried ($MgSO_4$), filtered, and concentrated to yield the crude alcohol which was directly used in the next step. LRMS (APCI+) calcd for $C_{10}H_7FNO^+$ [M+H−$H_2O^+$] 177, found 177.

Step 2: Synthesis of 2-(chloro(3-fluorophenyl)methyl)oxazole

To a vial charged with the crude alcohol (2.0 mmol, 1.0 equiv) was added $SOCl_2$ (0.6 mL). The mixture was then stirred at 70° C. for 4 hours. Upon completion, EtOAc (15 mL) was added to dilute and the organic phase was carefully washed by $Na_2CO_3$ solution and brine. the combined organic phase was dried ($MgSO_4$), filtered, and concentrated to yield the crude benzyl chloride which was directly used in the next step. LRMS (APCI+) m/z 212 (M+H). LRMS (APCI+) calcd for $C_{10}H_8ClFNO^+$ [$M+H^+$] 212, found 212.

Step 3: Synthesis of (3-fluorophenyl)(oxazol-2-yl)methanamine (Amine 2)

To a solution of the crude benzyl chloride in THF (1 mL) was added $NH_3$ (7 M in MeOH, 0.5 mL) at 23° C. The reaction was stirred at this temperature for 14 hours. Upon completion, the volatile was removed in vacuo and the crude amine (158 mg, 82%) was used directly in synthetic method 1 without further purification. LRMS (APCI+) calcd for $C_{10}H_{10}FN_2O^+$ [$M+H^+$] 212, found 212.

Example E

Preparation of 4-((2-(1H-pyrazol-4-yl)ethyl)amino)-5-chloro-6-methylpyrimidine-2-carboxylic acid (Intermediate 2-1)

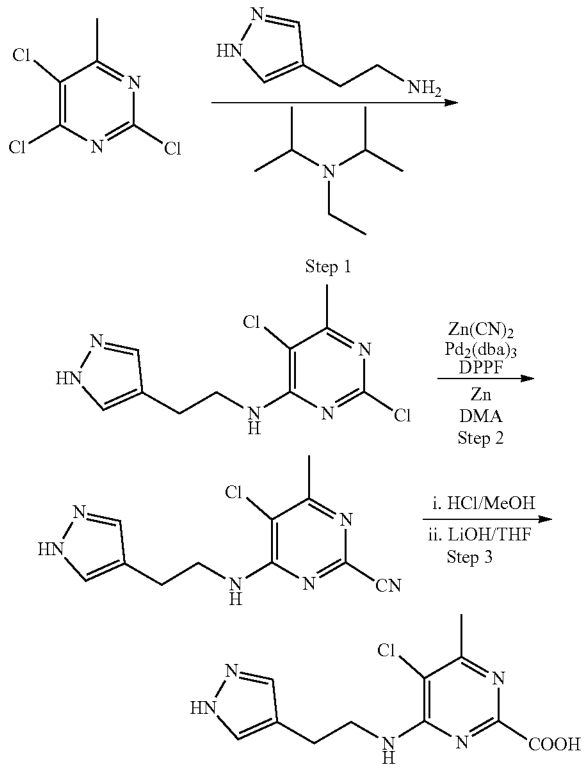

Intermediate 2-1

Step 1: Synthesis of N-(2-(1H-pyrazol-4-yl)ethyl)-2,5-dichloro-6-methylpyrimidin-4-amine To a solution of 2,4,5-trichloro-6-methylpyrimidine (1.58 g, 8.0 mmol) in iPrOH (20 mL) was added 2-(1H-pyrazol-4-yl)ethan-1-amine (934 mg, 8.4 mmol) and DIPEA (4.18 mL, 24 mmol) sequentially. The mixture was stirred at rt for 0.5 h. LC-MS showed complete conversion. Upon completion, iPrOH was removed under vacuum. EtOAc (20 mL) and $H_2O$ (20 mL) were added. The precipitate was collected by filtration to give the desired product (2.2 g, yield quantitative) as an off-white solid. LRMS (APCI+) 272.10 [$M+H^+$].

Step 2: Synthesis of 4-((2-(1H-pyrazol-4-yl)ethyl)amino)-5-chloro-6-methylpyrimidine-2-carbonitrile To N-(2-(1H-pyrazol-4-yl)ethyl)-2,5-dichloro-6-methylpyrimidin-4-amine (0.256 g, 1.0 mmol) in a round bottom flask was added DMA (4 mL), tris(dibenzylideneacetone) dipalladium (0.055 g, 0.1 mmol), 1,1'-bis(diphenylphosphino)ferrocene (0.046 g, 0.05 mmol), zinc cyanide (0.088 g, 0.7 mmol), and zinc dust (0.033 g, 0.53 mmol). The flask was capped, flushed with nitrogen, and stirred at 120° C. for 2 h. The reaction was cooled to room temperature, filtered through celite, and washed with dichloromethane (DCM). The filtrate was poured into water and extracted with DCM. The combined organic layers were dried ($Na_2SO_4$), filtered, and concentrated in vacuo. The residue was purified by Agilent RP-HPLC (20% to 100% MeCN linearly with 0.1% HCOOH) to give the desired product (0.160 g, yield 61%) as an off-white solid. LRMS (APCI+) 263.00 [$M+H^+$]. $^1H$ NMR (400 MHz, Chloroform-d) δ 7.55 (s, 1H), 5.73 (s, OH), 3.75 (q, J=6.5 Hz, 1H), 2.88 (t, J=6.9 Hz, 1H), 2.50 (s, 1H).

Step 3: Synthesis of 4-((2-(1H-pyrazol-4-yl)ethyl)amino)-5-chloro-6-methylpyrimidine-2-carboxylic acid To a nitrile compound 4-((2-(1H-pyrazol-4-yl)ethyl)amino)-5-chloro-6-methylpyrimidine-2-carbonitrile (155 mg, 0.592 mmol) stirring in 2 mL MeOH was added 2 mL conc. HCl, the mix was stirred at 50° C. for 1 h and concentrated to dryness. The residue was dissolved in 2 mL THF followed by addition of LiOH (1M, 2 mL, 2.0 mmol), the mixture was stirred at rt for 1 hour until the completion of esterification. The mix was extracted with 2 mL EtOAc, the aq. solution was acidified to pH 3 with 1 M HCl, then extracted with DCM (3×2 mL). The DCM solution was concentrated to give the desired product as an off-white solid (82 mg). The aqueous solution was purified by an Agilent HPLC eluted with 5 to 100% MeCN with 0.1% HCOOH over 40 min to give the pure product as a white solid (28 mg). The portions of product were combined to afford Intermediate 2-1 (110 mg, yield 67%). LRMS (APCI+) 282.10 [$M+H^+$].

Example E-2

Preparation of 4-((2-(1H-pyrazol-4-yl)ethyl)amino)-5-fluoro-6-methylpyrimidine-2-carboxylic acid (Intermediate 2-2)

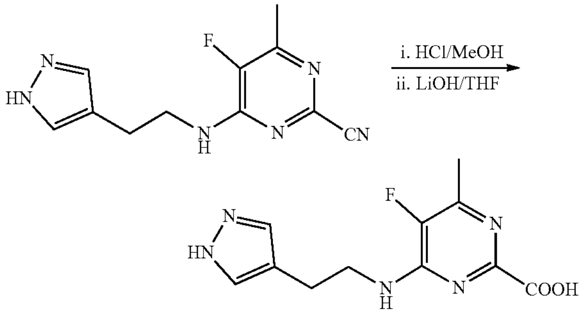

Intermediate 2-2

Intermediate 2-2 was prepared according to Step 3 of Example E.

Example 1

Representative example: Preparation of (4-((2-(1H-pyrazol-4-yl)ethyl)amino)-5,6-dimethylpyrimidin-2-yl)(3-(3-fluorophenyl)-3-hydroxyazetidin-1-yl) methanone

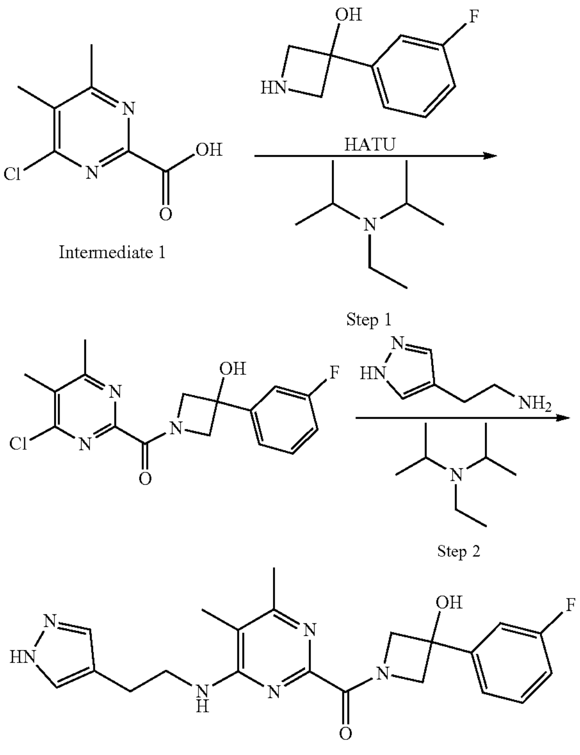

Intermediate 1
Compound 3

Step 1: Synthesis of (4-chloro-5,6-dimethylpyrimidin-2-yl)(3-(3-fluorophenyl)-3-hydroxyazetidin-1-yl) methanone To a solution of 4-chloro-5,6-dimethylpyrimidine-2-carboxylic acid (Intermediate 1, 30 mg, 0.16 mmol, 1.0 equiv), 3-(3-fluorophenyl)azetidin-3-ol HCl salt (34 mg, 0.17 mmol, 1.05 equiv), and Hexafluorophosphate azabenzotriazoie tetramethyl uronium (HATU, 70 mg, 0.19 mmol, 1.2 equiv) in DMF (1 mL) was added diisopropylethylamine (DIPEA, 0.08 mL, 0.48 mmol, 3.0 equiv) dropwise at 23° C. The resulting solution was stirred at this temperature for 30 min. LC-MS showed complete conversion. EtOAc (5 mL) and water (5 mL) were added. The organic phase was washed by half-saturated brine, dried ($MgSO_4$), filtered, and concentrated to give the crude amide coupling product (4-chloro-5,6-dimethylpyrimidin-2-yl)(3-(3-fluorophenyl)-3-hydroxyazetidin-1-yl)methanone which was directly carried to the next step. Step 2: Synthesis of (4-((2-(1H-pyrazol-4-yl) ethyl)amino)-5,6-dimethylpyrimidin-2-yl)(3-(3-fluorophenyl)-3-hydroxyazetidin-1-yl)methanone A solution of crude coupling product intermediate (4-chloro-5,6-dimethylpyrimidin-2-yl)(3-(3-fluorophenyl)-3-hydroxyazetidin-1-yl)methanone (0.16 mmol, 1.0 equiv), 2-(1H-pyrazol-4-yl)ethan-1-amine (54 mg, 0.48 mmol, 3.0 equiv), and DIPEA (0.08 mL, 0.48 mmol, 3.0 equiv) in McOH (0.5 mL)/i-PrOH (1 mL) was heated under microwave at 165° C. for 30 min. LC-MS showed complete conversion. The reaction was directly concentrated and subjected to reverse-phase HPLC separation ($H_2O$ (0.1% $HCO_2H$)/MeCN (0.1% $HCO_2H$), 100% to 40%) to yield the desired product (19 mg, 29%) as a colorless foam. (4-((2-(1H-pyrazol-4-yl)ethyl)amino)-5,6-dimethylpyrimidin-2-yl)(3-(3-fluorophenyl)-3-hydroxyazetidin-1-yl)methanone (Compound 3): $^1H$ NMR (400 MHz, Methanol-$d_4$) δ 7.49-7.37 (m, 2H), 7.42 (s, 2H), 7.33 (d, J=10.4 Hz, 1H), 7.06 (t, J=8.6 Hz, 1H), 4.95-4.88 (m, 1H), 4.82 (d, J=10.8 Hz, 1H), 4.48 (d, J=10.7 Hz, 1H), 4.36 (d, J=11.5 Hz, 1H), 3.70 (t, J=6.7 Hz, 2H), 2.84 (t, J=7.0 Hz, 2H), 2.45 (s, 3H), 2.10 (s, 3H). LRMS (APCI+) calcd for $C_{21}H_{24}FN_6O_2^+$ [M+$H^+$] 411.19, found 411.10.

The following compounds were prepared according to the procedures described above using in step 1 the amine reagent described in the table below.

| Compound No. | Amine in Step 1 | Structure, Name, and Data |
|---|---|---|
| 3 | 3-(3-fluorophenyl)azetidin-3-ol | 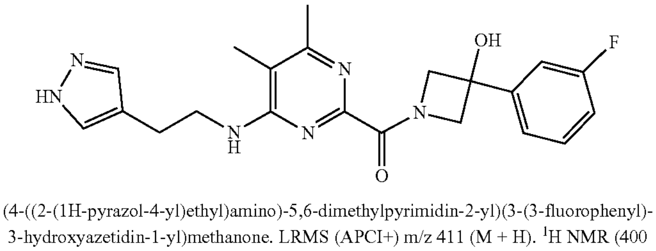 (4-((2-(1H-pyrazol-4-yl)ethyl)amino)-5,6-dimethylpyrimidin-2-yl)(3-(3-fluorophenyl)-3-hydroxyazetidin-1-yl)methanone. LRMS (APCI+) m/z 411 (M + H). $^1H$ NMR (400 MHz, Methanol-d4) δ 7.49-7.37 (m, 2H), 7.42 (s, 2H), 7.33 (d, J = 10.4 Hz, 1H), 7.06 (t, J = 8.6 Hz, 1H), 4.95-4.88 (m, 1H), 4.82 (d, J = 10.8 Hz, 1H), 4.48 (d, J = 10.7 Hz, 1H), 4.36 (d, J = 11.5 Hz, 1H), 3.70 (t, J = 6.7 Hz, 2H), 2.84 (t, J = 7.0 Hz, 2H), 2.45 (s, 3H), 2.10 (s, 3H). |

-continued

| Compound No. | Amine in Step 1 | Structure, Name, and Data |
|---|---|---|
| 4 | (R)-1-(6-fluoropyridin-2-yl)ethan-1-amine | 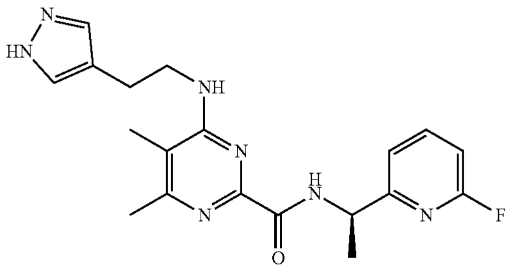<br>(R)-4-((2-(1H-pyrazol-4-yl)ethyl)amino)-N-(1-(6-fluoropyridin-2-yl)ethyl)-5,6-dimethylpyrimidine-2-carboxamide. LRMS (APCI+) m/z 384 (M + H). $^{1}$H NMR (400 MHz, Methanol-$d_4$) δ 7.94 (q, J = 8.0 Hz, 1H), 7.51 (s, 2H), 7.37 (dd, J = 7.4, 2.4 Hz, 1H), 6.99 (dd, J = 8.1, 2.5 Hz, 1H), 5.25 (q, J = 6.9 Hz, 1H), 3.83 (t, J = 7.2 Hz, 2H), 2.90 (t, J = 7.2 Hz, 2H), 2.44 (s, 3H), 2.09 (s, 3H), 1.59 (d, J = 6.9 Hz, 3H). |
| 5 | (rac)-1-(3-fluorophenyl)-N-methyl-1-(1-methyl-1H-imidazol-2-yl)methanamine(amine 1) | 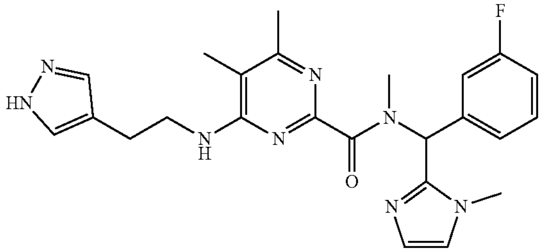<br>4-((2-(1H-pyrazol-4-yl)ethyl)amino)-N-((3-fluorophenyl)(1-methyl-1H-imidazol-2-yl)methyl)-N,5,6-trimethylpyrimidine-2-carboxamide. LRMS (APCI+) m/z 463 (M + H). (3:1 mixture of rotamers) $^{1}$H NMR (400 MHz, Methanol-$d_4$) δ 7.50-6.91 (m, 9H), 3.84 (s, 3H), 3.76-3.63 (m, 2H), 3.44 (s, 1H), 2.84 (t, J = 7.3 Hz, 2H), 2.77 (s, 3H), 2.44-2.34 (m, 2H), 2.14-2.00 (m, 3H). |
| 6 | 3-(piperidin-4-yl)-1H-indole | 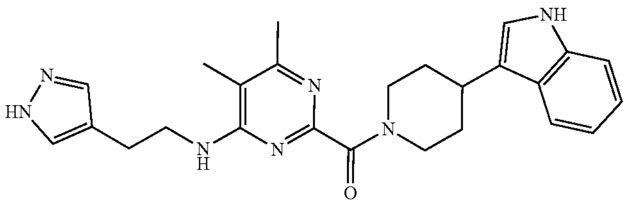<br>(4-(1H-indol-3-yl)piperidin-1-yl)(4-((2-(1H-pyrazol-4-yl)ethyl)amino)-5,6-dimethylpyrimidin-2-yl)methanone. LRMS (APCI+) m/z 444 (M + H). $^{1}$H NMR (400 MHz, Methanol-$d_4$) δ 7.61 (d, J = 7.6 Hz, 1H), 7.45 (s, 2H), 7.34 (d, J = 8.2 Hz, 1H), 7.10 (d, J = 8.0 Hz, 1H), 7.03-6.92 (m, 2H), 4.75 (d, J = 13.2 Hz, 1H), 3.70 (t, J = 6.9 Hz, 2H), 3.63 (d, J = 13.4 Hz, 1H), 3.28 (t, J = 12.5 Hz, 1H), 3.19 (t, J = 11.5 Hz, 1H), 3.07 (t, J = 12.7 Hz, 1H), 2.85 (t, J = 7.0 Hz, 2H), 2.39 (s, 3H), 2.19 (d, J = 13.7 Hz, 1H), 2.07 (s, 3H), 2.02 (d, J = 12.8 Hz, 1H), 1.85 (q, J = 12.8 Hz, 2H), 1.39 (d, J = 6.6 Hz, 1H). |

-continued

| Compound No. | Amine in Step 1 | Structure, Name, and Data |
|---|---|---|
| 7 | (rac)-3-(3-fluorophenyl)morpholine | 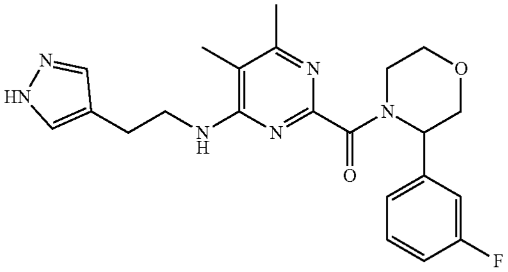 (4-((2-(1H-pyrazol-4-yl)ethyl)amino)-5,6-dimethylpyrimidin-2-yl)(3-(3-fluorophenyl)morpholino)methanone. LRMS (APCI+) m/z 425 (M + H). (1.6:1 mixture of rotamers) Major rotamer: $^1$H NMR (400 MHz, Methanol-$d_4$) δ 7.47-7.42 (m, 1H), 7.43 (s, 1H), 7.35-7.28 (m, 2H), 7.11-7.04 (m, 1H), 5.70 (d, J = 3.3 Hz, 1H), 4.58 (d, J = 12.4 Hz, 1H), 3.97 (dd, J = 12.6, 3.7 Hz, 2H), 3.82 (d, J = 11.4 Hz, 1H), 3.73-3.65 (m, 2H), 3.52-3.47 (m, 1H), 3.31-3.28 (m, 2H), 2.83 (t, J = 7.2 Hz, 2H), 2.40 (s, 3H), 2.08 (s, 3H). Minor rotamer: $^1$H NMR (400 MHz, Methanol-$d_4$) δ 7.43 (s, 2H), 7.40-7.36 (m, 3H), 7.02-6.95 (m, 1H), 4.79 (d, J = 2.8 Hz, 1H), 4.48-4.39 (m, 2H), 4.38 (s, 2H), 3.95-3.89 (m, 1H), 3.77-3.66 (m, 2H), 3.13-3.01 (m, 1H), 2.69 (t, J = 7.2 Hz, 2H), 2.39 (s, 3H), 2.04 (s, 3H). |
| 8 | (S)-1-(thiophen-2-yl)ethan-1-amine | 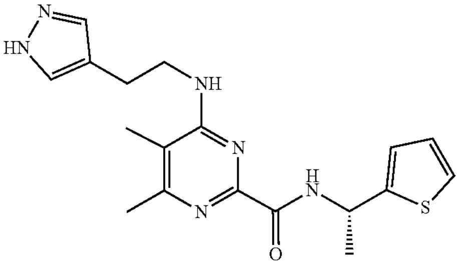 (S)-4-((2-(1H-pyrazol-4-yl)ethyl)amino)-5,6-dimethyl-N-(1-(thiophen-2-yl)ethyl)pyrimidine-2-carboxamide. LRMS (APCI+) m/z 371 (M + H). $^1$H NMR (400 MHz, Methanol-$d_4$) δ 7.41 (s, 2H), 7.32 (d, J = 5.0 Hz, 1H), 7.10 (d, J = 3.5 Hz, 1H), 7.00 (t, J = 4.3 Hz, 1H), 5.50 (q, J = 6.9 Hz, 1H), 3.76 (dtd, J = 28.1, 13.7, 7.4 Hz, 2H), 2.83 (t, J = 7.9 Hz, 2H), 2.43 (s, 3H), 2.08 (s, 3H), 1.71 (d, J = 6.8 Hz, 3H). |
| 10 | (S)-1-(3-fluorophenyl)ethan-1-amine | 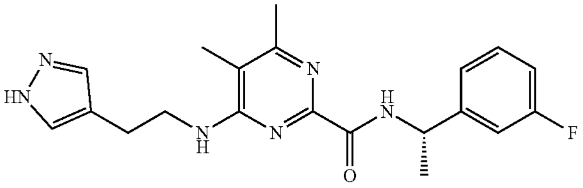 (S)-4-((2-(1H-pyrazol-4-yl)ethyl)amino)-N-(1-(3-fluorophenyl)ethyl)-5,6-dimethylpyrimidine-2-carboxamide. LRMS (APCI+) m/z 383 (M + H). $^1$H NMR (400 MHz, Methanol-$d_4$) δ 7.46 (s, 2H), 7.36 (td, J = 8.0, 5.9 Hz, 1H), 7.24 (dd, J = 7.8, 1.2 Hz, 1H), 7.18 (dt, J = 10.1, 2.1 Hz, 1H), 7.00 (td, J = 8.1, 2.0 Hz, 1H), 5.22 (q, J = 7.0 Hz, 1H), 3.80 (h, J = 6.1 Hz, 2H), 2.86 (t, J = 7.3 Hz, 2H), 2.43 (s, 3H), 2.08 (s, 3H), 1.61 (d, J = 7.0 Hz, 3H). |

-continued

| Compound No. | Amine in Step 1 | Structure, Name, and Data |
|---|---|---|
| 11 | 2-(3-fluorophenyl)propan-2-amine | 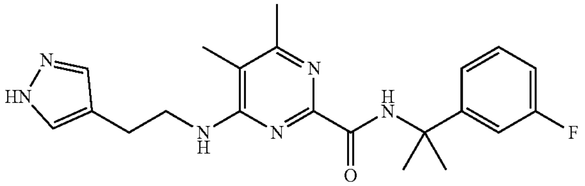 4-((2-(1H-pyrazol-4-yl)ethyl)amino)-N-(2-(3-fluorophenyl)propan-2-yl)-5,6-dimethylpyrimidine-2-carboxamide. LRMS (APCI+) m/z 397 (M + H). $^{1}$H NMR (400 MHz, Methanol-$d_4$) δ 7.46 (s, 2H), 7.38-7.26 (m, 2H), 7.20 (dt, J = 10.9, 2.1 Hz, 1H), 7.01-6.91 (m, 1H), 3.78 (t, J = 7.3 Hz, 2H), 2.87 (t, J = 7.3 Hz, 2H), 2.43 (s, 3H), 2.09 (s, 3H, 1.80 (s, 6H). |
| 12 | (rac)-3-(3-chlorophenyl)morpholine | 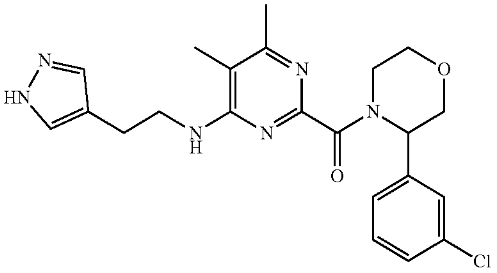 (4-((2-(1H-pyrazol-4-yl)ethyl)amino)-5,6-dimethylpyrimidin-2-yl)(3-(3-chlorophenyl)morpholino)methanone. LRMS (APCI+) m/z 441 (M + H). (1.5:1 mixture of rotamers) Major rotamer: $^{1}$H NMR (400 MHz, Methanol-$d_4$) δ 7.64 (s, 1H), 7.57 (s, 1H), 7.42 (s, 2H), 7.39-7.34 (m, 3H), 5.69 (d, J = 3.2 Hz, 1H), 4.57 (d, J = 12.5 Hz, 1H), 3.97 (dd, J = 12.4, 3.5 Hz, 2H), 3.87-3.79 (m, 1H), 3.77-3.65 (m, 2H), 3.32-3.26 (m, 1H), 2.83 (t, J = 7.2 Hz, 2H), 2.40 (s, 3H), 2.08 (s, 3H). Minor rotamer: $^{1}$H NMR (400 MHz, Methanol-$d_4$) δ 7.55 (s, 1H), 7.47 (d, J = 7.4 Hz, 1H), 7.37 (s, 2H), 7.31-7.22 (m, 2H), 4.77 (d, J = 2.8 Hz, 1H), 4.39 (d, J = 13.1 Hz, 1H), 3.95-3.89 (m, 1H), 3.74-3.68 (m, 4H), 3.56-3.42 (m, 1H), 3.12-2.98 (m, 1H), 2.70 (t, J = 7.2 Hz, 2H), 2.39 (s, 3H), 2.04 (s, 3H). |
| 13 | (R)-2-(3-chlorophenyl)pyrrolidine | 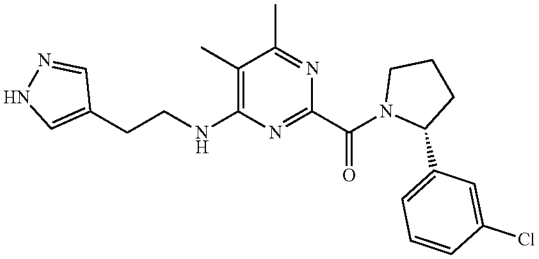 (R)-(4-((2-(1H-pyrazol-4-yl)ethyl)amino)-5,6-dimethylpyrimidin-2-yl)(2-(3-chlorophenyl)pyrrolidin-1-yl)methanone. LRMS (APCI+) m/z 425 (M + H). (1.4:1 mixture of rotamers) Minor rotamer: $^{1}$H NMR (400 MHz, Methanol-$d_4$) δ 7.49 (s, 2H), 7.38 (s, 1H), 7.36-7.23 (m, 3H), 5.27 (dd, J = 8.1, 4.3 Hz, 1H), 3.77 (q, J = 7.2 Hz, 2H), 3.65 (dt, J = 11.3, 6.9 Hz, 1H), 2.89 (t, J = 7.2 Hz, 2H), 2.52-2.43 (m, 2H), 2.41 (s, 3H), 2.09 (s, 3H), 2.08-2.02 (m, 3H). Major rotamer: $^{1}$H NMR (400 MHz, Methanol-$d_4$) δ 7.45 (s, 2H), 7.14 (t, J = 7.8 Hz, 1H), 7.07 (d, J = 8.5 Hz, 1H), 6.96 (d, J = 7.6 Hz, 1H), 6.86 (s, 1H), 5.10 (t, J = 6.7 Hz, 1H), 3.96 (dt, J = 12.8, 6.6 Hz, 1H), 3.89-3.80 (m, 2H), 3.42 (td, J = 7.0, 4.2 Hz, 2H), 2.68 (td, J = 7.2, 2.4 Hz, 2H), 2.23 (s, 3H), 2.01-1.86 (m, 3H), 1.95 (s, 3H). |

-continued

| Compound No. | Amine in Step 1 | Structure, Name, and Data |
|---|---|---|
| 14 | (R)-1-(thiophen-2-yl)ethan-1-amine | 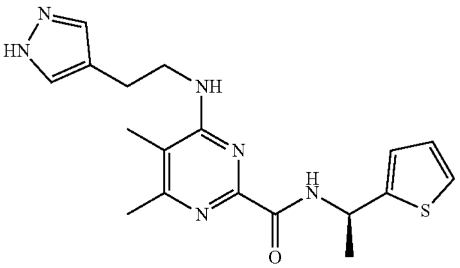 (R)-4-((2-(1H-pyrazol-4-yl)ethyl)amino)-5,6-dimethyl-N-(1-(thiophen-2-yl)ethyl)pyrimidine-2-carboxamide. LRMS (APCI+) m/z 371 (M + H). $^1H$ NMR (400 MHz, Methanol-$d_4$) δ 7.41 (s, 2H), 7.32 (d, J = 5.3 Hz, 1H), 7.10 (d, J = 3.5 Hz, 1H), 7.00 (dd, J = 5.0, 3.6 Hz, 1H), 5.50 (q, J = 6.8 Hz, 1H), 3.76 (dtd, J = 28.2, 13.6, 7.4 Hz, 2H), 2.83 (td, J = 7.4, 2.1 Hz, 2H), 2.43 (s, 3H), 2.08 (s, 3H), 1.71 (d, J = 6.8 Hz, 3H). |
| 15 | (R)-2-(3-fluorophenyl)pyrrolidine | 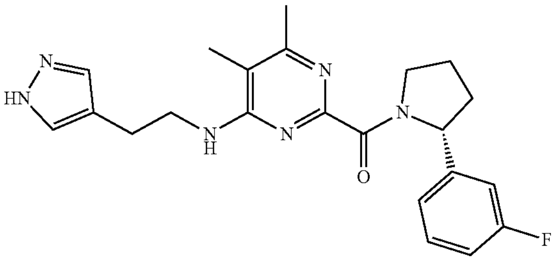 (R)-(4-((2-(1H-pyrazol-4-yl)ethyl)amino)-5,6-dimethylpyrimidin-2-yl)(2-(3-fluorophenyl)pyrrolidin-1-yl)methanone. LRMS (APCI+) m/z 409 (M + H). (1.2:1 mixture of rotamers) Major rotamer: $^1H$ NMR (400 MHz, Methanol-$d_4$) δ 7.44 (s, 2H), 7.35 (td, J = 8.0, 5.9 Hz, 1H), 7.20-7.15 (m, 1H), 6.98 (td, J = 8.1, 2.1 Hz, 1H), 6.71 (dt, J = 10.0, 2.1 Hz, 1H), 5.18 (dd, J = 7.5, 5.3 Hz, 1H), 3.90-3.72 (m, 3H), 3.40 (t, J = 7.3 Hz, 2H), 2.67 (td, J = 7.1, 2.0 Hz, 2H), 2.23 (s, 3H), 2.04 (p, J = 6.9 Hz, 2H), 1.96-1.89 (m, 1H), 1.93 (s, 3H). Minor rotamer: $^1H$ NMR (400 MHz, Methanol-$d_4$) δ 7.49 (s, 2H), 7.22-7.08 (m, 3H), 6.85-6.80 (m, 1H), 5.29 (dd, J = 8.2, 3.9 Hz, 1H), 3.99-3.86 (m, 2H), 3.69-3.60 (m, 1H), 2.88 (t, J = 7.2 Hz, 2H), 2.46 (ddd, J = 12.1, 6.0, 3.8 Hz, 2H), 2.41 (s, 3H), 2.10 (s, 3H), 2.00-1.94 (m, 3H). |
| 16 | (R)-3-phenylmorpholine | 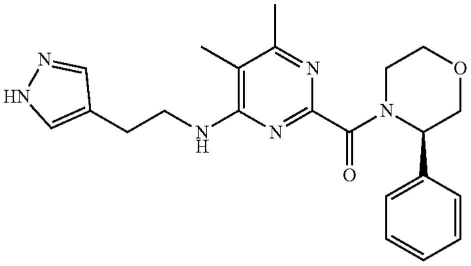 (R)-(4-((2-(1H-pyrazol-4-yl)ethyl)amino)-5,6-dimethylpyrimidin-2-yl)(3-phenylmorpholino)methanone. LRMS (APCI+) m/z 407 (M + H). (1.5:1 mixture of rotamers) Minor rotamer: $^1H$ NMR (400 MHz, Methanol-$d_4$) δ 7.51 (d, J = 7.6 Hz, 2H), 7.43 (s, 2H), 7.41 (s, 1H), 7.35-7.32 (m, 1H), 7.24 (t, J = 7.3 Hz, 1H), 4.80 (d, J = 3.0 Hz, 1H), 4.47 (d, J = 12.1 Hz, 1H), 4.38 (d, J = 13.7 Hz, 1H), 3.74 (dd, J = 11.8, 2.7 Hz, 1H), 3.67-3.60 (m, 2H), 3.49 (t, J = 7.2 Hz, 2H), 3.10 (td, J = 13.1, 3.9 Hz, 1H), 2.68 (t, J = 7.2 Hz, 2H), 2.38 (s, 3H), 2.03 (s, 3H). Major rotamer: $^1H$ NMR (400 MHz, Methanol-$d_4$) δ 7.62 (d, J = 7.6 Hz, 2H), 7.39 (s, 2H), 7.37 (s, 1H), 7.35-7.28 (m, 2H), 5.71 (d, J = 3.2 Hz, 1H), 4.60 (d, J = 12.3 Hz, 1H), 3.97 (td, J = 11.5, 10.2, 3.5 Hz, 2H), 3.85-3.77 (m, 1H), 3.71-3.65 (m, 2H), 3.32-3.25 (m, 2H), 2.82 (t, J = 7.3 Hz, 2H), 2.40 (s, 3H), 2.08 (s, 3H). |

-continued

| Compound No. | Amine in Step 1 | Structure, Name, and Data |
|---|---|---|
| 17 | (R)-1-phenylethan-1-amine | 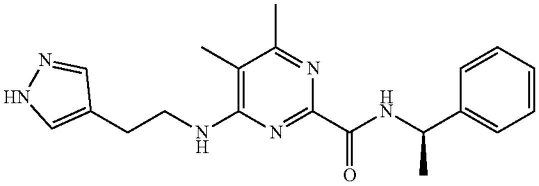 (R)-4-((2-(1H-pyrazol-4-yl)ethyl)amino)-5,6-dimethyl-N-(1-phenylethyl)pyrimidine-2-carboxamide. LRMS (APCI+) m/z 366 (M + H). $^1$H NMR (400 MHz, Methanol-$d_4$) δ 7.44 (s, 2H), 7.43-7.40 (m, 2H), 7.35 (t, J = 7.5 Hz, 2H), 7.28 (t, J = 7.2 Hz, 1H), 5.22 (q, J = 6.9 Hz, 1H), 3.78 (qt, J = 13.5, 7.4 Hz, 2H), 2.84 (t, J = 7.4 Hz, 2H), 2.43 (s, 3H), 2.08 (s, 3H), 1.61 (d, J = 6.9 Hz, 3H). |
| 18 | 3-(3-fluorophenyl)azetidine | 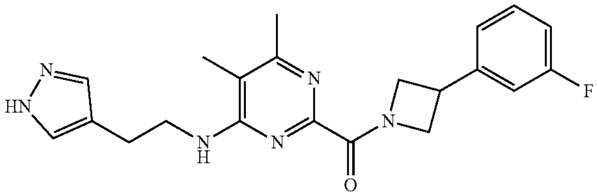 (4-((2-(1H-pyrazol-4-yl)ethyl)amino)-5,6-dimethylpyrimidin-2-yl)(3-(3-fluorophenyl)azetidin-1-yl)methanone. LRMS (APCI+) m/z 396 (M + H). $^1$H NMR (400 MHz, Methanol-$d_4$) δ 7.45-7.36 (m, 1H), 7.42 (s, 2H), 7.20 (d, J = 7.8 Hz, 1H), 7.15 (dt, J = 10.1, 2.1 Hz, 1H), 7.02 (td, J = 8.5, 2.6 Hz, 1H), 5.06 (t, J = 9.6 Hz, 1H), 4.71-4.64 (m, 1H), 4.61 (t, J = 9.7 Hz, 1H), 4.21 (dd, J = 10.7, 6.2 Hz, 1H), 4.00 (ddd, J = 15.0, 8.8, 6.2 Hz, 1H), 3.72 (t, J = 7.4 Hz, 2H), 2.84 (dd, J = 8.7, 6.5 Hz, 2H), 2.44 (s, 3H), 2.09 (s, 3H). |
| 19 | thiophen-2-ylmethanamine | 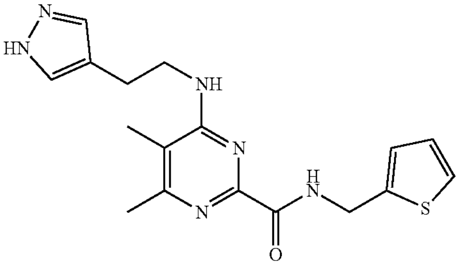 4-((2-(1H-pyrazol-4-yl)ethyl)amino)-5,6-dimethyl-N-(thiophen-2-ylmethyl)pyrimidine-2-carboxamide. LRMS (APCI+) m/z 397 (M + H). $^1$H NMR (400 MHz, Methanol-$d_4$) δ 7.43 (s, 2H), 7.32 (d, J = 5.2 Hz, 1H), 7.09 (d, J = 3.4 Hz, 1H), 6.98 (t, J = 4.4 Hz, 1H), 4.78 (s, 2H), 3.78 (t, J = 7.3 Hz, 2H), 2.84 (t, J = 7.3 Hz, 2H), 2.43 (s, 3H), 2.08 (s, 3H). |
| 20 | (rac)-(3-fluorophenyl)(1-methyl-1H-imidazol-2-yl)methanamine | 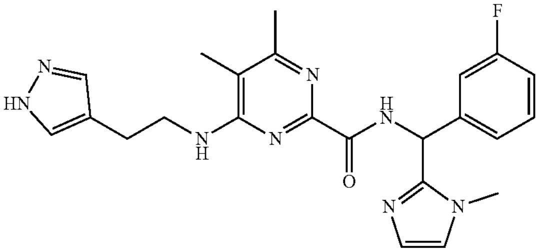 4-((2-(1H-pyrazol-4-yl)ethyl)amino)-N-((3-fluorophenyl)(1-methyl-1H-imidazol-2-yl)methyl)-5,6-dimethylpyrimidine-2-carboxamide. LRMS (APCI+) m/z 449 (M + H). $^1$H NMR (400 MHz, Methanol-$d_4$) δ 8.16 (s, 1H), 7.47 (s, 2H), 7.20 (dd, J = 7.7, 1.3 Hz, 1H), 7.18-7.05 (m, 4H), 6.54 (s, 1H), 3.85-3.72 (m, 2H), 3.70 (s, 3H), 2.84 (t, J = 7.5 Hz, 2H), 2.42 (s, 3H), 2.08 (s, 3H). |

-continued

| Compound No. | Amine in Step 1 | Structure, Name, and Data |
|---|---|---|
| 21 | 2-phenylpropan-2-amine | 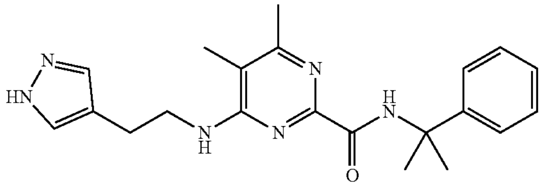 4-((2-(1H-pyrazol-4-yl)ethyl)amino)-5,6-dimethyl-N-(2-phenylpropan-2-yl)pyrimidine-2-carboxamide. LRMS (APCI+) m/z 380 (M + H). $^1$H NMR (400 MHz, Methanol-$d_4$) δ 7.51-7.45 (m, 2H), 7.43 (s, 2H), 7.37-7.30 (m, 2H), 7.27-7.20 (m, 1H), 3.76 (t, J = 7.3 Hz, 2H), 2.86 (t, J = 7.3 Hz, 2H), 2.43 (s, 3H), 2.10 (s, 3H), 1.82 (s, 6H). |
| 22 | 3-phenylazetidin-3-ol | 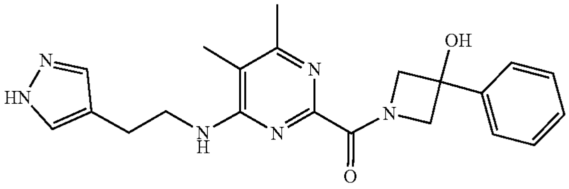 1-(4-methoxybenzyl)-3-(2-(2-methylbenzoyl)-2-azaspiro[3.3]heptan-6-yl)urea. LRMS (APCI+) m/z 393 (M + H). $^1$H NMR (400 MHz, Methanol-$d_4$) δ 7.56 (d, J = 7.7 Hz, 2H), 7.46-7.38 (m, 2H), 7.42 (s, 2H), 7.33 (t, J = 7.3 Hz, 1H), 4.95 (d, J = 10.8 Hz, 1H), 4.83 (d, J = 10.8 Hz, 1H), 4.53 (d, J = 11.0 Hz, 1H), 4.37 (d, J = 11.1 Hz, 1H), 3.72 (t, J = 7.5 Hz, 2H), 2.84 (t, J = 7.5 Hz, 2H), 2.45 (s, 3H), 2.10 (s, 3H). |
| 23 | (rac)-(3-fluorophenyl)(oxazol-2-yl)methanamine(amine 2) | 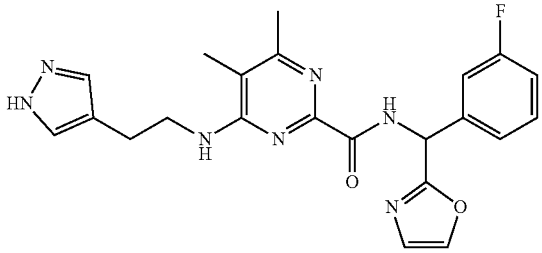 4-((2-(1H-pyrazol-4-yl)ethyl)amino)-N-((3-fluorophenyl)(oxazol-2-yl)methyl)-5,6-dimethylpyrimidine-2-carboxamide. LRMS (APCI+) m/z 437 (M + H). $^1$H NMR (400 MHz, Methanol-$d_4$) δ 8.21 (s, 2H), 7.92 (s, 1H), 7.49 (s, 2H), 7.38 (td, J = 7.9, 5.8 Hz, 1H), 7.27 (d, J = 7.9 Hz, 1H), 7.19 (d, J = 10.1 Hz, 1H), 7.05 (td, J = 8.6, 2.5 Hz, 1H), 6.36 (s, 1H), 3.76 (t, J = 7.7 Hz, 2H), 2.86 (t, J = 7.5 Hz, 2H), 2.43 (s, 3H), 2.09 (s, 3H). |

-continued

| Compound No. | Amine in Step 1 | Structure, Name, and Data |
|---|---|---|
| 24 | tert-butyl 3-(3-fluorophenyl)piperazine-1-carboxylate | 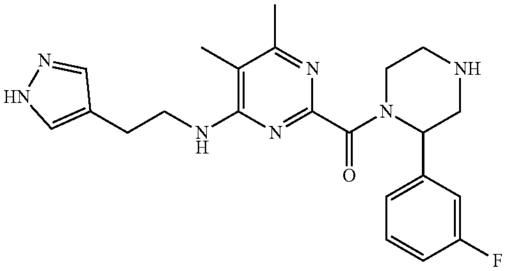 (4-((2-(1H-pyrazol-4-yl)ethyl)amino)-5,6-dimethylpyrimidin-2-yl)(2-(3-fluorophenyl)piperazin-1-yl)methanone. LRMS (APCI+) m/z 424 (M + H). (1.1:1 mixture of rotamers) $^1$H NMR (400 MHz, Methanol-$d_4$) δ 7.61-7.40 (m, 4H), 7.40-7.25 (m, 6H), 7.18 (t, J = 9.0 Hz, 1H), 7.08 (t, J = 9.0 Hz, 1H), 6.15 (s, 1H), 5.66 (s, 1H), 4.25 (d, J = 13.9 Hz, 1H), 4.15 (d, J = 13.9 Hz, 1H), 4.00 (d, J = 15.0 Hz, 1H), 3.88-3.72 (m, 1H), 3.72-3.57 (m, 2H), 3.53-3.45 (m, 2H), 3.39-3.32 (m, 2H), 3.30-3.21 (m, 6H), 2.91 (t, J = 6.7 Hz, 2H), 2.56 (t, J = 6.5 Hz, 2H), 2.47 (s, 3H), 2.45 (s, 3H), 2.14 (s, 3H), 2.06 (s, 3H). |
| 25 | 3-methyl-3-phenylmorpholine | 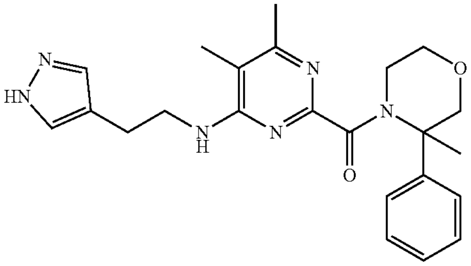 (4-((2-(1H-pyrazol-4-yl)ethyl)amino)-5,6-dimethylpyrimidin-2-yl)(3-methyl-3-phenylmorpholino)methanone. LRMS (APCI+) m/z 421 (M + H). |
| 26 | (R)-1-(2-chlorophenyl)ethan-1-amine | 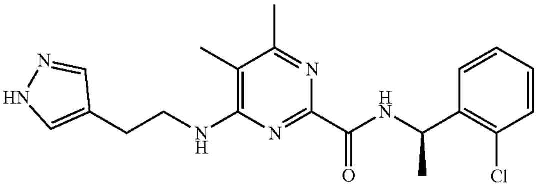 (R)-4-((2-(1H-pyrazol-4-yl)ethyl)amino)-N-(1-(2-chlorophenyl)ethyl)-5,6-dimethylpyrimidine-2-carboxamide. LRMS (APCI+) m/z 400 (M + H). $^1$H NMR (400 MHz, Methanol-$d_4$) δ 7.50 (dd, J = 7.3, 2.1 Hz, 1H), 7.47 (s, 2H), 7.41 (dd, J = 7.4, 1.8 Hz, 1H), 7.33-7.23 (m, 2H), 5.54 (q, J = 6.9 Hz, 1H), 3.79 (tq, J = 13.1, 7.3, 6.7 Hz, 2H), 2.86 (t, J = 7.3 Hz, 2H), 2.43 (s, 3H), 2.09 (s, 3H), 1.61 (d, J = 6.9 Hz, 3H). |
| 27 | 2-(3-fluorophenyl)-2-methylpropan-1-amine | 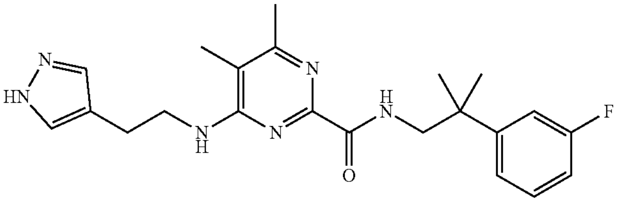 4-((2-(1H-pyrazol-4-yl)ethyl)amino)-N-(2-(3-fluorophenyl)-2-methylpropyl)-5,6-dimethylpyrimidine-2-carboxamide. LRMS (APCI+) m/z 411 (M + H). $^1$H NMR (400 MHz, Methanol-$d_4$) δ 7.38 (s, 2H), 7.36-7.26 (m, 2H), 7.21 (d, J = 10.6 Hz, 1H), 6.92 (t, J = 8.2 Hz, 1H), 3.64 (s, 2H), 3.56 (t, J = 7.1 Hz, 2H), 2.73 (t, J = 7.0 Hz, 2H), 2.40 (s, 3H, 2.05 (s, 3H), 1.40 (s, 6H). |

-continued

| Compound No. | Amine in Step 1 | Structure, Name, and Data |
|---|---|---|
| 28 | 4,4-difluoro-2-phenylpiperidine | 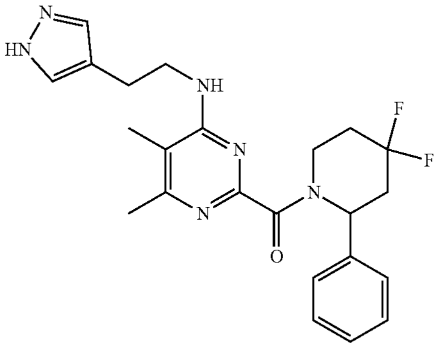 (4-((2-(1H-pyrazol-4-yl)ethyl)amino)-5,6-dimethylpyrimidin-2-yl)(4,4-difluoro-2-phenylpiperidin-1-yl)methanone. LRMS (APCI+) m/z 381 (M + H). (1.3:1 mixture of rotamers) $^1$H NMR (400 MHz, Methanol-$d_4$) δ 7.53-7.25 (m, 13H, 7.21 (t, J = 7.3 Hz, 1H), 6.17 (d, J = 6.5 Hz, 1H), 5.20 (d, J = 6.2 Hz, 1H), 4.76 (d, J = 14.1 Hz, 1H), 3.74 (q, J = 6.8 Hz, 3H), 3.63 (d, J = 15.2 Hz, 2H), 3.13-2.99 (m, 2H), 2.88 (t, J = 7.4 Hz, 3H), 2.59 (t, J = 7.3 Hz, 2H), 2.52-2.31 (m, 9H), 2.24-2.05 (m, 7H), 1.99 (s, 3H). |
| 29 | (S)-1-(2-chlorophenyl)-N-methylethan-1-amine | 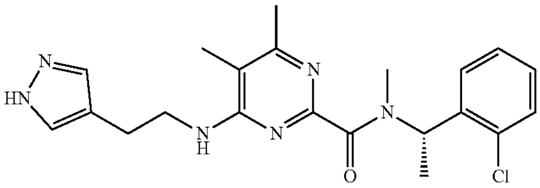 (S)-4-((2-(1H-pyrazol-4-yl)ethyl)amino)-N-(1-(2-chlorophenyl)ethyl)-N,5,6-trimethylpyrimidine-2-carboxamide. LRMS (APCI+) m/z 381 (M + H). (1.2:1 mixture of rotamers) Minor rotamer: $^1$H NMR (400 MHz, Methanol-$d_4$) δ 8.56 (s, 2H), 7.54 (s, 2H), 7.47 (s, 2H), 5.98 (q, J = 7.1 Hz, 1H), 3.70 (td, J = 7.1, 2.7 Hz, 2H), 2.85 (t, J = 7.2 Hz, 2H), 2.70 (s, 3H), 2.40 (s, 3H), 2.08 (s, 3H), 1.71 (d, J = 6.7 Hz, 3H). Major rotamer: $^1$H NMR (400 MHz, Methanol-$d_4$) δ 8.49 (s, 2H), 7.51 (d, J = 5.2 Hz, 2H), 7.42 (s, 2H), 5.01 (q, J = 6.9 Hz, 1H), 3.58 (h, J = 6.1 Hz, 2H), 2.82 (s, 3H), 2.73 (t, J = 7.3 Hz, 2H), 2.39 (s, 3H), 2.05 (s, 3H), 1.67 (d, J = 6.7 Hz, 3H). |
| 30 | (R)-1-(3-chloropyridin-2-yl)ethan-1-amine | 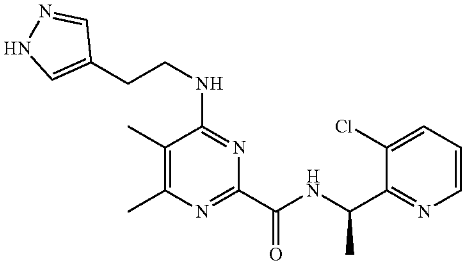 (R)-4-((2-(1H-pyrazol-4-yl)ethyl)amino)-N-(1-(3-chloropyridin-2-yl)ethyl)-5,6-dimethylpyrimidine-2-carboxamide. LRMS (APCI+) m/z 400 (M + H). $^1$H NMR (400 MHz, Methanol-$d_4$) δ 8.39 (dd, J = 4.7, 1.3 Hz, 1H), 7.90 (dd, J = 8.1, 1.3 Hz, 1H), 7.56 (s, 2H), 7.35 (dd, J = 8.1, 4.7 Hz, 1H), 5.69 (q, J = 6.7 Hz, 1H), 3.83 (td, J = 7.2, 3.8 Hz, 2H), 2.93 (t, J = 7.5 Hz, 2H), 2.45 (s, 3H), 2.10 (s, 3H), 1.56 (d, J = 6.6 Hz, 3H). |

-continued

| Compound No. | Amine in Step 1 | Structure, Name, and Data |
| --- | --- | --- |
| 31 | benzylamine | 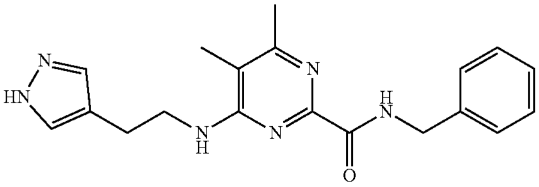<br>4-((2-(1H-pyrazol-4-yl)ethyl)amino)-N-benzyl-5,6-dimethylpyrimidine-2-carboxamide. LRMS (APCI+) m/z 352 (M + H). $^1$H NMR (400 MHz, Methanol-$d_4$) δ 7.41 (s, 2H), 7.41-7.31 (m, 4H), 7.31-7.25 (m, 1H), 4.62 (s, 2H), 3.76 (t, J = 7.3 Hz, 2H), 2.83 (t, J = 7.3 Hz, 2H), 2.42 (s, 3H), 2.07 (s, 3H). |
| 32 | 3-fluorobenzylamine | 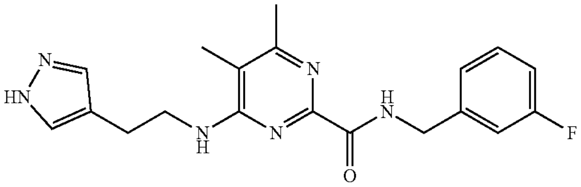<br>4-((2-(1H-pyrazol-4-yl)ethyl)amino)-N-(3-fluorobenzyl)-5,6-dimethylpyrimidine-2-carboxamide. LRMS (APCI+) m/z 370 (M + H). $^1$H NMR (400 MHz, Methanol-$d_4$) δ 7.45 (s, 2H, 7.36 (td, J = 8.0, 5.9 Hz, 1H), 7.20 (d, J = 7.7 Hz, 1H), 7.13 (dt, J = 9.9, 2.0 Hz, 1H), 7.00 (td, J = 8.6, 2.7 Hz, 1H), 4.63 (s, 2H), 3.80 (t, J = 7.3 Hz, 2H), 2.85 (t, J = 7.2 Hz, 2H), 2.44 (s, 3H), 2.09 (s, 3H). |
| 33 | 2,2,2-trifluoro-1-phenylethan-1-amine | 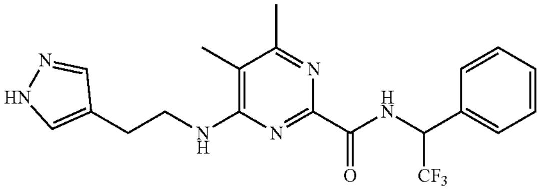<br>4-((2-(1H-pyrazol-4-yl)ethyl)amino)-5,6-dimethyl-N- (2,2,2-trifluoro-1-phenylethyl)pyrimidine-2-carboxamide. LRMS (APCI+) m/z 420 (M + H). $^1$H NMR (400 MHz, Methanol-$d_4$) δ 7.53 (dd, J = 6.8, 3.0 Hz, 2H), 7.49 (s, 2H), 7.46-7.42 (m, 3H), 5.87 (q, J = 8.0 Hz, 1H), 3.86-3.70 (m, 2H), 2.87 (t, J = 7.5 Hz, 2H), 2.44 (s, 3H), 2.09 (s, 3H). |
| 34 | 4-phenylpiperidin-4-ol | 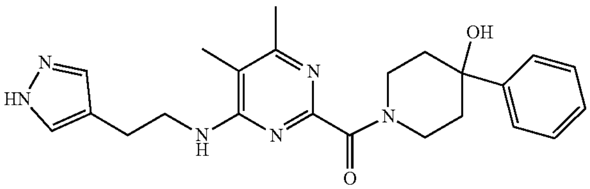<br>(4-((2-(1H-pyrazol-4-yl)ethyl)amino)-5,6-dimethylpyrimidin-2-yl)(4-hydroxy-4-phenylpiperidin-1-yl)methanone. LRMS (APCI+) m/z 421 (M + H). $^1$H NMR (400 MHz, Methanol-$d_4$) δ 7.49 (d, J = 7.8 Hz, 2H), 7.46 (s, 2H, 7.34 (t, J = 7.5 Hz, 2H), 7.29-7.20 (m, 1H), 4.62-4.52 (m, 1H), 3.74-3.66 (m, 2H), 3.59 (t, J = 12.9 Hz, 1H), 3.45 (d, J = 13.8 Hz, 1H), 3.37 (d, J = 10.0 Hz, 1H), 2.85 (t, J = 7.6 Hz, 2H), 2.40 (s, 3H), 2.15 (td, J = 13.0, 6.3 Hz, 2H), 2.08 (s, 3H), 1.86 (d, J = 14.0 Hz, 1H), 1.68 (d, J = 13.5 Hz, 1H). |

-continued

| Compound No. | Amine in Step 1 | Structure, Name, and Data |
|---|---|---|
| 35 | (R)-1-(thiophen-3-yl)ethan-1-amine | 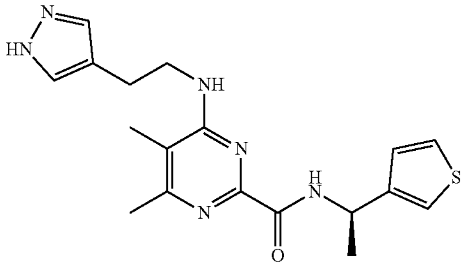 (R)-4-((2-(1H-pyrazol-4-yl)ethyl)amino)-5,6-dimethyl-N-(1-(thiophen-3-yl)ethyl)pyrimidine-2-carboxamide. LRMS (APCI+) m/z 371 (M + H). $^{1}$H NMR (400 MHz, Methanol-$d_4$) δ 7.45-7.39 (m, 1H), 7.41 (s, 2H), 7.33 (d, J = 2.8 Hz, 1H), 7.16 (dd, J = 5.0, 1.2 Hz, 1H), 5.32 (q, J = 6.8 Hz, 1H), 3.76 (tq, J = 13.5, 7.3, 6.7 Hz, 2H), 2.83 (t, J = 7.4 Hz, 2H), 2.44 (s, 3H), 2.08 (s, 3H), 1.64 (d, J = 6.9 Hz, 3H). |
| 36 | 1-(6-chloropyridin-2-yl)ethan-1-amine | 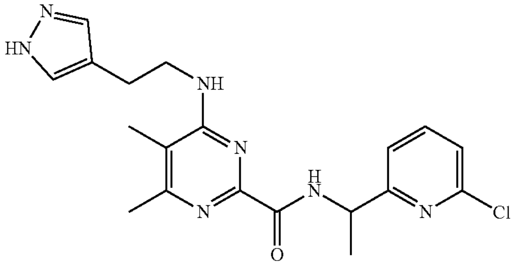 4-((2-(1H-pyrazol-4-yl)ethyl)amino)-N-(1-(6-chloropyridin-2-yl)ethyl)-5,6-dimethylpyrimidine-2-carboxamide. LRMS (APCI+) m/z 400 (M + H). $^{1}$H NMR (400 MHz, Methanol-$d_4$) δ 7.81 (t, J = 7.8 Hz, 1H), 7.50 (s, 2H), 7.43 (d, J = 7.6 Hz, 1H), 7.37 (d, J = 7.9 Hz, 1H), 5.24 (q, J = 6.8 Hz, 1H), 3.86 (q, J = 6.8 Hz, 2H), 2.92 (t, J = 7.1 Hz, 2H), 2.44 (s, 3H), 2.09 (s, 3H), 1.59 (d, J = 6.8 Hz, 3H). |
| 37 | (R)-1-(3-methylpyridin-2-yl)ethan-1-amine | 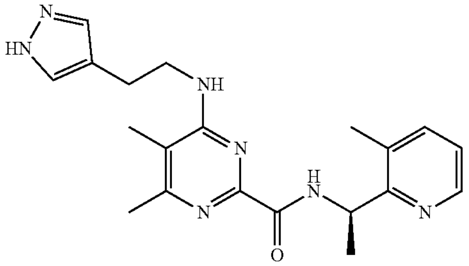 (R)-4-((2-(1H-pyrazol-4-yl)ethyl)amino)-5,6-dimethyl-N-(1-(3-methylpyridin-2-yl)ethyl)pyrimidine-2-carboxamide. LRMS (APCI+) m/z 421 (M + H). $^{1}$H NMR (400 MHz, Methanol-$d_4$) δ 8.30 (dd, J = 4.8, 1.5 Hz, 1H), 7.64 (d, J = 7.8 Hz, 1H), 7.55 (s, 2H), 7.22 (dd, J = 7.7, 4.8 Hz, 1H), 5.49 (q, J = 6.7 Hz, 1H), 3.83 (t, J = 7.5 Hz, 2H), 2.92 (t, J = 7.5 Hz, 2H), 2.47 (s, 3H), 2.45 (s, 3H), 2.10 (s, 3H), 1.53 (d, J = 6.6 Hz, 3H). |
| 38 | (R)-2-phenylpyrrolidine | 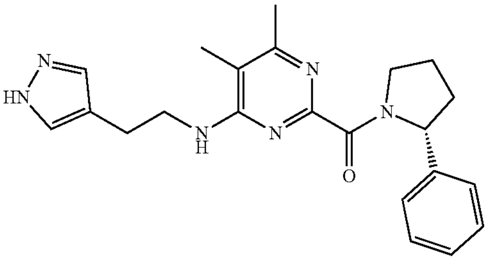 (R)-(4-((2-(1H-pyrazol-4-yl)ethyl)amino)-5,6-dimethylpyrimidin-2-yl)(2-phenylpyrrolidin-1-yl)methanone. LRMS (APCI+) m/z 391 (M + H). |

-continued

| Compound No. | Amine in Step 1 | Structure, Name, and Data |
|---|---|---|
| 39 | (R)-1-(3-fluorophenyl)ethan-1-amine | 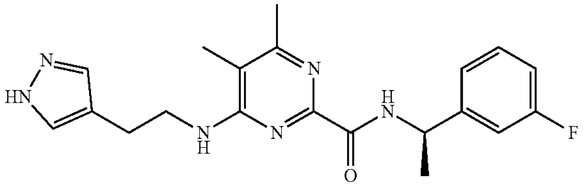 (R)-4-((2-(1H-pyrazol-4-yl)ethyl)amino)-N-(1-(3-fluorophenyl)ethyl)-5,6-dimethylpyrimidine-2-carboxamide. LRMS (APCI+) m/z 383 (M + H). $^1$H NMR (400 MHz, Methanol-$d_4$) δ 7.46 (s, 2H), 7.36 (td, J = 8.0, 5.9 Hz, 1H), 7.24 (dd, J = 7.8, 1.2 Hz, 1H), 7.18 (dt, J = 10.1, 2.1 Hz, 1H), 7.00 (td, J = 8.1, 2.0 Hz, 1H), 5.22 (q, J = 7.0 Hz, 1H), 3.80 (h, J = 6.1 Hz, 2H), 2.86 (t, J = 7.3 Hz, 2H), 2.43 (s, 3H), 2.08 (s, 3H), 1.61 (d, J = 7.0 Hz, 3H). |
| 40 | rac-(1-methyl-1H-imidazol-2-yl)(phenyl)methanamine | 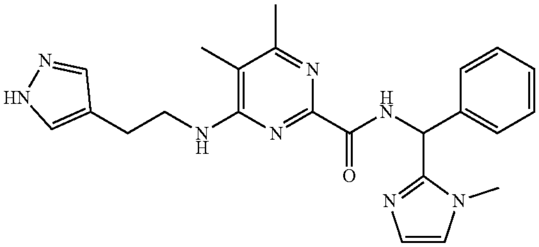 4-((2-(1H-pyrazol-4-yl)ethyl)amino)-5,6-dimethyl-N-((1-methyl-1H-imidazol-2-yl)(phenyl)methyl)pyrimidine-2-carboxamide. LRMS (APCI+) m/z 432 (M + H). $^1$H NMR (400 MHz, Methanol-$d_4$) δ 7.43 (s, 2H), 7.42-7.36 (m, 5H), 7.18 (d, J = 1.4 Hz, 1H), 7.09 (d, J = 1.4 Hz, 1H), 6.52 (s, 1H), 3.86-3.74 (m, 1H), 3.74-3.64 (m, 1H), 3.68 (s, 3H), 2.82 (t, J = 7.5 Hz, 2H), 2.42 (s, 3H), 2.08 (s, 3H). |
| 41 | 1-(3-fluorophenyl)-2-methylpropan-2-amine | 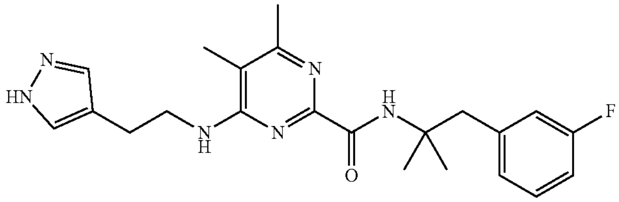 4-((2-(1H-pyrazol-4-yl)ethyl)amino)-N-(1-(3-fluorophenyl)-2-methylpropan-2-yl)-5,6-dimethylpyrimidine-2-carboxamide. LRMS (APCI+) m/z 411 (M + H). $^1$H NMR (400 MHz, Methanol-$d_4$) δ 7.37 (s, 2H), 7.25 (q, J = 8.1 Hz, 1H), 7.04 (d, J = 8.0 Hz, 1H), 6.94 (q, J = 9.3 Hz, 2H), 3.75 (t, J = 6.2 Hz, 2H), 3.18 (s, 2H), 2.81 (t, J = 7.0 Hz, 2H), 2.52 (s, 3H), 2.13 (s, 3H), 1.50 (s, 6H) |
| 42 | rac-trans-4-phenylpyrrolidin-3-ol | 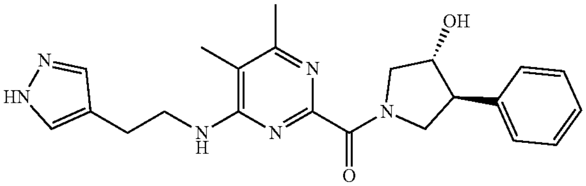 rac-(4-((2-(1H-pyrazol-4-yl)ethyl)amino)-5,6-dimethylpyrimidin-2-yl)(trans-3-hydroxy-4-phenylpyrrolidin-1-yl)methanone. LRMS (APCI+) m/z 407 (M + H). $^1$H NMR (400 MHz, Methanol-$d_4$) δ 7.49-7.19 (m, 7H), 4.46-4.31 (m, 1H), 4.20-4.01 (m, 1H), 3.96-3.80 (m, 2H), 3.76-3.62 (m, 2H), 3.61-3.47 (m, 1H), 3.43-3.29 (m, 1H), 2.91-2.75 (m, 2H), 2.41 (d, J = 4.1 Hz, 3H), 2.08 (d, J = 6.4 Hz, 3H). |

-continued

| Compound No. | Amine in Step 1 | Structure, Name, and Data |
|---|---|---|
| 43 | (R)-1-(6-methoxypyridin-2-yl)ethan-1-amine | 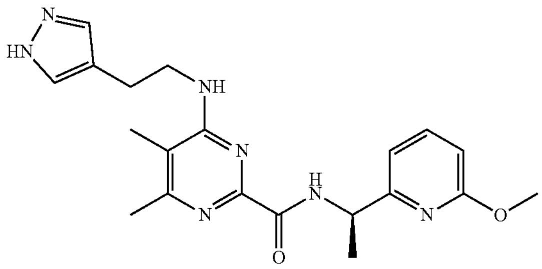 (R)-4-((2-(1H-pyrazol-4-yl)ethyl)amino)-N-(1-(6-methoxypyridin-2-yl)ethyl)-5,6-dimethylpyrimidine-2-carboxamide. LRMS (APCI+) m/z 396 (M + H). $^1$H NMR (400 MHz, Methanol-$d_4$) δ 7.65 (t, J = 7.8 Hz, 1H), 7.47 (s, 2H), 6.97 (d, J = 7.2 Hz, 1H), 6.70 (d, J = 8.3 Hz, 1H), 5.20 (q, J = 6.8 Hz, 1H), 3.88 (s, 3H), 3.80 (td, J = 7.1, 3.5 Hz, 2H), 2.87 (t, J = 7.3 Hz, 2H), 2.44 (s, 3H), 2.09 (s, 3H), 1.58 (d, J = 6.7 Hz, 3H). |
| 44 | 1-methyl-3-phenylpiperazine | 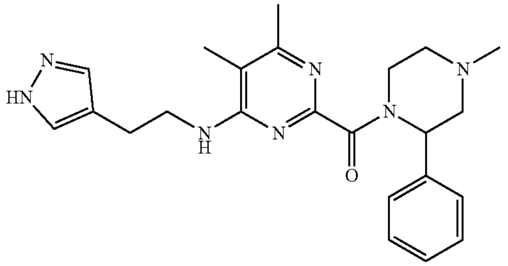 (4-((2-(1H-pyrazol-4-yl)ethyl)amino)-5,6-dimethylpyrimidin-2-yl)(4-methyl-2-phenylpiperazin-1-yl)methanone. LRMS (APCI+) m/z 420 (M + H). (1.4:1 mixture of rotamers) $^1$H NMR (400 MHz, Methanol-$d_4$) δ 7.57 (d, J = 7.7 Hz, 3H), 7.48 (d, J = 7.9 Hz, 4H), 7.40 (t, J = 7.5 Hz, 3H), 7.34 (t, J = 7.6 Hz, 3H), 7.25 (t, J = 7.4 Hz, 1H), 5.96 (s, 1H), 5.07 (s, 1H), 4.65 (d, J = 13.7 Hz, 1H), 3.83 (d, J = 12.6 Hz, 1H), 3.79-3.64 (m, 3H), 3.58-3.47 (m, 2H, 3.42-3.30 (m, 3H), 3.17-3.10 (m, 1H), 3.03 (t, J = 11.5 Hz, 1H), 2.91-2.78 (m, 6H), 2.61 (t, J = 7.3 Hz, 2H), 2.49 (s, 3H), 2.46 (s, 3H), 2.41 (s, 3H), 2.36 (s, 3H), 2.10 (s, 3H), 2.02 (s, 3H). |
| 45 | 1-benzylpiperazin-2-one | 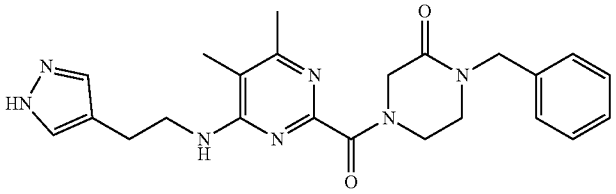 4-(4-((2-(1H-pyrazol-4-yl)ethyl)amino)-5,6-dimethylpyrimidine-2-carbonyl)-1-benzylpiperazin-2-one. LRMS (APCI+) m/z 434 (M + H). (1.5:1 mixture of rotamers) Major rotamer: $^1$H NMR (400 MHz, Methanol-$d_4$) δ 7.43 (s, 2H), 7.37-7.28 (m, 5H), 4.66 (s, 2H), 4.44 (s, 2H), 3.67-3.59 (m, 4H), 3.38 (s, 2H), 2.78 (t, J = 7.9 Hz, 2H), 2.37 (s, 3H), 2.06 (s, 3H). Minor rotamer: 1H NMR (400 MHz, Methanol-d4) d 7.50 (s, 2H), 7.39-7.26 (m, 5H), 4.66 (s, 2H), 4.26 (s, 2H, 3.70 (t, J = 7.7 Hz, 2H), 3.47 (s, 2H), 2.85 (t, J = 8.1 Hz, 2H), 2.41 (s, 3H), 2.09 (s, 3H). |

-continued

| Compound No. | Amine in Step 1 | Structure, Name, and Data |
|---|---|---|
| 46 | (rac)-(3-fluorophenyl)(pyridin-2-yl)methanamine | 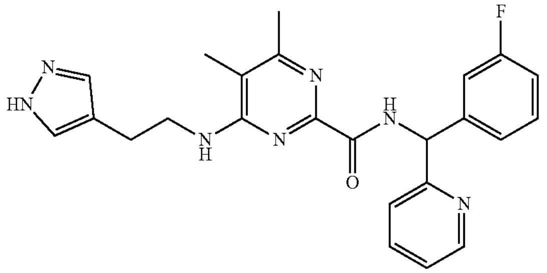 (rac)-4-((2-(1H-pyrazol-4-yl)ethyl)amino)-N-((3-fluorophenyl)(pyridin-2-yl)methyl)-5,6-dimethylpyrimidine-2-carboxamide. LRMS (APCI+) m/z 447 (M + H). $^1$H NMR (400 MHz, Methanol-$d_4$) δ 8.49 (dt, J = 4.7, 1.4 Hz, 1H), 7.82 (td, J = 7.7, 1.8 Hz, 1H), 7.54 (s, 2H), 7.51 (d, J = 7.8 Hz, 1H), 7.38-7.30 (m, 2H), 7.29-7.22 (m, 1H), 7.18 (dt, J = 10.0, 2.0 Hz, 1H), 6.99 (td, J = 8.2, 2.2 Hz, 1H), 6.30 (s, 1H), 3.84 (t, J = 7.5 Hz, 2H), 2.94 (td, J = 7.3, 3.2 Hz, 2H), 2.44 (s, 3H), 2.10 (s, 3H). |
| 47 | (R)-1-(pyridin-2-yl)ethan-1-amine | 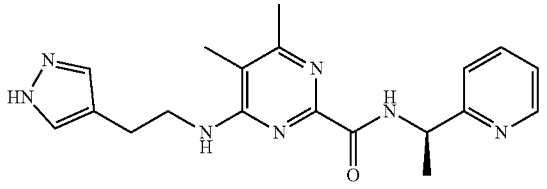 (R)-4-((2-(1H-pyrazol-4-yl)ethyl)amino)-5,6-dimethyl-N-(1-(pyridin-2-yl)ethyl)pyrimidine-2-carboxamide. LRMS (APCI+) m/z 367 (M + H). $^1$H NMR (400 MHz, Methanol-$d_4$) δ 8.48 (ddd, J = 5.0, 1.8, 0.9 Hz, 1H), 7.82 (td, J = 7.7, 1.8 Hz, 1H), 7.54 (s, 2H), 7.47 (dd, J = 7.9, 1.1 Hz, 1H), 7.32 (ddd, J = 7.5, 4.9, 1.1 Hz, 1H), 5.25 (q, J = 6.9 Hz, 1H), 3.83 (t, J = 7.4 Hz, 2H), 2.90 (t, J = 7.4 Hz, 2H), 2.45 (s, 3H), 2.10 (s, 3H), 1.60 (d, J = 6.9 Hz, 3H). |
| 48 | 3-(trifluoromethyl)azetidin-3-ol | 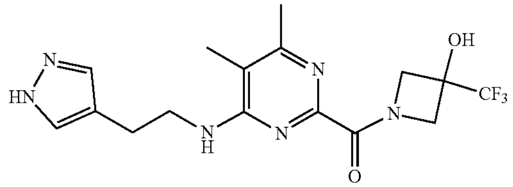 (4-((2-(1H-pyrazol-4-yl)ethyl)amino)-5,6-dimethylpyrimidin-2-yl)(3-hydroxy-3-(trifluoromethyl)azetidin-1-yl)methanone. LRMS (APCI+) m/z 385 (M + H). $^1$H NMR (400 MHz, Methanol-$d_4$) δ 7.49 (s, 2H, 4.97-4.88 (m, 1H), 4.64 (d, J = 11.6 Hz, 1H), 4.42 (d, J = 11.6 Hz, 1H), 4.12 (d, J = 11.6 Hz, 1H), 3.72 (t, J = 7.6 Hz, 2H), 2.86 (t, J = 6.6 Hz, 2H), 2.43 (s, 3H), 2.10 (s, 3H). |
| 49 | (R)-1-(3-fluorophenyl)-2-methoxyethan-1-amine | 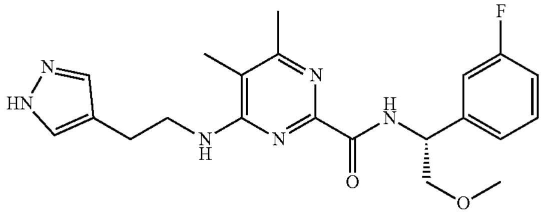 (R)-4-((2-(1H-pyrazol-4-yl)ethyl)amino)-N-(1-(3-fluorophenyl)-2-methoxyethyl)-5,6-dimethylpyrimidine-2-carboxamide. LRMS (APCI+) m/z 413 (M + H). $^1$H NMR (400 MHz, Methanol-$d_4$) δ 7.51 (s, 2H), 7.36 (td, J = 8.0, 5.9 Hz, 1H), 7.24 (d, J = 7.7 Hz, 1H), 7.18 (dt, J = 10.1, 2.0 Hz, 1H, 7.01 (td, J = 8.5, 2.5 Hz, 1H), 5.27 (t, J = 5.0 Hz, 1H), 3.85-3.75 (m, 4H), 3.37 (s, 3H), 2.89 (td, J = 7.1, 2.1 Hz, 2H), 2.44 (s, 3H), 2.10 (s, 3H). |

-continued

| Compound No. | Amine in Step 1 | Structure, Name, and Data |
|---|---|---|
| 50 | 2-phenylethan-1-amine | 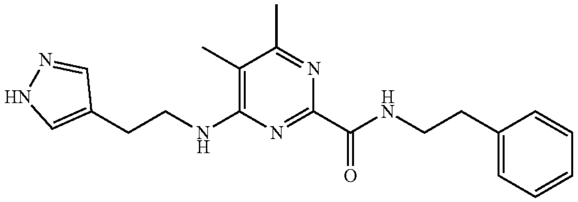 4-((2-(1H-pyrazol-4-yl)ethyl)amino)-5,6-dimethyl-N-phenethylpyrimidine-2-carboxamide. LRMS (APCI+) m/z 366 (M + H). $^1$H NMR (400 MHz, Methanol-$d_4$) δ 7.42 (s, 2H), 7.29 (d, J = 4.3 Hz, 4H), 7.20 (h, J = 4.3 Hz, 1H), 3.72 (t, J = 7.2 Hz, 2H), 3.67 (t, J = 7.1 Hz, 2H), 2.94 (t, J = 7.1 Hz, 2H), 2.80 (t, J = 7.1 Hz, 2H), 2.42 (s, 3H), 2.07 (s, 3H). |
| 51 | 3-(2,3-difluorophenyl)azetidin-3-ol | 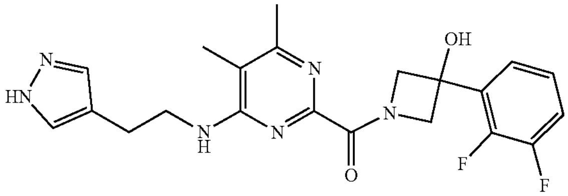 (4-((2-(1H-pyrazol-4-yl)ethyl)amino)-5,6-dimethylpyrimidin-2-yl)(3-(2,3-difluorophenyl)-3-hydroxyazetidin-1-yl)methanone. LRMS (APCI+) m/z 429 (M + H). $^1$H NMR (400 MHz, Methanol-$d_4$) δ 7.47 (s, 2H), 7.34-7.15 (m, 3H), 5.12 (d, J = 10.8 Hz, 1H), 4.89-4.83 (m, 1H, 4.68 (d, J = 11.6 Hz, 1H), 4.37 (d, J = 11.8 Hz, 1H), 3.80-3.69 (m, 2H), 2.92-2.82 (m, 2H), 2.44 (s, 3H), 2.09 (s, 3H). |
| 52 | (R)-3-phenylpyrrolidine | 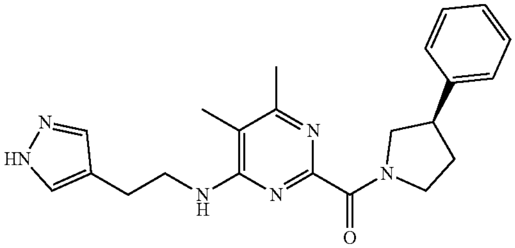 (R)-(4-((2-(1H-pyrazol-4-yl)ethyl)amino)-5,6-dimethylpyrimidin-2-yl)(3-phenylpyrrolidin-1-yl)methanone. LRMS (APCI+) m/z 391 (M + H). (1: 1 mixture of rotamers) $^1$H NMR (400 MHz, Methanol-$d_4$) δ 7.46 (s, 2H), 7.37 (s, 2H), 7.36-7.33 (m, 4H), 7.33-7.29 (m, 1H, 7.28 (s, 3H), 7.26-7.20 (m, 2H), 4.09 (dd, J = 11.6, 7.2 Hz, 1H), 3.95 (dd, J = 11.0, 7.4 Hz, 1H), 3.89 (ddd, J = 12.0, 8.3, 3.1 Hz, 1H), 3.78-3.58 (m, 9H), 3.55-3.45 (m, 2H), 2.85 (t, J = 7.2 Hz, 2H), 2.79 (t, J = 7.4 Hz, 2H), 2.42 (s, 3H), 2.40 (s, 3H), 2.39-2.31 (m, 2H), 2.19-2.10 (m, 2H), 2.09 (s, 3H), 2.07 (s, 3H). |
| 53 | (R)-1-(2-chlorophenyl)-N-methylethan-1-amine | 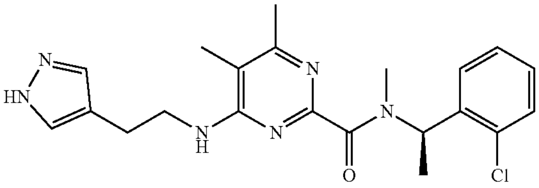 (R)-4-((2-(1H-pyrazol-4-yl)ethyl)amino)-N-(1-(2-chlorophenyl)ethyl)-N,5,6-trimethylpyrimidine-2-carboxamide. LRMS (APCI+) m/z 413 (M + H). (1.3:1 mixture of rotamers) Minor rotamer: $^1$H NMR (400 MHz, Methanol-$d_4$) δ 7.54 (dd, J = 6.9, 2.5 Hz, 1H), 7.43 (s, 2H), 7.40-7.36 (m, 2H), 7.26 (td, J = 7.5, 1.6 Hz, 1H), 5.39 (q, J = 6.9 Hz, 1H), 3.73-3.62 (m, 2H), 2.91 (s, 3H), 2.77-2.73 (m, 2H), 2.38 (s, 3H), 2.07 (s, 3H), 1.75 (d, J = 6.9 Hz, 3H). Major rotamer: $^1$H NMR (400 MHz, Methanol-$d_4$) δ 7.61 (dd, J = 7.2, 2.2 Hz, 1H), 7.48 (dd, J = 7.3, 1.9 Hz, 1H), 7.42 (s, 2H), 7.37-7.31 (m, 2H), 6.05 (q, J = 7.0 Hz, 1H), 3.63-3.51 (m, 2H), 2.79 (t, J = 7.4 Hz, 2H), 2.57 (s, 1H), 2.39 (s, 3H, 2.06 (s, 3H), 1.67 (d, J = 7.0 Hz, 3H). |

-continued

| Compound No. | Amine in Step 1 | Structure, Name, and Data |
|---|---|---|
| 54 | (R)-2-(2-fluorophenyl)pyrrolidine | 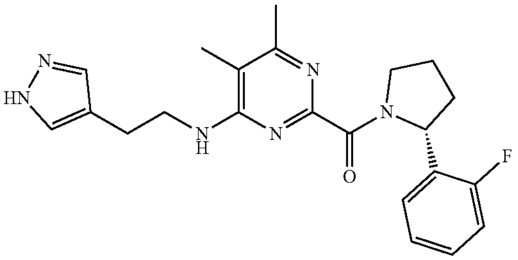 (R)-(4-((2-(1H-pyrazol-4-yl)ethyl)amino)-5,6-dimethylpyrimidin-2-yl)(2-(2-fluorophenyl)pyrrolidin-1-yl)methanone. LRMS (APCI+) m/z 409 (M + H). (1.3:1 mixture of rotamers) $^{1}$H NMR (400 MHz, Methanol-$d_4$) δ 7.50 (s, 2H), 7.44 (s, 2H), 7.35 (t, J = 7.6 Hz, 1H), 7.29 (q, J = 7.0 Hz, 1H), 7.17-7.07 (m, 3H), 7.04 (dt, J = 7.7, 3.9 Hz, 1H, 6.98 (t, J = 7.4 Hz, 1H), 6.87 (dd, J = 11.0, 8.2 Hz, 1H), 5.50 (dd, J = 7.5, 5.3 Hz, 2H), 3.99-3.81 (m, 3H), 3.80-3.63 (m, 3H), 3.45-3.38 (m, 2H), 2.89 (t, J = 7.2 Hz, 2H), 2.67 (t, J = 7.2 Hz, 2H), 2.53-2.36 (m, 5H), 2.21 (s, 3H), 2.14-1.95 (m, 9H), 1.92 (s, 3H). |
| 55 | (6-fluoropyridin-2-yl)methanamine | 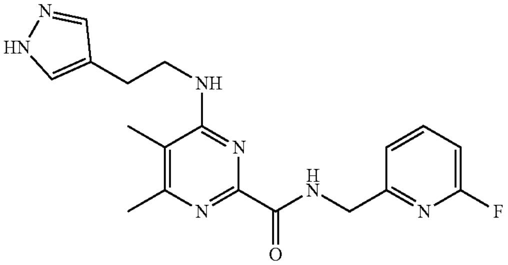 4-((2-(1H-pyrazol-4-yl)ethyl)amino)-N-((6-fluoropyridin-2-yl)methyl)-5,6-dimethylpyrimidine-2-carboxamide. LRMS (APCI+) m/z 370 (M + H). $^{1}$H NMR (400 MHz, Methanol-$d_4$) δ 7.93 (q, J = 8.0 Hz, 1H), 7.49 (s, 2H), 7.33 (d, J = 7.0 Hz, 1H), 6.97 (dt, J = 8.2, 1.5 Hz, 1H), 4.69 (s, 2H), 3.84 (t, J = 7.1 Hz, 2H), 2.89 (t, J = 7.2 Hz, 2H), 2.45 (s, 3H, 2.09 (s, 3H). |
| 56 | (R)-1-(3-fluoropyridin-2-yl)ethan-1-amine | 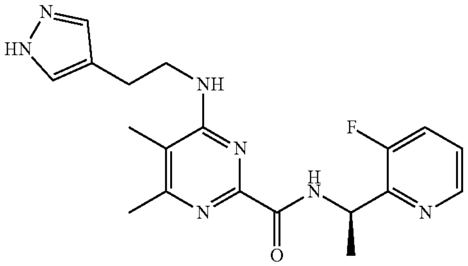 (R)-4-((2-(1H-pyrazol-4-yl)ethyl)amino)-N-(1-(3-fluoropyridin-2-yl)ethyl)-5,6-dimethylpyrimidine-2-carboxamide. LRMS (APCI+) m/z 384 (M + H). $^{1}$H NMR (400 MHz, Methanol-$d_4$) δ 8.31 (d, J = 4.7 Hz, 1H), 7.64 (t, J = 9.1 Hz, 1H), 7.55 (s, 2H), 7.40 (dt, J = 8.6, 4.5 Hz, 1H), 5.57 (q, J = 6.8 Hz, 1H), 3.82 (td, J = 7.3, 3.3 Hz, 2H), 2.92 (t, J = 7.5 Hz, 2H), 2.45 (s, 3H), 2.10 (s, 3H), 1.57 (d, J = 6.7 Hz, 3H). |

-continued

| Compound No. | Amine in Step 1 | Structure, Name, and Data |
|---|---|---|
| 57 | (3-(aminomethyl)azetidin-1-yl)(phenyl)methanone | 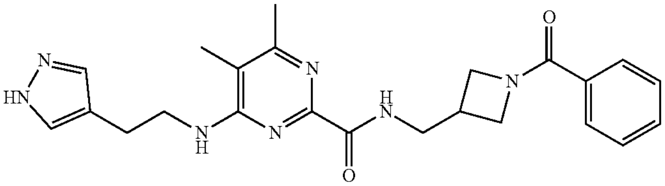 4-((2-(1H-pyrazol-4-yl)ethyl)amino)-N-((1-benzoylazetidin-3-yl)methyl)-5,6-dimethylpyrimidine-2-carboxamide. LRMS (APCI+) m/z 434 (M + H). $^1$H NMR (400 MHz, Methanol-$d_4$) δ 7.62 (d, J = 7.0 Hz, 2H), 7.56-7.40 (m, 3H), 7.49 (s, 2H), 4.46 (t, J = 9.1 Hz, 1H), 4.29 (t, J = 9.9 Hz, 1H), 4.24-4.15 (m, 1H), 4.06-3.97 (m, 1H), 3.83 (t, J = 5.8 Hz, 2H), 3.70 (d, J = 5.6 Hz, 2H), 3.10-2.99 (m, 1H), 2.87 (t, J = 7.7 Hz, 2H), 2.44 (s, 3H), 2.08 (s, 3H). |
| 58 | benzofuran-3-ylmethanamine | 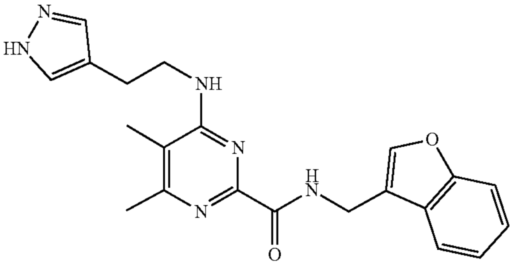 4-((2-(1H-pyrazol-4-yl)ethyl)amino)-N-(benzofuran-3-ylmethyl)-5,6-dimethylpyrimidine-2-carboxamide. LRMS (APCI+) m/z 391 (M + H). $^1$H NMR (400 MHz, Methanol-$d_4$) δ 7.81 (s, 1H), 7.75 (d, J = 7.7 Hz, 1H), 7.49 (d, J = 8.3 Hz, 1H, 7.39 (s, 2H), 7.31 (t, J = 7.7 Hz, 1H), 7.22 (t, J = 7.5 Hz, 1H), 4.77 (s, 2H), 3.88 (t, J = 7.2 Hz, 2H), 2.84 (t, J = 7.2 Hz, 2H), 2.51 (s, 3H), 2.12 (s, 3H). |
| 59 | (S)-1-phenylethan-1-amine | 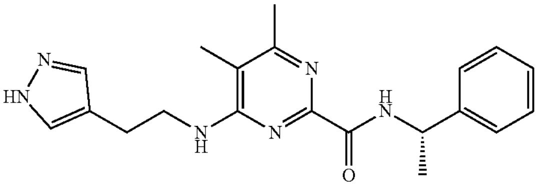 (S)-4-((2-(1H-pyrazol-4-yl)ethyl)amino)-5,6-dimethyl-N-(1-phenylethyl)pyrimidine-2-carboxamide. LRMS (APCI+) m/z 365 (M + H). $^1$H NMR (400 MHz, Methanol-$d_4$) δ 7.44 (s, 2H, 7.43-7.40 (m, 2H), 7.35 (t, J = 7.5 Hz, 2H), 7.28 (t, J = 7.2 Hz, 1H), 5.22 (q, J = 6.9 Hz, 1H), 3.78 (qt, J = 13.5, 7.4 Hz, 2H), 2.84 (t, J = 7.4 Hz, 2H), 2.43 (s, 3H), 2.08 (s, 3H), 1.61 (d, J = 6.9 Hz, 3H). |
| 60 | 3-benzylazetidin-3-ol | 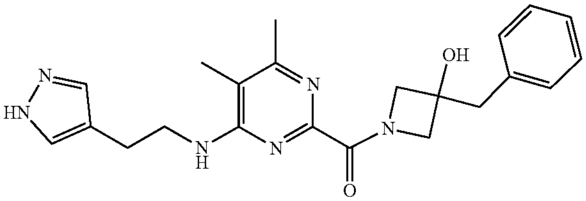 (4-((2-(1H-pyrazol-4-yl)ethyl)amino)-5,6-dimethylpyrimidin-2-yl)(3-benzyl-3-hydroxyazetidin-1-yl)methanone. LRMS (APCI+) m/z 407 (M + H). $^1$H NMR (400 MHz, Methanol-$d_4$) δ 7.43 (s, 2H), 7.34-7.19 (m, 5H), 4.69 (d, J = 10.7 Hz, 1H), 4.40 (d, J = 10.9 Hz, 1H), 4.26 (d, J = 10.7 Hz, 1H), 3.97 (d, J = 11.3 Hz, 1H), 3.76-3.65 (m, 2H), 3.07 (s, 2H), 2.83 (t, J = 6.5 Hz, 2H), 2.43 (s, 3H), 2.08 (s, 3H). |

-continued

| Compound No. | Amine in Step 1 | Structure, Name, and Data |
|---|---|---|
| 61 | (S)-3-phenylpyrrolidine | 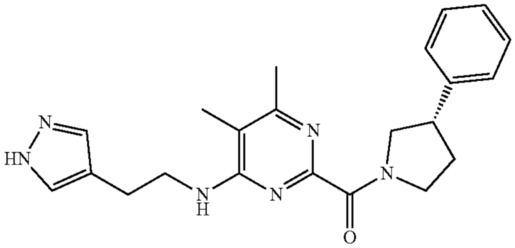 (S)-(4-((2-(1H-pyrazol-4-yl)ethyl)amino)-5,6-dimethylpyrimidin-2-yl)(3-phenylpyrrolidin-1-yl)methanone. LRMS (APCI+) m/z 391 (M + H). (1:1 mixture of rotamers) $^{1}$H NMR (400 MHz, Methanol-$d_4$) δ 7.46 (s, 2H), 7.37 (s, 2H), 7.36-7.33 (m, 4H), 7.33-7.29 (m, 1H, 7.28 (s, 3H), 7.26-7.20 (m, 2H), 4.09 (dd, J = 11.6, 7.2 Hz, 1H), 3.95 (dd, J = 11.0, 7.4 Hz, 1H), 3.89 (ddd, J = 12.0, 8.3, 3.1 Hz, 1H), 3.78-3.58 (m, 9H), 3.55-3.45 (m, 2H), 2.85 (t, J = 7.2 Hz, 2H), 2.79 (t, J = 7.4 Hz, 2H), 2.42 (s, 3H), 2.40 (s, 3H), 2.39-2.31 (m, 2H), 2.19-2.10 (m, 2H), 2.09 (s, 3H), 2.07 (s, 3H). |
| 62 | (2R,5R)-2-methyl-5-phenylmorpholine | 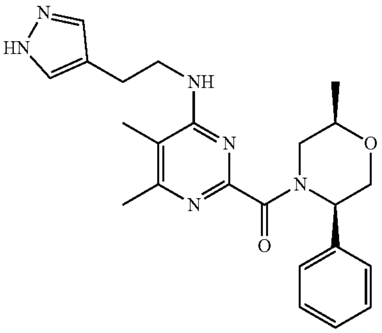 (4-((2-(1H-pyrazol-4-yl)ethyl)amino)-5,6-dimethylpyrimidin-2-yl)((2R,5R)-2-methyl-5-phenylmorpholino)methanone. LRMS (APCI+) m/z 421 (M + H). (1.3:1 mixture of rotamers) Minor rotamer: $^{1}$H NMR (400 MHz, Methanol-$d_4$) δ 7.50 (d, J = 7.6 Hz, 2H), 7.37 (s, 2H, 7.35-7.32 (m, 2H), 7.24 (t, J = 7.3 Hz, 1H), 4.76 (d, J = 3.0 Hz, 1H), 4.50 (d, J = 12.2 Hz, 1H), 4.41 (dd, J = 13.6, 2.6 Hz, 1H), 3.82-3.70 (m, 2H), 3.48 (t, J = 7.2 Hz, 2H), 2.72-2.61 (m, 3H), 2.39 (s, 3H), 2.03 (s, 3H), 1.18 (d, J = 6.2 Hz, 3H). Major rotamer: $^{1}$H NMR (400 MHz, Methanol-$d_4$) δ 7.61 (d, J = 7.6 Hz, 2H), 7.43 (s, 2H), 7.42-7.38 (m, 2H), 7.32-7.28 (m, 1H), 5.69 (d, J = 3.3 Hz, 1H), 4.62 (d, J = 12.3 Hz, 1H), 4.04 (td, J = 12.7, 3.5 Hz, 2H), 3.67 (t, J = 7.4 Hz, 2H), 2.94 (dd, J = 13.5, 10.7 Hz, 1H), 2.83 (t, J = 7.4 Hz, 2H), 2.40 (s, 3H), 2.08 (s, 3H), 1.03 (d, J = 6.2 Hz, 3H). |

-continued

| Compound No. | Amine in Step 1 | Structure, Name, and Data |
| --- | --- | --- |
| 63 | (S)-3-phenylmorpholine | 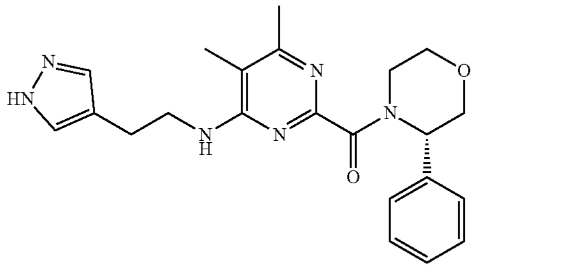 (S)-(4-((2-(1H-pyrazol-4-yl)ethyl)amino)-5,6-dimethylpyrimidin-2-yl)(3-phenylmorpholino)methanone. LRMS (APCI+) m/z 413 (M + H). (1.5:1 mixture of rotamers) Minor rotamer: $^{1}$H NMR (400 MHz, Methanol-d$_4$) δ 7.51 (d, J = 7.6 Hz, 2H), 7.43 (s, 2H), 7.41 (s, 1H), 7.35-7.32 (m, 1H), 7.24 (t, J = 7.3 Hz, 1H), 4.80 (d, J = 3.0 Hz, 1H), 4.47 (d, J = 12.1 Hz, 1H), 4.38 (d, J = 13.7 Hz, 1H), 3.74 (dd, J = 11.8, 2.7 Hz, 1H), 3.67-3.60 (m, 2H), 3.49 (t, J = 7.2 Hz, 2H), 3.10 (td, J = 13.1, 3.9 Hz, 1H), 2.68 (t, J = 7.2 Hz, 2H), 2.38 (s, 3H), 2.03 (s, 3H). Major rotamer: $^{1}$H NMR (400 MHz, Methanol-d$_4$) δ 7.62 (d, J = 7.6 Hz, 2H), 7.39 (s, 2H), 7.37 (s, 1H), 7.35-7.28 (m, 2H), 5.71 (d, J = 3.2 Hz, 1H), 4.60 (d, J = 12.3 Hz, 1H), 3.97 (td, J = 11.5, 10.2, 3.5 Hz, 2H), 3.85-3.77 (m, 1H), 3.71-3.65 (m, 2H), 3.32-3.25 (m, 2H), 2.82 (t, J = 7.3 Hz, 2H), 2.40 (s, 3H), 2.08 (s, 3H). |
| 64 | (R)-3-benzylmorpholine | 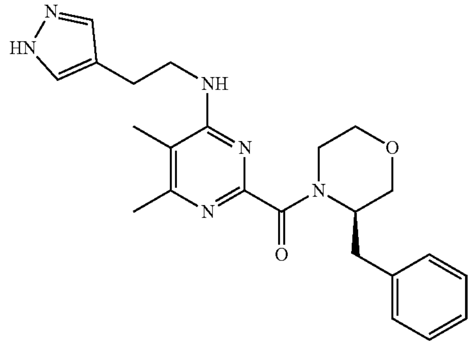 (R)-(4-((2-(1H-pyrazol-4-yl)ethyl)amino)-5,6-dimethylpyrimidin-2-yl)(3-benzylmorpholino)methanone. LRMS (APCI+) m/z 421 (M + H). (1.1:1 mixture of rotamers) $^{1}$H NMR (400 MHz, Methanol-d$_4$) δ 7.47 (s, 2H), 7.40 (s, 2H), 7.32 (dt, J = 14.9, 7.3 Hz, 4H), 7.24-7.14 (m, 4H), 6.95-6.88 (m, 2H), 4.72-4.64 (m, 1H), 4.36 (dd, J = 13.8, 2.8 Hz, 1H, 4.07 (dd, J = 11.6, 3.8 Hz, 1H), 3.90-3.83 (m, 1H), 3.80 (dd, J = 12.2, 5.2 Hz, 2H), 3.77-3.48 (m, 10H, 3.41 (dd, J = 13.3, 4.1 Hz, 1H), 3.29-3.05 (m, 5H), 2.82 (dt, J = 14.1, 7.2 Hz, 4H), 2.38 (s, 3H), 2.38 (s, 3H), 2.11 (s, 3H), 2.06 (s, 3H). |
| 65 | (R)-1-(benzofuran-3-yl)ethan-1-amine | 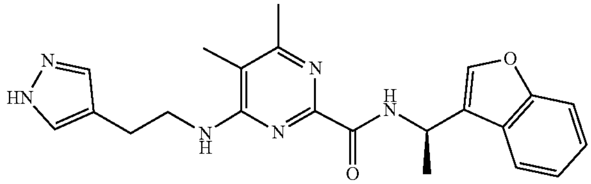 (R)-4-((2-(1H-pyrazol-4-yl)ethyl)amino)-N-(1-(benzofuran-3-yl)ethyl)-5,6-dimethylpyrimidine-2-carboxamide. LRMS (APCI+) m/z 405 (M + H). $^{1}$H NMR (400 MHz, Methanol-d$_4$) δ 7.79 (s, 1H), 7.67 (d, J = 7.8 Hz, 1H, 7.49 (d, J = 8.3 Hz, 1H), 7.33-7.26 (m, 1H), 7.29 (s, 2H), 7.19 (t, J = 7.5 Hz, 1H), 5.51 (q, J = 6.8 Hz, 1H), 3.69 (ddq, J = 20.7, 13.5, 7.3 Hz, 2H), 2.74 (t, J = 7.4 Hz, 2H), 2.43 (s, 3H), 2.07 (s, 3H), 1.75 (d, J = 6.8 Hz, 3H). |

-continued

| Compound No. | Amine in Step 1 | Structure, Name, and Data |
|---|---|---|
| 66 | (rac)-3-(2-fluorophenyl)pyrrolidine | 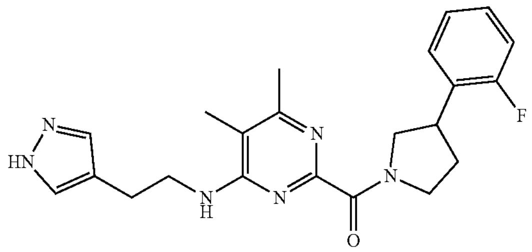 (rac)-(4-((2-(1H-pyrazol-4-yl)ethyl)amino)-5,6-dimethylpyrimidin-2-yl)(3-(2-fluorophenyl)pyrrolidin-1-yl)methanone. LRMS (APCI+) m/z 409 (M + H). (1:1 mixture of rotamers) $^1$H NMR (400 MHz, Methanol-$d_4$) δ 7.46 (s, 2H), 7.42-7.22 (m, 6H), 7.22-7.01 (m, 4H), 4.15-3.98 (m, 2H), 3.88 (ddd, J = 12.1, 8.3, 3.6 Hz, 1H), 3.81-3.59 (m, 11H, 2.85 (t, J = 7.2 Hz, 2H), 2.80 (t, J = 7.4 Hz, 2H), 2.48-2.30 (m, 8H), 2.26-2.13 (m, 2H), 2.10 (s, 3H), 2.08 (s, 3H). |
| 67 | 3-(4-fluorophenyl)morpholine | 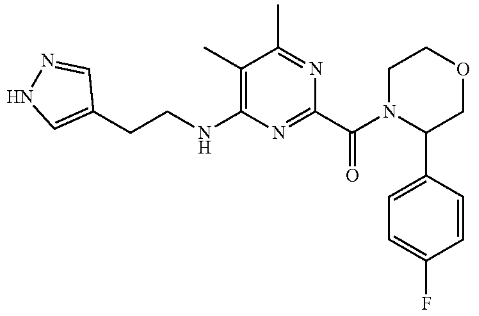 (4-((2-(1H-pyrazol-4-yl)ethyl)amino)-5,6-dimethylpyrimidin-2-yl)(3-(4-fluorophenyl)morpholino)methanone. LRMS (APCI+) m/z 425 (M + H). (1.5:1 mixture of rotamers) Minor rotamer: $^1$H NMR (400 MHz, Methanol-$d_4$) δ 7.54 (dd, J = 8.6, 5.3 Hz, 2H), 7.40 (s, 2H), 7.02 (t, J = 8.7 Hz, 2H), 4.77 (s, 1H), 4.43 (d, J = 12.2 Hz, 1H), 4.37 (d, J = 13.4 Hz, 1H), 3.74 (dd, J = 11.9, 2.8 Hz, 1H), 3.67-3.61 (m, 1H), 3.52 (t, J = 7.2 Hz, 2H), 3.12-3.00 (m, 2H), 2.70 (t, J = 7.2 Hz, 2H), 2.39 (s, 3H), 2.04 (s, 3H). Major rotamer: $^1$H NMR (400 MHz, Methanol-$d_4$) δ 7.65 (dd, J = 8.6, 5.4 Hz, 2H), 7.44 (s, 2H), 7.11 (t, J = 8.8 Hz, 2H), 5.71-5.66 (m, 1H), 4.55 (d, J = 12.4 Hz, 1H), 4.01-3.91 (m, 3H), 3.82 (d, J = 11.2 Hz, 1H), 3.71-3.62 (m, 3H), 2.82 (t, J = 7.3 Hz, 2H), 2.39 (s, 3H), 2.07 (s, 3H). |
| 68 | (rac)-1-(6-methoxypyridin-2-yl)ethan-1-amine | 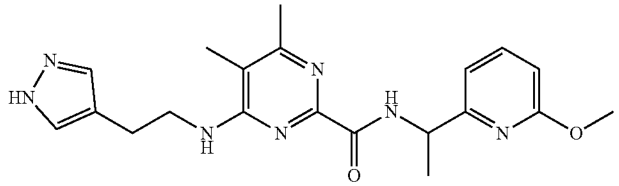 4-((2-(1H-pyrazol-4-yl)ethyl)amino)-N-(1-(6-methoxypyridin-2-yl)ethyl)-5,6-dimethylpyrimidine-2-carboxamide. LRMS (APCI+) m/z 396 (M + H). $^1$H NMR (400 MHz, Methanol-d4) δ 7.65 (t, J = 7.8 Hz, 1H), 7.47 (s, 2H), 6.97 (d, J = 7.2 Hz, 1H), 6.70 (d, J = 8.2 Hz, 1H), 5.20 (q, J = 6.8 Hz, 1H), 3.88 (s, 3H), 3.80 (td, J = 7.2, 3.6 Hz, 2H), 2.87 (t, J = 7.4 Hz, 2H), 2.44 (s, 3H), 2.09 (s, 3H), 1.58 (d, J = 6.7 Hz, 3H). |

-continued

| Compound No. | Amine in Step 1 | Structure, Name, and Data |
| --- | --- | --- |
| 69 | 2-(pyridin-2-yl)propan-2-amine | 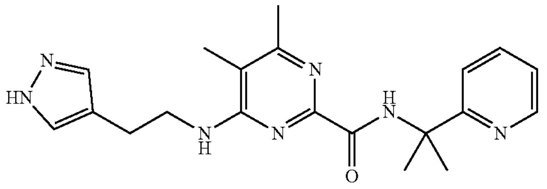 4-((2-(1H-pyrazol-4-yl)ethyl)amino)-5,6-dimethyl-N-(2-(pyridin-2-yl)propan-2-yl)pyrimidine-2-carboxamide. LRMS (APCI+) m/z 380 (M + H). $^1$H NMR (400 MHz, Methanol-$d_4$) δ 8.33 (ddd, J = 5.0, 1.8, 0.9 Hz, 1H), 7.85 (td, J = 7.8, 1.8 Hz, 1H), 7.62 (dt, J = 8.1, 1.0 Hz, 1H), 7.49 (s, 2H), 7.28 (ddd, J = 7.5, 4.9, 1.0 Hz, 1H), 3.90 (t, J = 7.3 Hz, 2H), 2.95 (t, J = 7.3 Hz, 2H), 2.46 (s, 3H), 2.11 (s, 3H), 1.85 (s, 6H). |
| 70 | 1-(5-chlorothiophen-2-yl)ethan-1-amine | 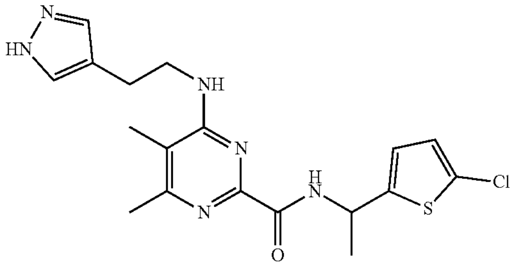 4-((2-(1H-pyrazol-4-yl)ethyl)amino)-N-(1-(5-chlorothiophen-2-yl)ethyl)-5,6-dimethylpyrimidine-2-carboxamide. LRMS (APCI+) m/z 405 (M + H). $^1$H NMR (400 MHz, Methanol-$d_4$) δ 7.45 (s, 2H), 6.90 (d, J = 3.9 Hz, 1H, 6.85 (d, J = 3.8 Hz, 1H), 5.40 (q, J = 6.9 Hz, 1H), 3.87-3.71 (m, 2H), 2.86 (t, J = 7.1 Hz, 2H), 2.43 (s, 3H), 2.08 (s, 3H), 1.68 (d, J = 6.8 Hz, 3H). |
| 71 | (rac)-2-benzylpyrrolidine | 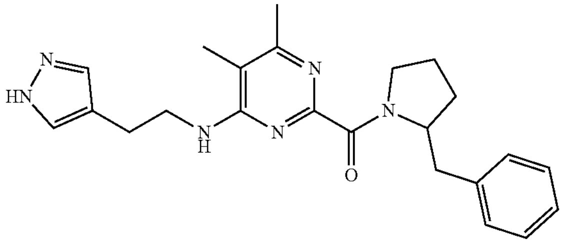 (rac)-(4-((2-(1H-pyrazol-4-yl)ethyl)amino)-5,6-dimethylpyrimidin-2-yl)(2-benzylpyrrolidin-1-yl)methanone. LRMS (APCI+) m/z 405 (M + H). |
| 72 | (S)-3-benzylmorpholine | 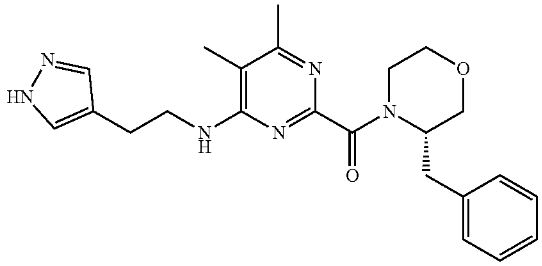 (S)-(4-((2-(1H-pyrazol-4-yl)ethyl)amino)-5,6-dimethylpyrimidin-2-yl)(3-benzylmorpholino)methanone. LRMS (APCI+) m/z 421 (M + H). (1.1:1 mixture of rotamers) $^1$H NMR (400 MHz, Methanol-$d_4$) δ 7.47 (s, 2H), 7.40 (s, 2H), 7.32 (dt, J = 14.9, 7.3 Hz, 4H), 7.24-7.14 (m, 4H), 6.95-6.88 (m, 2H), 4.72-4.64 (m, 1H), 4.36 (dd, J = 13.8, 2.8 Hz, 1H, 4.07 (dd, J = 11.6, 3.8 Hz, 1H), 3.90-3.83 (m, 1H), 3.80 (dd, J = 12.2, 5.2 Hz, 2H), 3.77-3.48 (m, 10H, 3.41 (dd, J = 13.3, 4.1 Hz, 1H), 3.29-3.05 (m, 5H), 2.82 (dt, J = 14.1, 7.2 Hz, 4H), 2.38 (s, 3H), 2.38 (s, 3H), 2.11 (s, 3H), 2.06 (s, 3H). |

-continued

| Compound No. | Amine in Step 1 | Structure, Name, and Data |
| --- | --- | --- |
| 73 | (S)-1-(6-fluoropyridin-2-yl)ethan-1-amine | 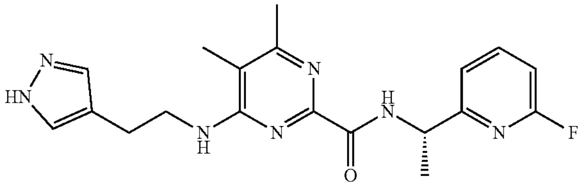 (S)-4-((2-(1H-pyrazol-4-yl)ethyl)amino)-N-(1-(6-fluoropyridin-2-yl)ethyl)-5,6-dimethylpyrimidine-2-carboxamide. LRMS (APCI+) m/z 384 (M + H). $^{1}$H NMR (400 MHz, Methanol-$d_4$) δ 7.94 (q, J = 8.0 Hz, 1H), 7.51 (s, 2H, 7.37 (dd, J = 7.5, 2.3 Hz, 1H), 6.99 (dd, J = 8.2, 2.4 Hz, 1H, 5.25 (q, J = 6.8 Hz, 1H), 3.83 (t, J = 7.2 Hz, 2H), 2.91 (t, J = 7.2 Hz, 2H), 2.44 (s, 3H), 2.09 (s, 3H), 1.59 (d, J = 6.9 Hz, 3H). |
| 74 | (3-(3-fluorophenyl)oxetan-3-yl)methanamine | 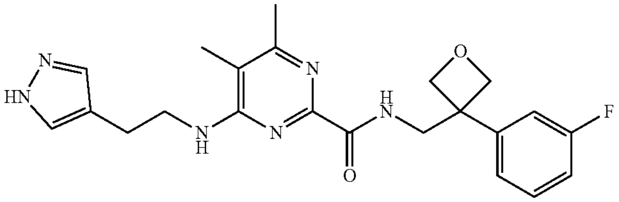 4-((2-(1H-pyrazol-4-yl)ethyl)amino)-N-((3-(3-fluorophenyl)oxetan-3-yl)methyl)-5,6-dimethylpyrimidine-2-carboxamide. LRMS (APCI+) m/z 425 (M + H). $^{1}$H NMR (400 MHz, Methanol-$d_4$) δ 7.42-7.33 (m, 1H), 7.39 (s, 2H), 7.03-6.93 (m, 3H), 4.96 (s, 4H), 4.00 (s, 2H), 3.69 (t, J = 6.4 Hz, 2H), 2.78 (t, J = 6.1 Hz, 2H), 2.42 (s, 3H), 2.07 (s, 3H). |
| 75 | (R)-1-(furan-2-yl)ethan-1-amine | 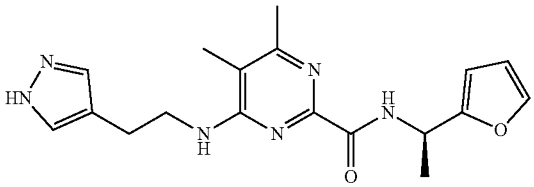 (R)-4-((2-(1H-pyrazol-4-yl)ethyl)amino)-N-(1-(furan-2-yl)ethyl)-5,6-dimethylpyrimidine-2-carboxamide. LRMS (APCI+) m/z 355 (M + H). $^{1}$H NMR (400 MHz, Methanol-$d_4$) δ 7.44 (s, 2H), 6.19 (d, J = 3.0 Hz, 1H), 5.97 (d, J = 3.0 Hz, 1H, 5.24 (q, J = 6.9 Hz, 1H), 3.83-3.67 (m, 2H), 2.84 (t, J = 7.4 Hz, 2H), 2.43 (s, 3H), 2.23 (s, 3H), 2.08 (s, 3H), 1.58 (d, J = 6.9 Hz, 3H). |
| 76 | 3-phenylazetidine | 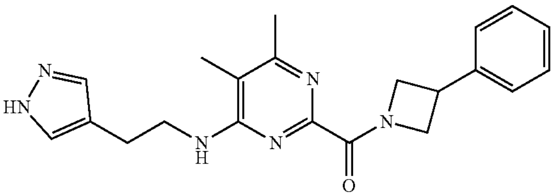 (4-((2-(1H-pyrazol-4-yl)ethyl)amino)-5,6-dimethylpyrimidin-2-yl)(3-phenylazetidin-1-yl)methanone. LRMS (APCI+) m/z 377 (M + H). $^{1}$H NMR (400 MHz, Methanol-$d_4$) δ 7.40 (s, 2H), 7.40-7.37 (m, 4H), 7.33-7.29 (m, 1H), 5.04 (t, J = 9.5 Hz, 1H), 4.67-4.58 (m, 2H), 4.22 (dd, J = 10.6, 6.1 Hz, 1H), 4.02-3.93 (m, 1H), 3.71 (t, J = 7.4 Hz, 2H), 2.83 (t, J = 7.4 Hz, 2H), 2.42 (s, 3H), 2.08 (s, 3H). |

-continued

| Compound No. | Amine in Step 1 | Structure, Name, and Data |
|---|---|---|
| 77 | 3-(2-fluorophenyl)azetidin-3-ol | 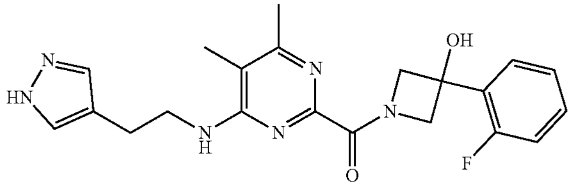 (4-((2-(1H-pyrazol-4-yl)ethyl)amino)-5,6-dimethylpyrimidin-2-yl)(3-(2-fluorophenyl)-3-hydroxyazetidin-1-yl)methanone. LRMS (APCI+) m/z 411 (M + H). $^{1}$H NMR (400 MHz, Methanol-$d_4$) δ 7.52-7.44 (m, 1H), 7.48 (s, 2H), 7.44-7.35 (m, 1H), 7.24 (t, J = 7.8 Hz, 1H), 7.17 (t, J = 10.2 Hz, 1H), 5.13 (d, J = 11.2 Hz, 1H), 4.87 (d, J = 11.2 Hz, 1H), 4.69 (d, J = 11.2 Hz, 1H), 4.37 (d, J = 10.9 Hz, 1H), 3.76 (t, J = 7.8 Hz, 2H), 2.86 (t, J = 6.6 Hz, 2H), 2.45 (s, 3H), 2.10 (s, 3H). |
| 78 | (R)-1-(6-methylpyridin-2-yl)ethan-1-amine | 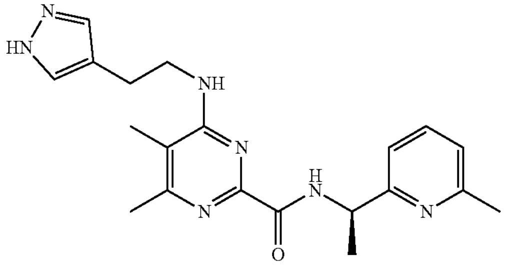 (R)-4-((2-(1H-pyrazol-4-yl)ethyl)amino)-5,6-dimethyl-N-(1-(6-methylpyridin-2-yl)ethyl)pyrimidine-2-carboxamide. LRMS (APCI+) m/z 380 (M + H). $^{1}$H NMR (400 MHz, Methanol-$d_4$) δ 7.69 (t, J = 7.7 Hz, 1H), 7.49 (s, 2H), 7.25 (d, J = 7.8 Hz, 1H), 7.18 (d, J = 7.7 Hz, 1H), 5.20 (q, J = 6.8 Hz, 1H), 3.86 (dt, J = 13.7, 6.9 Hz, 2H), 2.91 (t, J = 7.3 Hz, 2H, 2.48 (s, 3H), 2.45 (s, 3H), 2.10 (s, 3H), 1.58 (d, J = 6.8 Hz, 3H). |
| 79 | 3,3-difluoro-2,3-dihydro-1H-inden-1-amine | 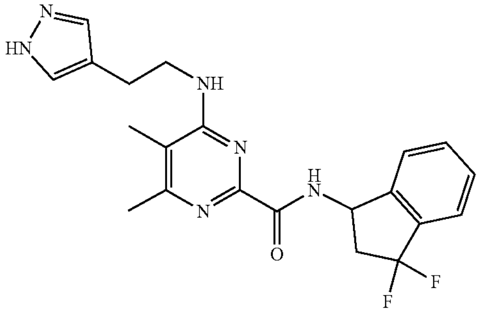 4-((2-(1H-pyrazol-4-yl)ethyl)amino)-N-(3,3-difluoro-2,3-dihydro-1H-inden-1-yl)-5,6-dimethylpyrimidine-2-carboxamide. LRMS (APCI+) m/z 413 (M + H). $^{1}$H NMR (400 MHz, Methanol-$d_4$) δ 7.66-7.46 (m, 4H), 7.39 (s, 2H), 5.72 (q, J = 6.3 Hz, 1H), 3.73 (dp, J = 27.9, 7.3, 6.8 Hz, 2H), 3.23-3.07 (m, 1H), 2.81 (t, J = 7.7 Hz, 2H), 2.68 (qd, J = 14.9, 6.1 Hz, 1H), 2.43 (s, 3H), 2.08 (s, 3H). |

-continued

| Compound No. | Amine in Step 1 | Structure, Name, and Data |
|---|---|---|
| 80 | 3-(2-chlorophenyl)morpholine | 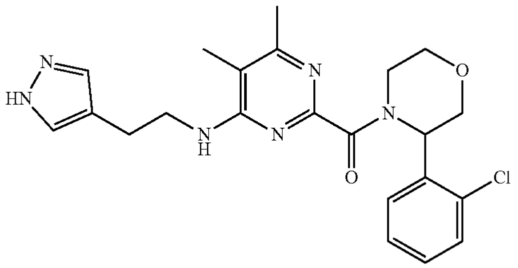 (4-((2-(1H-pyrazol-4-yl)ethyl)amino)-5,6-dimethylpyrimidin-2-yl)(3-(2-chlorophenyl)morpholino)methanone. LRMS (APCI+) m/z 441 (M + H). (1.1:1 mixture of rotamers) $^1$H NMR (400 MHz, Methanol-$d_4$) δ 7.80 (d, J = 7.9 Hz, 1H), 7.74 (d, J = 7.8 Hz, 1H, 7.52-7.42 (m, 3H), 7.38 (s, 2H), 7.35-7.22 (m, 4H), 7.17 (t, J = 7.4 Hz, 1H), 5.88-5.80 (m, 1H), 5.32 (s, 1H), 4.48 (d, J = 13.2 Hz, 1H), 4.40 (d, J = 12.3 Hz, 1H), 4.20-3.99 (m, 4H), 3.92 (d, J = 7.6 Hz, 1H), 3.84-3.59 (m, 6H), 3.45 (d, J = 11.0 Hz, 1H), 3.25 (p, J = 6.5 Hz, 2H), 2.84 (t, J = 7.3 Hz, 2H), 2.55 (t, J = 7.3 Hz, 2H), 2.39 (s, 3H), 2.32 (s, 3H, 2.08 (s, 3H), 2.01 (s, 3H). |
| 81 | 3-(trifluoromethoxy)azetidine | 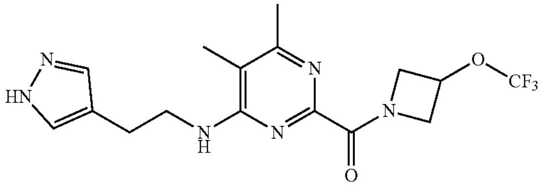 (4-((2-(1H-pyrazol-4-yl)ethyl)amino)-5,6-dimethylpyrimidin-2-yl)(3-(trifluoromethoxy)azetidin-1-yl)methanone. LRMS (APCI+) m/z 385 (M + H). $^1$H NMR (400 MHz, Methanol-$d_4$) δ 7.49 (s, 2H), 5.20 (s, 1H), 5.04 (d, J = 10.1 Hz, 1H), 4.75 (d, J = 12.0 Hz, 1H), 4.55 (d, J = 8.8 Hz, 1H), 4.24 (d, J = 12.1 Hz, 1H), 3.73 (t, J = 9.1 Hz, 2H), 2.86 (t, J = 6.6 Hz, 2H), 2.42 (s, 3H), 2.08 (s, 3H). |
| 82 | (S)-1-(3-fluorophenyl)-2-methoxyethan-1-amine | 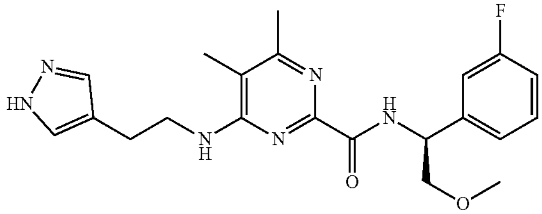 (S)-4-((2-(1H-pyrazol-4-yl)ethyl)amino)-N-(1-(3-fluorophenyl)-2-methoxyethyl)-5,6-dimethylpyrimidine-2-carboxamide. LRMS (APCI+) m/z 413 (M + H). $^1$H NMR (400 MHz, Methanol-$d_4$) δ 7.51 (s, 2H), 7.36 (td, J = 8.0, 5.9 Hz, 1H), 7.24 (d, J = 7.7 Hz, 1H), 7.18 (dt, J = 10.1, 2.0 Hz, 1H, 7.01 (td, J = 8.5, 2.5 Hz, 1H), 5.27 (t, J = 5.0 Hz, 1H), 3.85-3.75 (m, 4H), 3.37 (s, 3H), 2.89 (td, J = 7.1, 2.1 Hz, 2H), 2.44 (s, 3H), 2.10 (s, 3H).? |
| 83 | 2-(4-fluorophenyl)propan-2-amine | 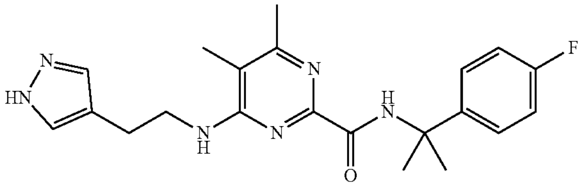 4-((2-(1H-pyrazol-4-yl)ethyl)amino)-N-(2-(4-fluorophenyl)propan-2-yl)-5,6-dimethylpyrimidine-2-carboxamide. LRMS (APCI+) m/z 397 (M + H). $^1$H NMR (400 MHz, Methanol-$d_4$) δ 7.56-7.42 (m, 4H), 7.04 (t, J = 8.2 Hz, 2H), 3.77 (t, J = 7.4 Hz, 2H), 2.87 (t, J = 7.0 Hz, 2H), 2.43 (s, 3H), 2.10 (s, 3H), 1.80 (s, 6H). |

-continued

| Compound No. | Amine in Step 1 | Structure, Name, and Data |
| --- | --- | --- |
| 84 | (3-phenylazetidin-3-yl)methanol | 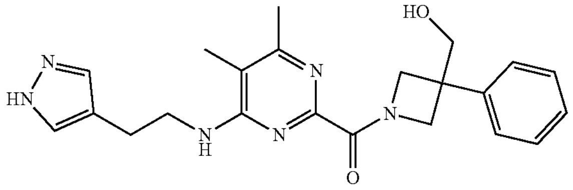 (4-((2-(1H-pyrazol-4-yl)ethyl)amino)-5,6-dimethylpyrimidin-2-yl)(3-(hydroxymethyl)-3-phenylazetidin-1-yl)methanone. LRMS (APCI+) m/z 407 (M + H). $^{1}$H NMR (400 MHz, Methanol-$d_4$) δ 7.54 (s, 2H), 7.38 (t, J = 6.9 Hz, 2H), 7.29 (d, J = 6.7 Hz, 1H), 7.13 (d, J = 7.0 Hz, 2H), 4.94 (d, J = 10.0 Hz, 1H), 4.82 (d, J = 10.0 Hz, 1H), 4.48 (d, J = 9.9 Hz, 1H), 4.36 (d, J = 10.7 Hz, 1H), 3.80 (t, J = 8.1 Hz, 2H), 3.73 (s, 2H), 2.90 (t, J = 7.2 Hz, 2H), 2.44 (s, 3H), 2.11 (s, 3H). |
| 85 | 4-(2-chloro-4-fluorobenzyl)tetrahydro-2H-pyran-4-amine | 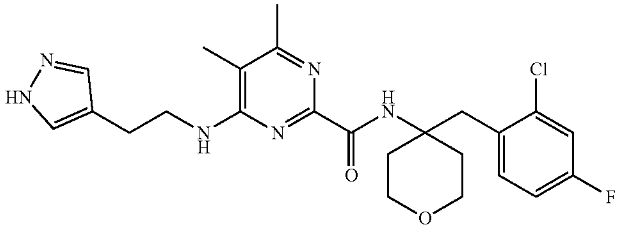 4-((2-(1H-pyrazol-4-yl)ethyl)amino)-N-(4-(2-chloro-4-fluorobenzyl)tetrahydro-2H-pyran-4-yl)-5,6-dimethylpyrimidine-2-carboxamide. LRMS (APCI+) m/z 487 (M + H). $^{1}$H NMR (400 MHz, Methanol-$d_4$) δ 7.36 (s, 2H), 7.24 (dd, J = 8.6, 6.2 Hz, 1H), 7.19 (dd, J = 8.7, 2.7 Hz, 1H), 6.94 (td, J = 8.3, 2.7 Hz, 1H), 3.80 (ddd, J = 12.1, 4.7, 2.0 Hz, 2H), 3.69-3.63 (m, 2H), 3.58 (td, J = 12.0, 1.9 Hz, 2H), 3.38-3.31 (m, 2H), 2.76 (t, J = 7.5 Hz, 2H), 2.44 (s, 3H), 2.21 (dd, J = 14.0, 2.2 Hz, 2H), 2.09 (s, 3H), 1.89 (ddd, J = 13.9, 12.1, 4.7 Hz, 2H). |
| 86 | (R)-2-(4-fluorophenyl)pyrrolidine | 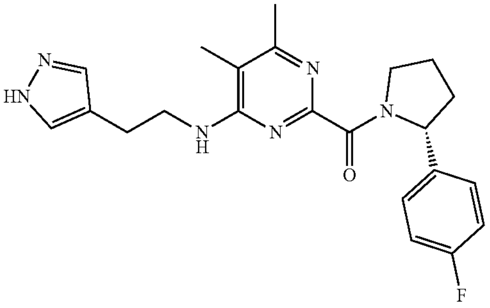 (R)-(4-((2-(1H-pyrazol-4-yl)ethyl)amino)-5,6-dimethylpyrimidin-2-yl)(2-(4-fluorophenyl)pyrrolidin-1-yl)methanone. LRMS (APCI+) m/z 409 (M + H). (1.4:1 mixture of rotamers) Major rotamer: $^{1}$H NMR (400 MHz, Methanol-$d_4$) δ 7.45 (s, 2H), 7.00-6.92 (m, 2H), 6.90-6.82 (m, 2H), 5.19-5.11 (m, 1H), 3.89-3.79 (m, 1H), 3.75 (td, J = 7.1, 2.8 Hz, 1H), 3.43 (td, J = 8.1, 7.5, 2.1 Hz, 2H), 2.67 (t, J = 7.2 Hz, 2H), 2.22 (s, 3H), 2.07-2.00 (m, 2H), 1.99-1.86 (m, 2H), 1.93 (s, 3H). Minor rotamer: $^{1}$H NMR (400 MHz, Methanol-$d_4$) δ 7.49 (s, 2H), 7.36 (dd, J = 8.5, 5.3 Hz, 2H, 7.05 (t, J = 8.8 Hz, 2H), 5.28 (dd, J = 8.0, 4.0 Hz, 1H), 3.99-3.86 (m, 3H), 3.84-3.79 (m, 1H), 2.88 (t, J = 7.3 Hz, 2H), 2.51-2.43 (m, 2H), 2.41 (s, 3H), 2.09 (s, 3H), 2.00-1.96 (m, 1H), 1.92-1.86 (m, 1H). |

-continued

| Compound No. | Amine in Step 1 | Structure, Name, and Data |
|---|---|---|
| 87 | (S)-1-(pyridin-4-yl)ethan-1-amine | 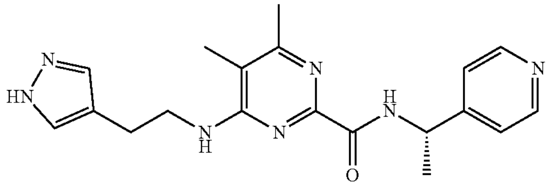 (S)-4-((2-(1H-pyrazol-4-yl)ethyl)amino)-5,6-dimethyl-N-(1-(pyridin-4-yl)ethyl)pyrimidine-2-carboxamide. LRMS (APCI+) m/z 366 (M + H). $^1$H NMR (400 MHz, Methanol-$d_4$) δ 8.54-8.48 (m, 2H), 7.51-7.48 (m, 2H), 7.49 (s 2H, 5.24 (q, J = 7.0 Hz, 1H), 3.83 (t, J = 7.1 Hz, 2H), 2.87 (t, J = 7.2 Hz, 2H), 2.44 (s, 3H), 2.09 (s, 3H), 1.64 (d, J = 7.1 Hz, 3H). |
| 88 | (6-methoxypyridin-2-yl)methanamine | 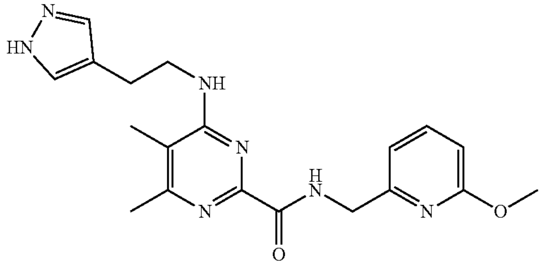 4-((2-(1H-pyrazol-4-yl)ethyl)amino)-N-((6-methoxypyridin-2-yl)methyl)-5,6-dimethylpyrimidine-2-carboxamide. LRMS (APCI+) m/z 391 (M + H). $^1$H NMR (400 MHz, Methanol-$d_4$) δ 7.64 (dd, J = 8.3, 7.3 Hz, 1H), 7.46 (s, 2H), 6.96 (d, J = 7.3 Hz, 1H), 6.69 (d, J = 8.3 Hz, 1H), 4.65 (s, 2H), 3.89 (s, 3H), 3.80 (t, J = 7.3 Hz, 2H), 2.87 (t, J = 7.3 Hz, 2H), 2.44 (s, 3H), 2.09 (s, 3H). |
| 89 | 3-methyl-3-phenylazetidine | 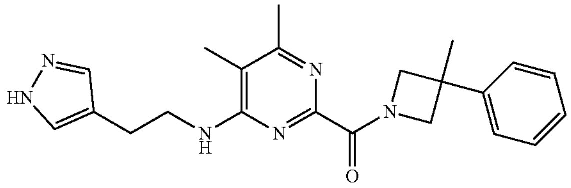 (4-((2-(1H-pyrazol-4-yl)ethyl)amino)-5,6-dimethylpyrimidin-2-yl)(3-methyl-3-phenylazetidin-1-yl)methanone. LRMS (APCI+) m/z 391 (M + H). $^1$H NMR (400 MHz, Methanol-$d_4$) δ 7.49 (s, 2H), 7.37 (t, J = 7.5 Hz, 2H), 7.25 (t, J = 7.3 Hz, 1H), 7.20 (d, J = 7.7 Hz, 2H), 4.88-4.84 (m, 1H), 4.65 (d, J = 10.1 Hz, 1H), 4.45 (d, J = 10.4 Hz, 1H), 4.23 (d, J = 10.3 Hz, 1H), 3.78 (t, J = 7.6 Hz, 2H), 2.88 (t, J = 7.6 Hz, 2H), 2.45 (s, 3H), 2.11 (s, 3H), 1.65 (s, 3H). |
| 90 | 1-(isoxazol-3-yl)ethan-1-amine | 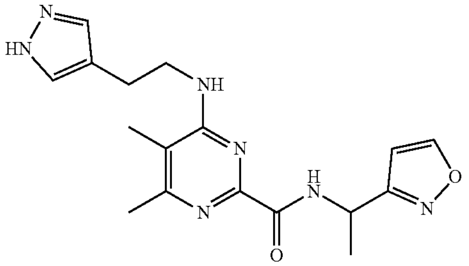 4-((2-(1H-pyrazol-4-yl)ethyl)amino)-N-(1-(isoxazol-3-yl)ethyl)-5,6-dimethylpyrimidine-2-carboxamide. LRMS (APCI+) m/z 356 (M + H). $^1$H NMR (400 MHz, Methanol-$d_4$) δ 8.63 (s, 1H), 7.51 (s, 2H), 6.55 (s, 1H), 5.39 (q, J = 7.0 Hz, 1H), 3.79 (h, J = 6.0 Hz, 2H), 2.86 (t, J = 7.4 Hz, 2H), 2.44 (s, 3H), 2.09 (s, 3H), 1.67 (d, J = 6.8 Hz, 3H). |

-continued

| Compound No. | Amine in Step 1 | Structure, Name, and Data |
|---|---|---|
| 91 | 3,3-difluoroazetidine | 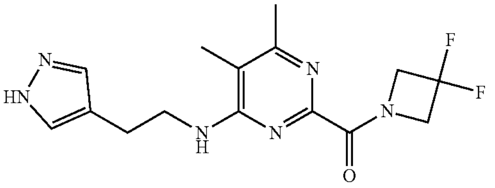<br>(4-((2-(1H-pyrazol-4-yl)ethyl)amino)-5,6-dimethylpyrimidin-2-yl)(3,3-difluoroazetidin-1-yl)methanone. LRMS (APCI+) m/z 337 (M + H). $^{1}$H NMR (400 MHz, Methanol-$d_4$) δ 7.49 (s, 2H), 5.01 (td, J = 12.1, 1.6 Hz, 2H), 4.53 (td, J = 12.3, 1.3 Hz, 2H), 3.72 (t, J = 7.3 Hz, 2H), 2.86 (t, J = 7.4 Hz, 3H), 2.43 (s, 3H), 2.09 (s, 3H). |
| 92 | 1-(4-fluorophenyl)-2-methoxy-N-methylethan-1-amine | 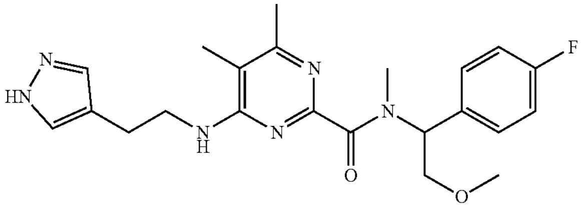<br>4-((2-(1H-pyrazol-4-yl)ethyl)amino)-N-(1-(4-fluorophenyl)-2-methoxyethyl)-N,5,6-trimethylpyrimidine-2-carboxamide. LRMS (APCI+) m/z 427 (M + H). |
| 93 | pyridin-2-ylmethanamine | 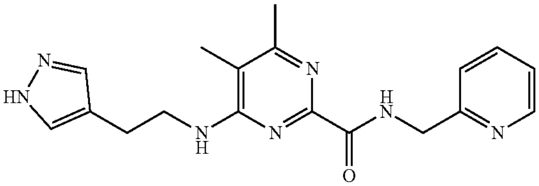<br>4-((2-(1H-pyrazol-4-yl)ethyl)amino)-5,6-dimethyl-N-(pyridin-2-ylmethyl)pyrimidine-2-carboxamide. LRMS (APCI+) m/z 352 (M + H). $^{1}$H NMR (400 MHz, Methanol-$d_4$) δ 8.50 (ddd, J = 5.0, 1.7, 0.9 Hz, 1H), 7.83 (td, J = 7.7, 1.8 Hz, 1H), 7.49 (s, 2H), 7.46 (d, J = 7.8 Hz, 1H), 7.34 (ddd, J = 7.6, 5.0, 1.1 Hz, 1H), 4.74 (s, 2H), 3.84 (t, J = 7.3 Hz, 2H), 2.88 (t, J = 7.3 Hz, 2H), 2.45 (s, 3H), 2.10 (s, 3H). |
| 94 | (3-phenyloxetan-3-yl)methanamine | 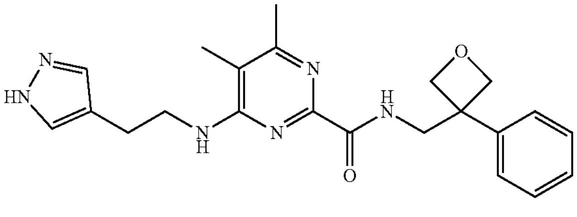<br>4-((2-(1H-pyrazol-4-yl)ethyl)amino)-5,6-dimethyl-N-((3-phenyloxetan-3-yl)methyl)pyrimidine-2-carboxamide. LRMS (APCI+) m/z 407 (M + H). $^{1}$H NMR (400 MHz, Methanol-$d_4$) δ 7.42-7.33 (m, 2H), 7.35 (s, 2H), 7.30-7.23 (m, 1H), 7.20-7.15 (m, 2H), 4.99 (d, J = 6.1 Hz, 2H), 4.87 (d, J = 6.1 Hz, 2H), 4.00 (s, 2H), 3.65 (t, J = 7.2 Hz, 2H), 2.76 (t, J = 7.2 Hz, 2H), 2.42 (s, 3H), 2.07 (s, 3H). |

-continued

| Compound No. | Amine in Step 1 | Structure, Name, and Data |
|---|---|---|
| 95 | (R)-1-(pyridin-4-yl)ethan-1-amine | 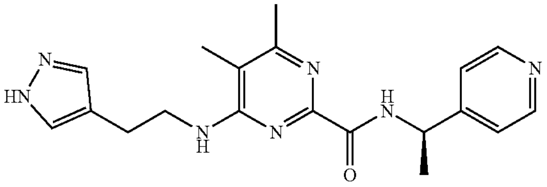 (R)-4-((2-(1H-pyrazol-4-yl)ethyl)amino)-5,6-dimethyl-N-(1-(pyridin-4-yl)ethyl)pyrimidine-2-carboxamide. LRMS (APCI+) m/z 366 (M + H). $^1$H NMR (400 MHz, Methanol-$d_4$) δ 8.54-8.48 (m, 2H), 7.51-7.48 (m, 2H), 7.49 (s 2H, 5.24 (q, J = 7.0 Hz, 1H), 3.83 (t, J = 7.1 Hz, 2H), 2.87 (t, J = 7.2 Hz, 2H), 2.44 (s, 3H), 2.09 (s, 3H), 1.64 (d, J = 7.1 Hz, 3H). |
| 96 | 4-phenylpiperidine-4-carbonitrile | 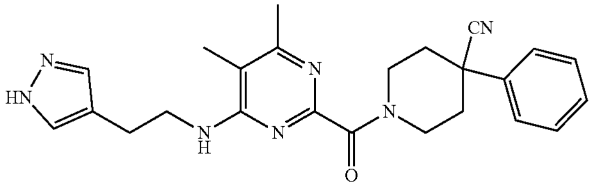 1-(4-((2-(1H-pyrazol-4-yl)ethyl)amino)-5,6-dimethylpyrimidine-2-carbonyl)-4-phenylpiperidine-4-carbonitrile. LRMS (APCI+) m/z 430 (M + H). $^1$H NMR (400 MHz, Methanol-$d_4$) δ 7.55 (d, J = 7.7 Hz, 2H), 7.50-7.41 (m, 4H, 7.41-7.33 (m, 1H), 4.85 (d, J = 12.5 Hz, 1H), 3.80-3.64 (m, 3H), 3.51 (t, J = 13.2 Hz, 1H), 3.27 (t, J = 12.7 Hz, 1H, 2.84 (t, J = 7.0 Hz, 2H), 2.39 (s, 3H), 2.32-2.15 (m, 3H), 2.11 (s, 1H), 2.08 (s, 3H). |
| 97 | 3-cyclopropylazetidin-3-ol | 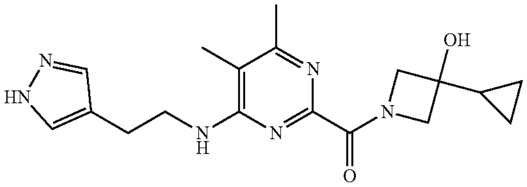 (4-((2-(1H-pyrazol-4-yl)ethyl)amino)-5,6-dimethylpyrimidin-2-yl)(3-cyclopropyl-3-hydroxyazetidin-1-yl)methanone. LRMS (APCI+) m/z 357 (M + H). $^1$H NMR (400 MHz, Methanol-$d_4$) δ 7.51 (s, 2H), 4.45 (q, J = 10.9 Hz, 2H, 4.04 (d, J = 11.1 Hz, 1H), 3.95 (d, J = 11.1 Hz, 1H), 3.73 (t, J = 7.6 Hz, 2H), 2.86 (t, J = 6.6 Hz, 2H), 2.44 (s, 3H), 2.10 (s, 3H), 1.32-1.21 (m, 1H), 0.56 (d, J = 8.6 Hz, 2H), 0.42 (q, J = 12.4, 11.3 Hz, 2H). |
| 98 | (rac)-(2-fluorophenyl)(1-methyl-1H-imidazol-2-yl)methanamine | 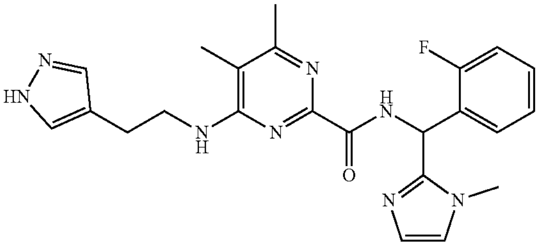 (rac)-4-((2-(1H-pyrazol-4-yl)ethyl)amino)-N-((2-fluorophenyl)(1-methyl-1H-imidazol-2-yl)methyl)-5,6-dimethylpyrimidine-2-carboxamide. LRMS (APCI+) m/z 449 (M + H). $^1$H NMR (400 MHz, Methanol-$d_4$) δ 8.18-8.12 (m, 1H), 7.47-7.38 (m, 2H), 7.45 (s, 2H), 7.26-7.15 (m, 2H), 7.05 (d, J = 1.4 Hz, 1H), 6.76 (s, 1H), 3.82 (dt, J = 13.3, 7.5 Hz, 1H), 3.77-3.66 (m, 1H), 3.74 (s, 3H), 2.84 (t, J = 7.5 Hz, 2H), 2.42 (s, 3H), 2.08 (s, 3H). |

-continued

| Compound No. | Amine in Step 1 | Structure, Name, and Data |
|---|---|---|
| 99 | (S)-1-(2-chlorophenyl)ethan-1-amine | 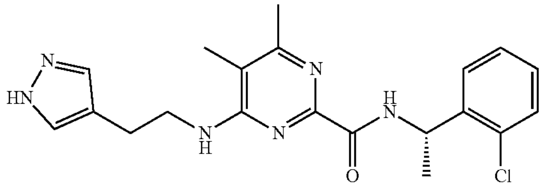 (S)-4-((2-(1H-pyrazol-4-yl)ethyl)amino)-N-(1-(2-chlorophenyl)ethyl)-5,6-dimethylpyrimidine-2-carboxamide. LRMS (APCI+) m/z 399 (M + H). $^1$H NMR (400 MHz, Methanol-$d_4$) δ 7.50 (dd, J = 7.3, 2.1 Hz, 1H), 7.47 (s, 2H), 7.41 (d, J = 7.2 Hz, 1H), 7.29 (pd, J = 7.4, 1.8 Hz, 2H), 5.54 (q, J = 7.0 Hz, 1H), 3.88-3.72 (m, 2H), 2.86 (t, J = 7.3 Hz, 2H), 2.43 (s, 3H), 2.09 (s, 3H), 1.61 (d, J = 6.9 Hz, 3H). |
| 100 | 3-(trifluoromethyl)azetidine | 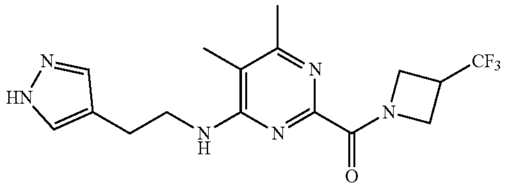 (4-((2-(1H-pyrazol-4-yl)ethyl)amino)-5,6-dimethylpyrimidin-2-yl)(3-(trifluoromethyl)azetidin-1-yl)methanone. LRMS (APCI+) m/z 369 (M + H). $^1$H NMR (400 MHz, Methanol-$d_4$) δ 7.48 (s, 2H), 4.88-4.84 (m, 1H), 4.72 (dd, J = 11.0, 5.6 Hz, 1H), 4.40 (t, J = 10.0 Hz, 1H), 4.20 (dd, J = 11.1, 5.5 Hz, 1H), 3.72 (t, J = 6.9 Hz, 2H), 3.58 (dtd, J = 12.4, 9.0, 4.5 Hz, 1H), 2.91-2.79 (m, 2H), 2.43 (s, 3H, 2.09 (s, 3H). |
| 101 | (R)-1-(5-methylfuran-2-yl)ethan-1-amine | 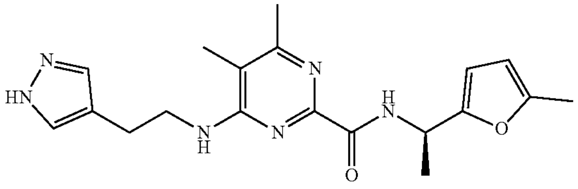 (R)-4-((2-(1H-pyrazol-4-yl)ethyl)amino)-5,6-dimethyl-N-(1-(5-methylfuran-2-yl)ethyl)pyrimidine-2-carboxamide. LRMS (APCI+) m/z 369 (M + H). $^1$H NMR (400 MHz, Methanol-$d_4$) δ 7.44 (s, 2H), 6.19 (d, J = 3.0 Hz, 1H), 5.97 (d, J = 3.0 Hz, 1H), 5.24 (q, J = 6.9 Hz, 1H), 3.83-3.67 (m, 2H, 2.84 (t, J = 7.4 Hz, 2H), 2.43 (s, 3H), 2.23 (s, 3H), 2.08 (s, 3H), 1.58 (d, J = 6.9 Hz, 3H). |
| 102 | 3-methoxy-3-phenylazetidine | 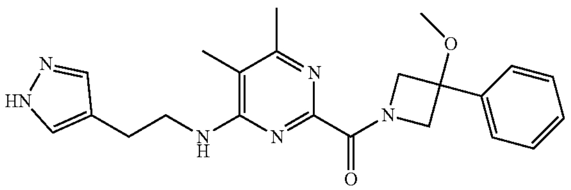 (4-((2-(1H-pyrazol-4-yl)ethyl)amino)-5,6-dimethylpyrimidin-2-yl)(3-methoxy-3-phenylazetidin-1-yl)methanone. LRMS (APCI+) m/z 407 (M + H). $^1$H NMR (400 MHz, Methanol-$d_4$) δ 7.48 (s, 2H), 7.45 (d, J = 7.0 Hz, 2H, 7.42-7.35 (m, 3H), 4.99-4.82 (m, 2H), 4.50 (d, J = 11.1 Hz, 1H), 4.40 (d, J = 11.3 Hz, 1H), 3.76 (t, J = 7.9 Hz, 2H, 3.07 (s, 3H), 2.87 (t, J = 8.0 Hz, 2H), 2.44 (s, 3H), 2.11 (s, 3H). |

-continued

| Compound No. | Amine in Step 1 | Structure, Name, and Data |
|---|---|---|
| 103 | 1-(thiazol-5-yl)ethan-1-amine | 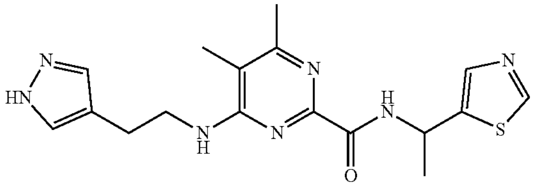<br>4-((2-(1H-pyrazol-4-yl)ethyl)amino)-5,6-dimethyl-N-(1-(thiazol-5-yl)ethyl)pyrimidine-2-carboxamide. LRMS (APCI+) m/z 372 (M + H). $^1$H NMR (400 MHz, Methanol-$d_4$) δ 8.93 (s, 1H), 7.88 (s, 1H), 7.46 (s, 2H), 5.58 (q, J = 6.9 Hz, 1H), 3.79 (tt, J = 8.9, 4.5 Hz, 2H), 2.85 (t, J = 7.2 Hz, 2H), 2.43 (s, 3H), 2.08 (s, 3H), 1.76 (d, J = 6.9 Hz, 3H). |
| 104 | (rac)-1-amino-2-phenylpropan-2-ol | 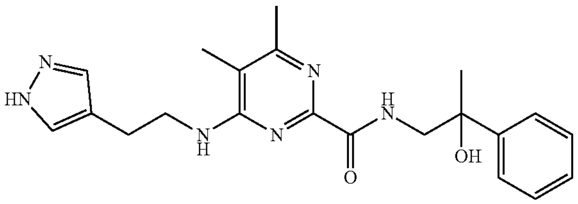<br>(rac)-4-((2-(1H-pyrazol-4-yl)ethyl)amino)-N-(2-hydroxy-2-phenylpropyl)-5,6-dimethylpyrimidine-2-carboxamide. LRMS (APCI+) m/z 395 (M + H). $^1$H NMR (400 MHz, Methanol-$d_4$) δ 7.59-7.53 (m, 2H), 7.49 (s, 2H), 7.32 (t, J = 7.7 Hz, 2H), 7.25-7.19 (m, 1H), 3.77 (d, J = 13.5 Hz, 1H), 3.69 (d, J = 13.5 Hz, 1H), 3.67 (t, J = 7.3 Hz, 2H), 2.82 (t, J = 7.2 Hz, 2H), 2.41 (s, 3H), 2.06 (s, 3H), 1.60 (s, 3H). |
| 105 | (1H-indazol-3-yl)methanamine | 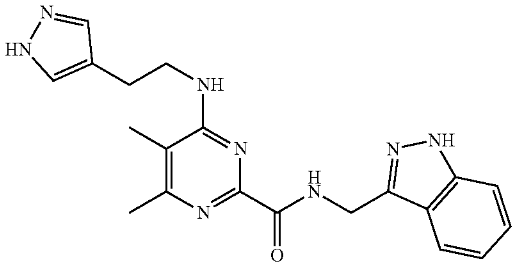<br>N-((1H-indazol-3-yl)methyl)-4-((2-(1H-pyrazol-4-yl)ethyl)amino)-5,6-dimethylpyrimidine-2-carboxamide. LRMS (APCI+) m/z 391 (M + H). $^1$H NMR (400 MHz, Methanol-$d_4$) δ 7.88 (d, J = 8.2 Hz, 1H), 7.51 (d, J = 8.5 Hz, 1H, 7.40 (s, 2H), 7.37 (d, J = 8.0 Hz, 1H), 7.11 (t, J = 7.5 Hz, 1H), 5.00 (s, 2H), 3.76 (t, J = 7.3 Hz, 2H), 2.81 (t, J = 7.3 Hz, 2H), 2.43 (s, 3H), 2.07 (s, 3H). |
| 107 | 3-ethyl-3-hydroxyazetidine | 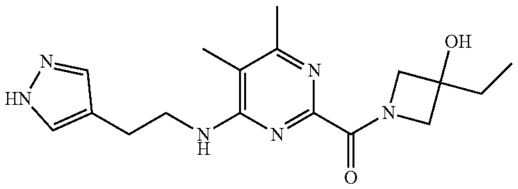<br>(4-((2-(1H-pyrazol-4-yl)ethyl)amino)-5,6-dimethylpyrimidin-2-yl)(3-ethyl-3-hydroxyazetidin-1-yl)methanone. LRMS (APCI+) m/z 345 (M + H). $^1$H NMR (400 MHz, Methanol-$d_4$) δ 7.50 (s, 2H), 4.52 (d, J = 10.7 Hz, 1H, 4.44 (d, J = 10.7 Hz, 1H), 4.11 (d, J = 10.9 Hz, 1H), 3.98 (d, J = 11.2 Hz, 1H), 3.73 (t, J = 7.3 Hz, 2H), 2.85 (d, J = 8.0 Hz, 2H), 2.43 (s, 3H), 2.09 (s, 3H), 1.80 (q, J = 8.4 Hz, 2H), 0.97 (t, J = 6.9 Hz, 3H). |

-continued

| Compound No. | Amine in Step 1 | Structure, Name, and Data |
|---|---|---|
| 108 | (rac)-1-(oxazol-2-yl)ethan-1-amine | 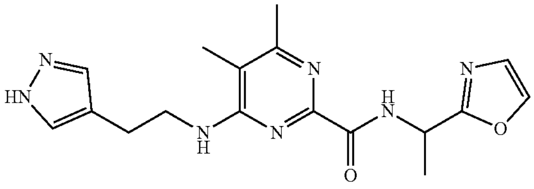 (rac)-4-((2-(1H-pyrazol-4-yl)ethyl)amino)-5,6-dimethyl-N-(1-(oxazol-2-yl)ethyl)pyrimidine-2-carboxamide. LRMS (APCI+) m/z 356 (M + H). $^{1}$H NMR (400 MHz, Methanol-$d_4$) δ 7.90 (s, 1H), 7.51 (s, 2H), 7.17 (s, 1H), 5.38 (q, J = 7.0 Hz, 1H), 3.81 (t, J = 7.3 Hz, 2H), 2.87 (t, J = 7.3 Hz, 2H), 2.44 (s, 3H), 2.09 (s, 3H), 1.69 (d, J = 6.9 Hz, 3H). |
| 109 | (R)-1-(5-fluoropyridin-3-yl)ethan-1-amine | 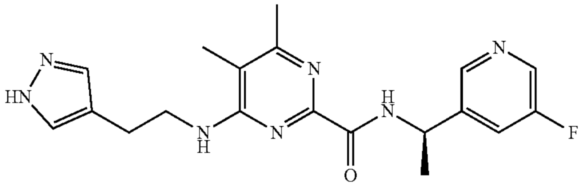 (R)-4-((2-(1H-pyrazol-4-yl)ethyl)amino)-N-(1-(5-fluoropyridin-3-yl)ethyl)-5,6-dimethylpyrimidine-2-carboxamide. LRMS (APCI+) m/z 384 (M + H). $^{1}$H NMR (400 MHz, Methanol-$d_4$) δ 8.51 (s, 1H), 8.38 (d, J = 2.7 Hz, 1H, 7.74 (dt, J = 9.7, 2.4 Hz, 1H), 7.48 (s, 2H), 5.30 (q, J = 7.1 Hz, 1H), 3.82 (td, J = 7.1, 2.5 Hz, 2H), 2.86 (t, J = 7.2 Hz, 2H), 2.43 (s, 3H), 2.08 (s, 3H), 1.67 (d, J = 7.1 Hz, 3H). |
| 110 | (rac)-1-(3-fluoropyridin-4-yl)ethan-1-amine | 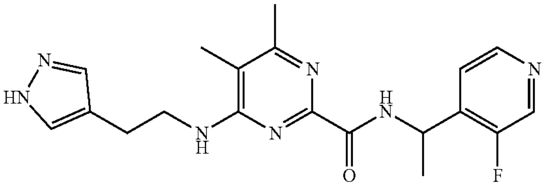 (rac)-4-((2-(1H-pyrazol-4-yl)ethyl)amino)-N-(1-(3-fluoropyridin-4-yl)ethyl)-5,6-dimethylpyrimidine-2-carboxamide. LRMS (APCI+) m/z 384 (M + H). $^{1}$H NMR (400 MHz, Methanol-$d_4$) δ 8.44 (s, 1H), 8.35 (s, 1H), 7.55-7.48 (m, 1H), 7.50 (s, 2H), 5.45 (q, J = 7.6 Hz, 1H), 3.82 (t, J = 7.4 Hz, 2H), 2.88 (t, J = 6.3 Hz, 2H), 2.43 (d, J = 2.6 Hz, 3H, 2.09 (s, 3H), 1.64 (d, J = 6.4 Hz, 3H). |
| 111 | 2,2-difluoro-2-phenylethan-1-amine | 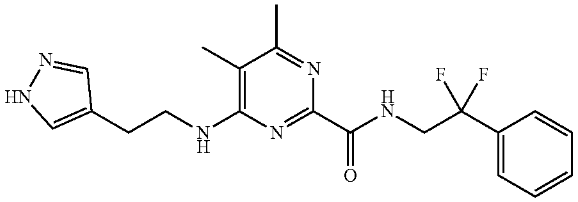 4-((2-(1H-pyrazol-4-yl)ethyl)amino)-N-(2,2-difluoro-2-phenylethyl)-5,6-dimethylpyrimidine-2-carboxamide. LRMS (APCI+) m/z 401 (M + H). $^{1}$H NMR (400 MHz, Methanol-$d_4$) δ 7.64-7.55 (m, 2H), 7.53-7.41 (m, 5H), 4.12 (t, J = 14.1 Hz, 2H), 3.74 (t, J = 7.3 Hz, 2H), 2.84 (t, J = 7.4 Hz, 2H), 2.43 (s, 3H), 2.08 (s, 3H). |

-continued

| Compound No. | Amine in Step 1 | Structure, Name, and Data |
|---|---|---|
| 112 | (R)-1-(benzofuran-2-yl)ethan-1-amine | 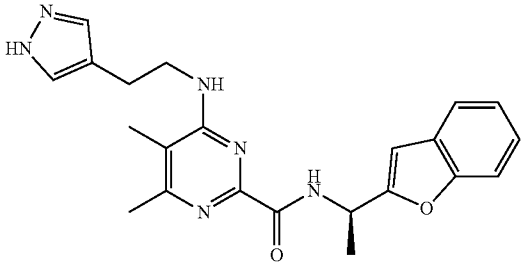 (R)-4-((2-(1H-pyrazol-4-yl)ethyl)amino)-N-(1-(benzofuran-2-yl)ethyl)-5,6-dimethylpyrimidine-2-carboxamide. LRMS (APCI+) m/z 405 (M + H). $^{1}$H NMR (400 MHz, Methanol-$d_4$) δ 7.55 (d, J = 7.6 Hz, 1H), 7.46 (s, 2H, 7.42 (d, J = 8.1 Hz, 1H), 7.29-7.23 (m, 1H), 7.21 (t, J = 7.3 Hz, 1H), 6.73 (s, 1H), 5.47 (q, J = 7.0 Hz, 1H), 3.78 (hept, J = 7.3, 6.7 Hz, 2H), 2.85 (t, J = 7.3 Hz, 2H), 2.43 (s, 3H, 2.08 (s, 3H), 1.72 (d, J = 6.9 Hz, 3H). |
| 113 | 2-(3-fluoropyridin-4-yl)ethan-1-amine | 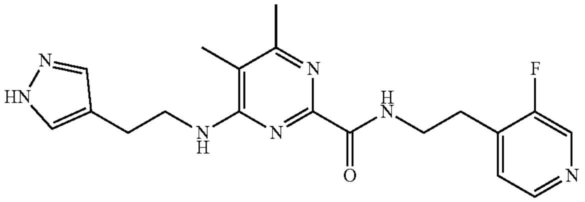 4-((2-(1H-pyrazol-4-yl)ethyl)amino)-N-(2-(3-fluoropyridin-4-yl)ethyl)-5,6-dimethylpyrimidine-2-carboxamide. LRMS (APCI+) m/z 384 (M + H). $^{1}$H NMR (400 MHz, Methanol-$d_4$) δ 8.36 (d, J = 1.9 Hz, 1H), 8.27 (d, J = 4.9 Hz, 1H), 7.47 (s, 2H), 7.43 (dd, J = 6.4, 4.9 Hz, 1H), 3.76 (dt, J = 8.8, 7.0 Hz, 4H), 3.09 (t, J = 6.8 Hz, 2H), 2.82 (t, J = 7.1 Hz, 2H), 2.42 (s, 3H), 2.07 (s, 3H). |
| 114 | 3-phenyloxetan-3-amine | 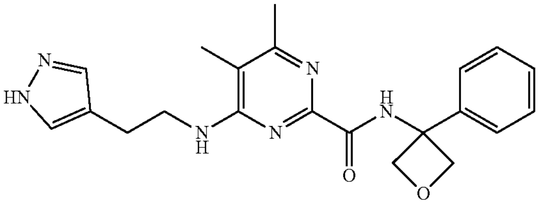 4-((2-(1H-pyrazol-4-yl)ethyl)amino)-5,6-dimethyl-N-(3-phenyloxetan-3-yl)pyrimidine-2-carboxamide. LRMS (APCI+) m/z 393 (M + H). $^{1}$H NMR (400 MHz, Methanol-$d_4$) δ 7.69-7.62 (m, 2H), 7.49 (s, 2H), 7.45-7.39 (m, 2H), 7.35-7.29 (m, 1H), 5.22 (d, J = 6.8 Hz, 2H), 4.95 (d, J = 6.8 Hz, 2H), 3.84 (t, J = 7.2 Hz, 2H), 2.88 (t, J = 7.2 Hz, 2H), 2.44 (s, 3H, 2.10 (s, 3H). |

-continued

| Compound No. | Amine in Step 1 | Structure, Name, and Data |
|---|---|---|
| 115 | 2-(3-fluorophenyl)azetidine | 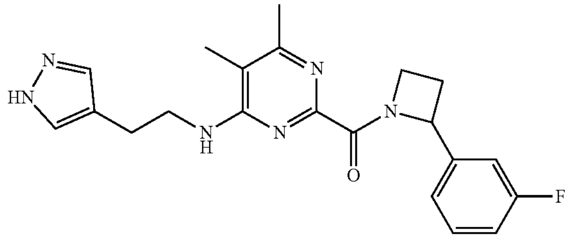<br>(4-((2-(1H-pyrazol-4-yl)ethyl)amino)-5,6-dimethylpyrimidin-2-yl)(2-(3-fluorophenyl)azetidin-1-yl)methanone. LRMS (APCI+) m/z 395 (M + H). (1.2:1 mixture of rotamers) $^1$H NMR (400 MHz, Methanol-$d_4$) δ 8.19 (s, 2H), 7.50 (s, 2H), 7.45 (s, 2H), 7.41 (td, J = 7.9, 5.8 Hz, 1H), 7.31-7.16 (m, 3H), 7.03 (td, J = 8.6, 2.6 Hz, 1H), 6.97 (d, J = 7.8 Hz, 1H), 6.93-6.83 (m, 2H), 5.91 (dd, J = 8.9, 5.7 Hz, 1H), 5.56 (dd, J = 9.2, 5.7 Hz, 1H), 4.83-4.69 (m, 1H), 4.64 (td, J = 9.7, 6.2 Hz, 1H), 4.40-4.23 (m, 2H), 3.77 (t, J = 7.2 Hz, 2H), 3.56 (dt, J = 13.9, 7.3 Hz, 1H), 3.43 (dt, J = 13.5, 7.4 Hz, 1H), 3.40-3.30 (m, 2H),2.97-2.84 (m, 4H, 2.72 (t, J = 7.3 Hz, 2H), 2.43 (s, 3H), 2.25 (s, 3H), 2.23-2.14 (m, 2H), 2.10 (s, 3H), 1.91 (s, 2H), 1.41-1.29 (m, 1H). |
| 116 | (R)-1-cyclohexylethan-1-amine | 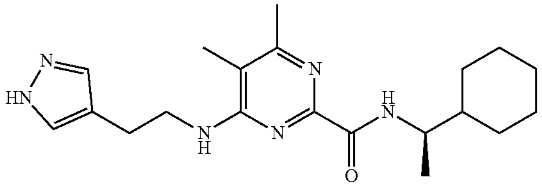<br>(R)-4-((2-(1H-pyrazol-4-yl)ethyl)amino)-N-(1-cyclohexylethyl)-5,6-dimethylpyrimidine-2-carboxamide. LRMS (APCI+) m/z 371 (M + H). $^1$H NMR (400 MHz, Methanol-$d_4$) δ 7.49 (s, 2H), 3.92 (p, J = 6.8 Hz, 1H), 3.83 (dt, J = 13.3, 7.4 Hz, 1H), 3.73 (dt, J = 13.3, 7.4 Hz, 1H), 2.87 (t, J = 7.4 Hz, 2H), 2.43 (s, 3H), 2.09 (s, 3H), 1.89-1.72 (m, 4H), 1.68 (d, J = 12.7 Hz, 1H), 1.50 (dddt, J = 11.8, 9.4, 6.3, 3.0 Hz, 1H), 1.34-1.25 (m, 2H), 1.23 (d, J = 6.8 Hz, 3H, 1.19-0.95 (m, 3H). |
| 117 | 3,5-difluoroaniline | 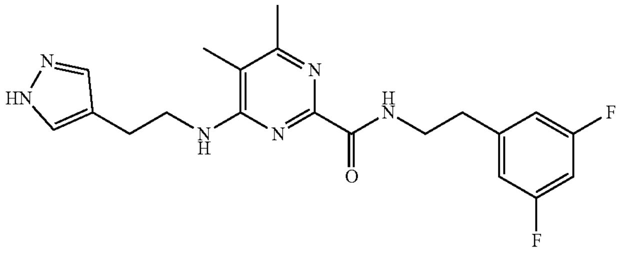<br>4-((2-(1H-pyrazol-4-yl)ethyl)amino)-N-(3,5-difluorophenyl)-5,6-dimethylpyrimidine-2-carboxamide. LRMS (APCI+) m/z 373 (M + H). $^1$H NMR (400 MHz, Methanol-$d_4$) δ 7.52 (s, 3H), 7.50 (s, 1H), 6.74 (t, J = 8.8 Hz, 1H, 3.85 (t, J = 6.7 Hz, 2H), 2.90 (t, J = 6.4 Hz, 2H), 2.46 (s, 3H), 2.11 (s, 3H). |
| 118 | (R)-1-(5-fluoropyridin-2-yl)ethan-1-amine | 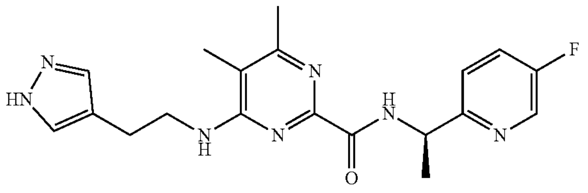<br>(R)-4-((2-(1H-pyrazol-4-yl)ethyl)amino)-N-(1-(5-fluoropyridin-2-yl)ethyl)-5,6-dimethylpyrimidine-2-carboxamide. LRMS (APCI+) m/z 384 (M + H). $^1$H NMR (400 MHz, Methanol-$d_4$) δ 8.34 (d, J = 2.9 Hz, 1H), 7.61 (td, J = 8.5, 2.9 Hz, 1H), 7.54 (s, 2H), 7.51 (dd, J = 8.7, 4.4 Hz, 1H, 5.28 (q, J = 6.8 Hz, 1H), 3.83 (t, J = 6.9 Hz, 2H), 2.91 (t, J = 7.5 Hz, 2H), 2.44 (s, 3H), 2.09 (s, 3H), 1.59 (d, J = 6.9 Hz, 3H). |

-continued

| Compound No. | Amine in Step 1 | Structure, Name, and Data |
|---|---|---|
| 119 | 4-(trifluoromethyl)piperidine | 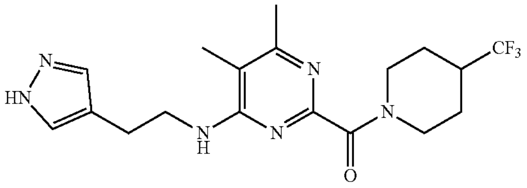 (4-((2-(1H-pyrazol-4-yl)ethyl)amino)-5,6-dimethylpyrimidin-2-yl)(4-(trifluoromethyl)piperidin-1-yl)methanone. LRMS (APCI+) m/z 397 (M + H). $^1$H NMR (400 MHz, Methanol-$d_4$) δ 7.46 (s, 2H), 4.73 (d, J = 12.9 Hz, 1H, 3.68 (t, J = 7.3 Hz, 2H), 3.14 (td, J = 13.2, 2.7 Hz, 1H), 2.89 (td, J = 13.2, 2.7 Hz, 1H), 2.83 (t, J = 7.4 Hz, 2H), 2.56 (tdp, J = 12.4, 8.4, 4.5 Hz, 1H), 2.38 (s, 3H), 2.07 (s, 3H), 2.03 (d, J = 13.5 Hz, 2H), 1.87 (d, J = 13.4 Hz, 1H), 1.62 (dtd, J = 17.9, 12.6, 6.1 Hz, 2H). |
| 120 | (3-fluoropyridin-2-yl)methanamine | 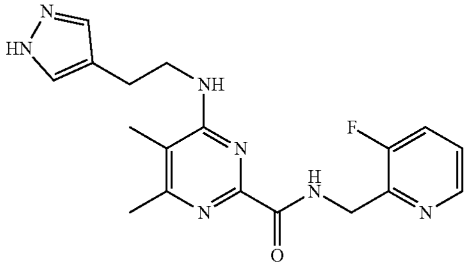 4-((2-(1H-pyrazol-4-yl)ethyl)amino)-N-((3-fluoropyridin-2-yl)methyl)-5,6-dimethylpyrimidine-2-carboxamide. LRMS (APCI+) m/z 370 (M + H). $^1$H NMR (400 MHz, Methanol-$d_4$) δ 8.32 (d, J = 4.7 Hz, 1H), 7.67-7.58 (m, 1H), 7.51 (s, 2H), 7.41 (dt, J = 8.7, 4.5 Hz, 1H), 4.82 (s, 2H), 3.82 (t, J = 7.4 Hz, 2H), 2.90 (t, J = 7.4 Hz, 2H), 2.44 (s, 3H), 2.09 (s, 3H). |
| 121 | 2-(pyridin-3-yl)propan-2-amine | 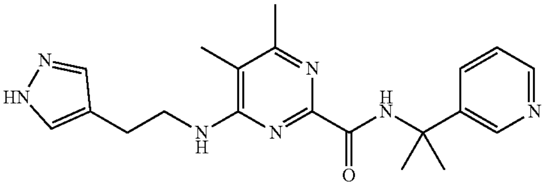 4-((2-(1H-pyrazol-4-yl)ethyl)amino)-5,6-dimethyl-N-(2-(pyridin-3-yl)propan-2-yl)pyrimidine-2-carboxamide. LRMS (APCI+) m/z 380 (M + H). $^1$H NMR (400 MHz, Methanol-$d_4$) δ 8.67 (s, 1H), 8.43 (s, 1H), 7.97 (dd, J = 8.2, 2.0 Hz, 1H), 7.49 (s, 2H), 7.43 (dd, J = 8.1, 4.8 Hz, 1H), 3.80 (t, J = 7.2 Hz, 2H), 2.88 (t, J = 7.2 Hz, 2H), 2.43 (s, 3H), 2.10 (s, 3H), 1.83 (s, 6H). |
| 122 | 3-amino-1,1,1-trifluoro-2-phenylpropan-2-ol | 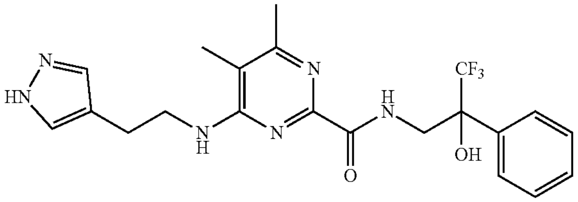 4-((2-(1H-pyrazol-4-yl)ethyl)amino)-5,6-dimethyl-N- (3,3,3-trifluoro-2-hydroxy-2-phenylpropyl)pyrimidine-2-carboxamide. LRMS (APCI+) m/z 449 (M + H). $^1$H NMR (400 MHz, Methanol-$d_4$) δ 7.67 (d, J = 6.9 Hz, 2H), 7.47 (s, 2H, 7.41-7.30 (m, 3H), 4.25 (d, J = 14.0 Hz, 1H), 4.07 (d, J = 14.0 Hz, 1H), 3.57 (td, J = 7.2, 3.9 Hz, 2H), 2.75 (t, J = 7.3 Hz, 2H), 2.38 (s, 3H), 2.03 (s, 3H). |

-continued

| Compound No. | Amine in Step 1 | Structure, Name, and Data |
|---|---|---|
| 123 | 2-azaspiro[3.3]heptane | 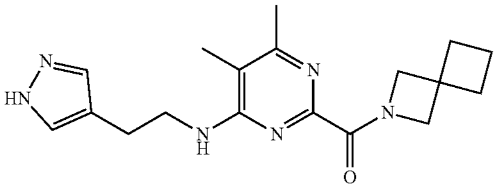 (4-((2-(1H-pyrazol-4-yl)ethyl)amino)-5,6-dimethylpyrimidin-2-yl)(2-azaspiro[3.3]heptan-2-yl)methanone. LRMS (APCI+) m/z 341 (M + H). $^1$H NMR (400 MHz, Methanol-$d_4$) δ 7.52 (s, 2H), 4.57 (s, 2H), 4.14 (s, 2H), 3.76 (t, J = 7.4 Hz, 2H), 2.87 (t, J = 7.5 Hz, 2H), 2.43 (s, 3H), 2.23 (q, J = 8.5 Hz, 4H), 2.10 (s, 3H), 1.95-1.78 (m, 2H). |
| 124 | (R)-1-(3-methoxypyridin-2-yl)ethan-1-amine | 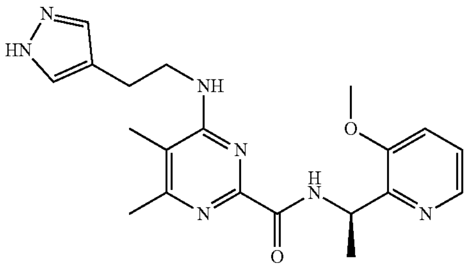 (R)-4-((2-(1H-pyrazol-4-yl)ethyl)amino)-N-(1-(3-methoxypyridin-2-yl)ethyl)-5,6-dimethylpyrimidine-2-carboxamide. LRMS (APCI+) m/z 396 (M + H). $^1$H NMR (400 MHz, Methanol-$d_4$) δ 8.03 (dd, J = 4.8, 1.2 Hz, 1H), 7.55 (s, 2H), 7.46 (dd, J = 8.3, 1.2 Hz, 1H), 7.32 (dd, J = 8.4, 4.7 Hz, 1H), 5.57 (q, J = 6.6 Hz, 1H), 3.95 (s, 3H), 3.84 (t, J = 7.0 Hz, 2H), 2.93 (t, J = 7.5 Hz, 2H), 2.45 (s, 3H), 2.10 (s, 3H, 1.50 (d, J = 6.7 Hz, 3H). |
| 125 | 3-methylazetidin-3-ol | 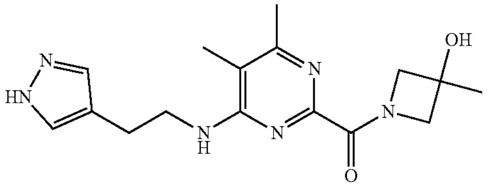 (4-((2-(1H-pyrazol-4-yl)ethyl)amino)-5,6-dimethylpyrimidin-2-yl)(3-hydroxy-3-methylazetidin-1-yl)methanone. LRMS (APCI+) m/z 331 (M + H). $^1$H NMR (400 MHz, Methanol-$d_4$) δ 7.50 (s, 2H), 4.50 (s, 2H), 4.07 (q, J = 11.3, 10.7 Hz, 2H), 3.72 (t, J = 6.4 Hz, 2H), 2.87 (t, J = 6.6 Hz, 2H), 2.43 (s, 3H), 2.09 (s, 3H), 1.51 (s, 3H). |

-continued

| Compound No. | Amine in Step 1 | Structure, Name, and Data |
|---|---|---|
| 126 | (R)-2-(pyrrolidin-2-yl)pyridine | 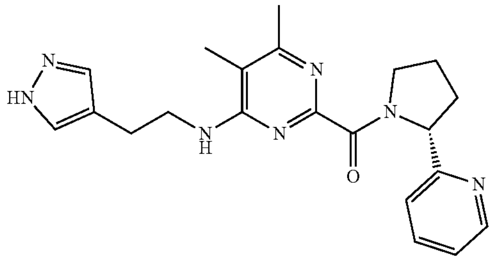 (R)-(4-((2-(1H-pyrazol-4-yl)ethyl)amino)-5,6-dimethylpyrimidin-2-yl)(2-(pyridin-2-yl)pyrrolidin-1-yl)methanone. LRMS (APCI+) m/z 392 (M + H). (1:1 mixture of rotamers) $^{1}$H NMR (400 MHz, Methanol-d4) δ 8.53 (d, J = 5.0 Hz, 1H), 8.34 (d, J = 5.0 Hz, 1H), 7.80 (td, J = 7.7, 1.6 Hz, 1H), 7.60 (td, J = 7.8, 1.7 Hz, 1H), 7.50 (s, 2H), 7.48 (d, J = 7.9 Hz, 1H), 7.44 (s, 2H), 7.32 (dd, J = 7.5, 5.0 Hz, 1H), 7.12 (dd, J = 7.5, 4.9 Hz, 1H), 7.07 (d, J = 7.9 Hz, 1H), 5.30 (td, J = 8.1, 3.9 Hz, 2H), 3.95-3.86 (m, 1H), 3.93 (t, J = 6.8 Hz, 2H), 3.81-3.72 (m, 3H), 3.33-3.27 (m, 2H), 2.88 (t, J = 7.3 Hz, 2H), 2.64 (t, J = 7.3 Hz, 2H), 2.53-2.43 (m, 2H), 2.42 (s, 3H), 2.24 (s, 3H), 2.10 (s, 3H), 2.08-1.97 (m, 6H), 1.93 (s, 3H). |
| 127 | (R)-1-(pyridin-3-yl)ethan-1-amine | 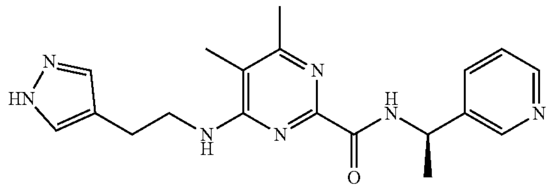 (R)-4-((2-(1H-pyrazol-4-yl)ethyl)amino)-5,6-dimethyl-N-(1-(pyridin-3-yl)ethyl)pyrimidine-2-carboxamide. LRMS (APCI+) m/z 366 (M + H). $^{1}$H NMR (400 MHz, Methanol-$d_4$) δ 8.64 (d, J = 2.2 Hz, 1H), 8.46 (dd, J = 4.8, 1.5 Hz, 1H), 7.93 (dt, J = 8.0, 1.9 Hz, 1H), 7.47 (s, 2H), 7.44 (dd, J = 8.0, 4.9 Hz, 1H), 5.28 (q, J = 7.0 Hz, 1H), 3.82 (t, J = 7.2 Hz, 2H), 2.86 (t, J = 7.2 Hz, 2H), 2.43 (s, 3H), 2.09 (s, 3H), 1.67 (d, J = 7.0 Hz, 3H). |
| 128 | (rac)-3-amino-1,1,1-trifluoropropan-2-ol | 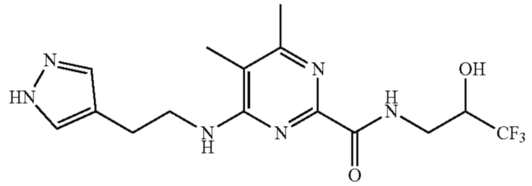 (rac)-4-((2-(1H-pyrazol-4-yl)ethyl)amino)-5,6-dimethyl-N- (3,3,3-trifluoro-2-hydroxypropyl)pyrimidine-2-carboxamide. LRMS (APCI+) m/z 373 (M + H). $^{1}$H NMR (400 MHz, Methanol-$d_4$) δ 7.51 (s, 2H), 4.25 (pd, J = 7.1, 3.9 Hz, 1H), 3.85 (dd, J = 13.9, 4.0 Hz, 1H), 3.78 (t, J = 7.3 Hz, 2H, 3.53 (dd, J = 13.9, 8.1 Hz, 1H), 2.86 (t, J = 7.3 Hz, 2H), 2.43 (s, 3H), 2.08 (s, 3H). |
| 129 | 2-(5-fluoropyridin-3-yl)ethan-1-amine | 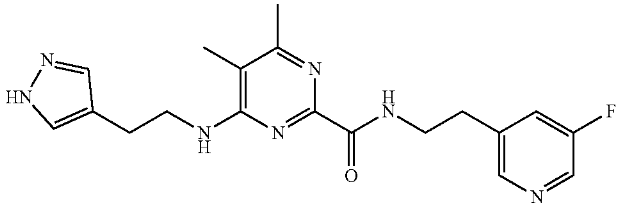 4-((2-(1H-pyrazol-4-yl)ethyl)amino)-N-(2-(5-fluoropyridin-3-yl)ethyl)-5,6-dimethylpyrimidine-2-carboxamide. LRMS (APCI+) m/z 384 (M + H). $^{1}$H NMR (400 MHz, Methanol-$d_4$) δ 8.33 (s, 1H), 8.30 (d, J = 2.7 Hz, 1H, 7.63 (dt, J = 9.5, 2.2 Hz, 1H), 7.47 (s, 2H), 3.77 (t, J = 7.1 Hz, 2H), 3.71 (t, J = 6.9 Hz, 2H), 3.03 (t, J = 6.9 Hz, 2H), 2.83 (t, J = 7.1 Hz, 2H), 2.42 (s, 3H), 2.07 (s, 3H). |

-continued

| Compound No. | Amine in Step 1 | Structure, Name, and Data |
|---|---|---|
| 130 | 1-(5-methylthiophen-2-yl)ethan-1-amine | 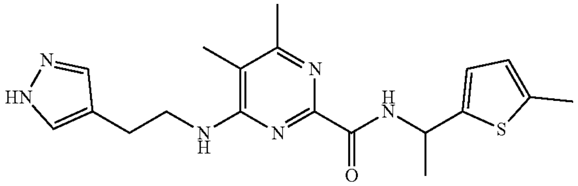 4-((2-(1H-pyrazol-4-yl)ethyl)amino)-5,6-dimethyl-N-(1-(5-methylthiophen-2-yl)ethyl)pyrimidine-2-carboxamide. LRMS (APCI+) m/z 385 (M + H). $^1$H NMR (400 MHz, Methanol-$d_4$) δ 7.42 (s, 2H), 6.85 (d, J = 3.4 Hz, 1H), 6.64 (d, J = 3.5 Hz, 1H), 5.39 (q, J = 6.8 Hz, 1H), 3.75 (dtd, J = 28.1, 13.8, 7.5 Hz, 2H), 2.84 (q, J = 6.7 Hz, 2H), 2.44 (s, 3H), 2.43 (s, 3H), 2.08 (s, 3H), 1.66 (d, J = 6.8 Hz, 3H). |
| 132 | 2-phenylazetidine | 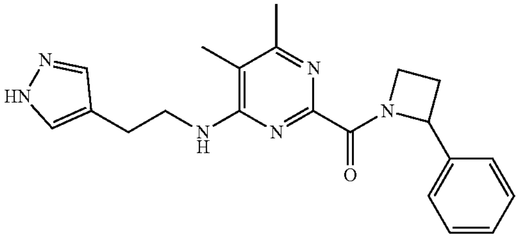 (4-((2-(1H-pyrazol-4-yl)ethyl)amino)-5,6-dimethylpyrimidin-2-yl)(2-phenylazetidin-1-yl)methanone. LRMS (APCI+) m/z 377 (M + H). (1:1 mixture of rotamers) $^1$H NMR (400 MHz, Methanol-$d_4$) δ 7.50 (s, 2H), 7.48-7.42 (m, 4H), 7.39 (t, J = 7.5 Hz, 2H), 7.32-7.25 (m, 1H), 7.23-7.17 (m, 2H), 7.17-7.10 (m, 3H), 5.90 (dd, J = 8.8, 5.7 Hz, 1H), 5.55 (dd, J = 9.2, 5.7 Hz, 1H), 4.84-4.73 (m, 1H), 4.70-4.57 (m, 1H), 4.41-4.22 (m, 2H), 3.77 (t, J = 7.3 Hz, 2H), 3.55 (dt, J = 13.8, 7.0 Hz, 1H), 3.54 (s, 1H), 3.48-3.39 (m, 1H), 3.04 (s, 1H), 2.90 (dt, J = 10.0, 8.2 Hz, 4H), 2.71 (t, J = 7.2 Hz, 2H), 2.43 (s, 3H), 2.29-2.16 (m, 3H), 2.11 (s, 3H), 1.89 (s, 3H). |
| 133 | pyridin-4-ylmethanamine | 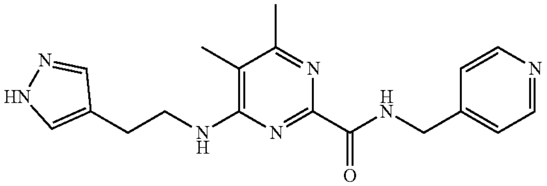 4-((2-(1H-pyrazol-4-yl)ethyl)amino)-5,6-dimethyl-N-(pyridin-4-ylmethyl)pyrimidine-2-carboxamide. LRMS (APCI+) m/z 352 (M + H). $^1$H NMR (400 MHz, Methanol-$d_4$) δ 8.50 (d, J = 4.8 Hz, 2H), 7.48 (s, 2H), 7.45 (d, J = 5.0 Hz, 2H, 4.69 (s, 2H), 3.84 (t, J = 7.2 Hz, 2H), 2.87 (t, J = 7.2 Hz, 2H), 2.45 (s, 3H), 2.10 (s, 3H). |
| 134 | (rac)-(3,4-difluorophenyl)(1-methyl-1H-imidazol-2-yl)methanamine | 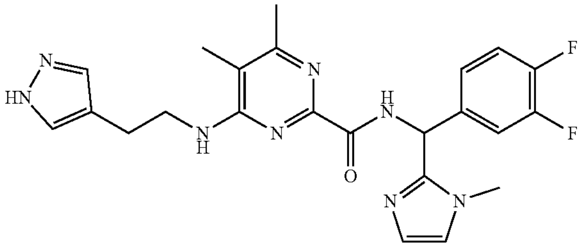 (rac)-4-((2-(1H-pyrazol-4-yl)ethyl)amino)-N-((3,4-difluorophenyl)(1-methyl-1H-imidazol-2-yl)methyl)-5,6-dimethylpyrimidine-2-carboxamide. LRMS (APCI+) m/z 467 (M + H). $^1$H NMR (400 MHz, Methanol-$d_4$) δ 7.50 (s, 2H), 7.38-7.18 (m, 3H), 7.16 (d, J = 1.4 Hz, 1H), 7.06 (d, J = 1.4 Hz, 1H), 6.51 (s, 1H), 3.78 (td, J = 7.2, 3.9 Hz, 2H), 3.70 (s, 3H), 2.85 (t, J = 7.5 Hz, 2H), 2.42 (s, 3H), 2.08 (s, 3H). |

-continued

| Compound No. | Amine in Step 1 | Structure, Name, and Data |
|---|---|---|
| 135 | cis-3-phenylcyclobutan-1-amine | 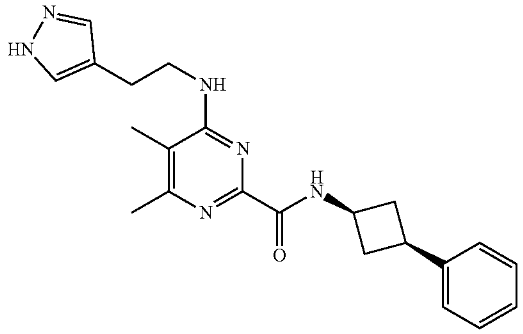 4-((2-(1H-pyrazol-4-yl)ethyl)amino)-5,6-dimethyl-N-(cis-3-phenylcyclobutyl)pyrimidine-2-carboxamide. LRMS (APCI+) m/z 391 (M + H). $^1$H NMR (400 MHz, Methanol-$d_4$) δ 7.50 (s, 2H), 7.31 (s, 2H), 7.30 (s, 2H), 7.19 (h, J = 4.2 Hz, 1H), 4.57-4.44 (m, 1H), 3.83 (t, J = 7.2 Hz, 2H), 3.31-3.23 (m, 1H), 2.87 (t, J = 7.2 Hz, 2H), 2.81 (td, J = 7.8, 3.0 Hz, 2H), 2.44 (s, 3H), 2.35-2.22 (m, 2H), 2.08 (s, 3H). |
| 136 | 2,2,2-trifluoro-1-(pyridin-3-yl)ethan-1-amine | 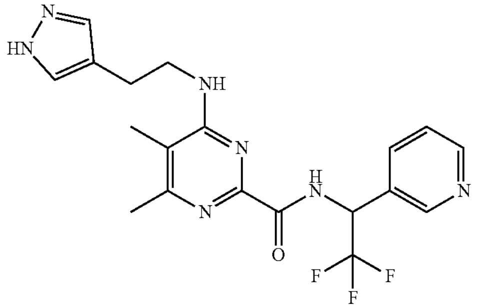 4-((2-(1H-pyrazol-4-yl)ethyl)amino)-5,6-dimethyl-N- (2,2,2-trifluoro-1-(pyridin-3-yl)ethyl)pyrimidine-2-carboxamide. LRMS (APCI+) m/z 420 (M + H). $^1$H NMR (400 MHz, Methanol-$d_4$) δ 8.79 (d, J = 2.1 Hz, 1H), 8.63 (dd, J = 4.9, 1.5 Hz, 1H), 8.08 (d, J = 8.1 Hz, 1H), 7.53 (dd, J = 8.0, 4.9 Hz, 1H), 7.49 (s, 2H), 6.09 (q, J = 8.1 Hz, 1H), 3.80 (td, J = 7.2, 1.5 Hz, 2H), 2.87 (t, J = 7.3 Hz, 2H), 2.44 (s, 3H), 2.09 (s, 3H). |
| 137 | (S)-1-(pyridin-2-yl)ethan-1-amine | 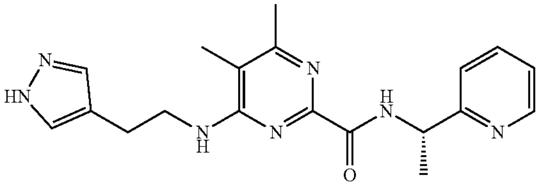 (S)-4-((2-(1H-pyrazol-4-yl)ethyl)amino)-5,6-dimethyl-N-(1-(pyridin-2-yl)ethyl)pyrimidine-2-carboxamide. LRMS (APCI+) m/z 366 (M + H). $^1$H NMR (400 MHz, Methanol-$d_4$) δ 8.48 (ddd, J = 4.9, 1.8, 0.9 Hz, 1H), 7.82 (td, J = 7.7, 1.8 Hz, 1H), 7.54 (s, 2H), 7.47 (dt, J = 7.9, 1.1 Hz, 1H), 7.32 (ddd, J = 7.6, 4.9, 1.1 Hz, 1H), 5.25 (q, J = 6.9 Hz, 1H), 3.83 (t, J = 7.4 Hz, 2H), 2.90 (t, J = 7.4 Hz, 2H), 2.45 (s, 3H), 2.10 (s, 3H), 1.60 (d, J = 6.9 Hz, 3H). |

-continued

| Compound No. | Amine in Step 1 | Structure, Name, and Data |
|---|---|---|
| 138 | 3-(trifluoromethyl)morpholine | 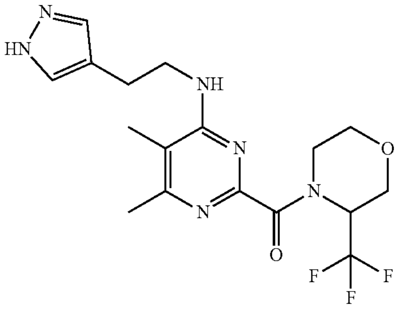 (4-((2-(1H-pyrazol-4-yl)ethyl)amino)-5,6-dimethylpyrimidin-2-yl)(3-(trifluoromethyl)morpholino)methanone. LRMS (APCI+) m/z 399 (M + H). (2.3:1 mixture of rotamers, major rotamer shown) $^1$H NMR (400 MHz, Methanol-$d_4$) δ 7.46 (s, 2H), 5.12 (qd, J = 8.9, 4.0 Hz, 1H), 4.29 (d, J = 13.1 Hz, 1H), 3.90-3.77 (m, 2H), 3.67 (td, J = 7.2, 2.6 Hz, 2H), 3.59-3.50 (m, 1H), 3.41 (d, J = 11.1 Hz, 1H), 3.40-3.30 (m, 1H), 2.83 (t, J = 7.0 Hz, 2H), 2.39 (s, 3H), 2.07 (s, 3H). |
| 139 | 2-fluoro-6-methylaniline | 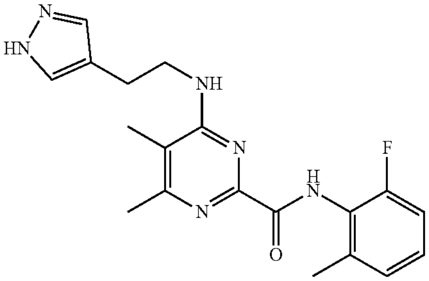 4-((2-(1H-pyrazol-4-yl)ethyl)amino)-N-(2-fluoro-6-methylphenyl)-5,6-dimethylpyrimidine-2-carboxamide. LRMS (APCI+) m/z 337 (M + H). $^1$H NMR (400 MHz, Methanol-$d_4$) δ 7.50 (s, 2H), 7.27 (td, J = 8.0, 5.4 Hz, 1H), 7.14 (d, J = 7.7 Hz, 1H), 7.07 (t, J = 9.2 Hz, 1H), 3.85 (t, J = 7.2 Hz, 2H), 2.90 (t, J = 7.2 Hz, 2H), 2.47 (s, 3H), 2.34 (s, 3H), 2.12 (s, 3H). |
| 140 | Aniline | 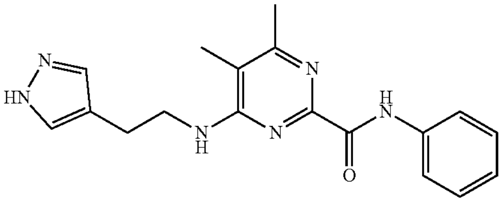 4-((2-(1H-pyrazol-4-yl)ethyl)amino)-5,6-dimethyl-N-phenylpyrimidine-2-carboxamide. LRMS (APCI+) m/z 337 (M + H). $^1$H NMR (400 MHz, Methanol-$d_4$) δ 7.76 (d, J = 8.0 Hz, 2H), 7.53 (s, 2H), 7.40 (t, J = 7.8 Hz, 2H), 7.18 (t, J = 7.5 Hz, 1H), 3.85 (t, J = 7.2 Hz, 2H), 2.91 (t, J = 7.2 Hz, 2H), 2.47 (s, 3H), 2.11 (s, 3H). |
| 141 | 2-(benzylsulfonyl)ethan-1-amine | 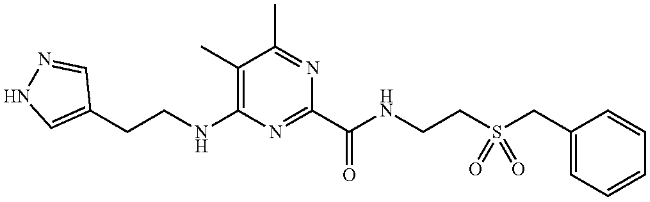 4-((2-(1H-pyrazol-4-yl)ethyl)amino)-N-(2-(benzylsulfonyl)ethyl)-5,6-dimethylpyrimidine-2-carboxamide. LRMS (APCI+) m/z 443 (M + H). $^1$H NMR (400 MHz, Methanol-$d_4$) δ 7.50 (s, 2H), 7.49-7.44 (m, 2H), 7.44-7.33 (m, 3H), 4.51 (s, 2H), 3.89 (t, J = 6.2 Hz, 2H), 3.79 (t, J = 6.5 Hz, 2H), 3.40-3.30 (m, 2H), 2.86 (t, J = 6.6 Hz, 2H), 2.43 (s, 3H), 2.07 (s, 3H). |

-continued

| Compound No. | Amine in Step 1 | Structure, Name, and Data |
|---|---|---|
| 142 | spiro[azetidine-3,3'-indolin]-2'-one | 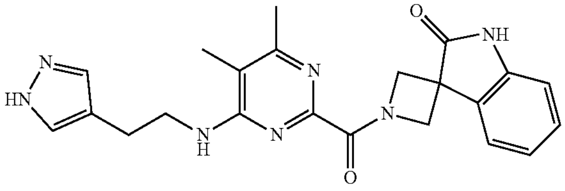 1-(4-((2-(1H-pyrazol-4-yl)ethyl)amino)-5,6-dimethylpyrimidine-2-carbonyl)spiro[azetidine-3,3′-indolin]-2′-one. LRMS (APCI+) m/z 418 (M + H). $^{1}$H NMR (400 MHz, Methanol-$d_4$) δ 7.62 (d, J = 7.5 Hz, 1H), 7.39 (s, 2H, 7.30 (td, J = 7.8, 1.2 Hz, 1H), 7.14 (td, J = 7.6, 1.0 Hz, 1H, 6.95 (d, J = 7.8 Hz, 1H), 5.03 (dd, J = 10.1, 1.3 Hz, 1H), 4.91-4.86 (m, 1H), 4.52 (dd, J = 10.3, 1.3 Hz, 1H), 4.38 (dd, J = 10.4, 1.4 Hz, 1H), 3.69 (t, J = 7.4 Hz, 2H), 2.82 (t, J = 7.4 Hz, 2H), 2.45 (s, 3H), 2.09 (s, 3H). |
| 143 | 4,4,4-trifluoro-3,3-dimethylbutan-1-amine | 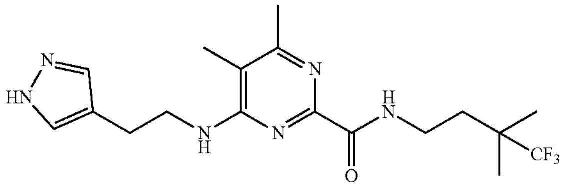 4-((2-(1H-pyrazol-4-yl)ethyl)amino)-5,6-dimethyl-N- (4,4,4-trifluoro-3,3-dimethylbutyl)pyrimidine-2-carboxamide. LRMS (APCI+) m/z 399 (M + H). $^{1}$H NMR (400 MHz, Methanol-$d_4$) δ 8.20 (s, 1H), 7.50 (s, 2H), 3.84 (d, J = 6.4 Hz, 2H), 3.52 (t, J = 7.3 Hz, 2H), 3.39-3.30 (m, 2H), 2.86 (d, J = 6.8 Hz, 2H), 2.44 (s, 3H), 2.08 (s, 3H), 1.87 (d, J = 7.3 Hz, 2H), 1.23 (s, 6H). |
| 144 | 3-fluoropyridin-4-amine | 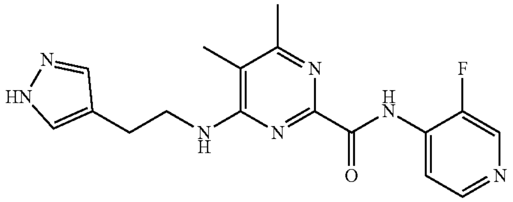 4-((2-(1H-pyrazol-4-yl)ethyl)amino)-N-(3-fluoropyridin-4-yl)-5,6-dimethylpyrimidine-2-carboxamide. LRMS (APCI+) m/z 356 (M + H). $^{1}$H NMR (400 MHz, DMSO-$d_6$) δ 8.62 (d, J = 2.4 Hz, 1H), 8.42 (d, J = 5.3 Hz, 1H), 7.48 (s, 2H), 7.25 (t, J = 5.6 Hz, 1H), 3.63 (q, J = 6.8 Hz, 2H), 2.78 (t, J = 7.5 Hz, 2H), 2.39 (s, 3H), 2.07 (s, 3H). |
| 145 | 1-(pyridin-2-yl)cyclobutan-1-amine | 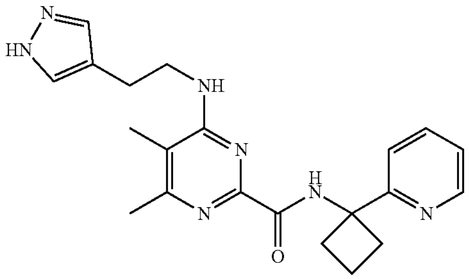 4-((2-(1H-pyrazol-4-yl)ethyl)amino)-5,6-dimethyl-N-(1-(pyridin-2-yl)cyclobutyl)pyrimidine-2-carboxamide. LRMS (APCI+) m/z 392 (M + H). $^{1}$H NMR (400 MHz, Methanol-$d_4$) δ 8.49 (d, J = 4.9 Hz, 1H), 7.84 (t, J = 7.7 Hz, 1H), 7.71 (d, J = 8.0 Hz, 1H), 7.51 (s, 2H), 7.29 (dd, J = 7.4, 5.0 Hz, 1H), 3.84 (t, J = 7.4 Hz, 2H), 2.91 (t, J = 7.3 Hz, 2H), 2.88-2.72 (m, 4H), 2.44 (s, 3H), 2.24 (qd, J = 9.9, 5.1 Hz, 1H), 2.17-1.96 (m, 1H), 2.10 (s, 3H). |

Example 1-2

Representative example: Preparation of (R)-4-chloro-N-(1-(6-fluoropyridin-2-yl)ethyl)-6,7-dihydro-5H-cyclopenta[d]pyrimidine-2-carboxamide

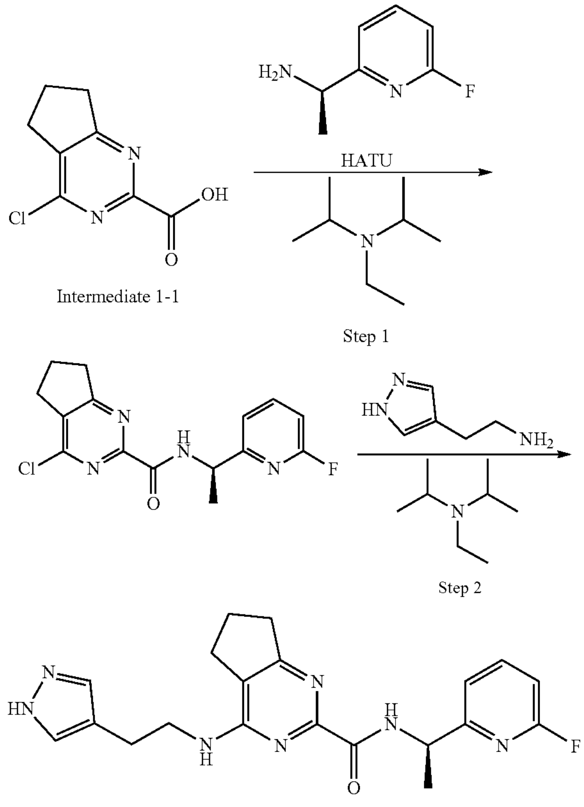

Copound 146

Step 1: Synthesis of (R)-4-chloro-N-(1-(6-fluoropyridin-2-yl)ethyl)-6,7-dihydro-5H-cyclopenta[d] pyrimidine-2-carboxamide To a solution of 4-chloro-6,7-dihydro-5H-cyclopenta[d]pyrimidine-2-carboxylic acid (55 mg, 0.277 mmol, 1.0 equiv), (R)-1-(6-fluoropyridin-2-yl)ethan-1-amine HCl salt (59 mg, 0.277 mmol, 1.0 equiv), and Hexafluorophosphate azabenzotriazole tetramethyl uronium (HATU, 111 mg, 0.291 mmol, 1.1 equiv) in DMF (1.5 mL) was added diisopropylethylamine (DIPEA, 0.52 mL, 1.39 mmol, 5.0 equiv) dropwise at 23° C. The resulting solution was stirred at this temperature for 30 min. LC-MS showed complete conversion. EtOAc (5 mL) and water (5 mL) were added. The organic phase was washed by brine, dried ($MgSO_4$), filtered, and concentrated to give the crude amide coupling product which was directly used in the next step without further purification.

Step 2: Synthesis of (R)-4-((2-(1H-pyrazol-4-yl) ethyl)amino)-N-(1-(6-fluoropyridin-2-yl)ethyl)-6,7-dihydro-5H-cyclopenta[d] pyrimidine-2-carboxamide A solution of crude coupling product intermediate (R)-4-chloro-N-(1-(6-fluoropyridin-2-yl)ethyl)-6,7-dihydro-5H-cyclopenta[d]pyrimidine-2-carboxamide (0.277 mmol, 1.0 equiv), 2-(1H-pyrazol-4-yl)ethan-1-amine (62 mg, 0.55 mmol, 2.0 equiv), and DIPEA (0.08 mL, 0.831 mmol, 3.0 equiv) in MeOH (0.5 mL)/i-PrOH (1 mL) was heated under microwave at 165° C. for 30 min. LC-MS showed complete conversion. The reaction was directly concentrated and subjected to reverse-phase HPLC separation (10% to 100% MeCN, 0.1% HCOOH linearly) to yield the desired product (45 mg, 41%) as a colorless foam. $^1$H NMR (400 MHz, Chloroform-d) δ 8.93 (d, J=8.2 Hz, 1H), 7.92 (s, 1H), 7.76 (q, J=7.8 Hz, 1H), 7.49 (s, 2H), 7.22 (dd, J=7.5, 2.2 Hz, 1H), 6.82 (dd, J=8.3, 2.6 Hz, 1H), 5.35 (p, J=7.1 Hz, 1H), 5.13 (s, 1H), 3.78 (h, J=6.7 Hz, 2H), 2.91 (dt, J=33.7, 7.3 Hz, 3H), 2.65 (t, J=7.4 Hz, 2H), 2.14 (d, J=31.2 Hz, 2H), 1.58 (d, J=6.8 Hz, 2H). LRMS (APCI+) 396.10 [M+H$^+$].

The following compounds were prepared according to the procedures described above using in step 1 the carboxylic acid and amine reagent described in the table below.

| Compound No. | Carboxylic Acid in Step 1 | Amine in Step 1 | Structure, Name, and Data |
|---|---|---|---|
| 146 | 4-chloro-6,7-dihydro-5H-cyclopenta[pyrimidine-2-carboxylic acid (Intermediate 1-1) | (R)-1-(6-fluoropyridin-2-yl)ethan-1-amine | 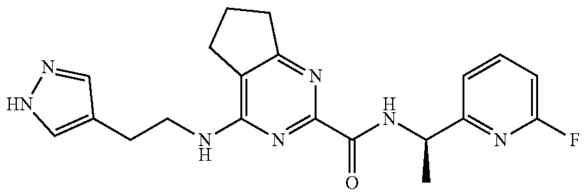 (R)-4-((2-(1H-pyrazol-4-yl)ethyl)amino)-N-(1-(6-fluoropyridin-2-yl)ethyl)-6,7-dihydro-5H-cyclopenta[d]pyrimidine-2-carboxamide LRMS (APCI+) m/z 396.1 (M + H). $^1$H NMR (400 MHz, Chloroform-d) δ 8.93 (d, J = 8.2 Hz, 1H), 7.92 (s, 1H), 7.76 (q, J = 7.8 Hz, 1H), 7.49 (s, 2H), 7.22 (dd, J = 7.5, 2.2 Hz, 1H), 6.82 (dd, J = 8.3, 2.6 Hz, 1H), 5.35 (p, J = 7.1 Hz, 1H), 5.13 (s, 1H), 3.78 (h, J = 6.7 Hz, 2H), 2.91 (dt, J = 33.7, 7.3 Hz, 3H), 2.65 (t, J = 7.4 Hz, 2H), 2.14 (d, J = 31.2 Hz, 2H), 1.58 (d, J = 6.8 Hz, 2H). |

-continued

| Compound No. | Carboxylic Acid in Step 1 | Amine in Step 1 | Structure, Name, and Data |
|---|---|---|---|
| 151 | 4-bromo-6-chloropicolinic acid (Intermediate 1-2) | (R)-1-(6-fluoropyridin-2-yl)ethan-1-amine | 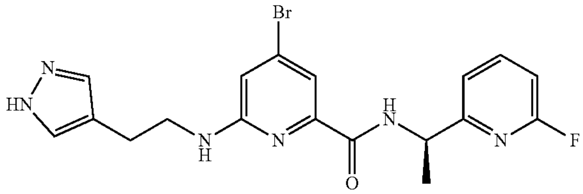 (R)-6-((2-(1H-pyrazol-4-yl)ethyl)amino)-4-bromo-N-(1-(6-fluoropyridin-2-yl)ethyl)picolinamide. LRMS (APCI+) m/z 433.1 (M + H). $^1$H NMR (400 MHz, Methanol-$d_4$) δ 7.94 (q, J = 7.9 Hz, 1H), 7.53 (s, 2H), 7.35 (s, 1H), 7.38-7.31 (m, 1H), 6.98 (dd, J = 8.2, 2.5 Hz, 1H), 6.86 (d, J = 1.5 Hz, 1H), 5.21 (q, J = 6.7 Hz, 1H), 3.65 (t, J = 7.1 Hz, 2H), 2.87 (t, J = 7.1 Hz, 2H), 1.57 (d, J = 6.8 Hz, 3H). |
| 152 | 4-methyl-6-chloropicolinic acid (Intermediate 1-3) | (R)-2-(3-fluorophenyl)pyrrolidine | 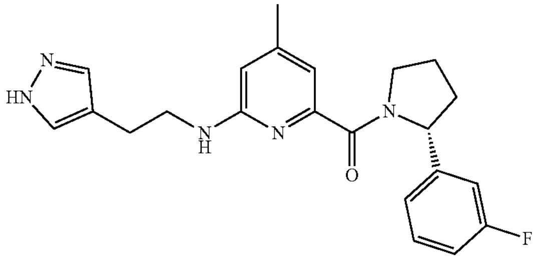 (R)-(6-((2-(1H-pyrazol-4-yl)ethyl)amino)-4-methylpyridin-2-yl) (2-(3-fluorophenyl)pyrrolidin-1-yl)methanone. LRMS (APCI+) m/z 394.1 (M + H). $^1$H NMR (400 MHz, Methanol-$d_4$) δ 7.49 (d, J = 10.8 Hz, 2H), 7.34 (td, J = 7.9, 5.9 Hz, 1H), 7.16 (td, J = 8.2, 6.4 Hz, 1H), 7.07 (dd, J = 10.1, 2.3 Hz, 1H), 6.96 (td, J = 8.5, 2.5 Hz, 1H), 6.86-6.76 (m, 1H), 6.76-6.66 (m, 1H), 6.43 (s, 0H), 6.22 (s, 0H), 5.55 (dd, J = 7.4, 3.2 Hz, 0H), 5.26 (dd, J = 7.9, 4.9 Hz, 1H), 4.05 (dt, J = 11.2, 6.7 Hz, 1H), 3.83 (ddt, J = 28.7, 11.7, 5.3 Hz, 1H), 3.59 (t, J = 7.1 Hz, 1H), 3.33-3.21 (m, 1H), 2.84 (t, J = 7.2 Hz, 1H), 2.71 (td, J = 7.1, 3.7 Hz, 1H), 2.51-2.36 (m, 1H), 2.26 (s, 2H), 2.06 (s, 1H), 1.93 (dddt, J = 27.0, 20.3, 12.0, 6.8 Hz, 3H). |

Example 2

Preparation of (R)-(4-((2-(1H-pyrazol-4-yl)ethyl) amino)-5,6-dimethylpyrimidin-2-yl)(2-(6-methylpyridin-2-yl)pyrrolidin-1-yl)methanone

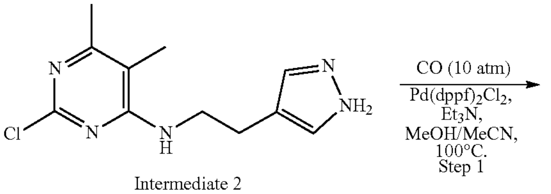

Intermediate 2

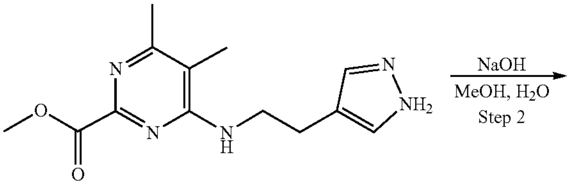

-continued

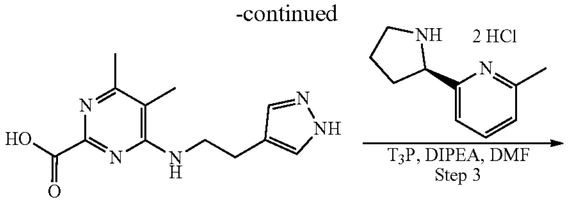

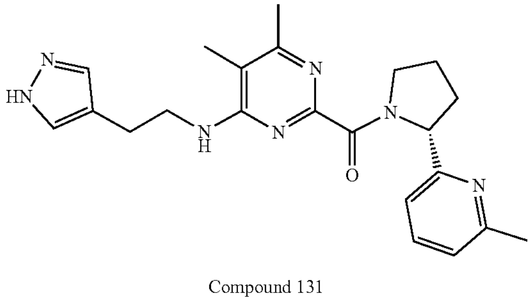

Compound 131

Step 1: Synthesis of methyl 4-((2-(1H-pyrazol-4-yl)ethyl)amino)-5,6-dimethylpyrimidine-2-carboxylate To a solution of 2-chloro-5,6-dimethyl-N-[2-(1H-pyrazol-4-yl)ethyl]pyrimidin-4-amine (Intermediate 2, 4.87 g, 19.3 mmol, 1.0 equiv) in McOH/MeCN (120 mL/30 mL) was added Pd(dppf)$Cl_2$ (2.83 g, 3.87 mmol, 0.2 equiv) and $Et_3N$ (3.90 g, 38.5 mmol, 2.0 equiv) in a pressure tank. The mixture was purged with nitrogen for 2 min and then was pressurized to 10 atm with carbon monoxide at 100° C. for 15 h. The reaction mixture was cooled to 23° C., filtered, concentrated, and purified by reverse phase column chromatography (Water (0.05% $NH_4HCO_3$)/MeCN, 7:3) to afford methyl 4,5-dimethyl-6-[[2-(1H-pyrazol-4-yl)ethyl]amino]pyrimidine-2-carboxylate (2.42 g, 45%) as a white solid.

Step 2: Synthesis of 4-((2-(1H-pyrazol-4-yl)ethyl)amino)-5,6-dimethylpyrimidine-2-carboxylic acid To a solution of methyl 4,5-dimethyl-6-[[2-(1H-pyrazol-4-yl)ethyl]amino]pyrimidine-2-carboxylate (2.42 g, 8.79 mmol, 1.0 equiv) in McOH (20 mL) at 0° C. was added NaOH (701.00 mg, 17.526 mmol, 1.99 equiv) in $H_2O$ (4 mL). The resulting mixture was stirred at 23° C. for 15 h. The resulting mixture was acidified to pH 5-6 with 1 N HCl. The precipitated solid was collected by filtration and dried in vacuo to obtain 4,5-dimethyl-6-[[2-(1H-pyrazol-4-yl)ethyl]amino]pyrimidine-2-carboxylic acid (2.2 g, 96%) as a white solid.

Step 3: Synthesis of (R)-(4-((2-(1H-pyrazol-4-yl)ethyl)amino)-5,6-dimethylpyrimidin-2-yl) (2-(6-methylpyridin-2-yl)pyrrolidin-1-yl)methanone To a stirred solution of 4,5-dimethyl-6-[[2-(1H-pyrazol-4-yl)ethyl]amino]pyrimidine-2-carboxylic acid (100 mg, 0.38 mmol, 1.0 equiv) in DMF (2 mL) was added 2-methyl-6-[(2R)-pyrrolidin-2-yl]pyridine dihydrochloride (90.00 mg, 0.383 mmol, 1.00 equiv), Propanephosphonic add anhydride (T3P, 370 mg, 1.16 mmol, 1.5 equiv, 50% in EtOAc) and diisopropylethylamine (250 mg, 1.93 mmol, 5.05 equiv). The resulting mixture was stirred at 23° C. for 15 h. Upon completion, the mixture was directly purified by reverse-phase prep-HPLC ($H_2O$ (10 MMOL/L $NH_4HCO_{3+}$ 0.1% $NH_3 \cdot H_2O$)/MeCN) to yield (R)-(4-((2-(1H-pyrazol-4-yl)ethyl)amino)-5,6-dimethylpyrimidin-2-yl)(2-(6-methylpyridin-2-yl)pyrrolidin-1-yl)methanone (Compound 131-48 mg, 31%) as an off-white solid. $^1$H NMR (400 MHz, DMSO-$d_6$) δ 12.55 (s, 1H), 7.69-6.87 (m, 5H), 6.81-6.59 (m, 1H), 5.05 (ddd, J=37.8, 8.1, 3.6 Hz, 1H), 4.12-3.34 (m, 4H), 2.82-2.62 (m, 2H), 2.52 (d, J=1.9 Hz, 3H), 2.38 (d, J=66.9 Hz, 3H), 2.29-1.72 (m, 7H). LRMS (APCI+) calcd for $C_{22}H_{28}N_7O^+[M+H^+]$ 406, found 406.

Example 3

Preparation of 4-((2-(1H-pyrazol-4-yl)ethyl)(phenethyl)amino)-5,6-dimethylpyrimidine-2-carboxamide

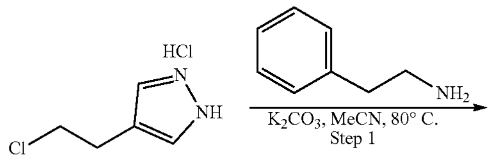

-continued

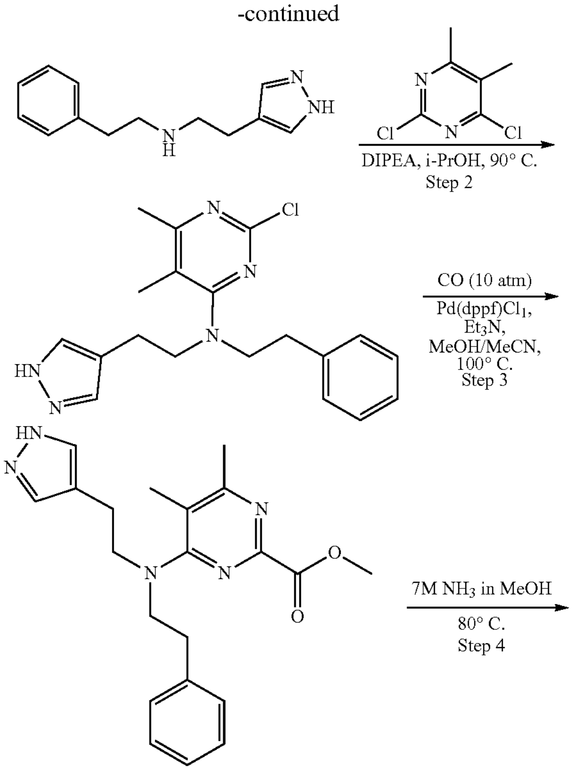

Intermediate 3

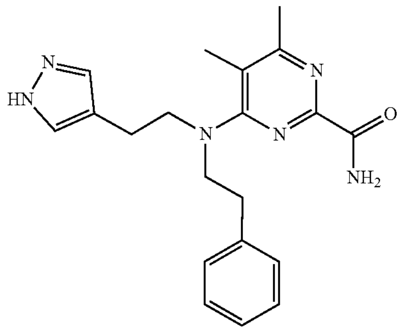

Compound 1

Step 1: Synthesis of N-(2-(1H-pyrazol-4-yl)ethyl)-2-phenylethan-1-amine

To a solution of phenylacetaldehyde (500 mg, 4.16 mmol, 1.0 equiv) in MeCN (10 mL) was added 4-(2-chloroethyl)-1H-pyrazole HCl salt (759 mg, 4.54 mmol, 1.09 equiv) and $K_2CO_3$ (1.10 g, 7.96 mmol, 1.91 equiv). The resulting mixture was stirred at 80° C. for 15 h. Upon completion, the mixture was cooled down to 23° C. and the solid was filtered. The filtrate was concentrated and purified by reverse phase column chromatography ($H_2O$ (0.05% $NH_4HCO_3$)/MeCN, 3:1) to afford (2-phenylethyl)[2-(1H-pyrazol-4-yl)ethyl]amine (230 mg, 26%) as a colorless oil.

Step 2: Synthesis of N-(2-(1H-pyrazol-4-yl)ethyl)-2-chloro-5,6-dimethyl-N-phenethylpyrimidin-4-amine To a stirred solution of (2-phenylethyl) [2-(1H-pyrazol-4-yl)ethyl]amine (230 mg, 1.07 mmol, 1.0 equiv) in i-PrOH (3 mL) was added 2,4-dichloro-5,6-dimethylpyrimidine (189 mg, 1.07 mmol, 1.0 equiv) and diisopropylethylamine (413 mg, 3.19 mmol, 3.0 equiv). The resulting mixture was stirred at 90° C. for 15 h. Upon completion, the reaction was directly concentrated and purified by reverse phase column chromatography ($H_2O$ (0.05% $NH_4HCO_3$)/MeCN, 1:3) to afford N-(2-(1H-pyrazol-4-yl)ethyl)-2-chloro-5,6-dimethyl-N-phenethylpyrimidin-4-amine (66 mg, 17%) as a white solid and 60 mg regio-isomer N-(2-(1H-pyrazol-4-yl)ethyl)-4-chloro-5,6-dimethyl-N-phenethylpyrimidin-2-amine.

N-(2-(1H-pyrazol-4-yl)ethyl)-2-chloro-5,6-dimethyl-N-phenethylpyrimidin-4-amine: $^1$H NMR (400 MHz, DMSO-$d_6$) δ 12.51 (s, 1H), 7.42 (s, 2H), 7.32-7.15 (m, 5H), 3.63-3.55 (m, 2H), 3.55-3.47 (m, 2H), 2.86-2.78 (m, 2H), 2.70-2.62 (m, 2H), 2.29 (s, 3H), 2.07 (s, 3H). Regio-isomer: $^1$H NMR (400 MHz, DMSO-$d_6$) δ 12.51 (s, 1H), 7.42 (s, 2H), 7.30 (t, J=7.4 Hz, 2H), 7.27-7.21 (m, 2H), 7.20 (t, J=7.1 Hz, 1H), 3.63 (dt, J=15.0, 7.6 Hz, 4H), 2.80 (t, J=7.7 Hz, 2H), 2.71-2.62 (m, 2H), 2.37 (s, 3H), 2.14 (s, 3H).

Step 3: Synthesis of methyl 4-((2-(1H-pyrazol-4-yl)ethyl)(phenethyl)amino)-5,6-dimethylpyrimidine-2-carboxylate (Intermediate 3)

To a solution of N-(2-(1H-pyrazol-4-yl)ethyl)-2-chloro-5,6-dimethyl-N-phenethylpyrimidin-4-amine (120 mg, 0.34 mmol, 1.0 equiv) in McOH/MeCN (4 mL/1 mL) was added Pd(dppf)$Cl_2$ (49 mg, 0.067 mmol, 0.2 equiv), $Et_3N$ (68 mg, 0.67 mmol, 2.0 equiv) in a pressure tank. The mixture was purged with nitrogen for 2 min and then was pressurized to 10 atm with carbon monoxide at 100° C. for 15 h. Upon completion, the reaction mixture was cooled to 23° C. and filtered to remove solid. The filtrate was concentrated and purified by reverse phase column chromatography ($H_2O$ (0.1% $NH_3 \cdot H_2O$)/MeCN=1:1) to afford methyl 4-((2-(1H-pyrazol-4-yl)ethyl)(phenethyl)amino)-5,6-dimethylpyrimidine-2-carboxylate (Intermediate 3, 120 mg, 94%) as a yellowish solid.

Step 4: Synthesis of 4-((2-(1H-pyrazol-4-yl)ethyl)(phenethyl)amino)-5,6-dimethylpyrimidine-2-carboxamide To a stirred solution of $NH_3$ (7 M in McOH, 1.00 mL) was added methyl 4-((2-(1H-pyrazol-4-yl)ethyl)(phenethyl)amino)-5,6-dimethylpyrimidine-2-carboxylate (Intermediate 3, 70 mg, 0.18 mmol, 1.0 equiv). The resulting mixture was stirred at 80° C. for 3 h. Upon completion, the reaction mixture was directly concentrated and purified by Prep-HPLC ($H_2O$ (10 MMOL/L $NH_4HCO_{3+0.1}$% $NH_3 \cdot H_2O$)/MeCN) to yield 4-((2-(1H-pyrazol-4-yl)ethyl)(phenethyl)amino)-5,6-dimethylpyrimidine-2-carboxamide (Compound 1-19.7 mg, 29%) as a white solid. $^1$H NMR (300 MHz, DMSO-$d_6$) δ 12.55 (s, 1H), 7.82 (s, 1H), 7.58 (s, 2H), 7.40-7.13 (m, 6H), 3.64 (dd, J=8.9, 6.3 Hz, 2H), 3.59-3.48 (m, 2H), 2.84 (t, J=7.6 Hz, 2H), 2.67 (t, J=7.7 Hz, 2H), 2.38 (s, 3H), 2.14 (s, 3H). LRMS (ESI+) calcd for $C_{20}H_{25}N_6O^+$ [M+H$^+$] 365, found 365.

Example 4

Preparation of 4-((2-(1H-pyrazol-4-yl)ethyl)(phenethyl)amino)-N,5,6-trimethylpyrimidine-2-carboxamide

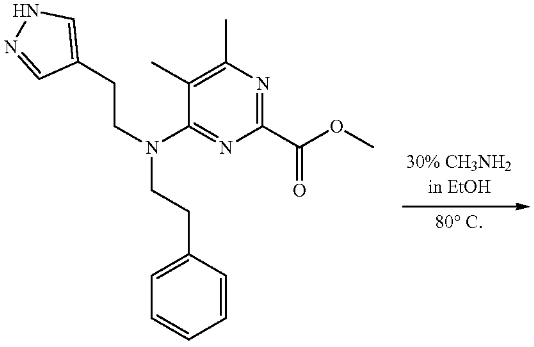

Intermediate 3

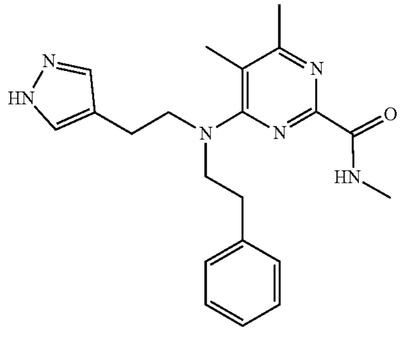

Compound 2

To a stirred solution of $CH_3NH_2$ (30% in EtOH, 1.00 mL) was added methyl 4-((2-(1H-pyrazol-4-yl)ethyl)(phenethyl)amino)-5,6-dimethylpyrimidine-2-carboxylate (Intermediate 3, 70 mg, 0.18 mmol, 1.0 equiv). The resulting mixture was stirred at 80° C. for 3 h. Upon completion, the reaction mixture was directly concentrated and purified by Prep-HPLC ($H_2O$ (10 mM $NH_4HCO_{3+0.1}$% $NH_3 \cdot H_2O$)/MeCN) to yield 4-((2-(1H-pyrazol-4-yl)ethyl)(phenethyl)amino)-N,5,6-trimethylpyrimidine-2-carboxamide (Compound 2-18.9 mg, 27%) as a white solid. $^1$H NMR (300 MHz, DMSO-$d_6$) δ 12.55 (s, 1H), 8.43 (d, J=5.1 Hz, 1 H), 7.45 (s, 2H), 7.28 (d, J=3.8 Hz, 4H), 7.27-7.13 (m, 1H), 3.64 (dd, J=8.9, 6.3 Hz, 2H), 3.59-3.49 (m, 2H), 2.90-2.77 (m, 5H), 2.67 (dd, J=8.8, 6.5 Hz, 2H), 2.39 (s, 3H), 2.13 (s, 3 H). LRMS (ESI+) calcd for $C_{21}H_{27}N_6O^+$ [M+H$^+$] 379, found 379.

Example 5

Preparation of 4-((2-(1H-pyrazol-4-yl)ethyl)(propyl)amino)-5,6-dimethylpyrimidine-2-carboxamide

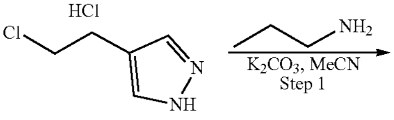

-continued

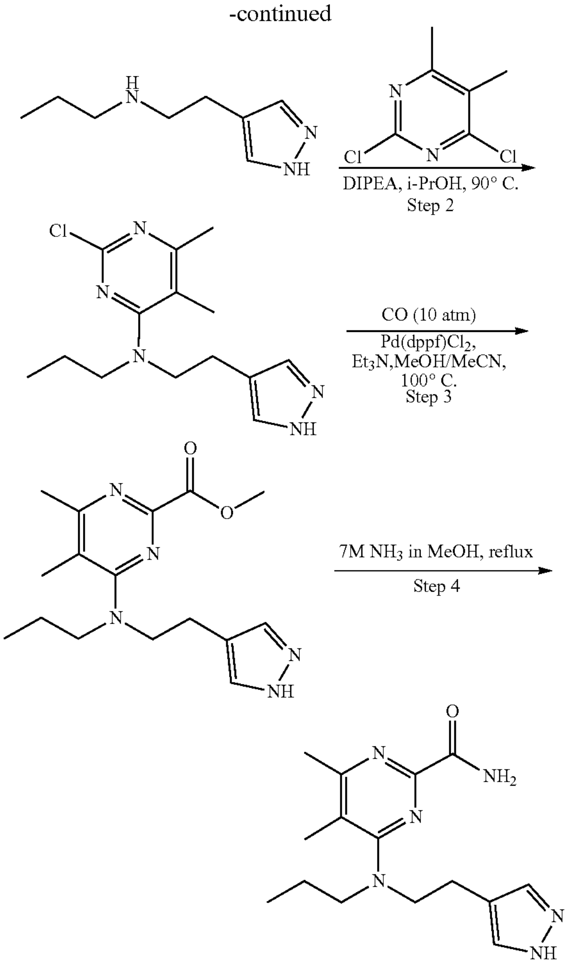

Compound 106

Step 1: Synthesis of N-(2-(1H-pyrazol-4-yl)ethyl)propan-1-amine

To a stirred solution of 4-(2-chloroethyl)-1H-pyrazole HCl salt (500 mg, 2.99 mmol, 1.0 equiv) in MeCN (5 mL) was added n-propylamine (353 mg, 5.97 mmol, 2.0 equiv) and $K_2CO_3$ (1.65 g, 11.9 mmol, 4.0 equiv). The resulting mixture was stirred at 80° C. for 15 h. Upon completion, the mixture was cooled down to 23° C. and filtered to remove solid. The filtrate was and purified by reverse phase column chromatography ($H_2O$ (0.05% $NH_4HCO_3$)/MeCN, 4:1) to afford N-(2-(1H-pyrazol-4-yl)ethyl)propan-1-amine (230 mg, 25%) as a yellowish oil.

Step 2: Synthesis of N-(2-(1H-pyrazol-4-yl)ethyl)-2-chloro-5,6-dimethyl-N-propylpyrimidin-4-amine To a solution of N-(2-(1H-pyrazol-4-yl)ethyl)propan-1-amine (230 mg, 1.50 mmol, 1.0 equiv) in i-PrOH (3 mL) was added 2,4-dichloro-5,6-dimethylpyrimidine (264 mg, 1.49 mmol, 1.0 equiv) and diisopropylethylamine (578 mg, 4.47 mmol, 2.98 equiv). The resulting mixture was stirred at 90° C. for 15 h. Upon completion, the reaction was directly concentrated and purified by reverse phase column chromatography ($H_2O$ (0.05% $NH_4HCO_3$)/MeCN, 3:2) to afford N-(2-(1H-pyrazol-4-yl)ethyl)-2-chloro-5,6-dimethyl-N-propylpyrimidin-4-amine (65 mg, 15%) as a white solid and 120 mg regio-isomer. N-(2-(1H-pyrazol-4-yl)ethyl)-2-chloro-5,6-dimethyl-N-propylpyrimidin-4-amine: $^1H$ NMR (300 MHz, DMSO-$d_6$) δ 12.54 (s, 1H), 7.43 (s, 2H), 3.56-3.45 (m, 2H), 3.32 (d, J=7.5 Hz, 2H), 2.70 (dd, J=8.9, 6.3 Hz, 2H), 2.30 (s, 3H), 2.10 (s, 3H), 1.55 (h, J=7.4 Hz, 2H), 0.84 (t, J=7.4 Hz, 3H). Regio-isomer: $^1H$ NMR (300 MHz, DMSO-$d_6$) δ 12.55 (s, 1H), 7.45 (s, 2H), 3.65 (dd, J=9.0, 6.4 Hz, 2H), 3.43 (t, J=7.5 Hz, 2H), 2.75-2.64 (m, 2H), 2.34 (s, 3H), 2.13 (s, 3H), 1.55 (h, J=7.4 Hz, 2H), 0.85 (t, J=7.4 Hz, 3H).

Step 3: Synthesis of methyl 4-((2-(1H-pyrazol-4-yl)ethyl)(propyl)amino)-5,6-dimethylpyrimidine-2-carboxylate To a solution of N-(2-(1H-pyrazol-4-yl)ethyl)-2-chloro-5,6-dimethyl-N-propylpyrimidin-4-amine (50 mg, 0.17 mmol, 1.0 equiv) in McOH/MeCN (8 mL/2 mL) was added $Pd(dppf)Cl_2$ (25 mg, 0.03 mmol, 0.2 equiv) and $Et_3N$ (34 mg, 0.34 mmol, 2.0 equiv) in a pressure tank. The mixture was purged with nitrogen for 2 min and then was pressurized to 10 atm with carbon monoxide at 100° C. for 15 h. Upon completion, the reaction mixture was cooled to 23° C. and filtered to remove solid. The filtrate was concentrated to yield crude methyl 4-((2-(1H-pyrazol-4-yl)ethyl)(propyl)amino)-5,6-dimethylpyrimidine-2-carboxylate (50 mg, 93%) as a brownish solid.

Step 4: Synthesis of 4-((2-(1H-pyrazol-4-yl)ethyl)(propyl)amino)-5,6-dimethylpyrimidine-2-carboxamide To a stirred solution of $NH_3$ (7 M in McOH, 1 mL) was added methyl 4-((2-(1H-pyrazol-4-yl)ethyl)(propyl)amino)-5,6-dimethylpyrimidine-2-carboxylate (50 mg, 0.16 mmol, 1.0 equiv). The resulting mixture was stirred at 80° C. for 15 h. Upon completion, the reaction mixture was directly concentrated and purified by reverse-phase prep-HPLC ($H_2O$ (0.05% $NH_4HCO_3$)/MeCN=3:2) to afford 4-((2-(1H-pyrazol-4-yl)ethyl)(propyl)amino)-5,6-dimethylpyrimidine-2-carboxamide (Compound 106-24.7 mg, 52%) as a white solid. $^1H$ NMR (300 MHz, DMSO-$d_6$) δ 12.55 (s, 1H), 7.80 (s, 1H), 7.56 (s, 1H), 7.46 (s, 2H), 3.54 (t, J=7.7 Hz, 2H), 3.35 (s, 2H), 2.71 (t, J=7.7 Hz, 2H), 2.39 (s, 3H), 2.16 (s, 3H), 1.56 (q, J=7.5 Hz, 2H), 0.90-0.79 (m, 3H). LRMS (ESI+) calcd for $C_{15}H_{23}N_6O^+$ [M+H$^+$] 303, found 303.

Example 6

Preparation of (S)-(4-(3-(1H-pyrazol-4-yl)pyrrolidin-1-yl)-5,6-dimethylpyrimidin-2-yl)(3-hydroxy-3-phenylazetidin-1-yl)methanone

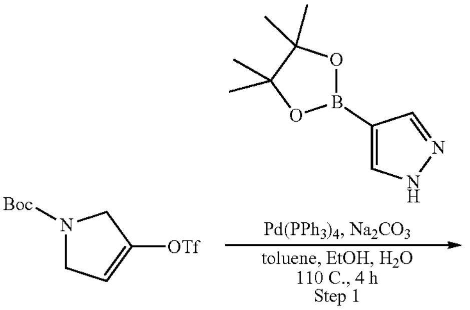

-continued

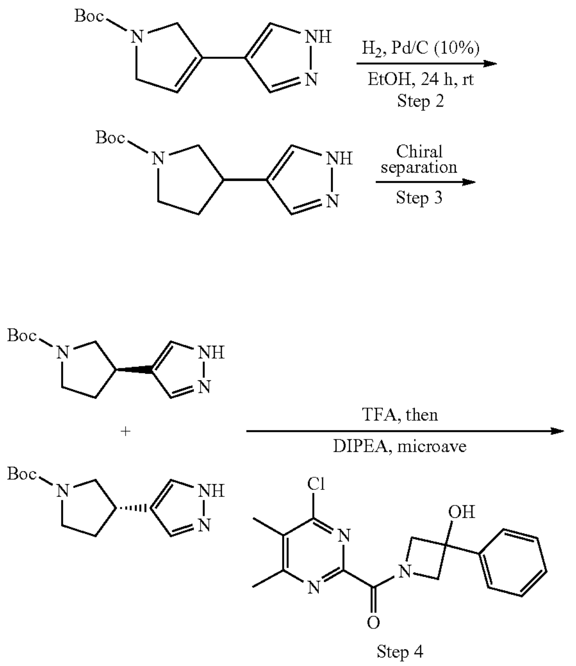

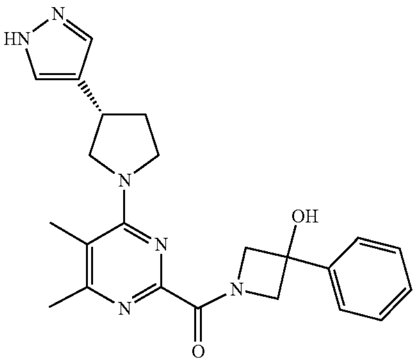

Compound 9

Step 1: Synthesis of tert-butyl 3-(1H-pyrazol-4-yl)-2,5-dihydro-1H-pyrrole-1-carboxylate To a solution of tert-butyl 3-(trifluoromethanesulfonyloxy)-2,5-dihydropyrrole-1-carboxylate (20.0 g, 63.0 mmol), 4-(tetramethyl-1,3,2-dioxaborolan-2-yl)-1H-pyrazol (24.5 g, 126.1 mmol), $Pd(PPh_3)_4$ (7.3 g, 6.3 mmol), sodium carbonate (13.4 g, 126 mmol) in 300 mL of toluene was added 40 mL of water and 40 mL of ethanol. The solution was heated at 110° C. for 4 hr, cooled to rt, and was poured into ether (1.5 L). It was washed with $NaHCO_3$, dried with $Na_2SO_4$, filtered and concentrated. The crude solid was purified by silica gel column chromatography (120 g biotage column, 20%-100% EtOAc/Hex then 10% McOH/DCM) provided product (9.0 g, 38.2 mmol, 60.6% yield) as a pale-yellow solid set-up. $R_f$=0.44 (50% EtOAc/hexanes). LRMS (ESI+) calcd for $C_{12}H_{18}N_3O_2^+$ [M+H$^+$] 236.1, found 236.2.

Step 2: Synthesis of tert-butyl 3-(1H-pyrazol-4-yl)pyrrolidine-1-carboxylate tert-butyl 3-(1H-pyrazol-4-yl)-2,5-dihydro-1H-pyrrole-1-carboxylate (8.4 g, 35.7 mmol) was dissolved in 50 mL of EtOH and hydrogenated over 10% Pd/C (400 mg) for 24 hours. LCMS indicated complete consumption of starting material. The reaction was filtered and concentrated to provide the product (8.2 g, 34.6 mmol, 96.8% yield) as a light-yellow oil.

Step 3: Chiral Separation of tert-butyl 3-(1H-pyrazol-4-yl)pyrrolidine-1-carboxylate The chiral hydrogenation product was purified using SFC (ChromegaChiral CCS from ES Industries, 2.0×25 cm, 100% McOH with 0.25% isopropylamine over 5 min).

Enantiomer 1: Retention Time 1.6 Mins $^1$H NMR (400 MHz, DMSO-d$_6$) δ 12.62 (s, 1H), 7.50 (s, 2H), 3.61 (dd, J=10.2, 7.2 Hz, 1H), 3.39 (ddd, J=11.1, 8.1, 3.3 Hz, 1H), 3.25 (qd, J=11.1, 10.6, 7.4 Hz, 2H), 3.07 (t, J=9.4 Hz, 1H), 2.14 (dtp, J=12.9, 6.3, 3.1 Hz, 1H), 1.91-1.75 (m, 1H), 1.40 (s, 9H). LRMS (ESI+) calcd for $C_{12}H_{20}N_3O_2^+$ [M+H$^+$] 238.1, found 238.2.

Enantiomer 2: Retention Time 3.6 Mins $^1$H NMR (400 MHz, DMSO-d$_6$) δ 12.62 (s, 1H), 7.50 (s, 2H), 3.61 (dd, J=10.2, 7.2 Hz, 1H), 3.39 (ddd, J=11.1, 8.1, 3.3 Hz, 1H), 3.32-3.15 (m, 2H), 3.07 (t, J=9.4 Hz, 1H), 2.13 (dtd, J=16.4, 9.3, 7.7, 4.9 Hz, 1H), 1.83 (ddt, J=13.2, 9.4, 6.1 Hz, 1H), 1.40 (s, 9H). LRMS (ESI+) calcd for $C_{12}H_{20}N_3O_2^+$ [M+H$^+$] 238.1, found 238.2.

Step 4: Synthesis of (S)-(4-(3-(1H-pyrazol-4-yl) pyrrolidin-1-yl)-5,6-dimethylpyrimidin-2-yl) (3-hydroxy-3-phenylazetidin-1-yl) methanone To a solution of Enantiomer 1 which was arbitrarily assigned to be tert-butyl (S)-3-(1H-pyrazol-4-yl)pyrrolidine-1-carboxylate (40 mg, 0.17 mmol, 2.8 equiv) in $CH_2Cl_2$ (1.0 mL) was added trifluoroacetic acid (0.1 mL). The mixture was stirred at this temperature for 30 min before volatile was removed in vacuo. The so-obtained crude (S)-4-(pyrrolidin-3-yl)-1H-pyrazole was transferred to a microwave vial charged with (4-chloro-5,6-dimethylpyrimidin-2-yl)(3-hydroxy-3-phenylazetidin-1-yl)methanone (20 mg, 0.06 mmol, 1.0 equiv, synthesized via Synthetic Method 1, Step 1), diisopropylethylamine (31 mg, 0.24 mmol, 5.0 equiv), and i-PrOH/MeOH (1.5 mL, 2:1). The reaction was heated at 165° C. under microwave irradiation for 30 min. Upon completion, the crude content was directly concentrated and subjected to reverse-phase HPLC separation (formic acid in $H_2O$/formic acid in MeCN, 100% to 0%) to yield (S)-(4-(3-(1H-pyrazol-4-yl)pyrrolidin-1-yl)-5,6-dimethylpyrimidin-2-yl)(3-hydroxy-3-phenylazetidin-1-yl) methanone (Compound 9-13 mg, 32%) as a colorless foam. $^1$H NMR (400 MHz, Methanol-d$_4$) δ 7.63-7.53 (m, 4H), 7.41 (t, J=7.6 Hz, 2H), 7.32 (t, J=7.4 Hz, 1H), 4.49 (d, J=11.1 Hz, 1H), 4.35 (d, J=11.1 Hz, 1H), 4.08 (t, J=8.6 Hz, 1H), 3.86 (s, 2H), 3.70 (t, J=9.6 Hz, 1H), 3.44 (t, J=8.0 Hz, 2H), 3.37 (s, 2H), 2.46 (s, 3H), 2.36 (s, 3H), 2.03 (p, J=10.9, 10.1 Hz, 1H). LRMS (APCI+) calcd for $C_{23}H_{27}N_6O_2^+$[M+H$^+$] 419.2, found 419.1.

Example 7

Representative example: Preparation of (R)-4-((2-(1H-pyrazol-4-yl)ethyl)amino)-5-chloro-N-(1-(6-fluoropyridin-2-yl)ethyl)-6-methylpyrimidine-2-carboxamide

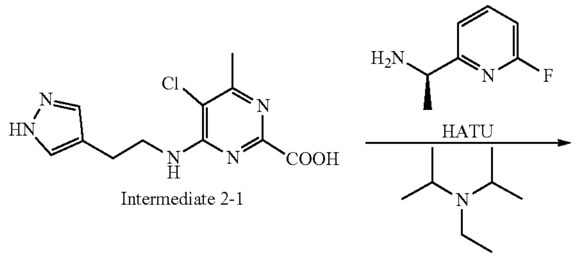

Intermediate 2-1

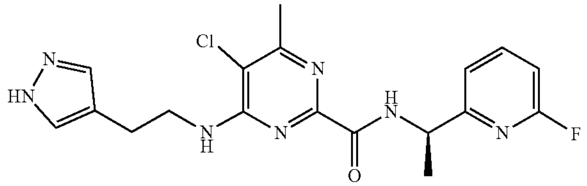

Compound 147

To a solution of 4-((2-(1H-pyrazol-4-yl)ethyl)amino)-5-chloro-6-methylpyrimidine-2-carboxylic acid (Intermediate 2-1, 28 mg, 0.100 mmol, 1.0 equiv), (R)-1-(6-fluoropyridin-2-yl)ethan-1-amine HCl salt (28 mg, 0.12 mmol, 1.2 equiv), and hexafluorophosphate azabeuzotriazoie tetramethyl uronium (HATU, 57 mg, 0.15 mmol, 1.5 equiv) in DMF (1 mL) was added diisopropylethylamine (DIPEA, 0.053 mL, 0.3 mmol, 5.0 equiv) dropwise at 23° C. The resulting solution was stirred at this temperature for 30 min. LC-MS showed complete conversion. EtOAc (3 mL) and water (3 mL) were added. The organic phase was washed by half-saturated brine, dried ($MgSO_4$), filtered, and concentrated. The residue was subjected to reverse-phase HPLC separation (20% to 100% MeCN in water with 0.1% HCOOH over 40 min) to yield (R)-4-((2-(1H-pyrazol-4-yl)ethyl)amino)-5-chloro-N-(1-(6-fluoropyridin-2-yl)ethyl)-6-methylpyrimidine-2-carboxamide (Compound 147-40 mg, yield 74%) as an off-white solid. $^1$H NMR (400 MHz, Methanol-$d_4$) δ 7.93 (q, J=7.9 Hz, 1H), 7.52 (s, 2H), 7.36 (dd, J=7.5, 2.2 Hz, 1H), 6.98 (dd, J=8.1, 2.4 Hz, 1H), 5.24 (q, J=6.8 Hz, 1H), 3.82 (t, J=7.2 Hz, 2H), 2.88 (t, J=7.2 Hz, 2H), 2.49 (s, 3H), 1.59 (d, J=6.8 Hz, 3H).

The following compounds were prepared according to the procedures described above using the carboxylic acid and amine reagent described in the table below.

| Compound No. | Carboxylic Acid | Amine | Structure, Name, and Data |
|---|---|---|---|
| 147 | 4-((2-(1H-pyrazol-4-yl)ethyl)amino)-5-chloro-6-methylpyrimidine-2-carboxylic acid (Intermediate 2-1) | (R)-1-(6-fluoropyridin-2-yl)ethan-1-amine | 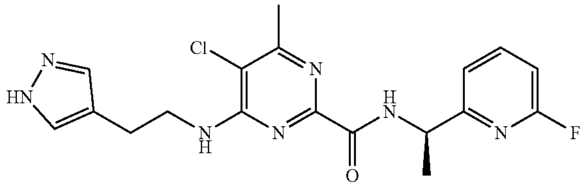 (R)-4-((2-(1H-pyrazol-4-yl)ethyl)amino)-5-chloro-N-(1-(6-fluoropyridin-2-yl)ethyl)-6-methylpyrimidine-2-carboxamide LRMS (APCI+) m/z 404.1 (M + H). $^1$H NMR (400 MHz, Methanol-$d_4$) δ 7.93 (q, J = 7.9 Hz, 1H), 7.52 (s, 2H), 7.36 (dd, J = 7.5, 2.2 Hz, 1H), 6.98 (dd, J = 8.1, 2.4 Hz, 1H), 5.24 (q, J = 6.8 Hz, 1H), 3.82 (t, J = 7.2 Hz, 2H), 2.88 (t, J = 7.2 Hz, 2H), 2.49 (s, 3H), 1.59 (d, J = 6.8 Hz, 3H). |
| 148 | 4-((2-(1H-pyrazol-4-yl)ethyl)amino)-5-chloro-6-methylpyrimidine-2-carboxylic acid (Intermediate 2-1) | (R)-2-(3-fluorophenyl)pyrrolidine | 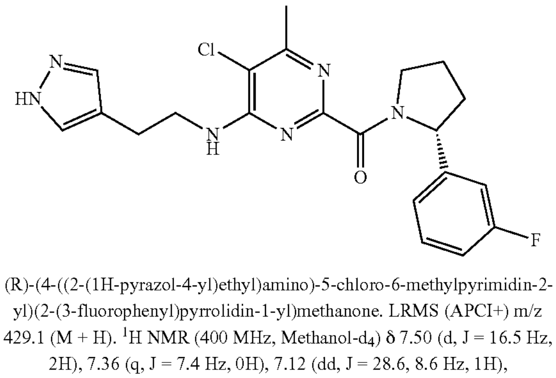 (R)-(4-((2-(1H-pyrazol-4-yl)ethyl)amino)-5-chloro-6-methylpyrimidin-2-yl)(2-(3-fluorophenyl)pyrrolidin-1-yl)methanone. LRMS (APCI+) m/z 429.1 (M + H). $^1$H NMR (400 MHz, Methanol-$d_4$) δ 7.50 (d, J = 16.5 Hz, 2H), 7.36 (q, J = 7.4 Hz, 0H), 7.12 (dd, J = 28.6, 8.6 Hz, 1H), 6.98 (t, J = 8.4 Hz, 0H), 6.87-6.71 (m, 2H), 5.14 (t, J = 6.5 Hz, 1H), 3.90 (ddt, J = 34.7, 12.9, 7.0 Hz, 1H), 3.77 (s, 1H), 3.63 (s, 0H), 3.42 (t, J = 7.3 Hz, 1H), 2.89 (t, J = 7.2 Hz, 1H), 2.68 (t, J = 7.2 Hz, 1H), 2.52-2.40 (m, 2H), 2.31 (s, 2H), 2.13-1.99 (m, 1H), 1.99 (s, 2H), 1.95 (t, J = 6.3 Hz, 0H). |

-continued

| Compound No. | Carboxylic Acid | Amine | Structure, Name, and Data |
|---|---|---|---|
| 149 | 4-((2-(1H-pyrazol-4-yl)ethyl)amino)-5-fluoro-6-methylpyrimidine-2-carboxylic acid (Intermediate 2-2) | (R)-1-(6-fluoropyridin-2-yl)ethan-1-amine | 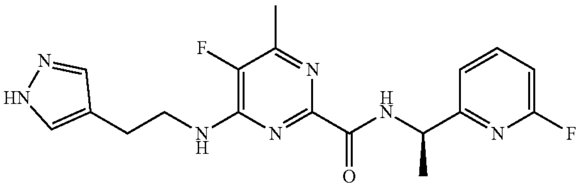<br>(R)-(4-((2-(1H-pyrazol-4-yl)ethyl)amino)-5-fluoro-N-(1-(6-fluoropyridin-2-yl)ethyl)-6-methylpyrimidine-2-carboxamide LRMS (APCI+) m/z 388.1 (M + H). $^1$H NMR (400 MHz, Methanol-$d_4$) δ 7.94 (q, J = 7.9 Hz, 1H), 7.54 (s, 2H), 7.37 (dd, J = 7.4, 2.2 Hz, 1H), 6.99 (dd, J = 8.2, 2.4 Hz, 1H), 5.23 (q, J = 6.8 Hz, 1H), 3.81 (t, J = 7.2 Hz, 2H), 2.89 (t, J = 7.2 Hz, 2H), 2.39 (d, J = 2.7 Hz, 3H), 2.17 (s, 1H), 1.59 (d, J = 6.7 Hz, 3H). |
| 150 | 4-((2-(1H-pyrazol-4-yl)ethyl)amino)-5-fluoro-6-methylpyrimidine-2-carboxylic acid (Intermediate 2-2) | (R)-2-(3-fluorophenyl)pyrrolidine | 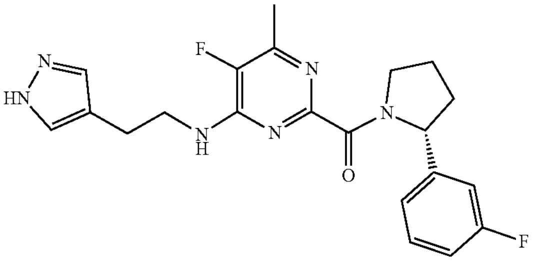<br>(R)-(4-((2-(1H-pyrazol-4-yl)ethyl)amino)-5-fluoro-6-methylpyrimidin-2-yl) (2-(3-fluorophenyl)pyrrolidin-1-yl)methanone. LRMS (APCI+) m/z 413.1 (M + H). $^1$H NMR (400 MHz, Methanol-$d_4$) δ 7.49 (d, J = 17.5 Hz, 2H), 7.36 (q, J = 7.3 Hz, 0H), 7.17 (d, J = 6.8 Hz, 1H), 6.79 (dt, J = 21.0, 10.6 Hz, 2H), 5.27 (s, 0H), 5.14 (t, J = 6.6 Hz, 1H), 3.90 (ddt, J = 25.3, 12.2, 6.2 Hz, 1H), 3.73 (s, 2H), 3.59 (s, 1H), 3.44-3.29 (m, 2H), 2.88 (t, J = 7.2 Hz, 1H), 2.68 (t, J = 7.5 Hz, 1H), 2.47 (dq, J = 13.9, 7.2 Hz, 1H), 2.37 (s, 1H), 2.22-2.15 (m, 2H), 2.05 (s, 1H), 1.97 (dd, J = 17.5, 9.1 Hz, 1H). |

Biological Example 1

NMN Fluorescence Biochemical and NAD Cellular Assay

A. Human Recombinant Enzyme Assay

Compounds described herein were assayed for their ability to stimulate the synthesis of nicotinamide mononucleotide (NMN) by the enzyme NAMPT. The human recombinant enzyme assay measures the activation of the enzyme activity by compounds using recombinant enzyme and substrates in a buffered cell-free system. The assay conditions closely mimic cellular environments. Dose responses were measured using an assay to detect the formation of nicotinamide mono-nucleotide. All experiments were performed in the 384-well format. Generally, 0.5 μL of DMSO containing varying concentrations of the test compound was mixed with 10 μL of the enzyme reagent solution. Enzyme reactions were initiated with the addition of 10 μL of a solution containing the substrates. The final assay conditions were as follows: 6 nM human NAMPT, 2.5 mM ATP, 2011M PRPP and 15011M nicotinamide in 50 mM HEPES, pH 7.2, 1 mM DTT, 1 mM CHAPS 50 mM NaCl, 100 mM $MgCl_2$. Following an incubation of 60 min at ambient temperature, 10 μL of 20% acetophenone in DMSO was added, followed by 10 μL of 2 M KOH and 40 μL of formic acid. The plates were read for fluorescence (Excitation/Emission=355 nm/460 nm) using an EnVision plate reader after 40 mins of incubation at ambient temperature. The potency measurements for compounds, are quantified and represented as $AC_{1.4}$ (the concentration of compounds that generates 40% higher activity over basal) and $EC_{50}$ (concentration of the compound that gives half-maximal activation). Table A shows the $AC_{1.4}$ and $EC_{50}$ data and for the tested compounds.

TABLE A

| Compound No. | $AC_{1.4}$ Human (μM) | $EC_{50}$ Human (μM) |
|---|---|---|
| 1 | 0.003 | 0.131 |
| 2 | 0.007 | 0.1555 |
| 3 | 0.0165 | 0.653 |
| 4 | 0.02 | 0.1055 |
| 5 | 0.0235 | 0.449 |
| 6 | 0.0385 | 1.839 |
| 7 | 0.029 | 0.3255 |
| 8 | 0.0325 | 0.1825 |
| 9 | 0.044 | 0.633 |
| 10 | 0.046 | 0.52 |
| 11 | 0.0465 | 0.282 |
| 12 | 0.048 | 0.5145 |
| 13 | 0.035 | 3.7435 |

TABLE A-continued

| Compound No. | $AC_{1.4}$ Human (μM) | $EC_{50}$ Human (μM) |
|---|---|---|
| 14 | 0.054 | 0.156 |
| 15 | 0.051 | 0.39 |
| 16 | 0.0585 | 0.621 |
| 17 | 0.0715 | 0.549 |
| 18 | 0.0745 | 0.597 |
| 19 | 0.075 | 0.4995 |
| 20 | 0.062 | 0.848 |
| 21 | 0.0815 | 0.5505 |
| 22 | 1.956 | 12.761 |
| 23 | 0.0955 | 3.2415 |
| 24 | 0.0955 | 0.77 |
| 25 | 0.106 | 0.8715 |
| 26 | 0.1215 | 0.429 |
| 27 | 0.1305 | 1.6305 |
| 28 | 0.144 | 1.356 |
| 29 | 0.1725 | 1.8735 |
| 30 | 0.1725 | 0.741 |
| 31 | 0.192 | 1.6095 |
| 32 | 0.193 | 0.929 |
| 33 | 0.2615 | 1.3775 |
| 34 | 2.839 | 17.651 |
| 35 | 0.231 | 0.617 |
| 36 | 0.2015 | 0.8815 |
| 37 | 0.2055 | 1.192 |
| 38 | 0.1635 | 3.8305 |
| 39 | 0.21 | 1.512 |
| 40 | 0.214 | 1.266 |
| 41 | 0.2615 | 2.871 |
| 42 | 0.265 | 2.9235 |
| 43 | 0.273 | 0.827 |
| 44 | 0.275 | 1.8355 |
| 45 | 0.277 | 3.5165 |
| 46 | 0.2845 | 2.3535 |
| 47 | 0.2915 | 1.9985 |
| 48 | 0.2925 | 6.835 |
| 49 | 0.3055 | 2.1035 |
| 50 | 0.311 | 2.079 |
| 51 | 0.327 | 1.876 |
| 52 | 0.3305 | 1.7765 |
| 53 | 0.3335 | 2.604 |
| 54 | 0.35 | 2.371 |
| 55 | 0.375 | 4.678 |
| 56 | 0.439 | 1.374 |
| 57 | 0.396 | 2.8765 |
| 58 | 0.406 | 0.788 |
| 59 | 0.4045 | 3.0805 |
| 60 | 0.4085 | 3.7485 |
| 61 | 0.409 | 2.113 |
| 62 | 0.4295 | 3.2105 |
| 63 | 0.4315 | 2.285 |
| 64 | 0.458 | 2.1605 |
| 65 | 0.4805 | 1.686 |
| 66 | 4.5565 | 16.307 |
| 67 | 0.505 | 3.8615 |
| 68 | 0.563 | 1.644 |
| 69 | 0.5395 | 4.181 |
| 70 | 0.5795 | 3.1245 |
| 71 | 0.5835 | 6.0665 |
| 72 | 0.625 | 3.527 |
| 73 | 0.6455 | 3.2365 |
| 74 | 0.715 | 8.007 |
| 75 | 0.7725 | 2.625 |
| 76 | 0.773 | 6.8315 |
| 77 | 0.8835 | 13.73 |
| 78 | 0.81 | 5.623 |
| 79 | 0.8395 | 4.624 |
| 80 | 0.877 | 10.399 |
| 81 | 0.891 | 5.9785 |
| 82 | 0.966 | 3.9925 |
| 83 | 0.9695 | 14.4735 |
| 84 | 31.857 | 40.186 |
| 85 | 1.072 | 8.3455 |
| 86 | 1.1115 | 8.0415 |
| 87 | 1.1375 | 13.342 |
| 88 | 1.1435 | 7.2145 |
| 89 | 4.9195 | 37.3495 |
| 90 | 1.17 | 9.2395 |
| 91 | 0.9345 | 7.7595 |
| 92 | 1.1995 | 5.678 |
| 93 | 1.244 | 14.898 |
| 94 | 1.271 | 8.133 |
| 95 | 1.2975 | 10.97 |
| 96 | 1.3075 | 8.5145 |
| 97 | 6.337 | 22.291 |
| 98 | 1.3275 | 5.1525 |
| 99 | 1.5915 | 19.97 |
| 100 | 6.3085 | 40.2145 |
| 101 | 1.519 | 4.092 |
| 102 | 2.0105 | 12.9455 |
| 103 | 1.6375 | 21.4845 |
| 104 | 1.6495 | 11.3035 |
| 105 | 1.669 | 2.5205 |
| 106 | 1.7115 | 32.734 |
| 107 | 2.339 | 13.991 |
| 108 | 1.7855 | 18.0665 |
| 109 | 1.933 | 11.211 |
| 110 | 1.9815 | 16.177 |
| 111 | 1.9995 | 18.489 |
| 112 | 2.084 | 2.966 |
| 113 | 2.084 | 18.2565 |
| 114 | 2.1125 | 23.0915 |
| 115 | 2.136 | 10.7 |
| 116 | 2.9705 | 29.602 |
| 117 | 2.2385 | 47.5795 |
| 118 | 2.384 | 11.754 |
| 119 | 32.854 | 47.194 |
| 120 | 2.443 | 15.159 |
| 121 | 2.5075 | 22.0545 |
| 122 | 2.574 | 16.724 |
| 123 | 2.581 | 26.389 |
| 124 | 2.6905 | 11.974 |
| 125 | 4.313 | 22.028 |
| 126 | 3.1455 | 13.4295 |
| 127 | 32.9385 | 60.0485 |
| 128 | 3.235 | 28.029 |
| 129 | 3.249 | 21.3385 |
| 130 | 3.2975 | 41.0095 |
| 131 | 3.487 | 10.7915 |
| 132 | 3.5055 | 13.1015 |
| 133 | 3.5315 | 28.907 |
| 134 | 3.578 | 26.1965 |
| 135 | 3.7335 | 17.4745 |
| 136 | 3.778 | 50.1845 |
| 137 | 3.794 | 34.501 |
| 138 | 4.125 | 30.698 |
| 139 | 3.809 | 28.545 |
| 140 | 4.0885 | 18.379 |
| 141 | 3.8305 | 20.3335 |
| 142 | 4.3845 | 31.7825 |
| 143 | 4.433 | 45.983 |
| 144 | 4.755 | 18.431 |
| 145 | 4.9555 | 22.4285 |
| 146 | 2.7 | n.d. |
| 147 | <0.003 | n.d. |
| 148 | >31 | n.d. |
| 149 | 0.02 | n.d. |
| 150 | 0.12 | n.d. |
| 152 | 12.6 | n.d. |

n.d. = not determined

B. Cellular NAD+ Modulation Assay.

The compounds described herein were also assayed for their ability to stimulate the endogenous NAMPT in a native cellular environment in the cellular NAD+ modulation assay, which measures the ability of the compound to modulate cellular NAD levels. Increased levels of NAD are expected by compounds that permeate the cells and activate the catalytic activity of the endogenous NAMPT.

Neuroblastoma SH-SY5Y cells were grown in 1:1 mixture of Eagle's Minimum Essential Medium and F12

Medium, along with 10% fetal bovine serum, in a humidified incubator with an atmosphere of 95% air and 5% $CO_2$ at 37° C. The assays were initiated by plating 20 µL of SH-SY5Y cells in culture medium with 0.1% fetal bovine serum, at a density of 5000 cells per well to a 384-well Corning™ BioCoat™ Poly-D-Lysine Multiwell Plates. The plates were incubated in the 37° C. incubators for a period of 5 hours. Compounds in DMSO were added to the plates in a volume of 120 nL using the Labcyte Echo Liquid Handlers. 5 µL of a 1.5 uM Doxorubicin solution in assay medium is added to each well. The plates are then incubated for 40 hours. 30 µL of a readout-solution containing 0.2 U/mL Diaphorase enzyme, 40 uM resazurin, 10 uM FMN, 0.8 U/mL Alcohol dehydrogenase, 3% ethanol, 0.4 mg/mL bovine serum albumin, 0.2% Triton X-100 in 100 mM Tris-HCl, 30 mM EDTA, pH 8.4. The plates were read for fluorescence (Excitation/Emission=540 nm/590 nm) using an EnVision plate reader after 60 mins of incubation at ambient temperature. Table B shows the $AC_{0.3}$ and $EC_{50}$ data for the tested compounds.

TABLE B

| Compound No. | SY5Y (human) NAD Cell Dox $AC_{0.3}$ (µM) | SY5Y (human) NAD Cell Dox $EC_{50}$ (µM) |
|---|---|---|
| 4 | 0.07 | 0.11 |
| 5 | 2.68 | 1.76 |
| 7 | 0.19 | 0.19 |
| 10 | 0.2 | 0.47 |
| 13 | 0.24 | 0.23 |
| 14 | 0.28 | 0.48 |
| 15 | 0.26 | 0.19 |
| 16 | 0.41 | 0.33 |
| 17 | 0.24 | 0.44 |
| 20 | 2.97 | 8.79 |
| 21 | 0.13 | 0.28 |
| 22 | 7.15 | 8.84 |
| 23 | 1.57 | 3.25 |
| 24 | 2.49 | 2.26 |
| 26 | 0.26 | 0.72 |
| 27 | 0.28 | 0.74 |
| 30 | 0.88 | 1.60 |
| 147 | 0.02 | n.d. |
| 149 | 0.01 | n.d. |
| 151 | 0.17 | n.d. |

n.d. = not determined

What is claimed is:

1. A compound of formula (A):

(A)

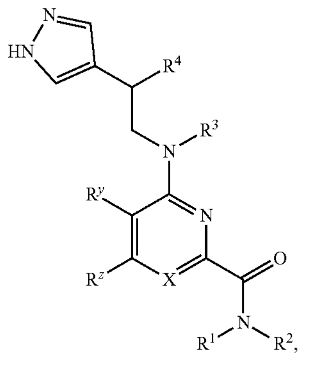

or a pharmaceutically acceptable salt thereof, wherein:

X is N or CH;

$R^1$ and $R^2$ are each independently H, optionally substituted $C_{1-6}$alkyl, optionally substituted $C_{3-10}$cycloalkyl, optionally substituted $C_{6-20}$aryl, optionally substituted 3-15 membered heterocyclyl, or optionally substituted 5-20 membered heteroaryl;

or $R^1$ and $R^2$ are taken together with the nitrogen to which they are attached to form an optionally substituted 3-15 membered heterocyclyl;

$R^3$ is H or optionally substituted $C_{1-6}$alkyl, and $R^4$ is H;

or $R^3$ and $R^4$ taken together are —$CH_2CH_2$—; and $R^y$ and $R^z$ are each independently H, halo, or optionally substituted $C_{1-6}$alkyl;

or $R^y$ and $R^z$ are taken together with the carbon atoms to which they are attached to form an optionally substituted non-aromatic cyclic ring containing 3 to 10 carbon atoms.

2. The compound of claim 1, or a pharmaceutically acceptable salt thereof, wherein X is N, such that the compound of formula (A) is a compound of formula (I):

(I)

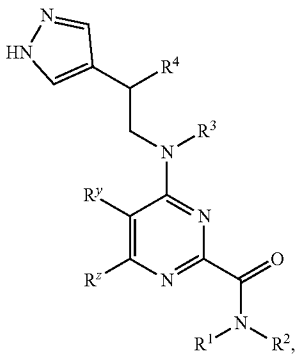

or a pharmaceutically acceptable salt thereof.

3. The compound of claim 1- or 2, or a pharmaceutically acceptable salt thereof, wherein the compound of formula (A) is a compound of formula (I):

(I)

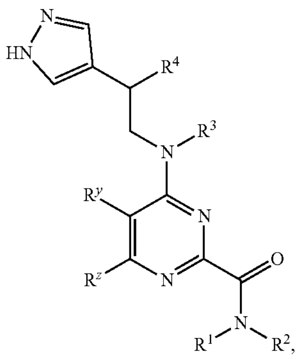

or a pharmaceutically acceptable salt thereof, wherein:

$R^1$ and $R^2$ are each independently H, optionally substituted $C_{1-6}$alkyl, optionally substituted $C_{3-10}$cycloalkyl, optionally substituted $C_{6-20}$aryl, optionally substituted 3-15 membered heterocyclyl, or optionally substituted 5-20 membered heteroaryl;

or $R^1$ and $R^2$ are taken together with the nitrogen to which they are attached to form an optionally substituted 3-15 membered heterocyclyl;

$R^3$ is H or optionally substituted $C_{1-6}$alkyl, and $R^4$ is H; or $R^3$ and $R^4$ taken together are —$CH_2CH_2$—; and $R^y$ and $R^z$ are each independently optionally substituted $C_{1-6}$alkyl.

4. The compound of claim 2, or a pharmaceutically acceptable salt thereof, wherein $R^3$ is H and $R^4$ is H, such that the compound of formula (I) is a compound of formula (I-A):

(I-A)

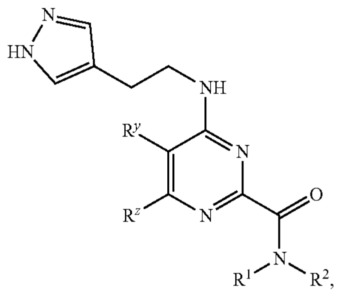

or a pharmaceutically acceptable salt thereof.

5. The compound of claim 4, or a pharmaceutically acceptable salt thereof, wherein $R^y$ is methyl and $R^z$ is methyl, such that the compound of formula (I-A) is a compound of formula (I-A1):

(I-A1)

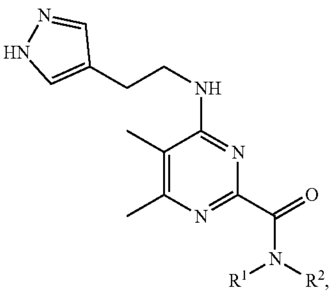

or a pharmaceutically acceptable salt thereof.

6. The compound of claim 4, or a pharmaceutically acceptable salt thereof, wherein $R^z$ is methyl, such that the compound of formula (I-A) is a compound of formula (I-A2):

(I-A2)

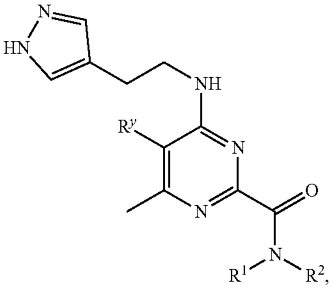

or a pharmaceutically acceptable salt thereof, wherein $R^y$ is halo.

7. The compound of claim 4, or a pharmaceutically acceptable salt thereof, having the formula (I-A3):

(I-A3)

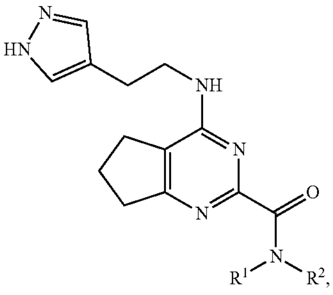

or a pharmaceutically acceptable salt thereof.

8. The compound of claim 2, or a pharmaceutically acceptable salt thereof, wherein $R^3$ and $R^4$ taken together are —$CH_2CH_2$—, such that the compound of formula (I) is a compound of formula (I-B):

(I-B)

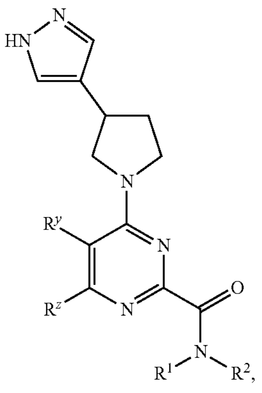

or a pharmaceutically acceptable salt thereof.

9. The compound of claim 8, or a pharmaceutically acceptable salt thereof, wherein $R^y$ is methyl and $R^z$ is methyl, such that the compound of formula (I-B) is a compound of formula (I-B1):

(I-B1)

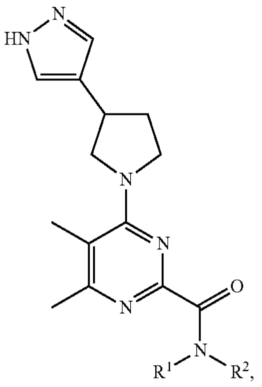

or a pharmaceutically acceptable salt thereof.

10. The compound of claim 1, or a pharmaceutically acceptable salt thereof, wherein X is CH, such that the compound of formula (A) is a compound of formula (II):

(II)

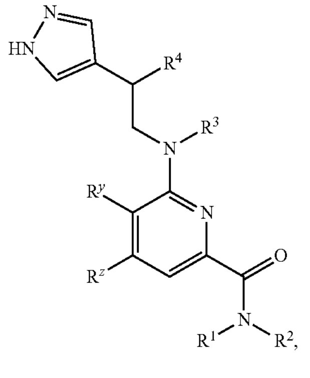

or a pharmaceutically acceptable salt thereof.

11. The compound of claim 10, or a pharmaceutically acceptable salt thereof, wherein $R^y$ is H, such that the compound of formula (II) is a compound of formula (II-A):

(II-A)

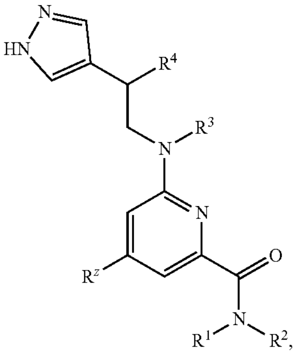

or a pharmaceutically acceptable salt thereof.

12. The compound of claim 1, or a pharmaceutically acceptable salt thereof, wherein $R^1$ and $R^2$ are each independently H, optionally substituted $C_{1-6}$alkyl, optionally substituted $C_{3-10}$cycloalkyl, optionally substituted $C_{6-20}$aryl, optionally substituted 3-15 membered heterocyclyl, or optionally substituted 5-20 membered heteroaryl.

13. The compound of claim 1, or a pharmaceutically acceptable salt thereof, wherein $R^1$ and $R^2$ are each independently H.

14. The compound of claim 1, or a pharmaceutically acceptable salt thereof, wherein one of $R^1$ and $R^2$ is H and the other of $R^1$ and $R^2$ is optionally substituted $C_{1-6}$alkyl.

15. The compound of claim 1, or a pharmaceutically acceptable salt thereof, wherein $R^1$ and $R^2$ are each independently optionally substituted $C_{1-6}$alkyl.

16. The compound of claim 14, or a pharmaceutically acceptable salt thereof, wherein the $C_{1-6}$alkyl of $R^1$ and $R^2$ are, independently of each other and independently at each occurrence, unsubstituted or are substituted with one or more $R^m$, wherein $R^m$ is, independently at each occurrence, —OH, halo, optionally substituted $C_{1-6}$alkoxy, optionally substituted sulfonyl, optionally substituted $C_{3-10}$cycloalkyl, optionally substituted 3-15 membered heterocyclyl, optionally substituted $C_{6-20}$aryl, or optionally substituted 5-20 membered heteroaryl.

17. The compound of claim 14, or a pharmaceutically acceptable salt thereof, wherein the $C_{1-6}$alkyl of $R^1$ and $R^2$ are, independently of each other and independently at each occurrence, unsubstituted or are substituted with one to five $R^m$, wherein each $R^m$ is, independently at each occurrence selected from the group consisting of: —OH, halo, $C_{1-6}$alkoxy, sulfonyl, $C_{3-10}$cycloalkyl, 3-15 membered heterocyclyl, $C_{6-10}$aryl, and 5-10 membered heteroaryl, wherein the $C_{1-6}$alkoxy, sulfonyl, $C_{3-10}$cycloalkyl, 3-15 membered heterocyclyl, $C_{6-10}$aryl, and 5-10 membered heteroaryl of $R^m$ are, independently at each occurrence, optionally substituted with 1 to 5 $R^n$, wherein $R^n$ is, independently at each occurrence, halo, —OH, $C_{1-6}$alkyl, $C_{1-6}$alkoxy, —C(O)—$C_{6-10}$aryl, —$C_{1-6}$alkyl-$C_{6-10}$aryl, or $C_{6-10}$aryl, wherein the $C_{6-10}$aryl of $R^n$ is, independently at each occurrence, optionally substituted with one or more halo.

18. The compound of claim 1, or a pharmaceutically acceptable salt thereof, wherein one of $R^1$ and $R^2$ is H and the other of $R^1$ and $R^2$ is optionally substituted $C_{3-10}$cycloalkyl.

19. The compound of claim 18, or a pharmaceutically acceptable salt thereof, wherein the $C_{3-10}$cycloalkyl of $R^1$ or $R^2$ is unsubstituted or is substituted with one or more halo or $C_{6-20}$aryl.

20. The compound of claim 1, or a pharmaceutically acceptable salt thereof, wherein one of $R^1$ and $R^2$ is H and the other of $R^1$ and $R^2$ is optionally substituted $C_{6-20}$aryl.

21. The compound of claim 20, or a pharmaceutically acceptable salt thereof, wherein the $C_{6-20}$aryl of $R^1$ or $R^2$ is unsubstituted or is substituted with one or more halo or $C_{1-6}$alkyl.

22. The compound of claim 1, or a pharmaceutically acceptable salt thereof, wherein one of $R^1$ and $R^2$ is H and the other of $R^1$ and $R^2$ is optionally substituted 5-20 membered heteroaryl.

23. The compound of claim 22, or a pharmaceutically acceptable salt thereof, wherein the 5-20 membered heteroaryl of $R^1$ or $R^2$ is unsubstituted or is substituted with one or more halo.

24. The compound of claim 1, or a pharmaceutically acceptable salt thereof, wherein $R^1$ and $R^2$ are taken together with the nitrogen to which they are attached to form an optionally substituted 3-15 membered heterocyclyl.

25. The compound of claim 24, or a pharmaceutically acceptable salt thereof, wherein the optionally substituted 3-15 membered heterocyclyl is an optionally substituted azetidinyl, an optionally substituted pyrrolidinyl, an optionally substituted piperidinyl, an optionally substituted piperazinyl, an optionally substituted morpholinyl, an optionally substituted spiro[azetidine-3,3'-indolin]-2'-on-yl, or an optionally substituted 2-azaspiro[3.3]heptanyl.

26. The compound of claim 24, or a pharmaceutically acceptable salt thereof, wherein the 3-15 membered heterocyclyl formed by $R^1$ and $R^2$ is unsubstituted or is substituted with one or more $R^s$, wherein $R^s$ is, independently at each occurrence, halo, —OH, —CN, oxo, optionally substituted $C_{1-6}$alkyl, optionally substituted $C_{1-6}$alkoxy, optionally substituted $C_{3-10}$cycloalkyl, optionally substituted 3-15 membered heterocyclyl, optionally substituted $C_{6-20}$aryl, or optionally substituted 5-20 membered heteroaryl.

27. The compound of claim 24, or a pharmaceutically acceptable salt thereof, wherein the 3-15 membered heterocyclyl formed by $R^1$ and $R^2$ is unsubstituted or is substituted with one or more $R^s$, wherein $R^s$ is, independently at each occurrence, halo, —OH, —CN, oxo, $C_{1-6}$alkyl, $C_{1-6}$alkoxy, $C_{3-10}$cycloalkyl, 3-15 membered heterocyclyl, $C_{6-10}$aryl, or 5-10 membered heteroaryl wherein the $C_{1-6}$alkyl, $C_{1-6}$alkoxy, $C_{3-10}$cycloalkyl, 3-15 membered heterocyclyl, $C_{6-10}$aryl, and 5-10 membered heteroaryl of $R^s$ are, independently at each occurrence, optionally substituted with one or more halo, —OH, $C_{1-6}$alkyl, or $C_{6-10}$aryl.

28. A compound selected from the group consisting of:
| No. | Structure |
|---|---|
| 1 | 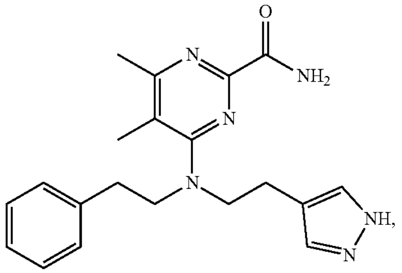 [SMILES: Cc1nc(C(N)=O)nc(N(CCc2ccccc2)CCc2cn[nH]c2)c1C] |
| 2 | 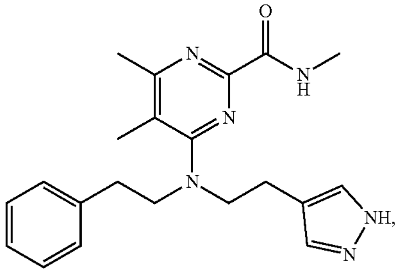 [SMILES: CNC(=O)c1nc(C)c(C)c(N(CCc2ccccc2)CCc2cn[nH]c2)n1] |
| 3 | 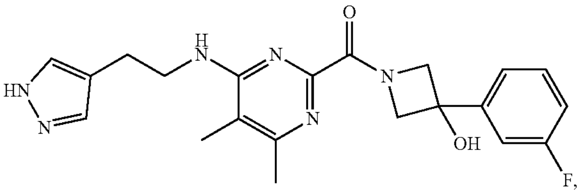 [SMILES: Cc1nc(C(=O)N2CC(O)(c3cccc(F)c3)C2)nc(NCCc2cn[nH]c2)c1C] |
| 4 | 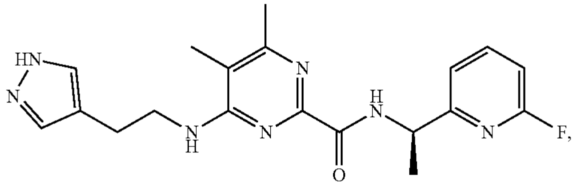 [SMILES: Cc1nc(C(=O)N[C@H](C)c2cccc(F)n2)nc(NCCc2cn[nH]c2)c1C] |
| 5 | 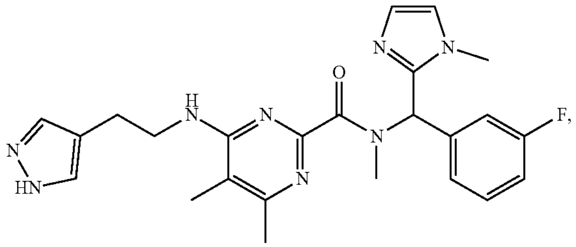 [SMILES: Cc1nc(C(=O)N(C)C(c2cccc(F)c2)c2nccn2C)nc(NCCc2cn[nH]c2)c1C] |

-continued
| No. | Structure |
|---|---|
| 6 | 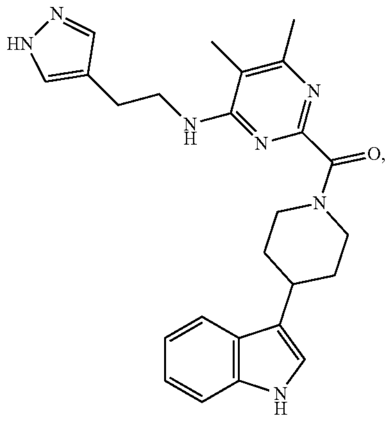 [SMILES: Cc1nc(C(=O)N2CCC(c3c[nH]c4ccccc34)CC2)nc(NCCc2cn[nH]c2)c1C] |
| 7 | 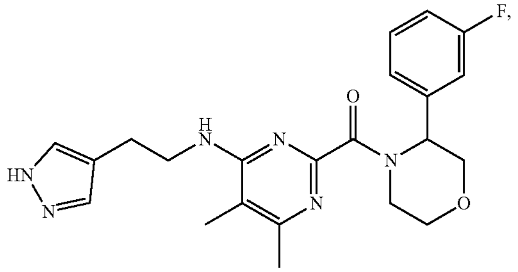 |
| 8 | 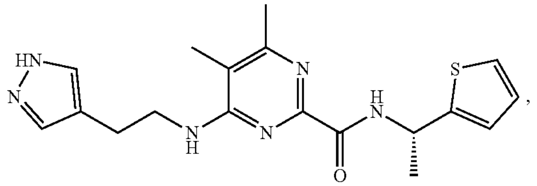 [SMILES: Cc1nc(C(=O)N[C@@H](C)c2cccs2)nc(NCCc2cn[nH]c2)c1C] |
| 9 | 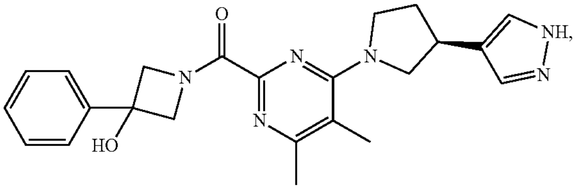 [SMILES: Cc1nc(C(=O)N2CC(O)(c3ccccc3)C2)nc(N2CC[C@@H](c3cn[nH]c3)C2)c1C] |
| 10 | 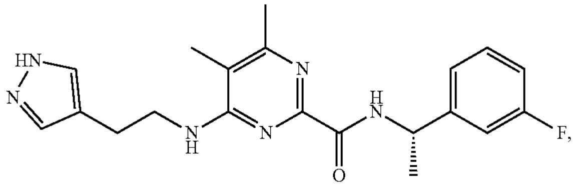 [SMILES: Cc1nc(C(=O)N[C@@H](C)c2cccc(F)c2)nc(NCCc2cn[nH]c2)c1C] |
| 11 | 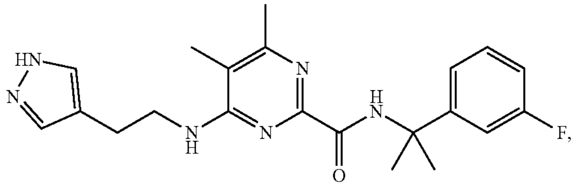 [SMILES: Cc1nc(C(=O)NC(C)(C)c2cccc(F)c2)nc(NCCc2cn[nH]c2)c1C] |

-continued
| No. | Structure |
|---|---|
| 12 | 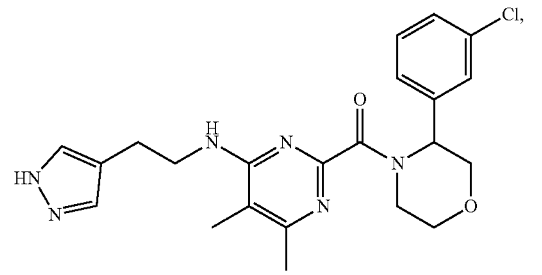 [SMILES: Cc1nc(C(=O)N2CCOCC2c2cccc(Cl)c2)nc(NCCc2cn[nH]c2)c1C] |
| 13 | 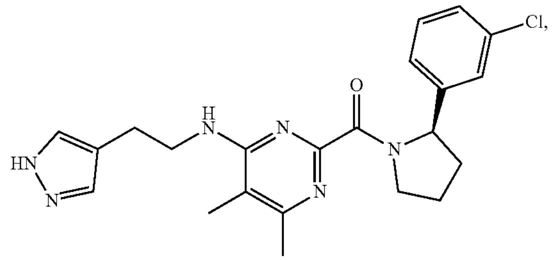 [SMILES: Cc1nc(C(=O)N2CCC[C@@H]2c2cccc(Cl)c2)nc(NCCc2cn[nH]c2)c1C] |
| 14 | 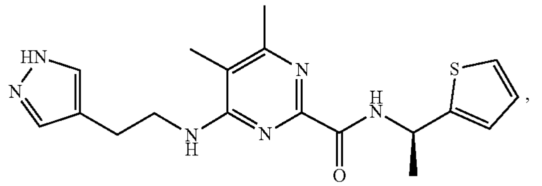 [SMILES: Cc1nc(C(=O)N[C@H](C)c2cccs2)nc(NCCc2cn[nH]c2)c1C] |
| 15 | 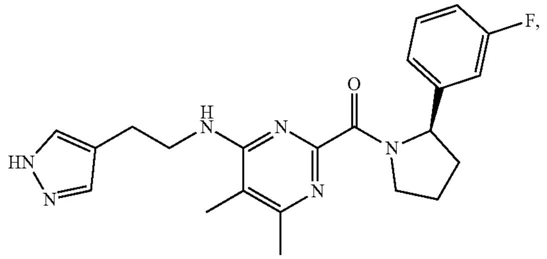 |
| 16 | 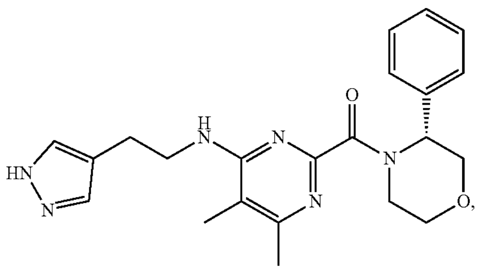 [SMILES: Cc1nc(C(=O)N2CCOC[C@H]2c2ccccc2)nc(NCCc2cn[nH]c2)c1C] |
| 17 | 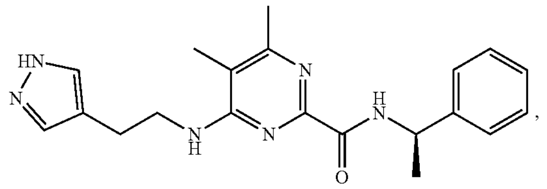 |

-continued
| No. | Structure |
| --- | --- |
| 18 | 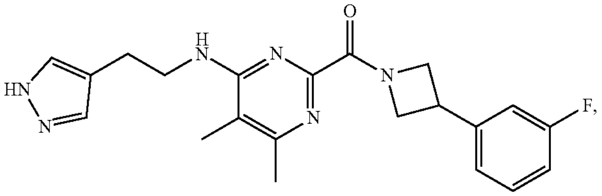 [SMILES: Cc1nc(C(=O)N2CC(c3cccc(F)c3)C2)nc(NCCc2cn[nH]c2)c1C] |
| 19 | 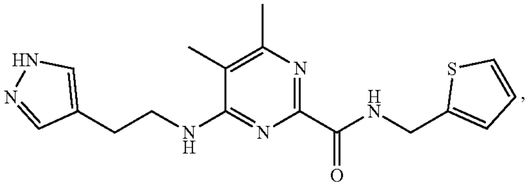 [SMILES: Cc1nc(C(=O)NCc2cccs2)nc(NCCc2cn[nH]c2)c1C] |
| 20 | 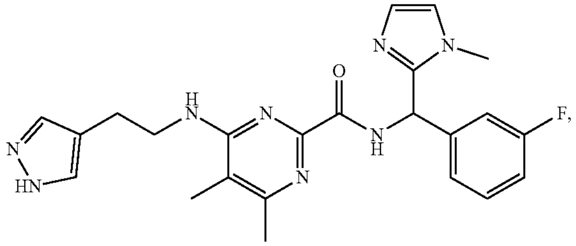 |
| 21 | 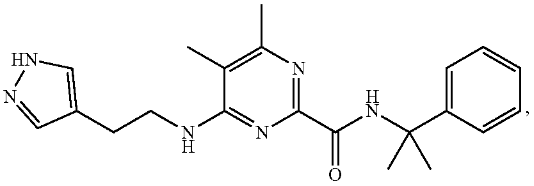 |
| 22 | 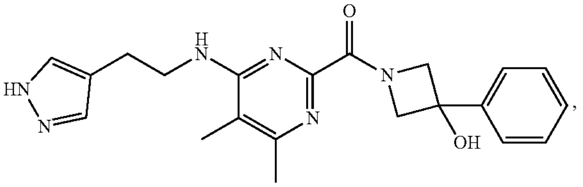 [SMILES: Cc1nc(C(=O)N2CC(O)(c3ccccc3)C2)nc(NCCc2cn[nH]c2)c1C] |
| 23 | 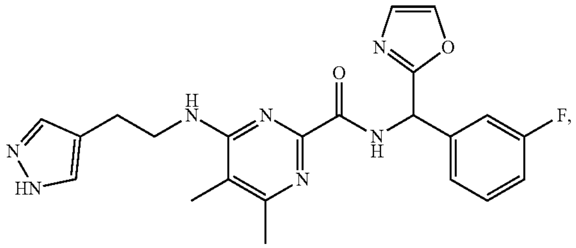 [SMILES: Cc1nc(C(=O)NC(c2cccc(F)c2)c2ncco2)nc(NCCc2cn[nH]c2)c1C] |
| 24 | 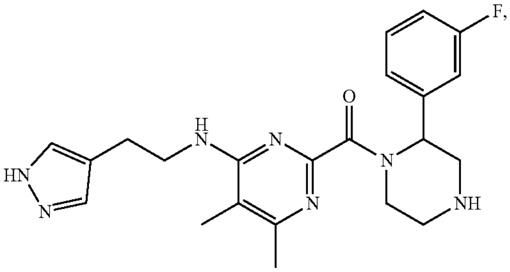 |

-continued
| No. | Structure |
| --- | --- |
| 25 | 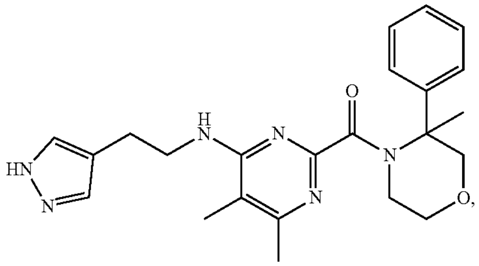 [SMILES: Cc1nc(C(=O)N2CCOCC2(C)c2ccccc2)nc(NCCc2cn[nH]c2)c1C] |
| 26 | 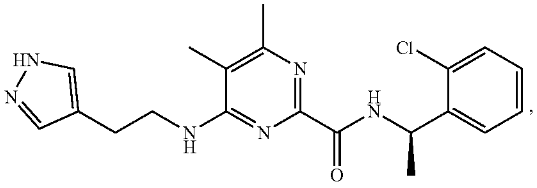 |
| 27 | 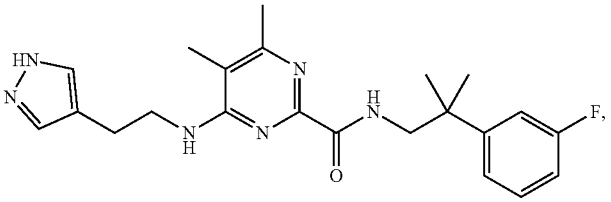 [SMILES: Cc1nc(C(=O)NCC(C)(C)c2cccc(F)c2)nc(NCCc2cn[nH]c2)c1C] |
| 28 | 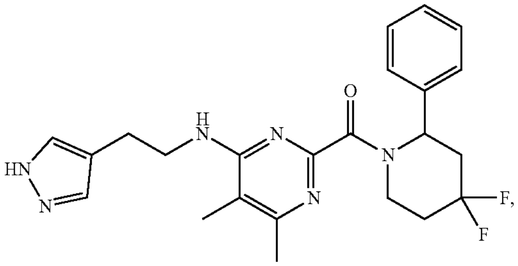 [SMILES: Cc1nc(C(=O)N2CCC(F)(F)CC2c2ccccc2)nc(NCCc2cn[nH]c2)c1C] |
| 29 | 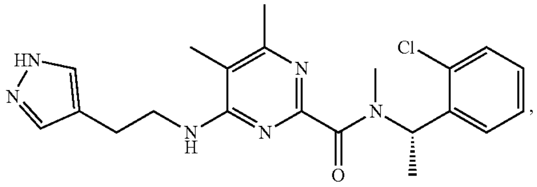 [SMILES: Cc1nc(C(=O)N(C)[C@@H](C)c2ccccc2Cl)nc(NCCc2cn[nH]c2)c1C] |
| 30 | 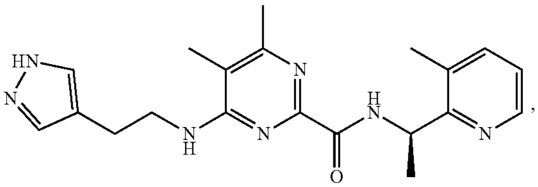 [SMILES: Cc1cccnc1[C@@H](C)NC(=O)c1nc(C)c(C)c(NCCc2cn[nH]c2)n1] |
| 31 | 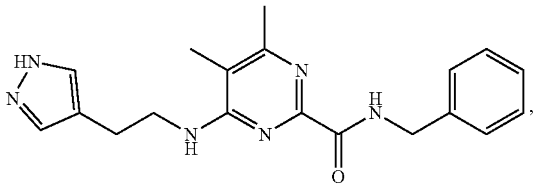 |

-continued
| No. | Structure |
|---|---|
| 32 | 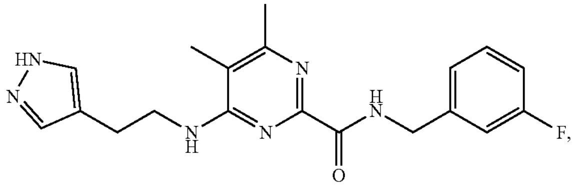 F, |
| 33 | 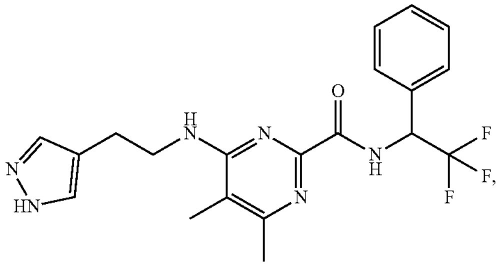 F, |
| 34 | 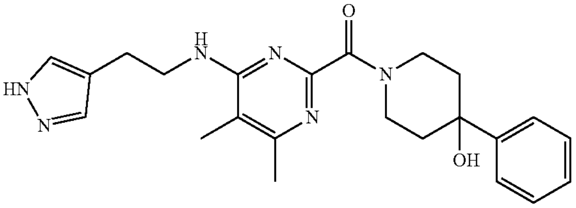 , |
| 35 | 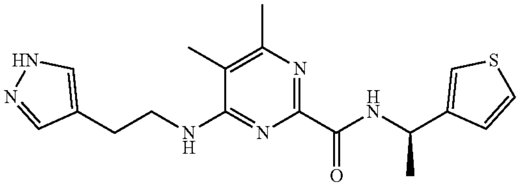 , |
| 36 | 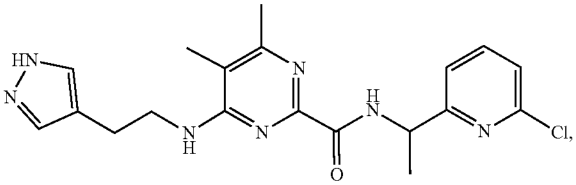 Cl, |
| 37 | 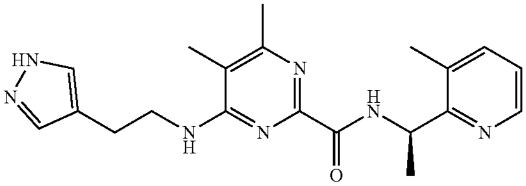 , |
| 38 | 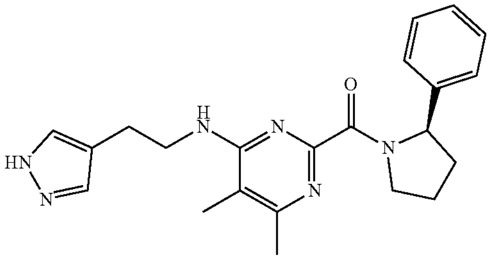 , |

-continued
| No. | Structure |
|---|---|
| 39 | 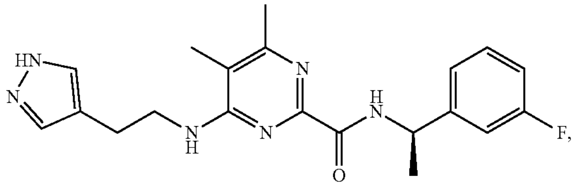 [SMILES: Cc1nc(C(=O)N[C@H](C)c2cccc(F)c2)nc(NCCc2cn[nH]c2)c1C] |
| 40 | 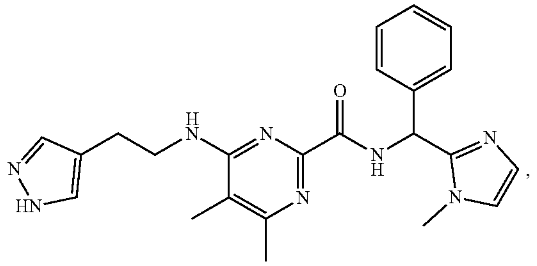 [SMILES: Cc1nc(C(=O)NC(c2ccccc2)c2nccn2C)nc(NCCc2cn[nH]c2)c1C] |
| 41 | 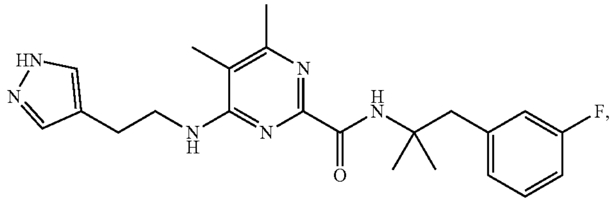 [SMILES: Cc1nc(C(=O)NC(C)(C)Cc2cccc(F)c2)nc(NCCc2cn[nH]c2)c1C] |
| 42 | 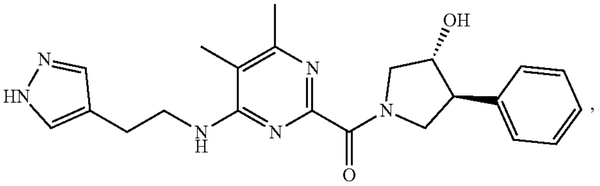 [SMILES: Cc1nc(C(=O)N2C[C@H](c3ccccc3)[C@@H](O)C2)nc(NCCc2cn[nH]c2)c1C] |
| 43 | 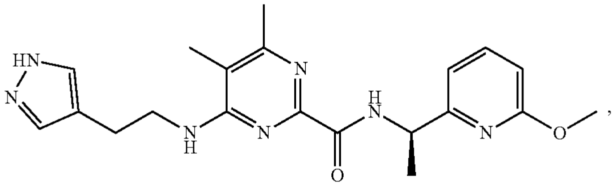 [SMILES: COc1cccc([C@@H](C)NC(=O)c2nc(C)c(C)c(NCCc3cn[nH]c3)n2)n1] |
| 44 | 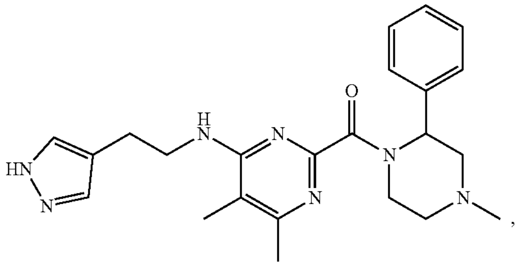 [SMILES: Cc1nc(C(=O)N2CCN(C)CC2c2ccccc2)nc(NCCc2cn[nH]c2)c1C] |
| 45 | 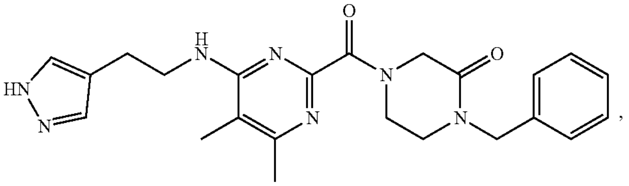 [SMILES: Cc1nc(C(=O)N2CCN(Cc3ccccc3)C(=O)C2)nc(NCCc2cn[nH]c2)c1C] |

-continued
| No. | Structure |
| --- | --- |
| 46 | 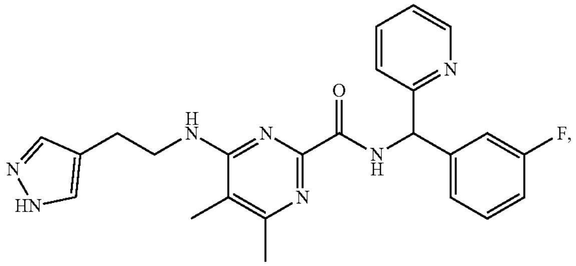 [SMILES: Cc1nc(C(=O)NC(c2cccc(F)c2)c2ccccn2)nc(NCCc2cn[nH]c2)c1C] |
| 47 | 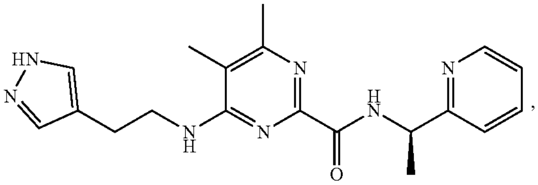 [SMILES: Cc1nc(C(=O)N[C@H](C)c2ccccn2)nc(NCCc2cn[nH]c2)c1C] |
| 48 | 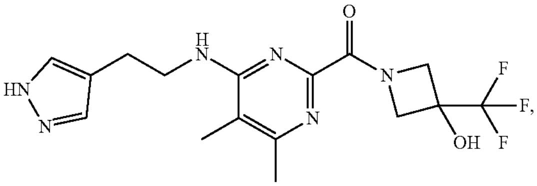 [SMILES: Cc1nc(C(=O)N2CC(O)(C(F)(F)F)C2)nc(NCCc2cn[nH]c2)c1C] |
| 49 | 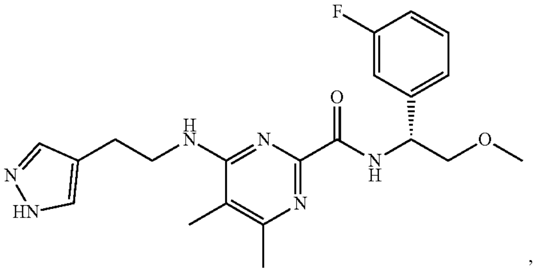 [SMILES: COC[C@H](NC(=O)c1nc(C)c(C)c(NCCc2cn[nH]c2)n1)c1cccc(F)c1] |
| 50 | 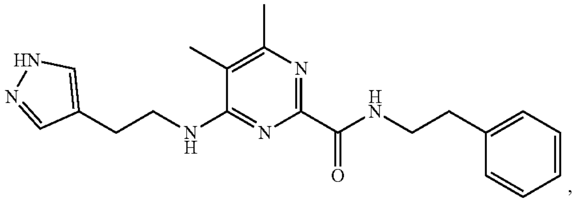 [SMILES: Cc1nc(C(=O)NCCc2ccccc2)nc(NCCc2cn[nH]c2)c1C] |
| 51 | 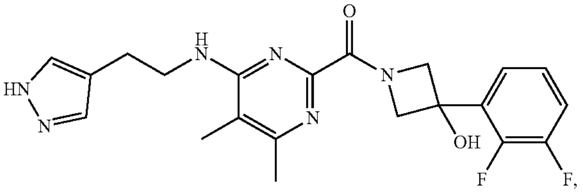 [SMILES: Cc1nc(C(=O)N2CC(O)(c3cccc(F)c3F)C2)nc(NCCc2cn[nH]c2)c1C] |
| 52 | 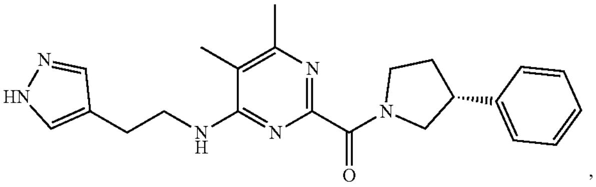 [SMILES: Cc1nc(C(=O)N2CC[C@H](c3ccccc3)C2)nc(NCCc2cn[nH]c2)c1C] |

-continued
| No. | Structure |
| --- | --- |
| 53 | 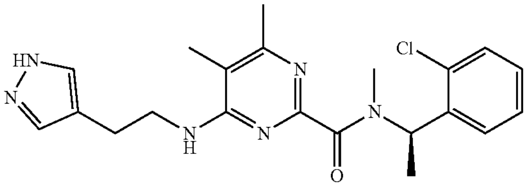 , |
| 54 | 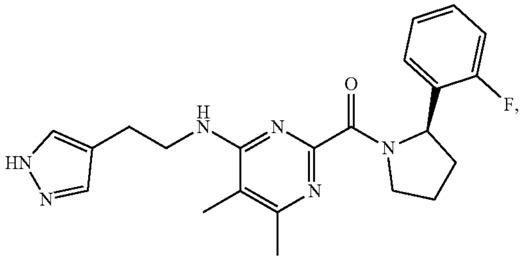 [SMILES: Cc1nc(C(=O)N2CCC[C@@H]2c2ccccc2F)nc(NCCc2cn[nH]c2)c1C] |
| 55 | 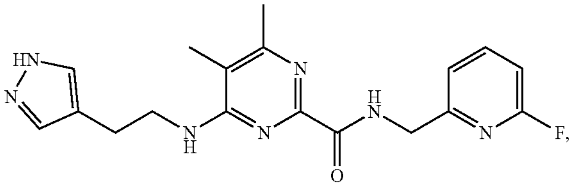 [SMILES: Cc1nc(C(=O)NCc2cccc(F)n2)nc(NCCc2cn[nH]c2)c1C] |
| 56 | 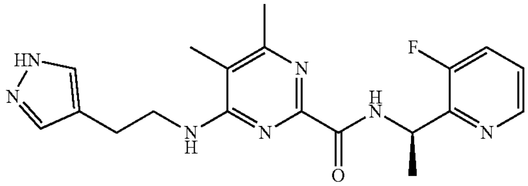 , |
| 57 | 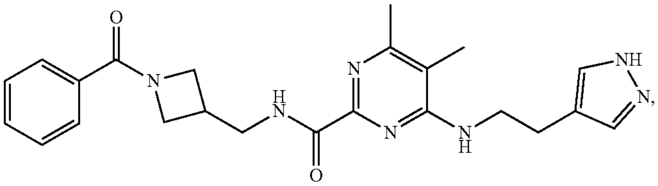 [SMILES: Cc1nc(C(=O)NCC2CN(C(=O)c3ccccc3)C2)nc(NCCc2cn[nH]c2)c1C] |
| 58 | 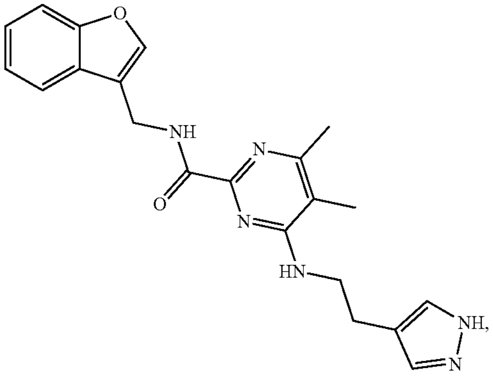 [SMILES: Cc1nc(C(=O)NCc2coc3ccccc23)nc(NCCc2cn[nH]c2)c1C] |

-continued
| No. | Structure |
|---|---|
| 59 | 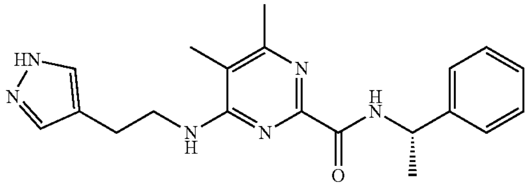 , |
| 60 | 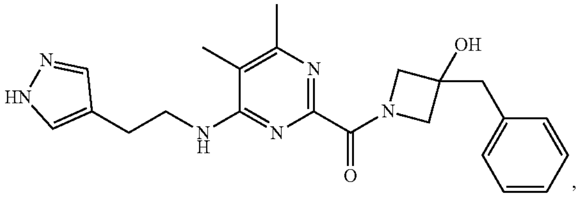 [SMILES: Cc1nc(C(=O)N2CC(O)(Cc3ccccc3)C2)nc(NCCc2cn[nH]c2)c1C] , |
| 61 | 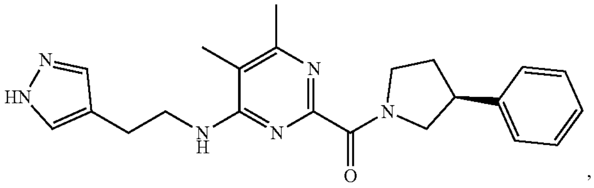 [SMILES: Cc1nc(C(=O)N2CC[C@@H](c3ccccc3)C2)nc(NCCc2cn[nH]c2)c1C] , |
| 62 | 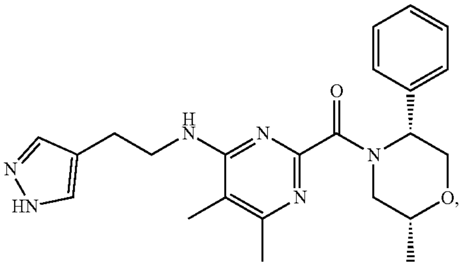 [SMILES: Cc1nc(C(=O)N2C[C@@H](C)OC[C@H]2c2ccccc2)nc(NCCc2cn[nH]c2)c1C] , |
| 63 | 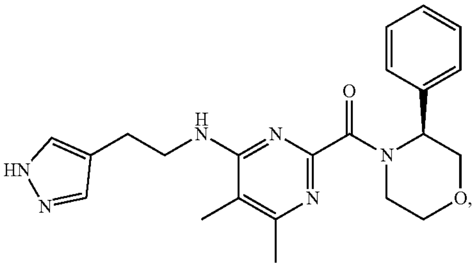 [SMILES: Cc1nc(C(=O)N2CCOC[C@@H]2c2ccccc2)nc(NCCc2cn[nH]c2)c1C] , |
| 64 | 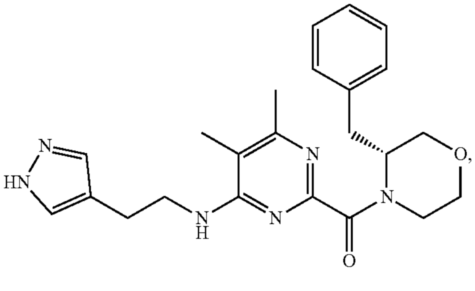 [SMILES: Cc1nc(C(=O)N2CCOC[C@H]2Cc2ccccc2)nc(NCCc2cn[nH]c2)c1C] , |

-continued
| No. | Structure |
|---|---|
| 65 | 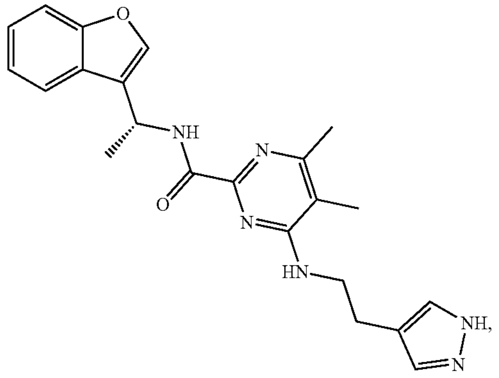 [SMILES: Cc1nc(C(=O)N[C@H](C)c2coc3ccccc23)nc(NCCc2cn[nH]c2)c1C] |
| 66 | 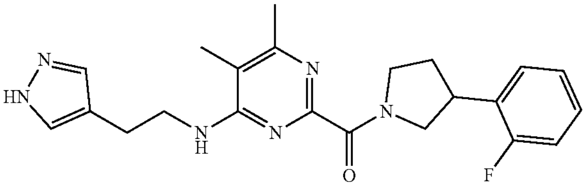 , |
| 67 | 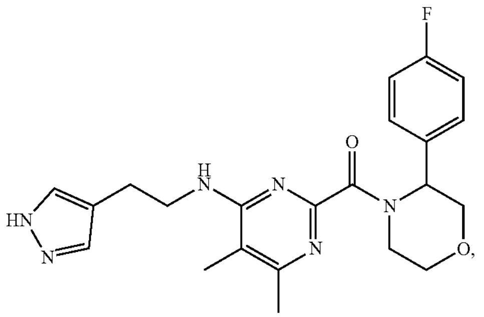 [SMILES: Cc1nc(C(=O)N2CCOCC2c2ccc(F)cc2)nc(NCCc2cn[nH]c2)c1C] |
| 68 | 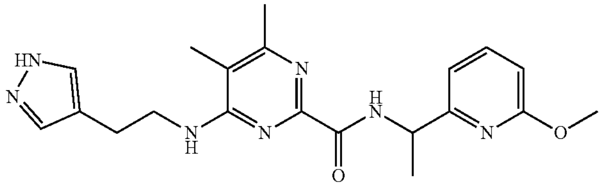 , |
| 69 | 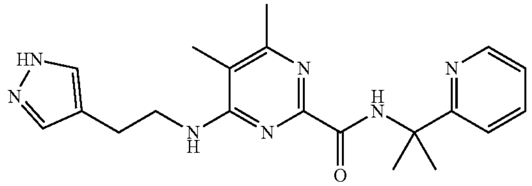 , |
| 70 | 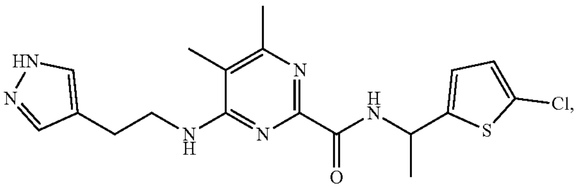 [SMILES: Cc1nc(C(=O)NC(C)c2ccc(Cl)s2)nc(NCCc2cn[nH]c2)c1C] |

-continued
| No. | Structure |
|---|---|
| 71 | 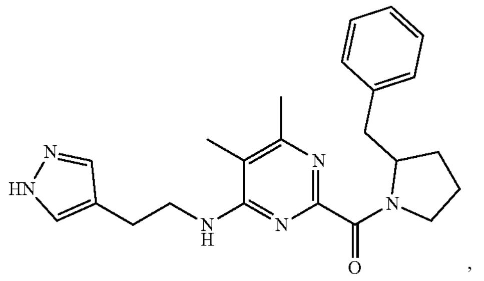 [SMILES: Cc1nc(C(=O)N2CCCC2Cc2ccccc2)nc(NCCc2cn[nH]c2)c1C] |
| 72 | 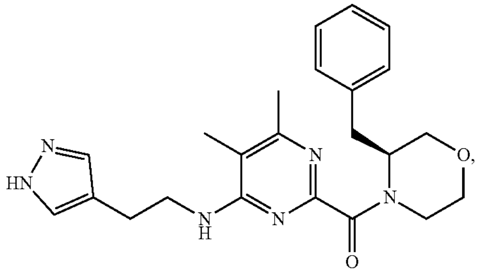 [SMILES: Cc1nc(C(=O)N2CCOC[C@@H]2Cc2ccccc2)nc(NCCc2cn[nH]c2)c1C] |
| 73 | 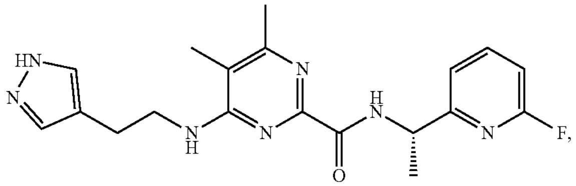 [SMILES: Cc1nc(C(=O)N[C@@H](C)c2cccc(F)n2)nc(NCCc2cn[nH]c2)c1C] |
| 74 | 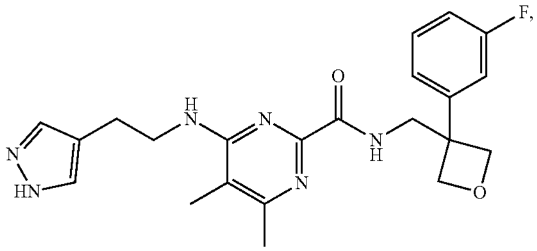 [SMILES: Cc1nc(C(=O)NCC2(c3cccc(F)c3)COC2)nc(NCCc2cn[nH]c2)c1C] |
| 75 | 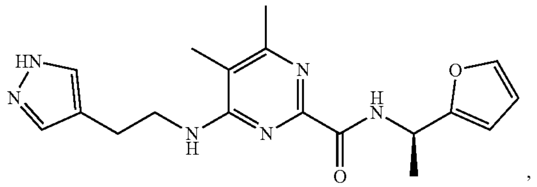 [SMILES: Cc1nc(C(=O)N[C@H](C)c2ccco2)nc(NCCc2cn[nH]c2)c1C] |
| 76 | 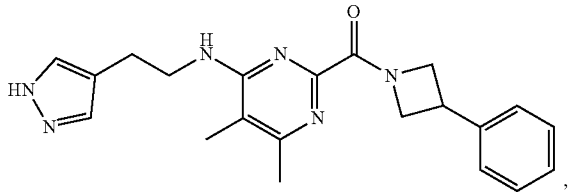 [SMILES: Cc1nc(C(=O)N2CC(c3ccccc3)C2)nc(NCCc2cn[nH]c2)c1C] |

-continued
| No. | Structure |
|---|---|
| 77 | 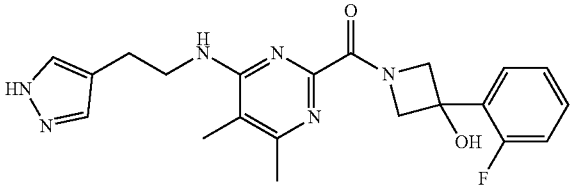 , |
| 78 | 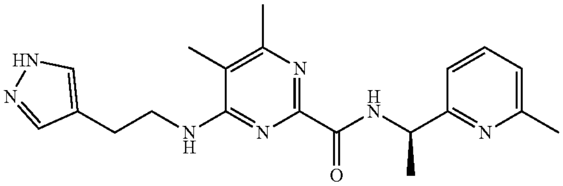 , |
| 79 | 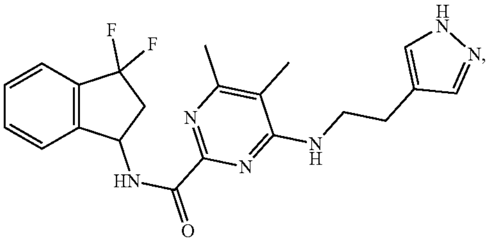 [SMILES: Cc1nc(C(=O)NC2CC(F)(F)c3ccccc32)nc(NCCc2cn[nH]c2)c1C] |
| 80 | 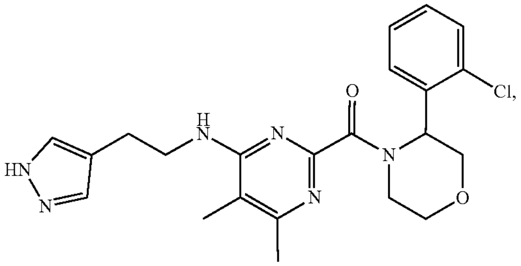 [SMILES: Cc1nc(C(=O)N2CCOCC2c2ccccc2Cl)nc(NCCc2cn[nH]c2)c1C] |
| 81 | 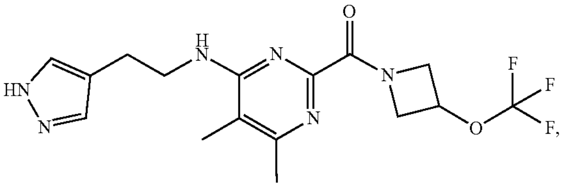 [SMILES: Cc1nc(C(=O)N2CC(OC(F)(F)F)C2)nc(NCCc2cn[nH]c2)c1C] |
| 82 | 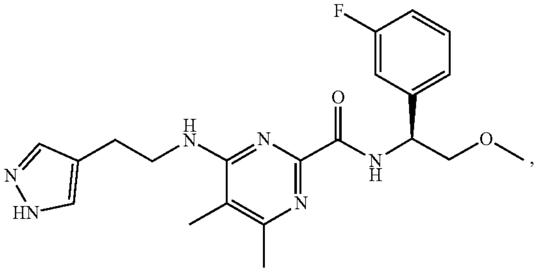 [SMILES: COC[C@@H](NC(=O)c1nc(C)c(C)c(NCCc2cn[nH]c2)n1)c1cccc(F)c1] , |
| 83 | 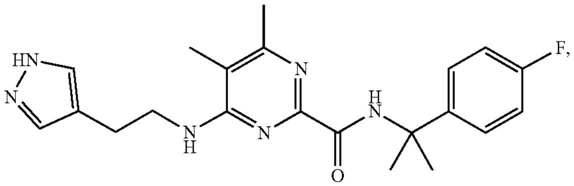 [SMILES: Cc1nc(C(=O)NC(C)(C)c2ccc(F)cc2)nc(NCCc2cn[nH]c2)c1C] |

-continued
| No. | Structure |
| --- | --- |
| 84 | 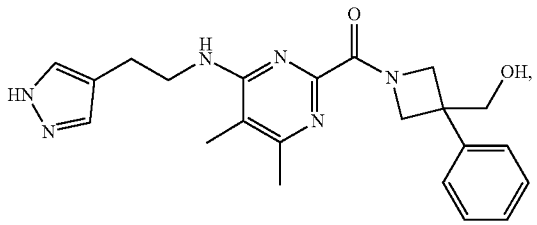 [SMILES: Cc1nc(C(=O)N2CC(CO)(c3ccccc3)C2)nc(NCCc2cn[nH]c2)c1C] |
| 85 | 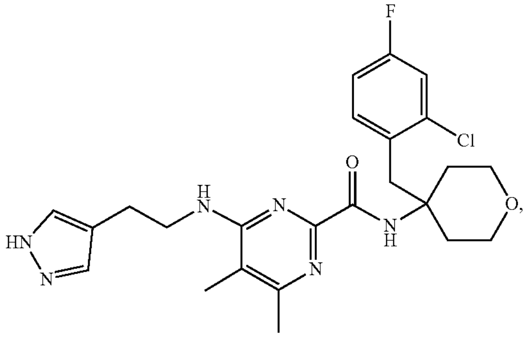 [SMILES: Cc1nc(C(=O)NC2(Cc3ccc(F)cc3Cl)CCOCC2)nc(NCCc2cn[nH]c2)c1C] |
| 86 | 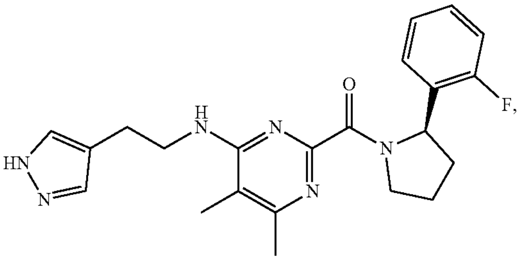 [SMILES: Cc1nc(C(=O)N2CCC[C@@H]2c2ccccc2F)nc(NCCc2cn[nH]c2)c1C] |
| 87 | 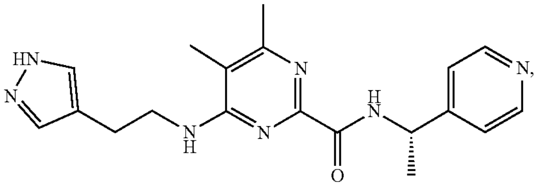 [SMILES: Cc1nc(C(=O)N[C@@H](C)c2ccncc2)nc(NCCc2cn[nH]c2)c1C] |
| 88 | 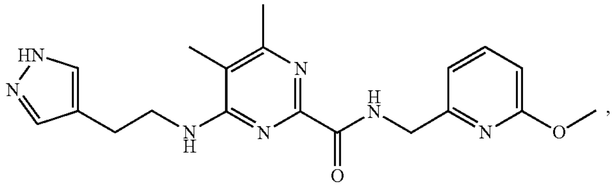 [SMILES: COc1cccc(CNC(=O)c2nc(C)c(C)c(NCCc3cn[nH]c3)n2)n1] |
| 89 | 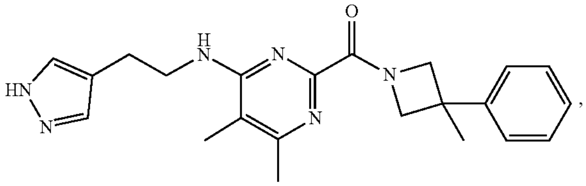 [SMILES: Cc1nc(C(=O)N2CC(C)(c3ccccc3)C2)nc(NCCc2cn[nH]c2)c1C] |

-continued
| No. | Structure |
| --- | --- |
| 90 | 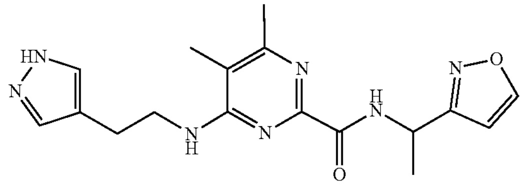, |
| 91 | 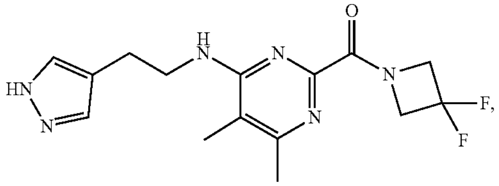 [SMILES: Cc1nc(C(=O)N2CC(F)(F)C2)nc(NCCc2cn[nH]c2)c1C] |
| 92 | 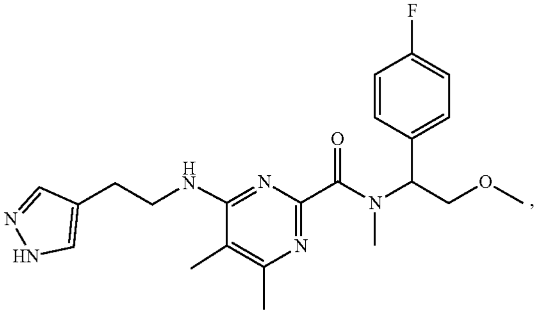 [SMILES: COCC(c1ccc(F)cc1)N(C)C(=O)c1nc(C)c(C)c(NCCc2cn[nH]c2)n1] |
| 93 | 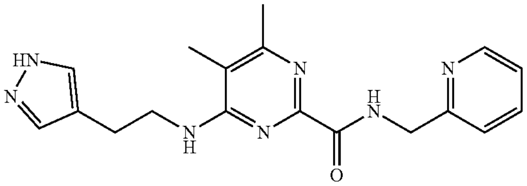, |
| 94 | 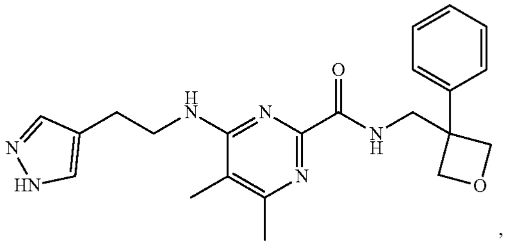, |
| 95 | 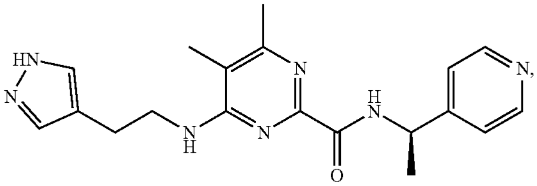 [SMILES: Cc1nc(C(=O)N[C@H](C)c2ccncc2)nc(NCCc2cn[nH]c2)c1C] |
| 96 | 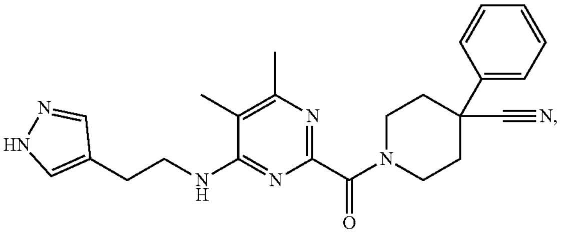 [SMILES: Cc1nc(C(=O)N2CCC(C#N)(c3ccccc3)CC2)nc(NCCc2cn[nH]c2)c1C] |

-continued
| No. | Structure |
| --- | --- |
| 97 | 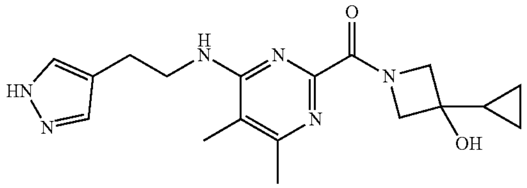, |
| 98 | 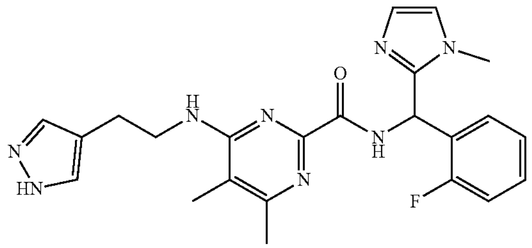, |
| 99 | 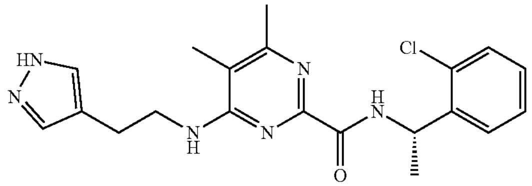, |
| 100 | 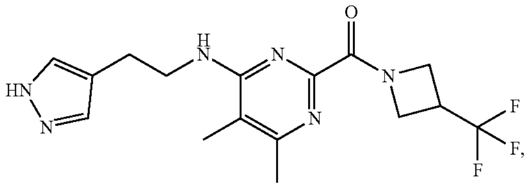 [SMILES: Cc1nc(C(=O)N2CC(C(F)(F)F)C2)nc(NCCc2cn[nH]c2)c1C] |
| 101 | 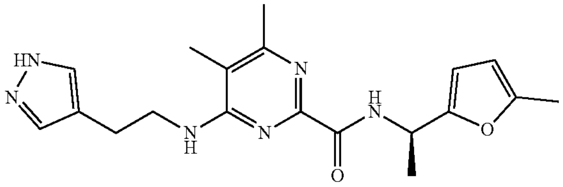, |
| 102 | 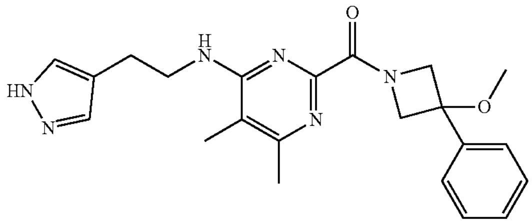, |
| 103 | 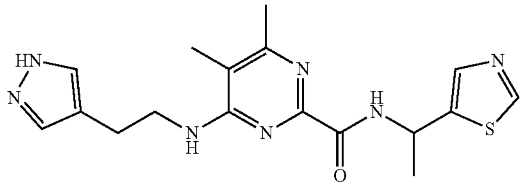, |

-continued
| No. | Structure |
|---|---|
| 104 | 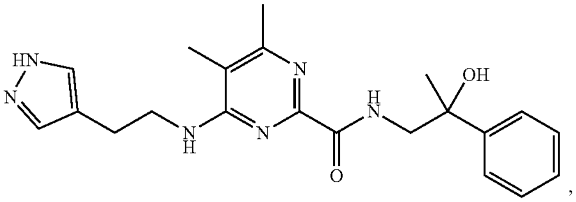 [SMILES: Cc1nc(C(=O)NCC(C)(O)c2ccccc2)nc(NCCc2cn[nH]c2)c1C] |
| 105 | 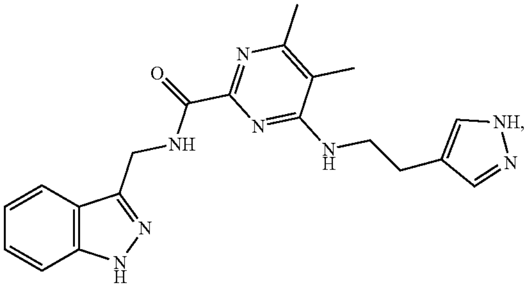 [SMILES: Cc1nc(C(=O)NCc2n[nH]c3ccccc23)nc(NCCc2cn[nH]c2)c1C] |
| 106 | 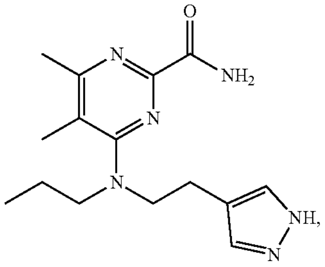 [SMILES: CCCN(CCc1cn[nH]c1)c1nc(C(N)=O)nc(C)c1C] |
| 107 | 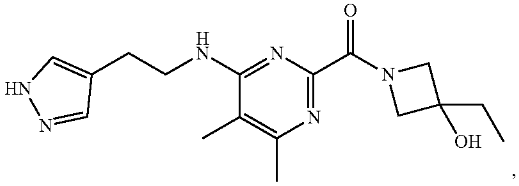 [SMILES: CCC1(O)CN(C(=O)c2nc(C)c(C)c(NCCc3cn[nH]c3)n2)C1] |
| 108 | 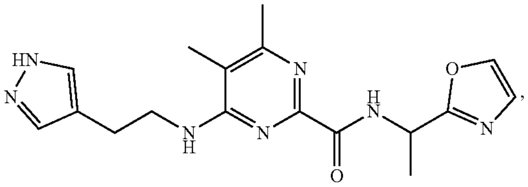 [SMILES: Cc1nc(C(=O)NC(C)c2ncco2)nc(NCCc2cn[nH]c2)c1C] |
| 109 | 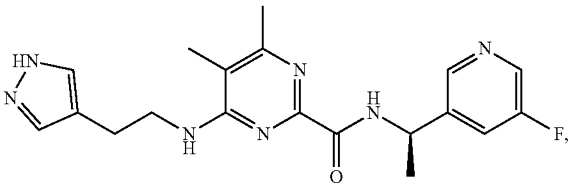 [SMILES: Cc1nc(C(=O)N[C@H](C)c2cncc(F)c2)nc(NCCc2cn[nH]c2)c1C] |
| 110 | 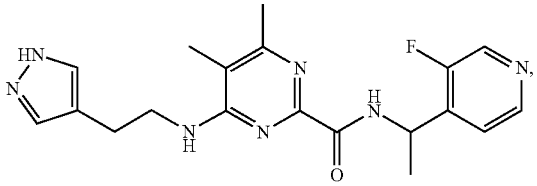 [SMILES: Cc1nc(C(=O)NC(C)c2ccncc2F)nc(NCCc2cn[nH]c2)c1C] |

-continued
| No. | Structure |
|---|---|
| 111 | 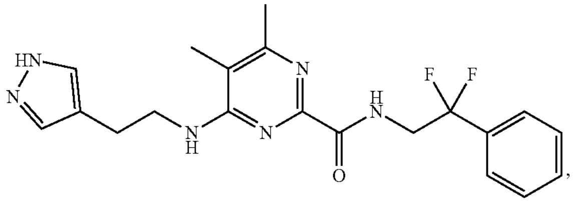 [SMILES: Cc1nc(C(=O)NCC(F)(F)c2ccccc2)nc(NCCc2cn[nH]c2)c1C] |
| 112 | 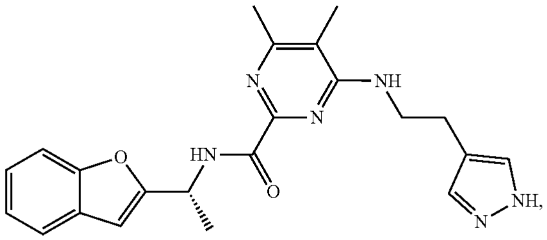 [SMILES: Cc1nc(C(=O)N[C@H](C)c2cc3ccccc3o2)nc(NCCc2cn[nH]c2)c1C] |
| 113 | 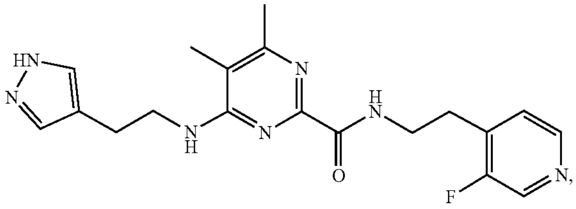 [SMILES: Cc1nc(C(=O)NCCc2ccncc2F)nc(NCCc2cn[nH]c2)c1C] |
| 114 | 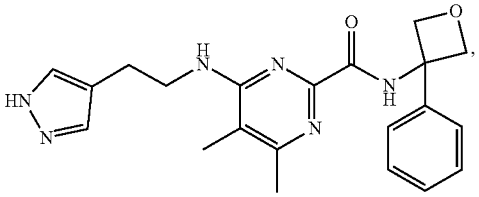 [SMILES: Cc1nc(C(=O)NC2(c3ccccc3)COC2)nc(NCCc2cn[nH]c2)c1C] |
| 115 | 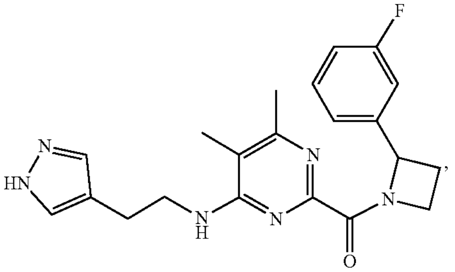 [SMILES: Cc1nc(C(=O)N2CCC2c2cccc(F)c2)nc(NCCc2cn[nH]c2)c1C] |
| 116 | 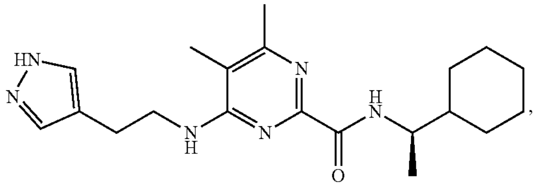 [SMILES: Cc1nc(C(=O)N[C@H](C)C2CCCCC2)nc(NCCc2cn[nH]c2)c1C] |

-continued
| No. | Structure |
|---|---|
| 117 | 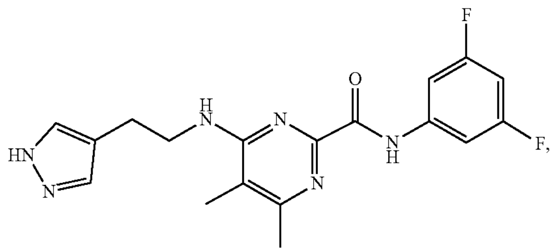 [SMILES: Cc1nc(C(=O)Nc2cc(F)cc(F)c2)nc(NCCc2cn[nH]c2)c1C] |
| 118 | 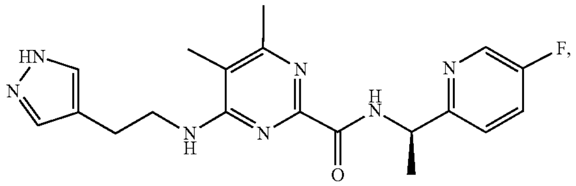 [SMILES: Cc1nc(C(=O)N[C@H](C)c2ccc(F)cn2)nc(NCCc2cn[nH]c2)c1C] |
| 119 | 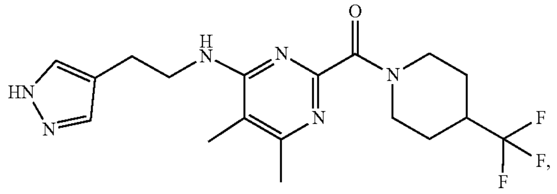 [SMILES: Cc1nc(C(=O)N2CCC(C(F)(F)F)CC2)nc(NCCc2cn[nH]c2)c1C] |
| 120 | 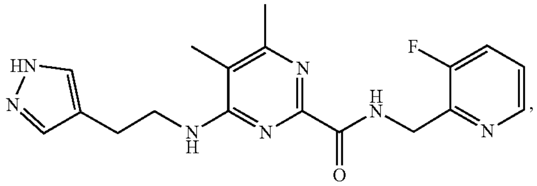 [SMILES: Cc1nc(C(=O)NCc2ncccc2F)nc(NCCc2cn[nH]c2)c1C] |
| 121 | 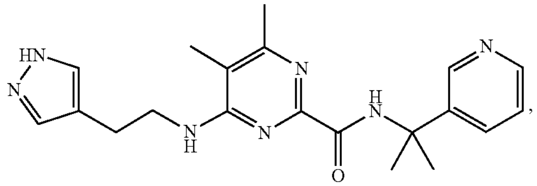 [SMILES: Cc1nc(C(=O)NC(C)(C)c2cccnc2)nc(NCCc2cn[nH]c2)c1C] |
| 122 | 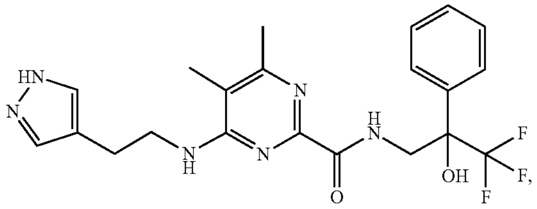 [SMILES: Cc1nc(C(=O)NCC(O)(c2ccccc2)C(F)(F)F)nc(NCCc2cn[nH]c2)c1C] |
| 123 | 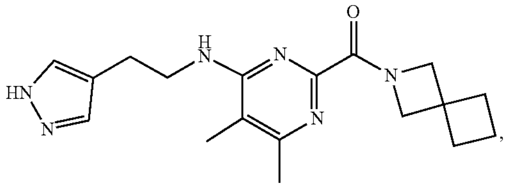 [SMILES: Cc1nc(C(=O)N2CC3(CCC3)C2)nc(NCCc2cn[nH]c2)c1C] |

-continued
| No. | Structure |
|---|---|
| 124 | 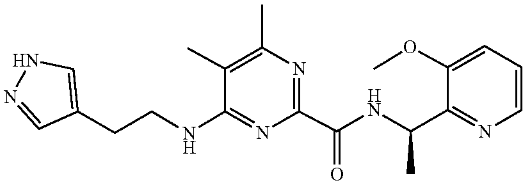, |
| 125 | 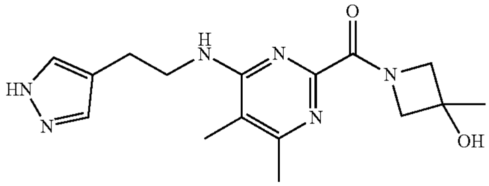, |
| 126 | 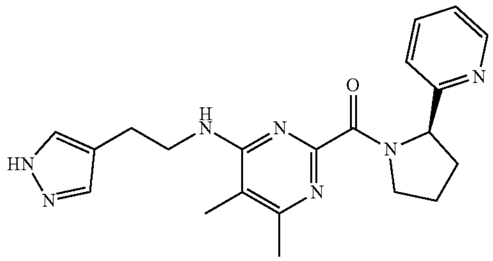, |
| 127 | 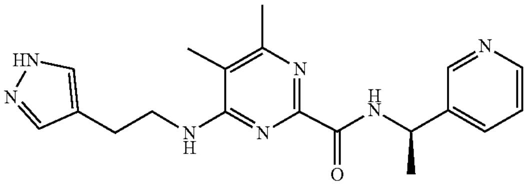, |
| 128 | 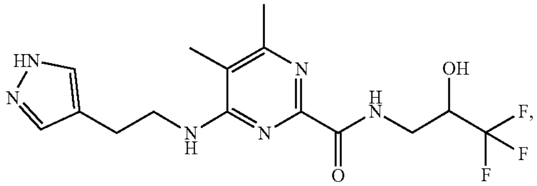 [SMILES: Cc1nc(C(=O)NCC(O)C(F)(F)F)nc(NCCc2cn[nH]c2)c1C], |
| 129 | 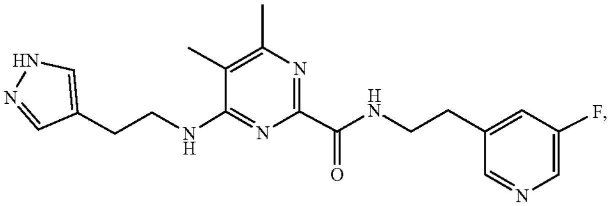 [SMILES: Cc1nc(C(=O)NCCc2cncc(F)c2)nc(NCCc2cn[nH]c2)c1C], |
| 130 | 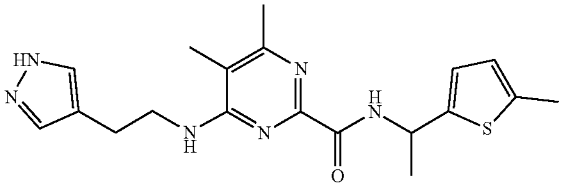, |

-continued
| No. | Structure |
|---|---|
| 131 | 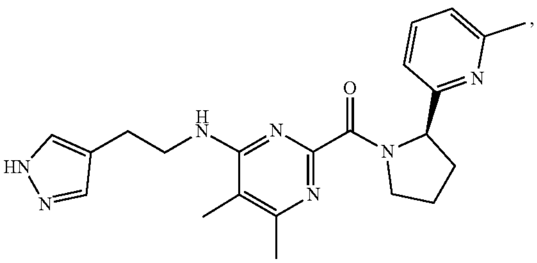 [SMILES: Cc1cccc([C@H]2CCCN2C(=O)c2nc(C)c(C)c(NCCc3cn[nH]c3)n2)n1], |
| 132 | 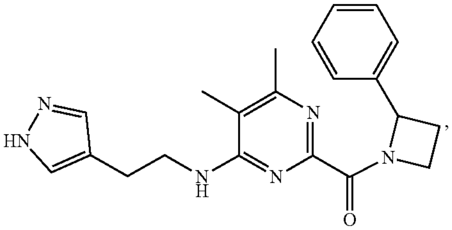 [SMILES: Cc1nc(C(=O)N2CCC2c2ccccc2)nc(NCCc2cn[nH]c2)c1C], |
| 133 | 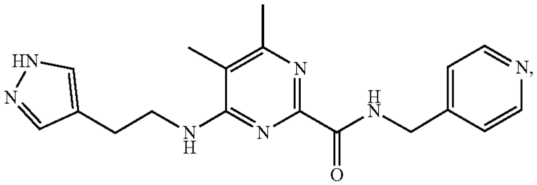 [SMILES: Cc1nc(C(=O)NCc2ccncc2)nc(NCCc2cn[nH]c2)c1C], |
| 134 | 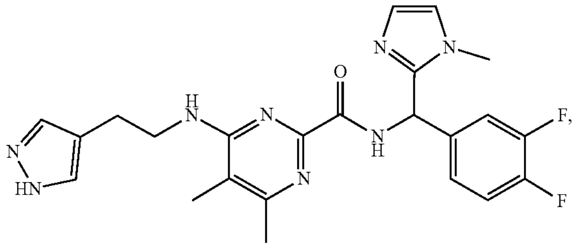 [SMILES: Cc1nc(C(=O)NC(c2ccc(F)c(F)c2)c2nccn2C)nc(NCCc2cn[nH]c2)c1C], |
| 135 | 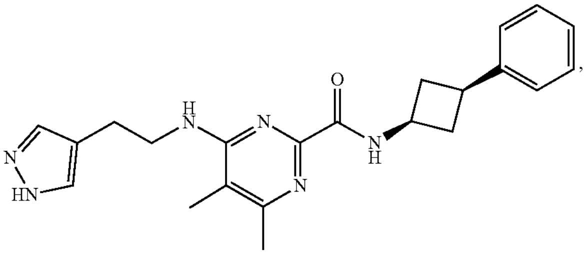 [SMILES: Cc1nc(C(=O)N[C@H]2C[C@@H](c3ccccc3)C2)nc(NCCc2cn[nH]c2)c1C], |
| 136 | 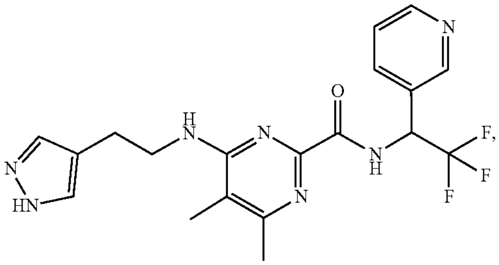 [SMILES: Cc1nc(C(=O)NC(c2cccnc2)C(F)(F)F)nc(NCCc2cn[nH]c2)c1C], |

-continued
| No. | Structure |
| --- | --- |
| 137 | 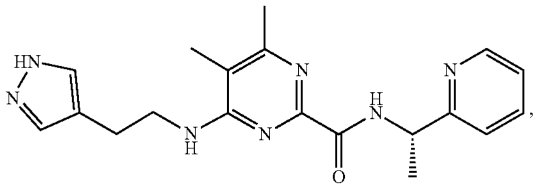 |
| 138 | 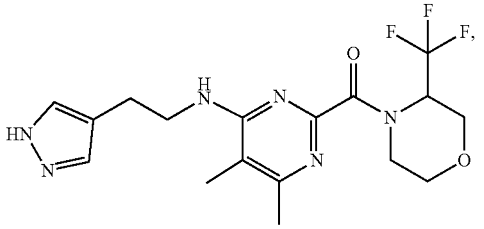 [SMILES: Cc1nc(C(=O)N2CCOCC2C(F)(F)F)nc(NCCc2cn[nH]c2)c1C] |
| 139 | 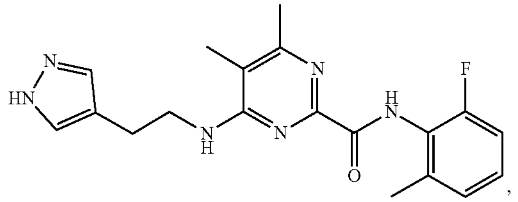 [SMILES: Cc1cccc(F)c1NC(=O)c1nc(C)c(C)c(NCCc2cn[nH]c2)n1] |
| 140 | 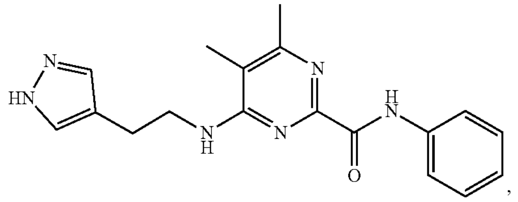 [SMILES: Cc1nc(C(=O)Nc2ccccc2)nc(NCCc2cn[nH]c2)c1C] |
| 141 | 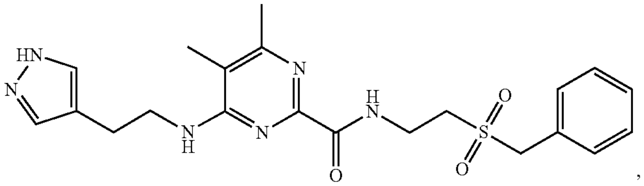 [SMILES: Cc1nc(C(=O)NCCS(=O)(=O)Cc2ccccc2)nc(NCCc2cn[nH]c2)c1C] |
| 142 | 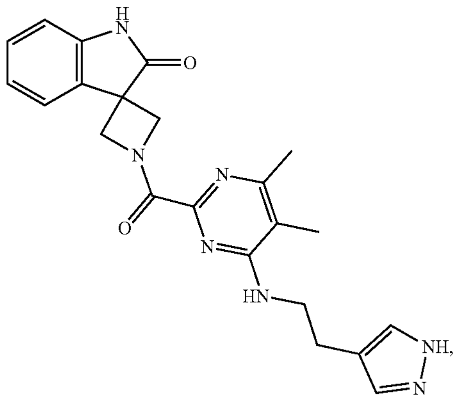 [SMILES: Cc1nc(C(=O)N2CC3(C2)C(=O)Nc2ccccc23)nc(NCCc2cn[nH]c2)c1C] |

-continued
| No. | Structure |
| --- | --- |
| 143 | 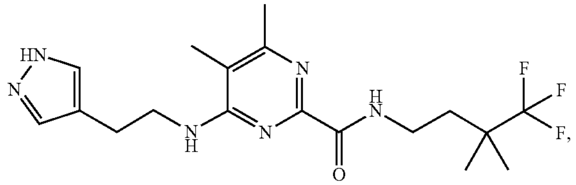 [SMILES: Cc1nc(C(=O)NCCC(C)(C)C(F)(F)F)nc(NCCc2cn[nH]c2)c1C] |
| 144 | 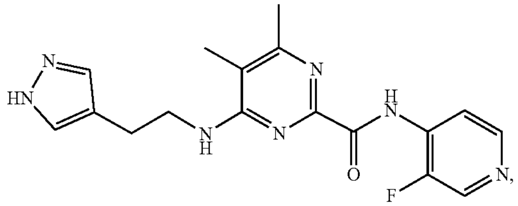 [SMILES: Cc1nc(C(=O)Nc2ccncc2F)nc(NCCc2cn[nH]c2)c1C] |
| 145 | 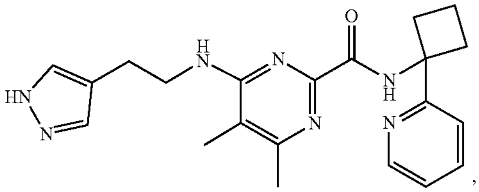 [SMILES: Cc1nc(C(=O)NC2(c3ccccn3)CCC2)nc(NCCc2cn[nH]c2)c1C] |
| 146 | 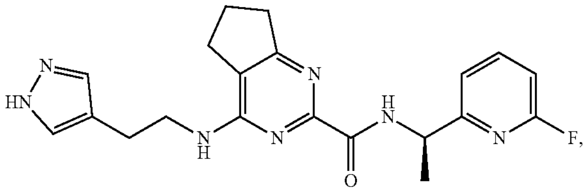 [SMILES: C[C@@H](NC(=O)c1nc2c(c(NCCc3cn[nH]c3)n1)CCC2)c1cccc(F)n1] |
| 147 | 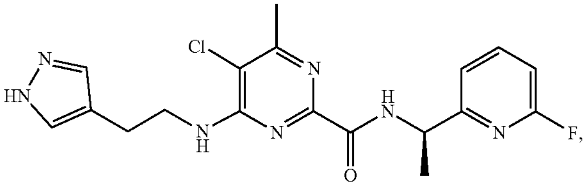 [SMILES: Cc1nc(C(=O)N[C@H](C)c2cccc(F)n2)nc(NCCc2cn[nH]c2)c1Cl] |
| 148 | 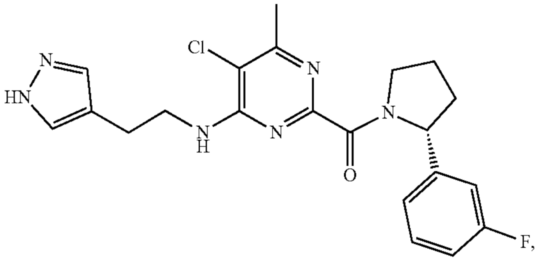 |
| 149 | 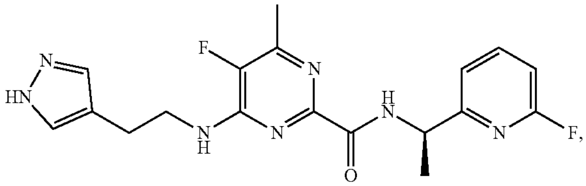 [SMILES: Cc1nc(C(=O)N[C@H](C)c2cccc(F)n2)nc(NCCc2cn[nH]c2)c1F] |

-continued
| No. | Structure |
|---|---|
| 150 | 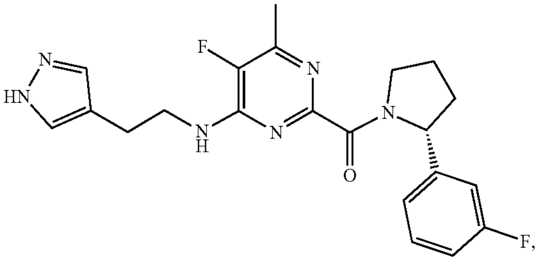 [SMILES: Cc1nc(C(=O)N2CCC[C@@H]2c2cccc(F)c2)nc(NCCc2cn[nH]c2)c1F] |
| 151 | 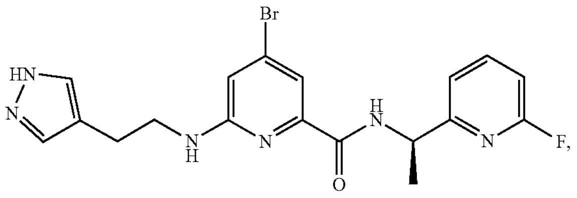 and |
| 152 | 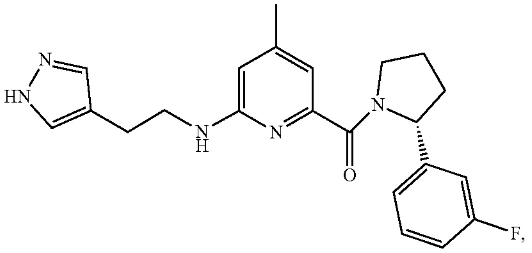 [SMILES: Cc1cc(NCCc2cn[nH]c2)nc(C(=O)N2CCC[C@@H]2c2cccc(F)c2)c1] |
or a pharmaceutically acceptable salt thereof.
29. A compound selected from the group consisting of:
| No. | Structure |
|---|---|
| 1 | 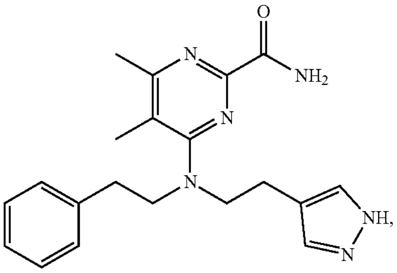 [SMILES: Cc1nc(C(N)=O)nc(N(CCc2ccccc2)CCc2cn[nH]c2)c1C] |
| 2 | 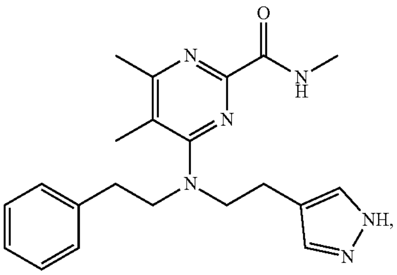 [SMILES: CNC(=O)c1nc(C)c(C)c(N(CCc2ccccc2)CCc2cn[nH]c2)n1] |

-continued
| No. | Structure |
|---|---|
| 3 | 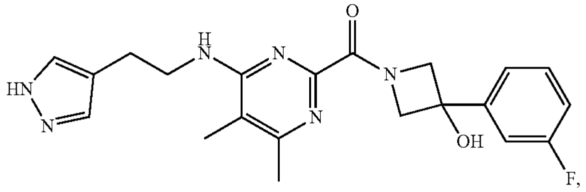 [SMILES: Cc1nc(C(=O)N2CC(O)(c3cccc(F)c3)C2)nc(NCCc2cn[nH]c2)c1C] |
| 4 | 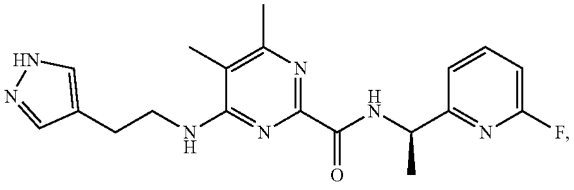 [SMILES: Cc1nc(C(=O)N[C@H](C)c2cccc(F)n2)nc(NCCc2cn[nH]c2)c1C] |
| 5 | 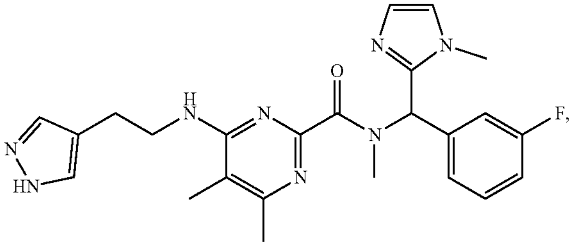 [SMILES: Cc1nc(C(=O)N(C)C(c2cccc(F)c2)c2nccn2C)nc(NCCc2cn[nH]c2)c1C] |
| 6 | 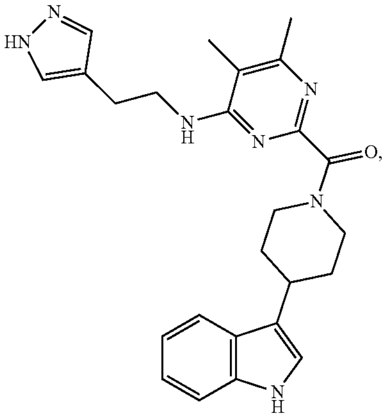 [SMILES: Cc1nc(C(=O)N2CCC(c3c[nH]c4ccccc34)CC2)nc(NCCc2cn[nH]c2)c1C] |
| 7 | 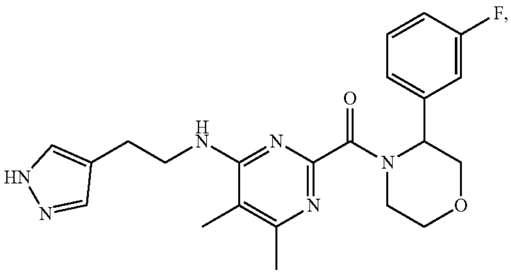 [SMILES: Cc1nc(C(=O)N2CCOCC2c2cccc(F)c2)nc(NCCc2cn[nH]c2)c1C] |
| 8 | 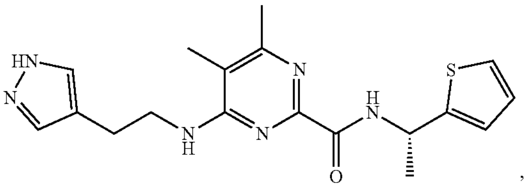 [SMILES: Cc1nc(C(=O)N[C@@H](C)c2cccs2)nc(NCCc2cn[nH]c2)c1C] , |

-continued
| No. | Structure |
|---|---|
| 9 | 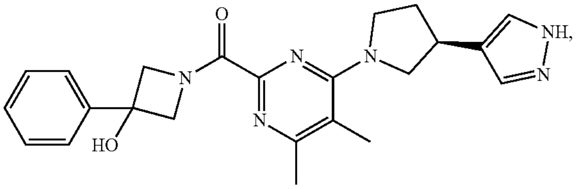 [SMILES: Cc1nc(C(=O)N2CC(O)(c3ccccc3)C2)nc(N2CC[C@@H](c3cn[nH]c3)C2)c1C] |
| 10 | 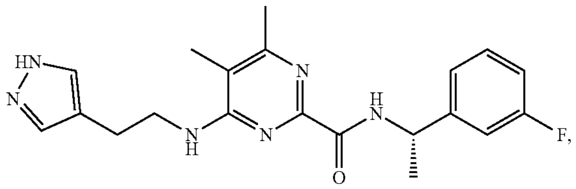 [SMILES: Cc1nc(C(=O)N[C@@H](C)c2cccc(F)c2)nc(NCCc2cn[nH]c2)c1C] |
| 11 | 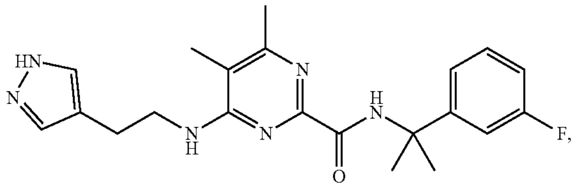 [SMILES: Cc1nc(C(=O)NC(C)(C)c2cccc(F)c2)nc(NCCc2cn[nH]c2)c1C] |
| 12 | 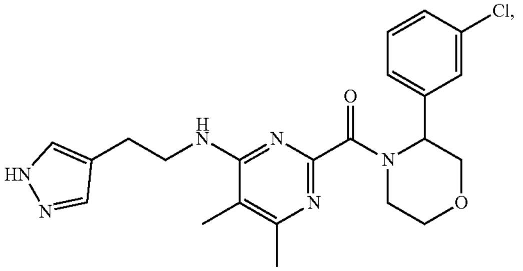 [SMILES: Cc1nc(C(=O)N2CCOCC2c2cccc(Cl)c2)nc(NCCc2cn[nH]c2)c1C] |
| 13 | 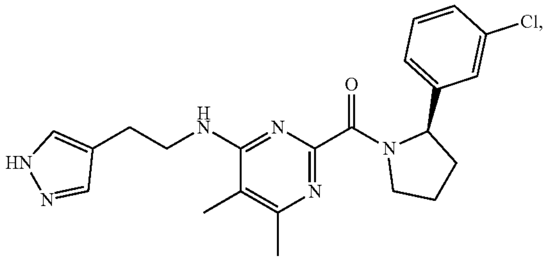 [SMILES: Cc1nc(C(=O)N2CCC[C@@H]2c2cccc(Cl)c2)nc(NCCc2cn[nH]c2)c1C] |
| 14 | 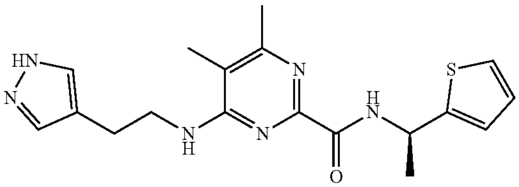 ' |
| 15 | 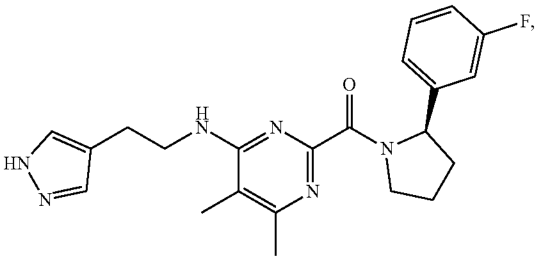 |

-continued
| No. | Structure |
| --- | --- |
| 16 | 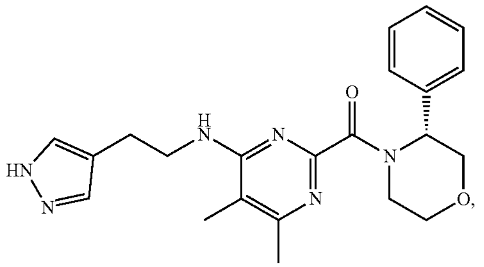 [SMILES: Cc1nc(C(=O)N2CCOC[C@H]2c2ccccc2)nc(NCCc2cn[nH]c2)c1C] |
| 17 | 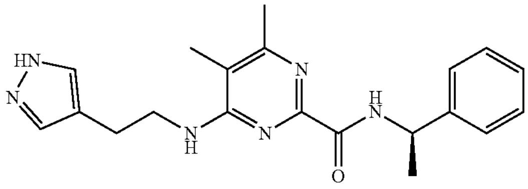 , |
| 18 | 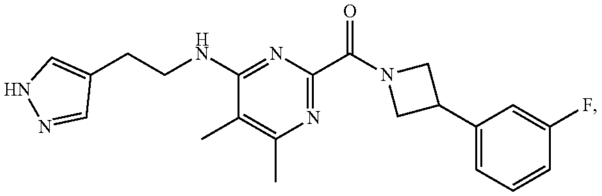 [SMILES: Cc1nc(C(=O)N2CC(c3cccc(F)c3)C2)nc(NCCc2cn[nH]c2)c1C] |
| 19 | 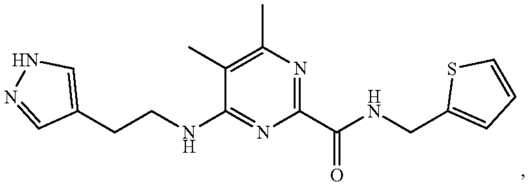 [SMILES: Cc1nc(C(=O)NCc2cccs2)nc(NCCc2cn[nH]c2)c1C] , |
| 20 | 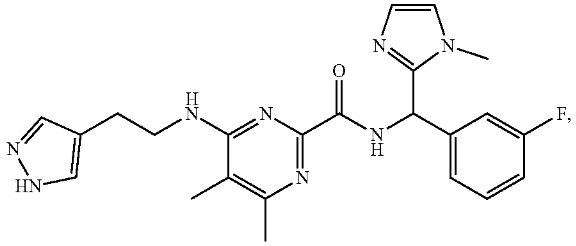 [SMILES: Cc1nc(C(=O)NC(c2cccc(F)c2)c2nccn2C)nc(NCCc2cn[nH]c2)c1C] |
| 21 | 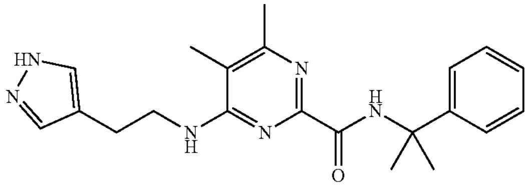 , |
| 22 | 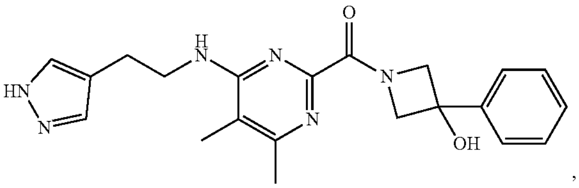 [SMILES: Cc1nc(C(=O)N2CC(O)(c3ccccc3)C2)nc(NCCc2cn[nH]c2)c1C] , |

-continued
| No. | Structure |
| --- | --- |
| 23 | 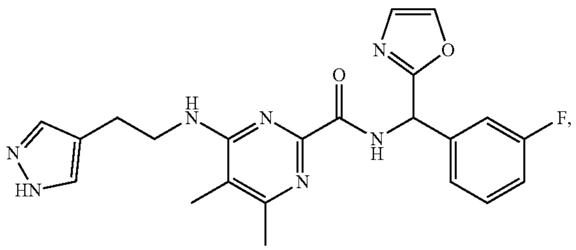 [SMILES: Cc1nc(C(=O)NC(c2cccc(F)c2)c2ncco2)nc(NCCc2cn[nH]c2)c1C] |
| 24 | 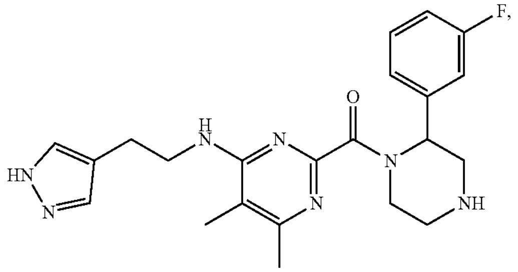 [SMILES: Cc1nc(C(=O)N2CCNCC2c2cccc(F)c2)nc(NCCc2cn[nH]c2)c1C] |
| 25 | 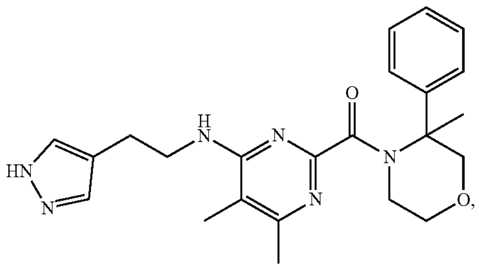 [SMILES: Cc1nc(C(=O)N2CCOCC2(C)c2ccccc2)nc(NCCc2cn[nH]c2)c1C] |
| 26 | 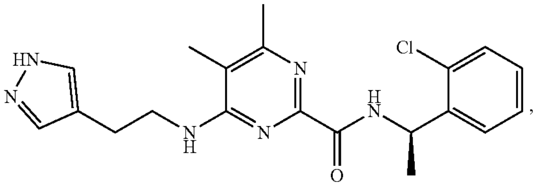 |
| 27 | 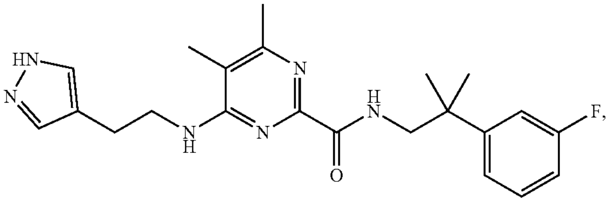 [SMILES: Cc1nc(C(=O)NCC(C)(C)c2cccc(F)c2)nc(NCCc2cn[nH]c2)c1C] |
| 28 | 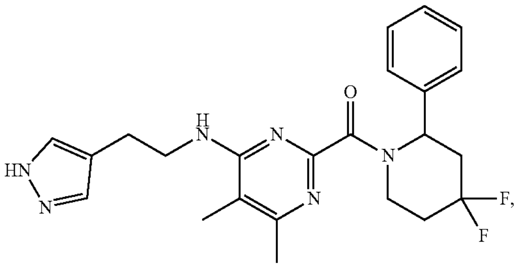 [SMILES: Cc1nc(C(=O)N2CCC(F)(F)CC2c2ccccc2)nc(NCCc2cn[nH]c2)c1C] |

-continued
| No. | Structure |
|---|---|
| 29 | 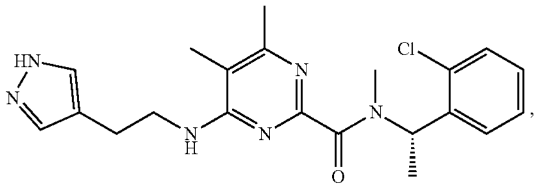 [SMILES: Cc1nc(C(=O)N(C)[C@@H](C)c2ccccc2Cl)nc(NCCc2cn[nH]c2)c1C] |
| 30 | 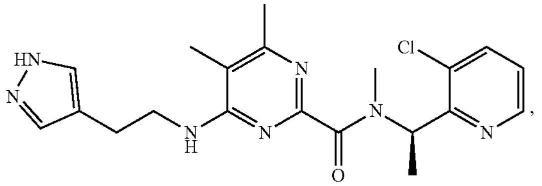 |
| 31 | 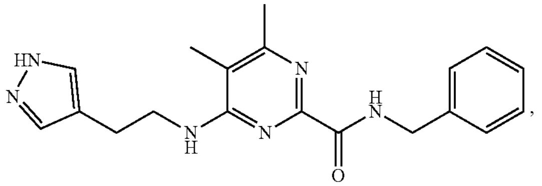 |
| 32 | 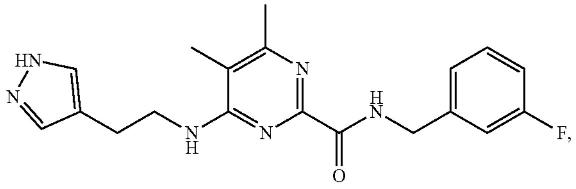 [SMILES: Cc1nc(C(=O)NCc2cccc(F)c2)nc(NCCc2cn[nH]c2)c1C] |
| 33 | 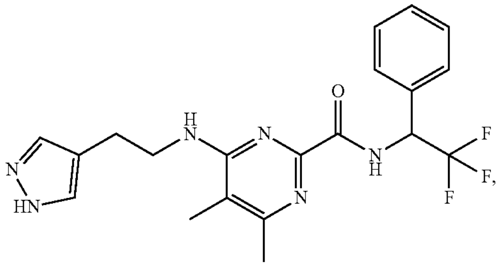 [SMILES: Cc1nc(C(=O)NC(c2ccccc2)C(F)(F)F)nc(NCCc2cn[nH]c2)c1C] |
| 34 | 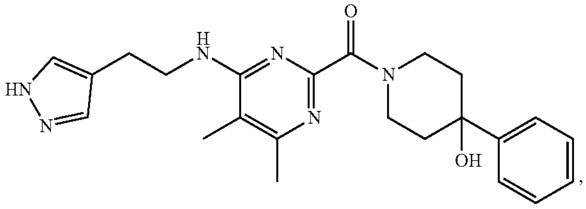 [SMILES: Cc1nc(C(=O)N2CCC(O)(c3ccccc3)CC2)nc(NCCc2cn[nH]c2)c1C] |
| 35 | 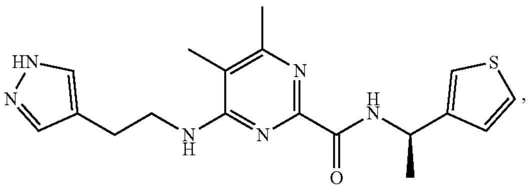 [SMILES: Cc1nc(C(=O)N[C@H](C)c2ccsc2)nc(NCCc2cn[nH]c2)c1C] |

-continued
| No. | Structure |
|---|---|
| 36 | 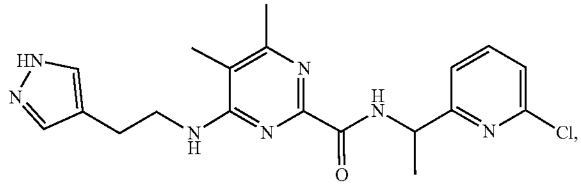 [SMILES: Cc1nc(C(=O)NC(C)c2cccc(Cl)n2)nc(NCCc2cn[nH]c2)c1C] Cl, |
| 37 | 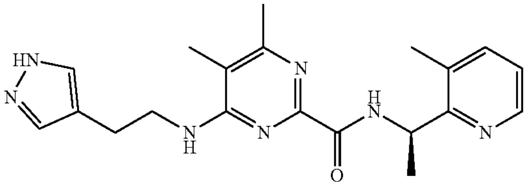 , |
| 38 | 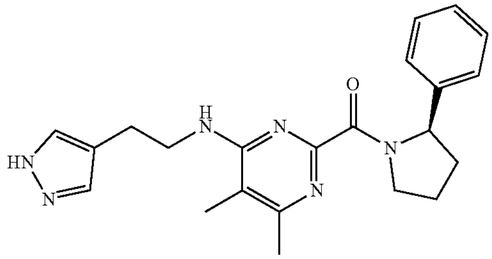 , |
| 39 | 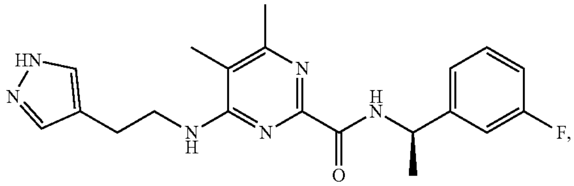 [SMILES: Cc1nc(C(=O)N[C@H](C)c2cccc(F)c2)nc(NCCc2cn[nH]c2)c1C] F, |
| 40 | 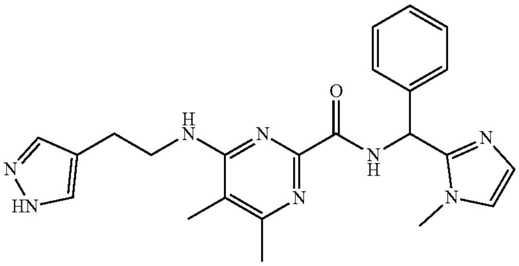 , |
| 41 | 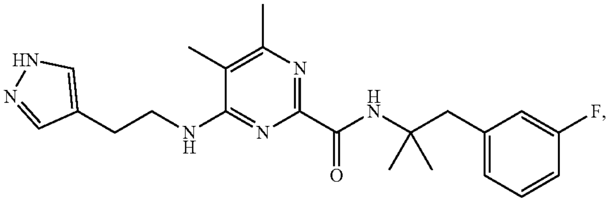 [SMILES: Cc1nc(C(=O)NC(C)(C)Cc2cccc(F)c2)nc(NCCc2cn[nH]c2)c1C] F, |
| 42 | 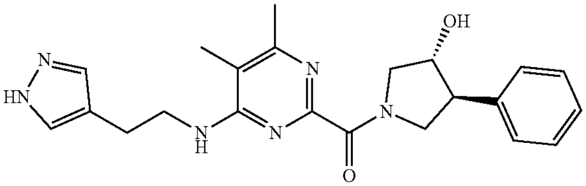 , |

-continued
| No. | Structure |
|---|---|
| 43 | 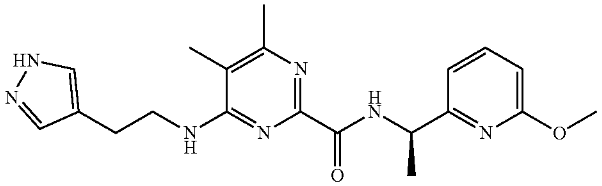 , |
| 44 | 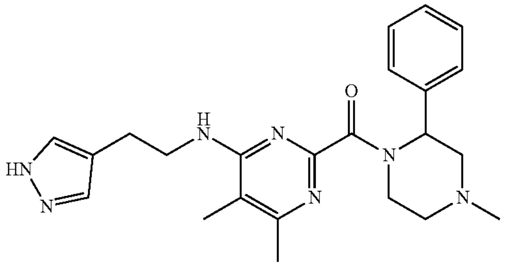 , |
| 45 | 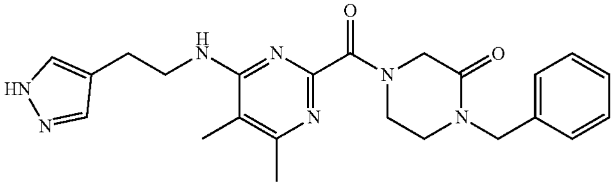 , |
| 46 | 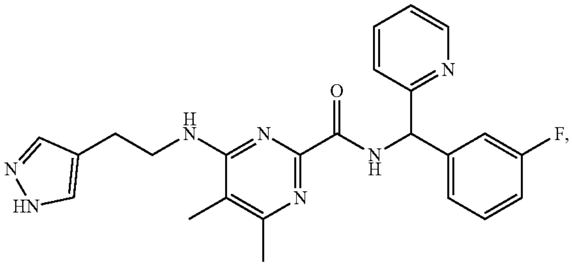 [SMILES: Cc1nc(C(=O)NC(c2cccc(F)c2)c2ccccn2)nc(NCCc2cn[nH]c2)c1C] , |
| 47 | 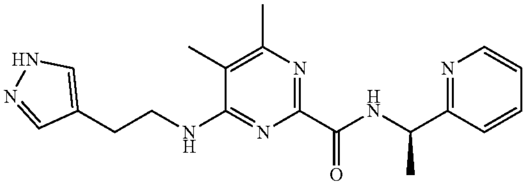 , |
| 48 | 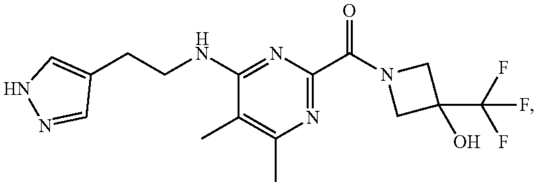 [SMILES: Cc1nc(C(=O)N2CC(O)(C(F)(F)F)C2)nc(NCCc2cn[nH]c2)c1C] , |

-continued
| No. | Structure |
|---|---|
| 49 | 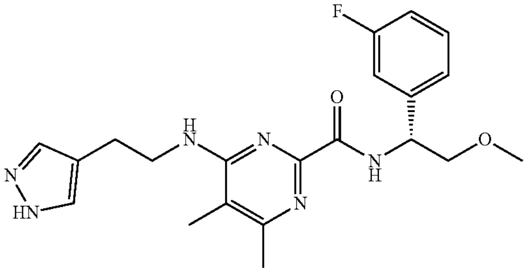, |
| 50 | 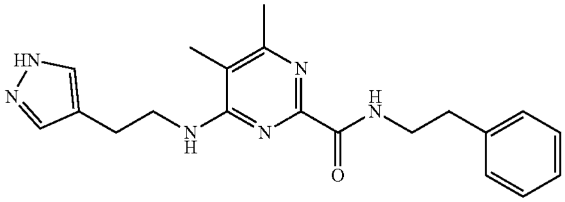, |
| 51 | 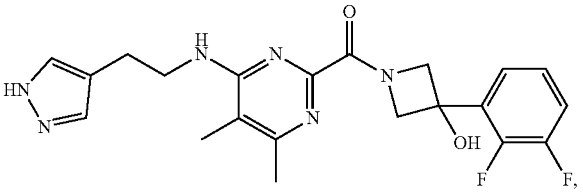 [SMILES: Cc1nc(C(=O)N2CC(O)(c3cccc(F)c3F)C2)nc(NCCc2cn[nH]c2)c1C] |
| 52 | 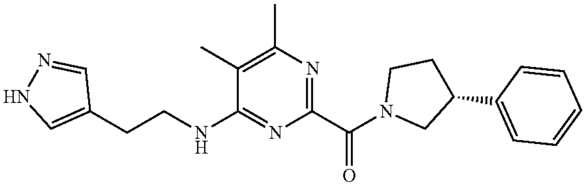, |
| 53 | 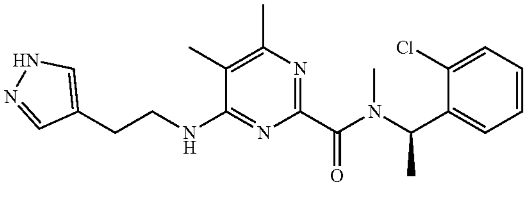, |
| 54 | 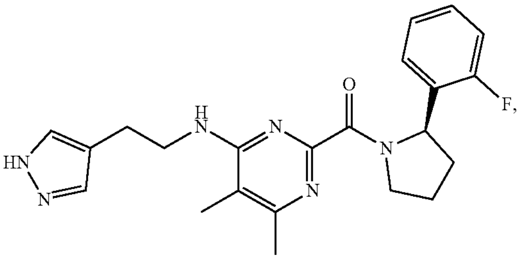 [SMILES: Cc1nc(C(=O)N2CCC[C@@H]2c2ccccc2F)nc(NCCc2cn[nH]c2)c1C] |
| 55 | 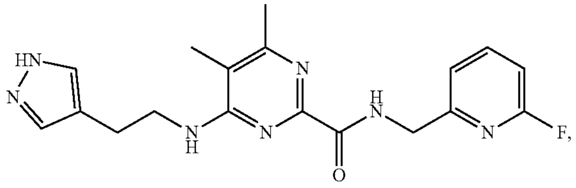 [SMILES: Cc1nc(C(=O)NCc2cccc(F)n2)nc(NCCc2cn[nH]c2)c1C] |

-continued
| No. | Structure |
|---|---|
| 56 | 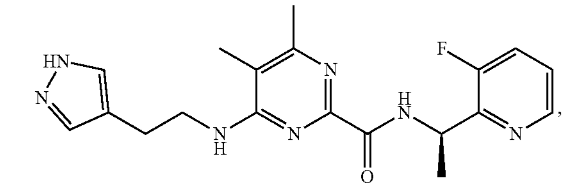 |
| 57 | 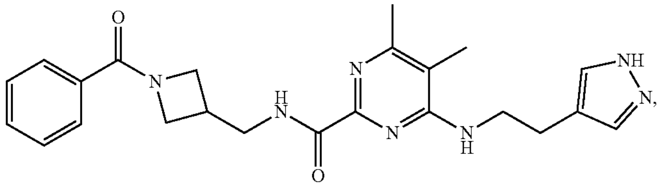 [SMILES: Cc1nc(C(=O)NCC2CN(C(=O)c3ccccc3)C2)nc(NCCc2cn[nH]c2)c1C] |
| 58 | 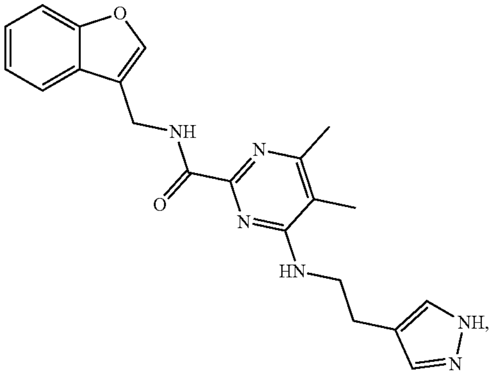 [SMILES: Cc1nc(C(=O)NCc2coc3ccccc23)nc(NCCc2cn[nH]c2)c1C] |
| 59 | 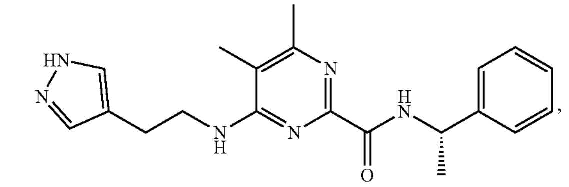 [SMILES: Cc1nc(C(=O)N[C@@H](C)c2ccccc2)nc(NCCc2cn[nH]c2)c1C] |
| 60 | 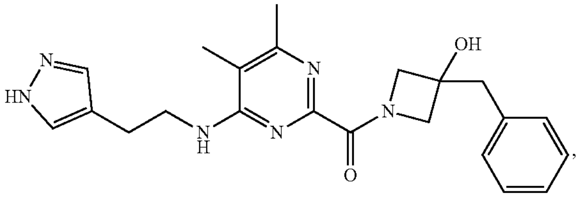 [SMILES: Cc1nc(C(=O)N2CC(O)(Cc3ccccc3)C2)nc(NCCc2cn[nH]c2)c1C] |
| 61 | 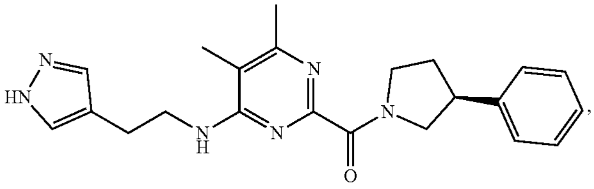 [SMILES: Cc1nc(C(=O)N2CC[C@@H](c3ccccc3)C2)nc(NCCc2cn[nH]c2)c1C] |

-continued
| No. | Structure |
|---|---|
| 62 | 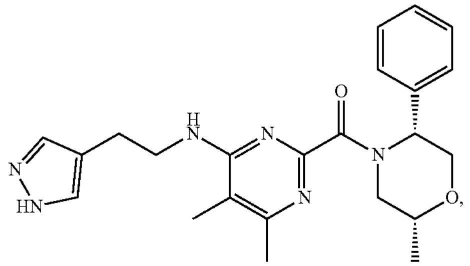 [SMILES: Cc1nc(C(=O)N2C[C@@H](C)OC[C@H]2c2ccccc2)nc(NCCc2cn[nH]c2)c1C] |
| 63 | 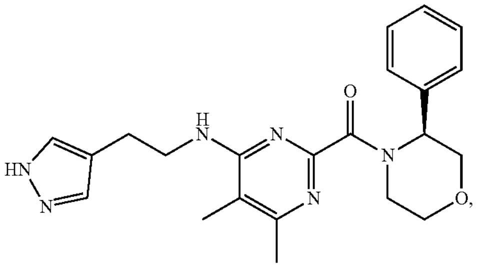 |
| 64 | 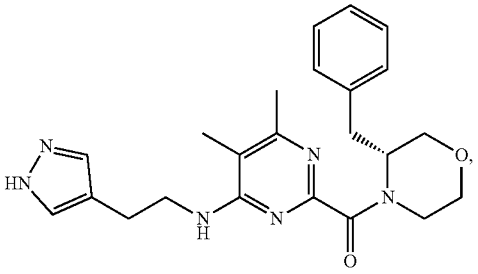 [SMILES: Cc1nc(C(=O)N2CCOC[C@H]2Cc2ccccc2)nc(NCCc2cn[nH]c2)c1C] |
| 65 | 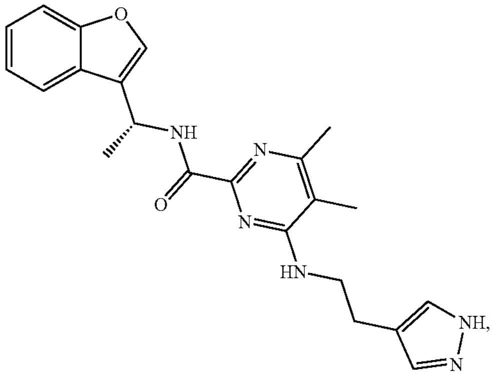 [SMILES: Cc1nc(C(=O)N[C@H](C)c2coc3ccccc23)nc(NCCc2cn[nH]c2)c1C] |
| 66 | 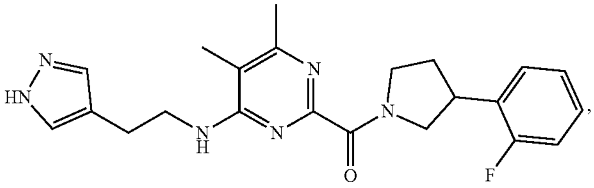 [SMILES: Cc1nc(C(=O)N2CCC(c3ccccc3F)C2)nc(NCCc2cn[nH]c2)c1C] |

-continued
| No. | Structure |
|---|---|
| 67 | 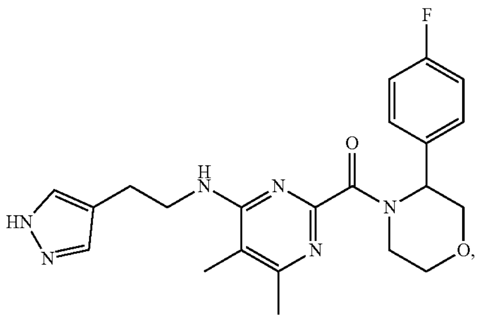 [SMILES: Cc1nc(C(=O)N2CCOCC2c2ccc(F)cc2)nc(NCCc2cn[nH]c2)c1C] |
| 68 | 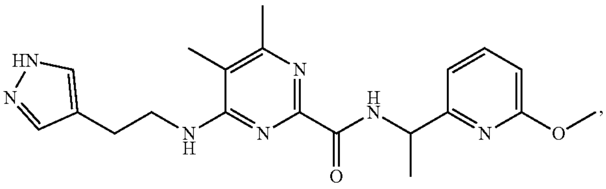 [SMILES: COc1cccc(C(C)NC(=O)c2nc(C)c(C)c(NCCc3cn[nH]c3)n2)n1] |
| 69 | 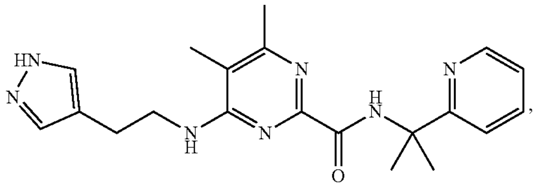 [SMILES: Cc1nc(C(=O)NC(C)(C)c2ccccn2)nc(NCCc2cn[nH]c2)c1C] |
| 70 | 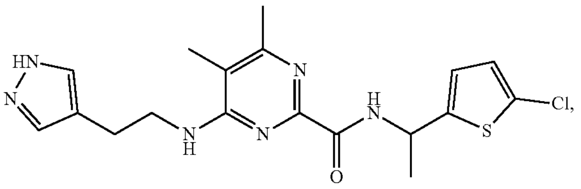 [SMILES: Cc1nc(C(=O)NC(C)c2ccc(Cl)s2)nc(NCCc2cn[nH]c2)c1C] |
| 71 | 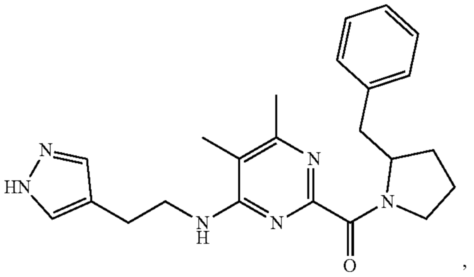 [SMILES: Cc1nc(C(=O)N2CCCC2Cc2ccccc2)nc(NCCc2cn[nH]c2)c1C] |
| 72 | 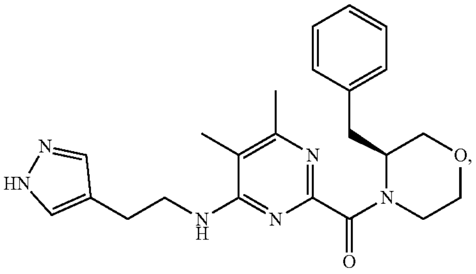 [SMILES: Cc1nc(C(=O)N2CCOC[C@@H]2Cc2ccccc2)nc(NCCc2cn[nH]c2)c1C] |

-continued
| No. | Structure |
|---|---|
| 73 | 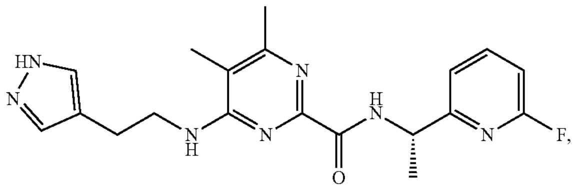 F, |
| 74 | 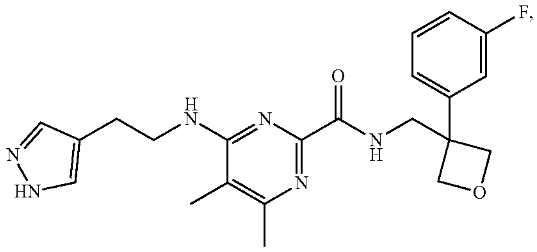 |
| 75 | 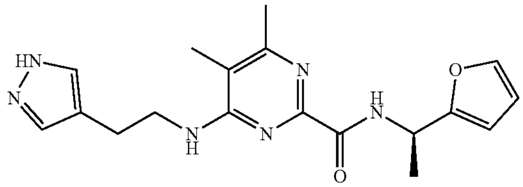 , |
| 76 | 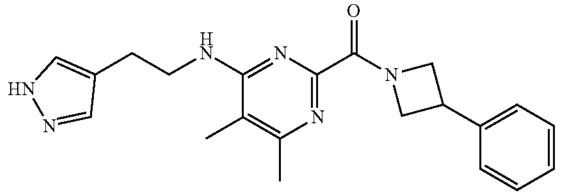 , |
| 77 | 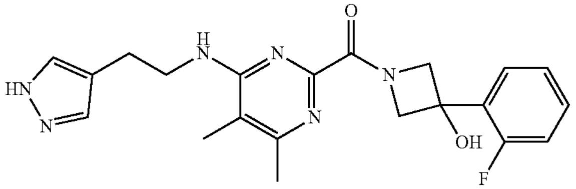 , |
| 78 | 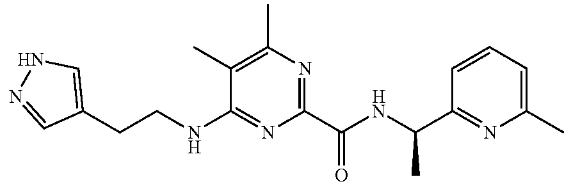 , |
| 79 | 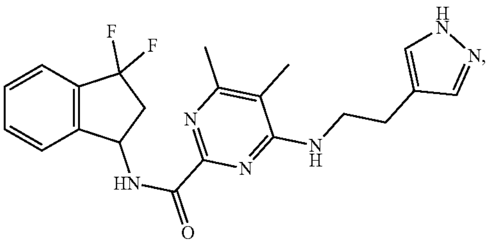 |

-continued
| No. | Structure |
| --- | --- |
| 80 | 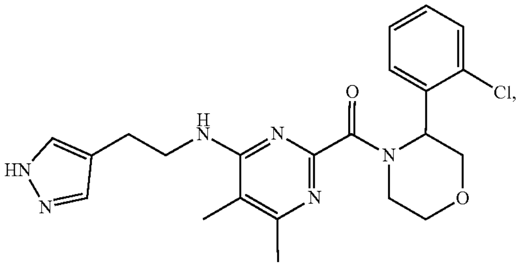 [SMILES: Cc1nc(C(=O)N2CCOCC2c2ccccc2Cl)nc(NCCc2cn[nH]c2)c1C] |
| 81 | 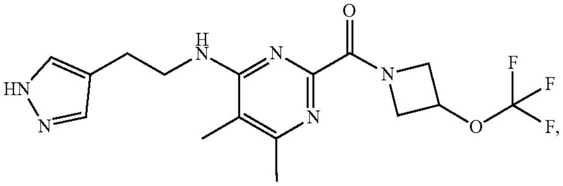 [SMILES: Cc1nc(C(=O)N2CC(OC(F)(F)F)C2)nc(NCCc2cn[nH]c2)c1C] |
| 82 | 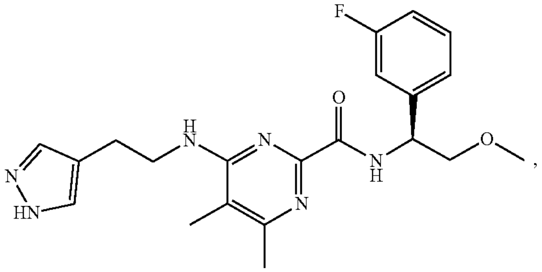 [SMILES: COC[C@@H](NC(=O)c1nc(C)c(C)c(NCCc2cn[nH]c2)n1)c1cccc(F)c1] |
| 83 | 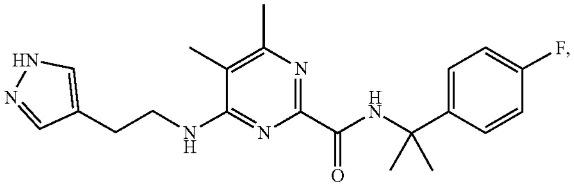 [SMILES: Cc1nc(C(=O)NC(C)(C)c2ccc(F)cc2)nc(NCCc2cn[nH]c2)c1C] |
| 84 | 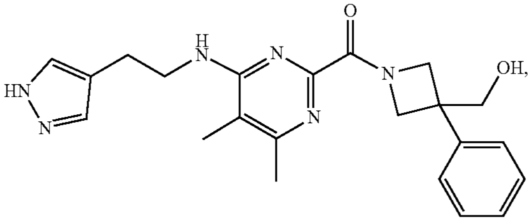 [SMILES: Cc1nc(C(=O)N2CC(CO)(c3ccccc3)C2)nc(NCCc2cn[nH]c2)c1C] |
| 85 | 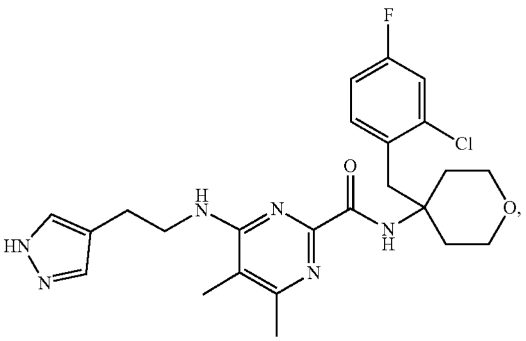 [SMILES: Cc1nc(C(=O)NC2(Cc3ccc(F)cc3Cl)CCOCC2)nc(NCCc2cn[nH]c2)c1C] |

-continued
| No. | Structure |
|---|---|
| 86 | 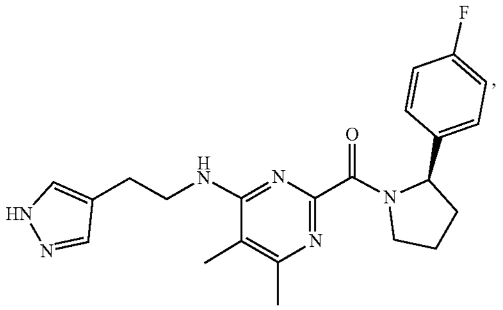 [SMILES: Cc1nc(C(=O)N2CCC[C@@H]2c2ccc(F)cc2)nc(NCCc2cn[nH]c2)c1C] |
| 87 | 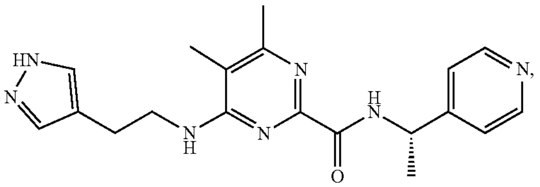 [SMILES: Cc1nc(C(=O)N[C@@H](C)c2ccncc2)nc(NCCc2cn[nH]c2)c1C] |
| 88 | 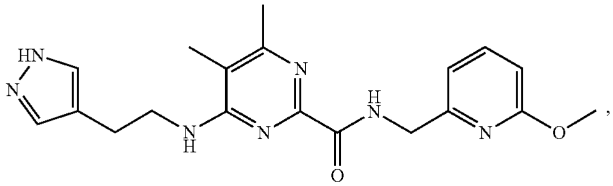 [SMILES: COc1cccc(CNC(=O)c2nc(C)c(C)c(NCCc3cn[nH]c3)n2)n1] |
| 89 | 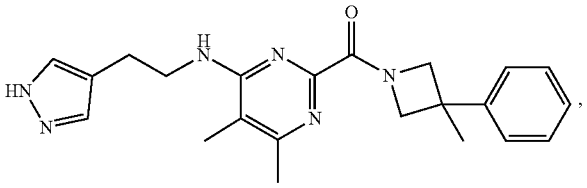 [SMILES: Cc1nc(C(=O)N2CC(C)(c3ccccc3)C2)nc(NCCc2cn[nH]c2)c1C] |
| 90 | 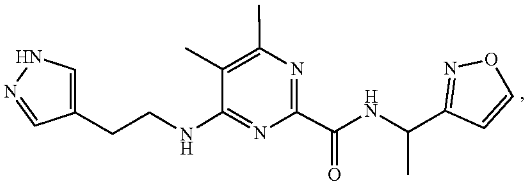 [SMILES: Cc1nc(C(=O)NC(C)c2ccon2)nc(NCCc2cn[nH]c2)c1C] |
| 91 | 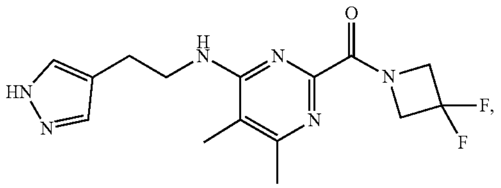 [SMILES: Cc1nc(C(=O)N2CC(F)(F)C2)nc(NCCc2cn[nH]c2)c1C] |

-continued
| No. | Structure |
|---|---|
| 92 | 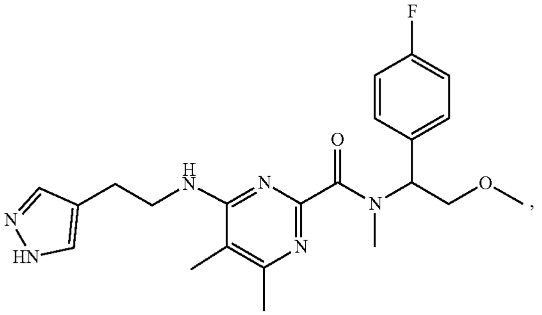 [SMILES: COCC(c1ccc(F)cc1)N(C)C(=O)c1nc(C)c(C)c(NCCc2cn[nH]c2)n1] |
| 93 | 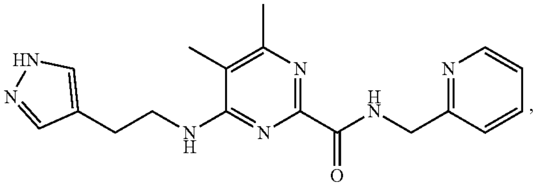 [SMILES: Cc1nc(C(=O)NCc2ccccn2)nc(NCCc2cn[nH]c2)c1C] |
| 94 | 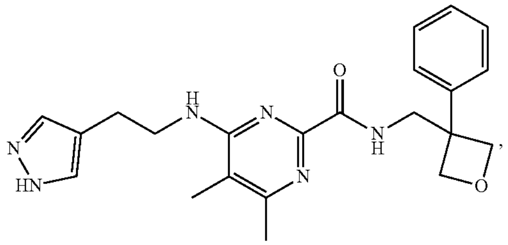 [SMILES: Cc1nc(C(=O)NCC2(c3ccccc3)COC2)nc(NCCc2cn[nH]c2)c1C] |
| 95 | 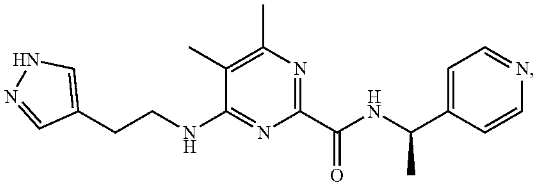 [SMILES: Cc1nc(C(=O)N[C@H](C)c2ccncc2)nc(NCCc2cn[nH]c2)c1C] |
| 96 | 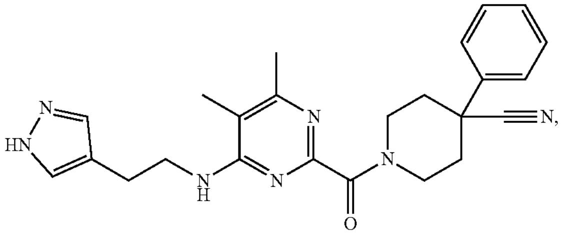 [SMILES: Cc1nc(C(=O)N2CCC(C#N)(c3ccccc3)CC2)nc(NCCc2cn[nH]c2)c1C] |
| 97 | 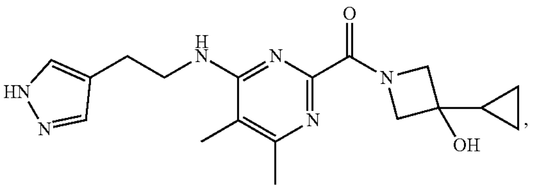 [SMILES: Cc1nc(C(=O)N2CC(O)(C3CC3)C2)nc(NCCc2cn[nH]c2)c1C] |

-continued
| No. | Structure |
|---|---|
| 98 | 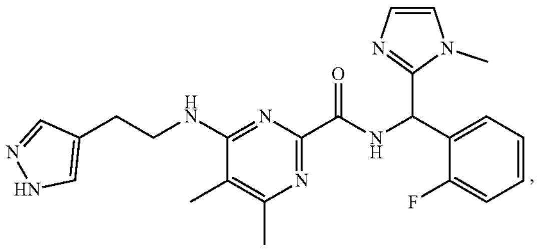 [SMILES: Cc1nc(C(=O)NC(c2ccccc2F)c2nccn2C)nc(NCCc2cn[nH]c2)c1C] |
| 99 | 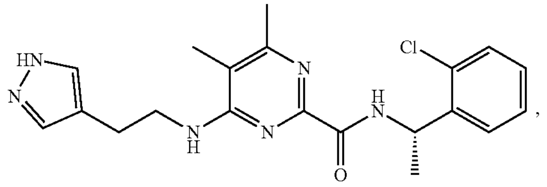 [SMILES: Cc1nc(C(=O)N[C@@H](C)c2ccccc2Cl)nc(NCCc2cn[nH]c2)c1C] |
| 100 | 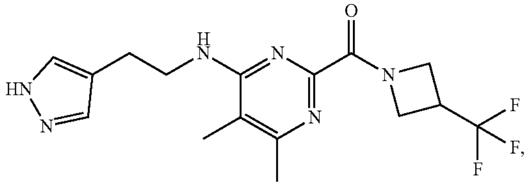 [SMILES: Cc1nc(C(=O)N2CC(C(F)(F)F)C2)nc(NCCc2cn[nH]c2)c1C] |
| 101 | 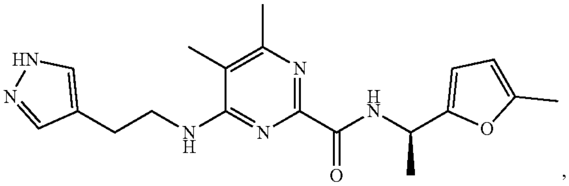 [SMILES: Cc1ccc([C@@H](C)NC(=O)c2nc(C)c(C)c(NCCc3cn[nH]c3)n2)o1] |
| 102 | 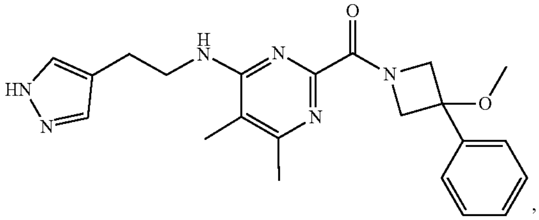 [SMILES: COC1(c2ccccc2)CN(C(=O)c2nc(C)c(C)c(NCCc3cn[nH]c3)n2)C1] |
| 103 | 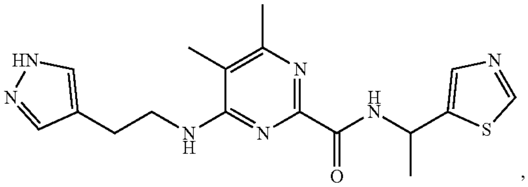 [SMILES: Cc1nc(C(=O)NC(C)c2cncs2)nc(NCCc2cn[nH]c2)c1C] |
| 104 | 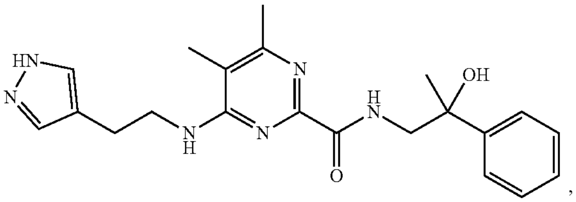 [SMILES: Cc1nc(C(=O)NCC(C)(O)c2ccccc2)nc(NCCc2cn[nH]c2)c1C] |

-continued
| No. | Structure |
|---|---|
| 105 | 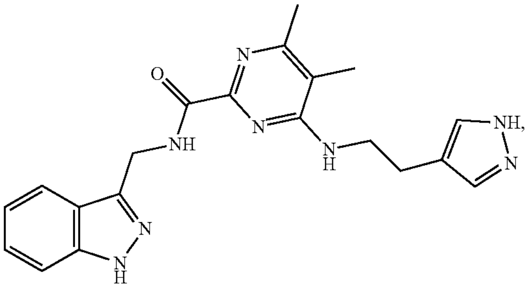 [SMILES: Cc1nc(C(=O)NCc2n[nH]c3ccccc23)nc(NCCc2cn[nH]c2)c1C] |
| 106 | 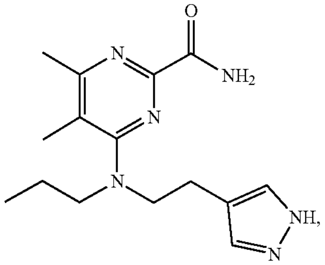 [SMILES: CCCN(CCc1cn[nH]c1)c1nc(C(N)=O)nc(C)c1C] |
| 107 | 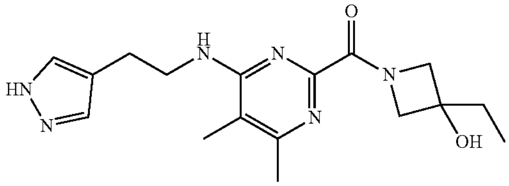 , |
| 108 | 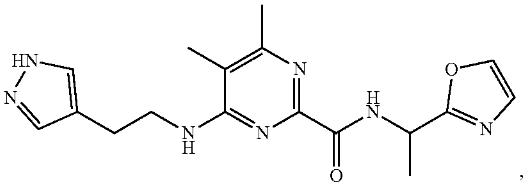 , |
| 109 | 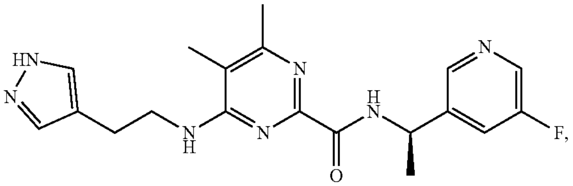 [SMILES: Cc1nc(C(=O)N[C@H](C)c2cncc(F)c2)nc(NCCc2cn[nH]c2)c1C] |
| 110 | 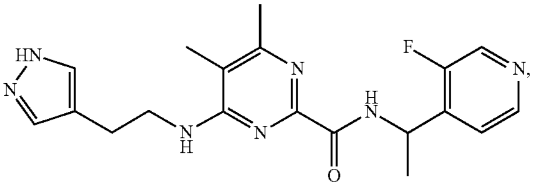 [SMILES: Cc1nc(C(=O)NC(C)c2ccncc2F)nc(NCCc2cn[nH]c2)c1C] |
| 111 | 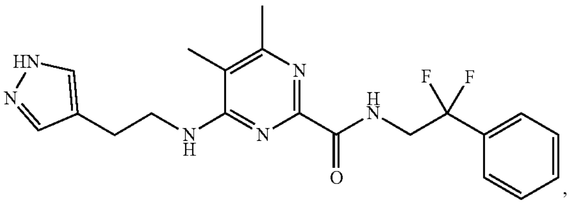 [SMILES: Cc1nc(C(=O)NCC(F)(F)c2ccccc2)nc(NCCc2cn[nH]c2)c1C] , |

-continued
| No. | Structure |
| --- | --- |
| 112 | 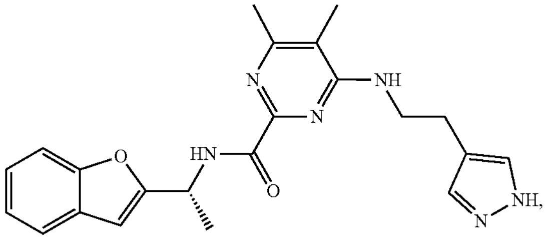 [SMILES: Cc1nc(C(=O)N[C@H](C)c2cc3ccccc3o2)nc(NCCc2cn[nH]c2)c1C] |
| 113 | 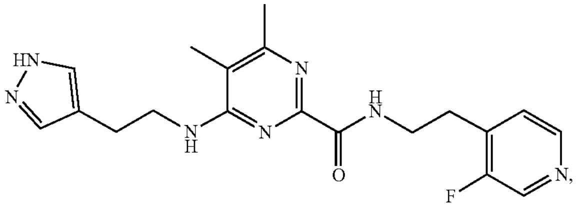 [SMILES: Cc1nc(C(=O)NCCc2ccncc2F)nc(NCCc2cn[nH]c2)c1C] |
| 114 | 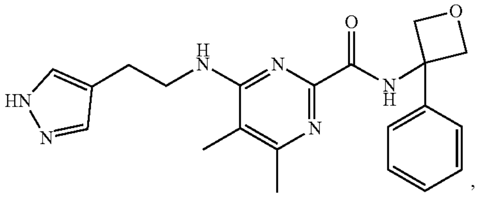 [SMILES: Cc1nc(C(=O)NC2(c3ccccc3)COC2)nc(NCCc2cn[nH]c2)c1C] |
| 115 | 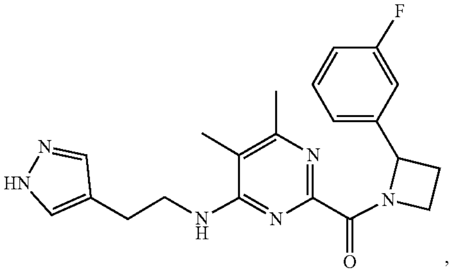 [SMILES: Cc1nc(C(=O)N2CCC2c2cccc(F)c2)nc(NCCc2cn[nH]c2)c1C] |
| 116 | 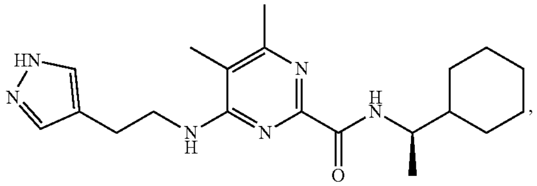 [SMILES: Cc1nc(C(=O)N[C@H](C)C2CCCCC2)nc(NCCc2cn[nH]c2)c1C] |
| 117 | 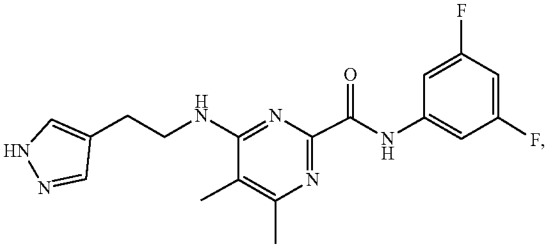 [SMILES: Cc1nc(C(=O)Nc2cc(F)cc(F)c2)nc(NCCc2cn[nH]c2)c1C] |
| 118 | 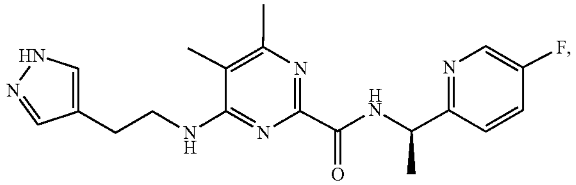 [SMILES: Cc1nc(C(=O)N[C@H](C)c2ccc(F)cn2)nc(NCCc2cn[nH]c2)c1C] |

-continued
| No. | Structure |
|---|---|
| 119 | 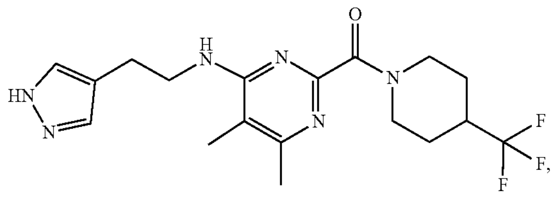 [SMILES: Cc1nc(C(=O)N2CCC(C(F)(F)F)CC2)nc(NCCc2cn[nH]c2)c1C] |
| 120 | 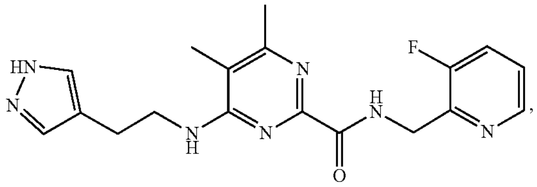 [SMILES: Cc1nc(C(=O)NCc2ncccc2F)nc(NCCc2cn[nH]c2)c1C] |
| 121 | 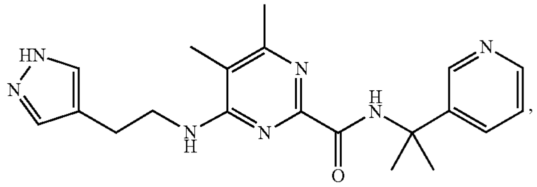 [SMILES: Cc1nc(C(=O)NC(C)(C)c2cccnc2)nc(NCCc2cn[nH]c2)c1C] |
| 122 | 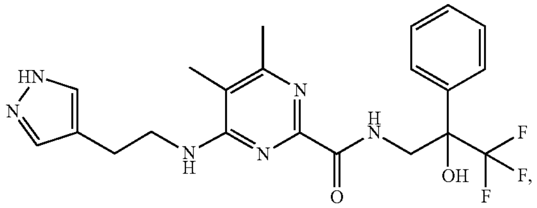 [SMILES: Cc1nc(C(=O)NCC(O)(c2ccccc2)C(F)(F)F)nc(NCCc2cn[nH]c2)c1C] |
| 123 | 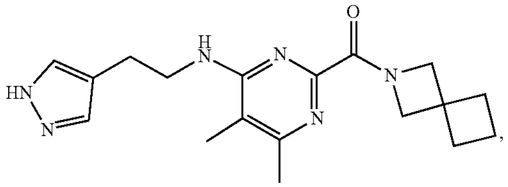 [SMILES: Cc1nc(C(=O)N2CC3(CCC3)C2)nc(NCCc2cn[nH]c2)c1C] |
| 124 | 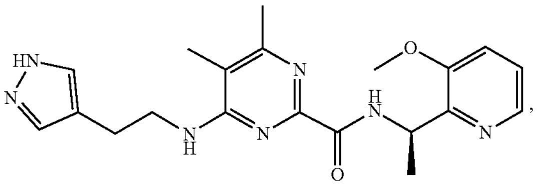 [SMILES: COc1cccnc1[C@@H](C)NC(=O)c1nc(C)c(C)c(NCCc2cn[nH]c2)n1] |
| 125 | 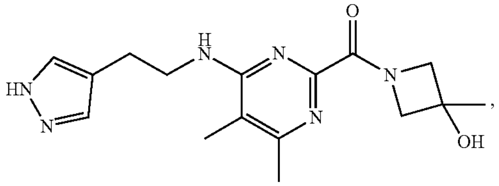 |

-continued
| No. | Structure |
|---|---|
| 126 | 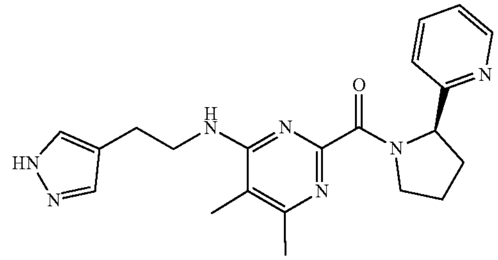 , |
| 127 | 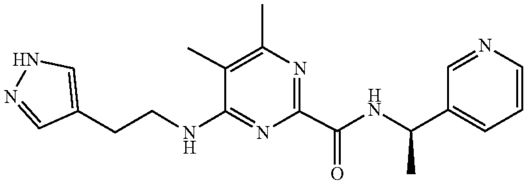 , |
| 128 | 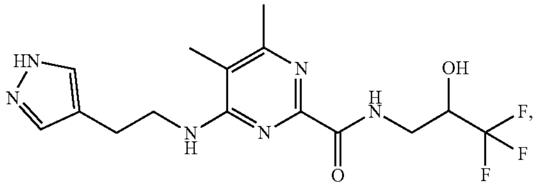 [SMILES: Cc1nc(C(=O)NCC(O)C(F)(F)F)nc(NCCc2cn[nH]c2)c1C] , |
| 129 | 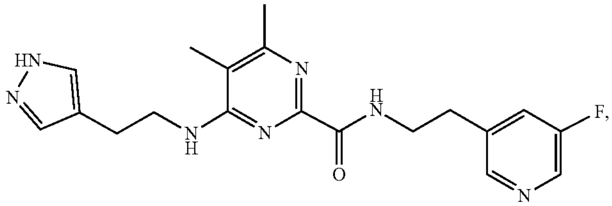 [SMILES: Cc1nc(C(=O)NCCc2cncc(F)c2)nc(NCCc2cn[nH]c2)c1C] , |
| 130 | 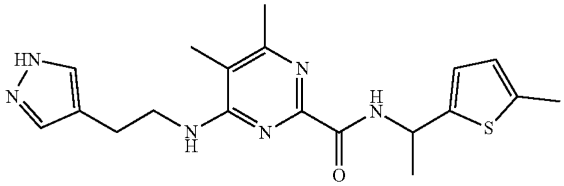 , |
| 131 | 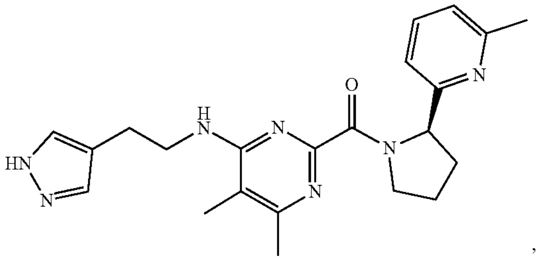 [SMILES: Cc1cccc([C@H]2CCCN2C(=O)c2nc(C)c(C)c(NCCc3cn[nH]c3)n2)n1] , |
| 132 | 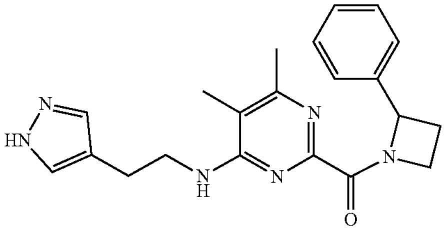 , |

-continued
| No. | Structure |
|---|---|
| 133 | 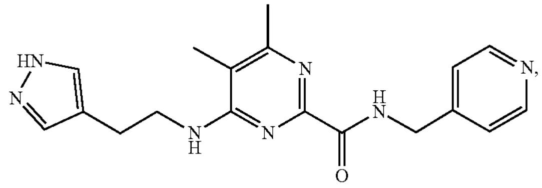 [SMILES: Cc1nc(C(=O)NCc2ccncc2)nc(NCCc2cn[nH]c2)c1C] |
| 134 | 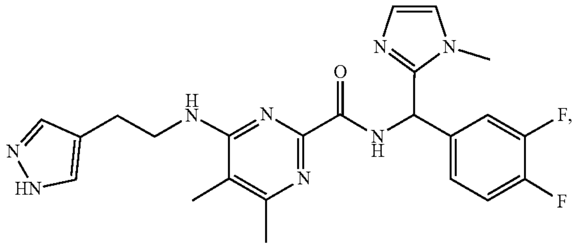 [SMILES: Cc1nc(C(=O)NC(c2ccc(F)c(F)c2)c2nccn2C)nc(NCCc2cn[nH]c2)c1C] |
| 135 | 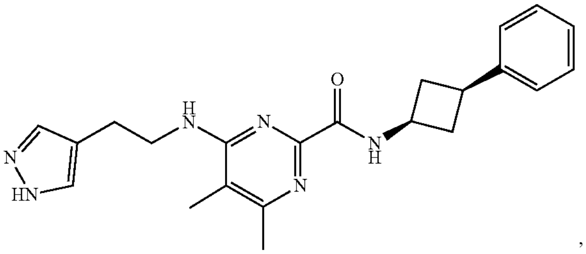 [SMILES: Cc1nc(C(=O)N[C@H]2C[C@@H](c3ccccc3)C2)nc(NCCc2cn[nH]c2)c1C] , |
| 136 | 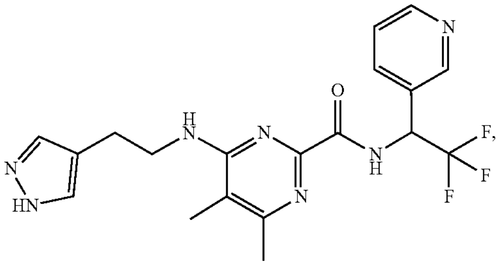 [SMILES: Cc1nc(C(=O)NC(c2cccnc2)C(F)(F)F)nc(NCCc2cn[nH]c2)c1C] |
| 137 | 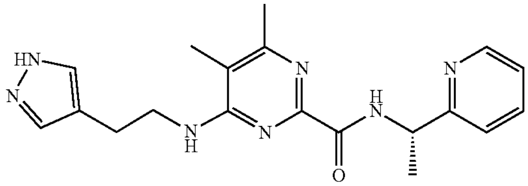 , |
| 138 | 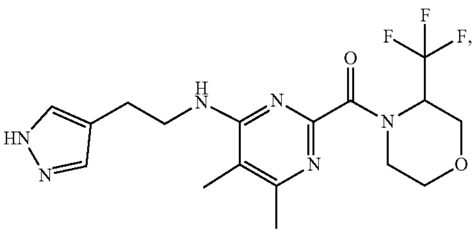 [SMILES: Cc1nc(C(=O)N2CCOCC2C(F)(F)F)nc(NCCc2cn[nH]c2)c1C] |

-continued
| No. | Structure |
| --- | --- |
| 139 | 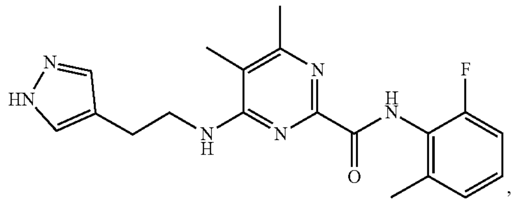 [SMILES: Cc1cccc(F)c1NC(=O)c1nc(C)c(C)c(NCCc2cn[nH]c2)n1] , |
| 140 | 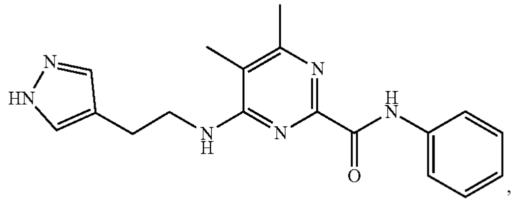 [SMILES: Cc1nc(C(=O)Nc2ccccc2)nc(NCCc2cn[nH]c2)c1C] , |
| 141 | 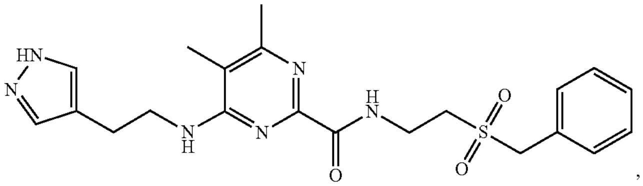 [SMILES: Cc1nc(C(=O)NCCS(=O)(=O)Cc2ccccc2)nc(NCCc2cn[nH]c2)c1C] , |
| 142 | 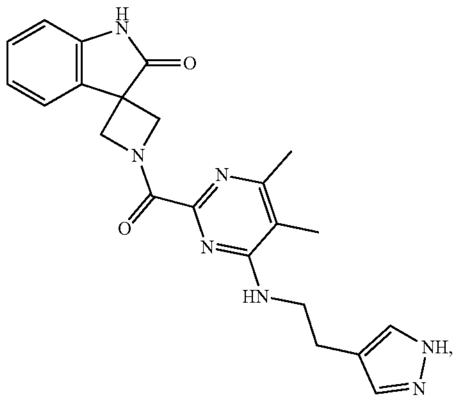 [SMILES: Cc1nc(C(=O)N2CC3(C2)C(=O)Nc2ccccc23)nc(NCCc2cn[nH]c2)c1C] , |
| 143 | 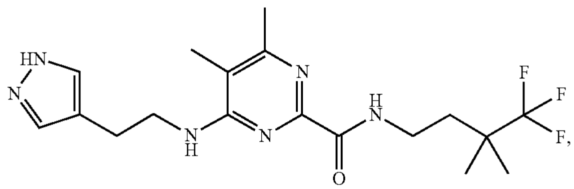 [SMILES: Cc1nc(C(=O)NCCC(C)(C)C(F)(F)F)nc(NCCc2cn[nH]c2)c1C] , |
| 144 | 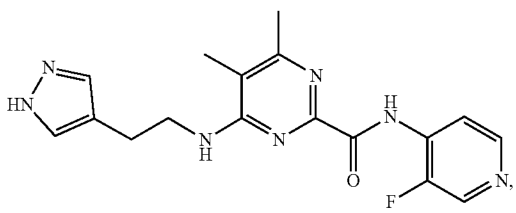 [SMILES: Cc1nc(C(=O)Nc2ccncc2F)nc(NCCc2cn[nH]c2)c1C] , |
and -continued

| No. | Structure |
| --- | --- |
| 145 | 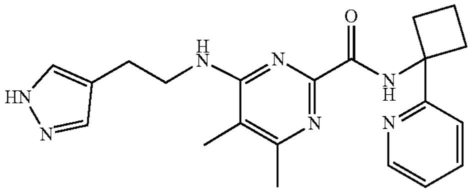, |

or a pharmaceutically acceptable salt thereof.

30. A pharmaceutical composition comprising a compound of claim 1, or a pharmaceutically acceptable salt thereof, and a pharmaceutically acceptable excipient.

31. A method of treating a disease or condition mediated by NAMPT activity in a subject in need thereof, comprising administering to the subject a compound of claim 1, or a pharmaceutically acceptable salt thereof.

32. The method of claim 31, wherein the disease or condition is selected from the group consisting of cancer, a hyperproliferative disease or condition, an inflammatory disease or condition, a metabolic disorder, a cardiac disease or condition, chemotherapy-induced tissue damage, a renal disease, a metabolic disease, a neurological disease or injury, a neurodegenerative disorder or disease, diseases caused by impaired stem cell function, diseases caused by DNA damage, primary mitochondrial disorders, or a muscle disease and muscle-wasting disorder.

33. The method of claim 31, wherein the disease or condition is selected from the group consisting of obesity, atherosclerosis, insulin resistance, type 2 diabetes, cardiovascular disease, Alzheimer's disease, Huntington's disease, Parkinson's disease, amyotrophic lateral sclerosis, depression, Down syndrome, neonatal nerve injury, aging, axonal degeneration, carpal tunnel syndrome, Guillain-Barre syndrome, nerve damage, polio (poliomyelitis), and spinal cord injury.

* * * * *